(12) United States Patent
Baell et al.

(10) Patent No.: US 8,114,893 B2
(45) Date of Patent: Feb. 14, 2012

(54) COMPOUNDS AND METHODS OF USE

(75) Inventors: Jonathan Bayldon Baell, Bundoora (AU); Chinh Thien Bui, Balwyn North (AU); Peter Colman, East Melbourne (AU); Danette A. Dudley, Pacifica, CA (US); Wayne J. Fairbrother, Burlingame, CA (US); John A. Flygare, Burlingame, CA (US); Guillaume Laurent Lessene, Coburg (AU); Chudi Ndubaku, San Francisco, CA (US); George Nikolakopoulos, Thomastown (AU); Carl Steven Rye, CR Epsom (GB); Brad Edmund Sleebs, Reservoir (AU); Brian John Smith, Sunbury (AU); Keith Geoffrey Watson, Surry Hills (AU); Steven W. Elmore, Northbrook, IL (US); Andrew M. Petros, Mundelein, IL (US); Andrew J. Souers, Evanston, IL (US); Peter Czabotar, Melbourne (AU)

(73) Assignees: Genentech, Inc., South San Francisco, CA (US); Abbott Laboratories, Abbott Park, IL (US); The Walter and Eliza Hall Medical Research Institute, Parkville (AU)

( * ) Notice: Subject to any disclaimer, the term of this patent is extended or adjusted under 35 U.S.C. 154(b) by 0 days.

(21) Appl. No.: 12/641,063

(22) Filed: Dec. 17, 2009

(65) Prior Publication Data

US 2010/0190782 A1 Jul. 29, 2010

Related U.S. Application Data

(60) Provisional application No. 61/139,479, filed on Dec. 19, 2008.

(51) Int. Cl.
| | | |
|---|---|---|
| *C07D 417/14* | (2006.01) | |
| *A61K 31/5377* | (2006.01) | |
| *A61K 31/538* | (2006.01) | |
| *A61K 31/496* | (2006.01) | |
| *A61K 31/498* | (2006.01) | |
| *A61K 31/4709* | (2006.01) | |

(52) U.S. Cl. ............. 514/314; 514/249; 514/230.5; 514/233.8; 514/253.06; 514/266.21; 514/367; 514/213.01; 514/262.1; 514/255.05; 544/235; 544/363; 544/128; 544/353; 544/284; 544/262; 544/405; 548/159; 540/593; 546/165

(58) Field of Classification Search .............. 540/593; 544/235, 363, 128, 353, 105, 284, 262, 405; 546/165; 548/159; 514/314, 249, 230.1, 514/595, 233.8, 253.06, 266.21, 367, 213.01, 514/262.1, 255.05, 230.5
See application file for complete search history.

(56) References Cited

U.S. PATENT DOCUMENTS

| | | | |
|---|---|---|---|
| 4,107,167 | A | 8/1978 | Lorenz et al. |
| 6,699,857 | B1 | 3/2004 | Stoltefuss et al. |
| 7,091,227 | B2 | 8/2006 | Scott et al. |
| 2009/0054402 | A1 | 2/2009 | Wang et al. |
| 2009/0124616 | A1 | 5/2009 | Song et al. |
| 2010/0210622 | A1 | 8/2010 | Baell et al. |

FOREIGN PATENT DOCUMENTS

WO WO 2009/039553 4/2009

OTHER PUBLICATIONS

ISA, International Search Report and Written Opinion dated Feb. 23, 2010 for International application PCT/US2009/068400.

*Primary Examiner* — Joseph Kosack
*Assistant Examiner* — Matthew Coughlin
(74) *Attorney, Agent, or Firm* — Jones Day

(57) ABSTRACT

In one aspect, the present invention provides for a compound of Formula I

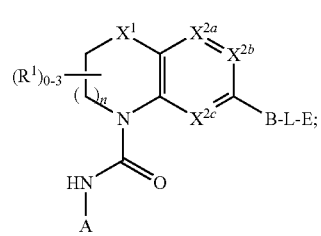

in which in Formula I, the variables $X^1$, $X^{2a}$, $X^{2b}$, $X^{2c}$, $R^1$, B, L, E, A and the subscript n are as defined herein. In another aspect, the present invention provides for pharmaceutical compositions comprising compounds of Formula I as well as methods for using compounds of Formula I for the treatment of diseases and conditions (e.g., cancer, thrombocythemia, etc) characterized by the expression or over-expression of Bcl-2 anti-apoptotic proteins, e.g., of anti-apoptotic Bcl-$x_L$ proteins.

20 Claims, 7 Drawing Sheets

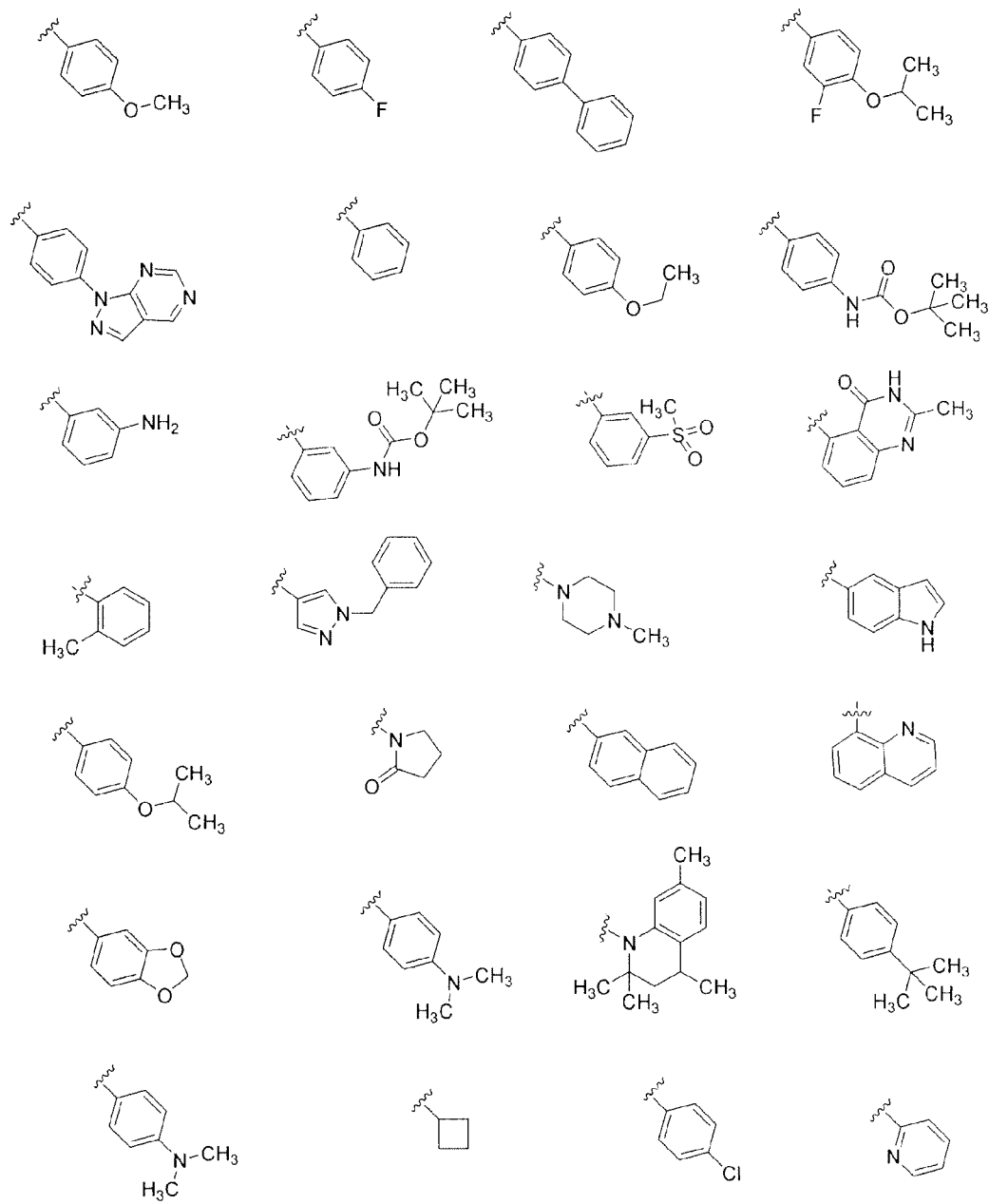
Figure 2-A

Figure 2-B
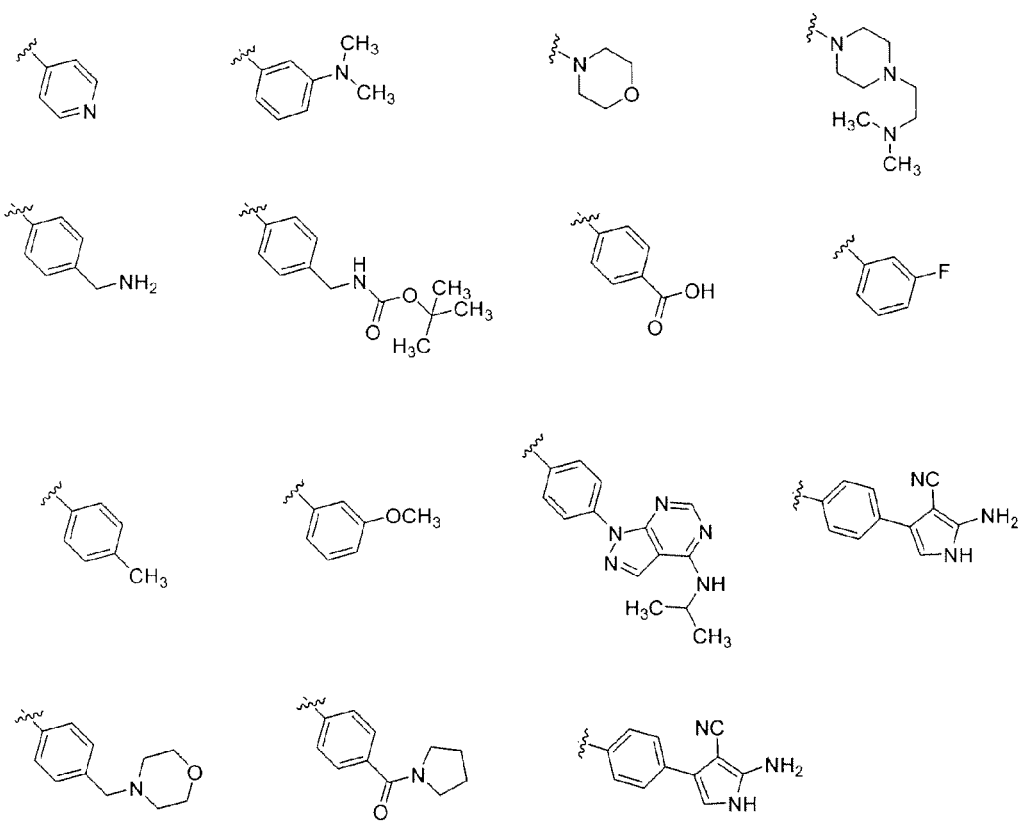

Figure 2-C
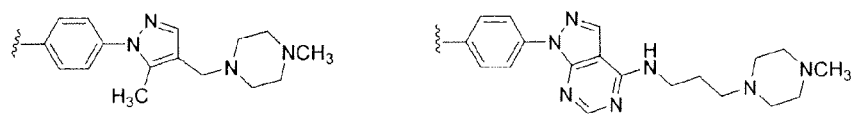
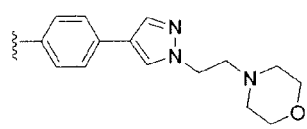 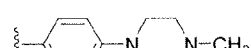 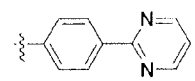
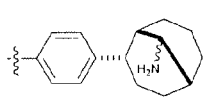 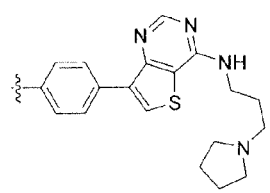 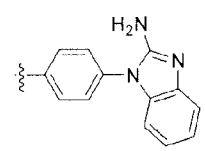
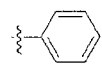 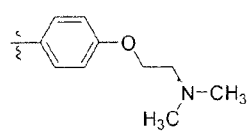 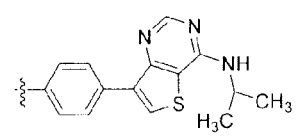
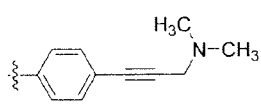  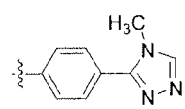
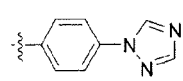 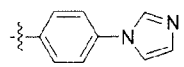 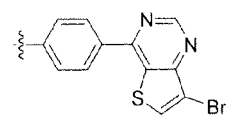
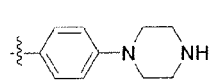 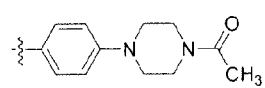 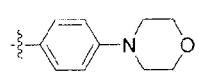

Figure 2-D
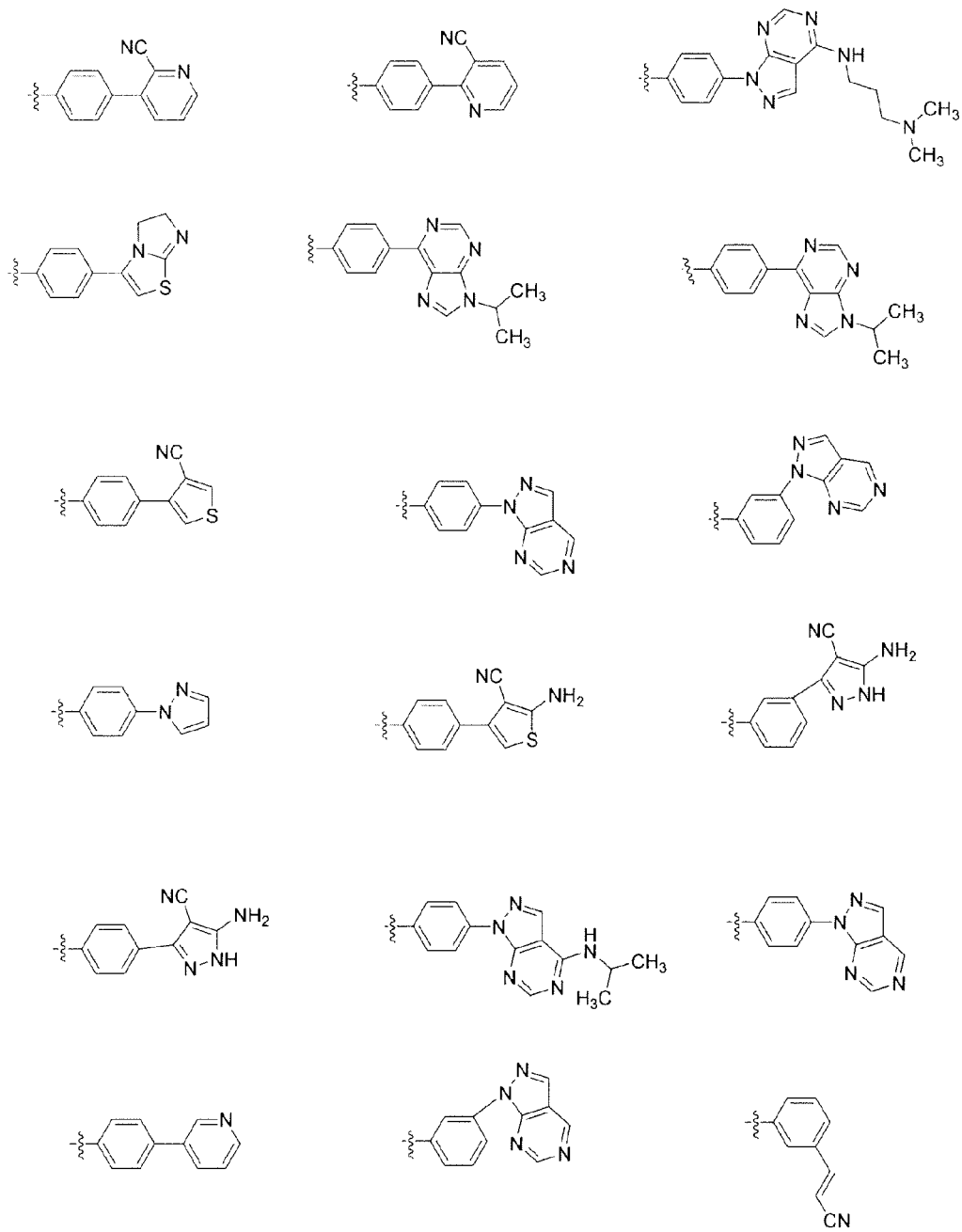

Figure 2-E
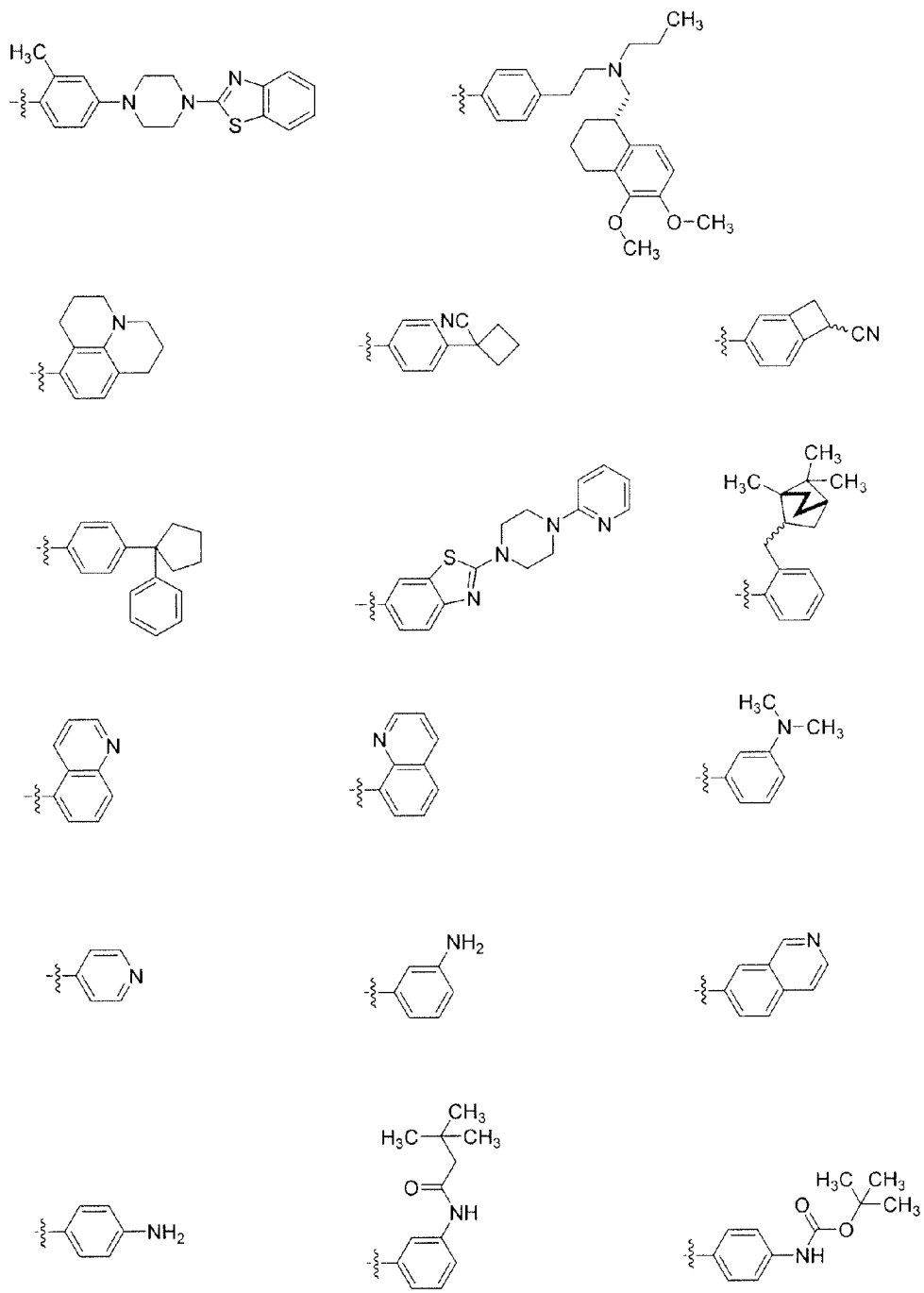

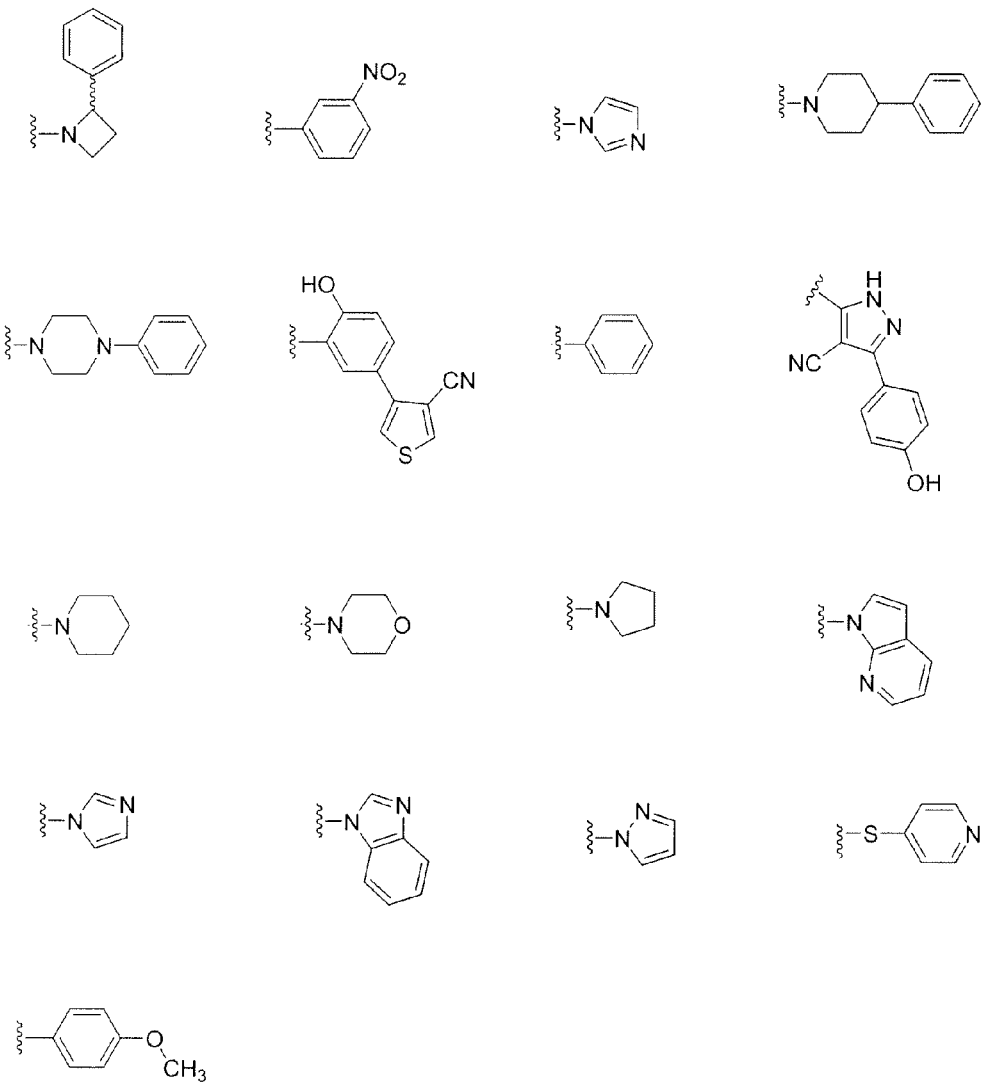
Figure 2-F

COMPOUNDS AND METHODS OF USE

CROSS-REFERENCE TO RELATED APPLICATIONS

This application claims the benefit of U.S. Provisional Application No. 61/139,479, filed Dec. 19, 2008, the content of which is hereby incorporated by reference in its entirety.

BACKGROUND OF INVENTION

Apoptosis is now recognized as an essential biological process for tissue homeostasis of all living species. In mammals in particular, it has been shown to regulate early embryonic development. Later in life, cell death is a default mechanism by which potentially dangerous cells (e.g., cells carrying cancerous defects) are removed. Several apoptotic pathways have been uncovered, and one of the most important involves the Bcl-2 family of proteins, which are key regulators of the mitochondrial (also called "intrinsic") pathway of apoptosis. See, Danial, N. N. and Korsmeyer, S. J. *Cell* (2004) 116, 205-219. The structural homology domains BH1, BH2, BH3 and BH4 are characteristic of this family of proteins. The Bcl-2 family of proteins can be further classified into three subfamilies depending on how many of the homology domains each protein contains and on its biological activity (i.e., whether it has pro- or anti-apoptotic function).

The first subgroup contains proteins having all 4 homology domains, i.e., BH1, BH2, BH3 and BH4. Their general effect is anti-apoptotic, that is to preserve a cell from starting a cell death process. Proteins such as, for example, Bcl-2, Bcl-w, Bcl-$x_L$, Mcl-1 and Bfl-1/A1 are members of this first subgroup. Proteins belonging to the second subgroup contain the three homology domains BH1, BH2 and BH3, and have a pro-apoptotic effect. The two main representative proteins of this second subgroup are Bax and Bak. Finally, the third subgroup is composed of proteins containing only the BH3 domain and members of this subgroup are usually referred to as "BH3-only proteins." Their biological effect on the cell is pro-apoptotic. Bim, Bid, Bad, Bik, Noxa, Hrk, Bmf, and Puma are examples of this third subfamily of proteins. The exact mechanism by which the Bcl-2 family proteins regulate cell death is still not entirely known and understanding this mechanism is an active area of research in the science community. In one hypothesis of regulation of cell death by Bcl-2 family proteins, the BH3-only proteins are further categorized as either "activator" (e.g., Bim and Bid) or "sensitizer" (e.g., Bad, Bik, Noxa, Hrk, Bmf, and Puma) proteins depending on their regulatory function.

The key to tissue homeostasis is achieving the delicate balance in the interactions among the three subgroups of protein in cells. Recent studies have tried to elucidate the mechanisms by which pro-apoptotic and anti-apoptotic subgroups of Bcl-2 family proteins interact to allow a cell to undergo programmed cell death. After receiving intra- or extra-cellular signals in cells, post-translational or transcriptional activation of BH3-only proteins occurs. The BH3-only proteins are the primary inducers of an apoptotic cascade that includes, as one step, the activation of the pro-apoptotic proteins Bax and Bak on the mitochondrial membrane in cells. Upon activation of Bax and/or Bak that are either already anchored to the mitochondrial membrane or migrate to this membrane, Bax and/or Bak oligomerize to result in mitochondrial outer membrane permeabilization (MOMP), the release of cytochrome C, and downstream activation of effector caspases, to ultimately result in cell apoptosis. Some researchers hypothesize that certain BH3-only proteins (e.g., Puma, Bim, Bid) are "activators" in that these proteins directly engage pro-apoptotic proteins Bax and Bak to initiate MOMP, while other BH3-only proteins (e.g., Bad, Bik and Noxa) are "sensitizers" and induce Bax and Bak oligomerization indirectly by binding anti-apoptotic proteins (e.g., Bcl-2, Bcl-$x_L$, Bcl-w, Mcl-1) and displacing and "freeing-up" the "activator" BH3-only proteins, which subsequently bind to and activate pro-apoptotic proteins (e.g., Bax, Bak) to induce cell death. Other researchers suggest that anti-apoptotic proteins engage and seqeuester Bax and Bak directly and all BH3-only proteins regulates this interaction by binding to anti-apoptotic proteins (e.g., Bcl-2, Bcl-$x_L$, Bcl-w, Mcl-1) which results in the release Bax and Bak. See, Adams, J. M. and Cory S. *Oncogene* (2007) 26, 1324-1337; Willis, S. N. et al. *Science* (2007) 315, 856-859. Although, the exact interactions through which the anti- and pro-apoptotic Bcl-2 family proteins regulate apoptosis remain under debate, there is a large body of scientific evidence to show that compounds which inhibit the binding of BH3-only proteins to anti-apoptotic Bcl-2 family proteins promote apoptosis in cells.

Dysregulated apoptotic pathways have been implicated in the pathology of many significant diseases such as neurodegenerative conditions (up-regulated apoptosis), such as for example, Alzheimer's disease; and proliferative diseases (down-regulated apoptosis) such as for example, cancer, autoimmune diseases and pro-thrombotic conditions.

In one aspect, the implication that down-regulated apoptosis (and more particularly the Bcl-2 family of proteins) is involved in the onset of cancerous malignancy has revealed a novel way of targeting this still elusive disease. Research has shown, for example, the anti-apoptotic proteins, Bcl-2 and Bcl-$x_L$, are over-expressed in many cancer cell types. See, Zhang J. Y., *Nature Reviews/Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. The effect of this deregulation is the survival of altered cells which would otherwise have undergone apoptosis in normal conditions. The repetition of these defects associated with unregulated proliferation is thought to be the starting point of cancerous evolution. Additionally, research has shown that BH3-only proteins can act as tumor suppressors when expressed in diseased animals.

These findings as well as numerous others have made possible the emergence of new strategies in drug discovery for targeting cancer: If a small molecule that could mimic the effect of BH3-only proteins were able to enter the cell and overcome the anti-apoptotic protein over-expression, then it could be possible to reset the apoptotic process. This strategy can have the advantage that it can alleviate the problem of drug resistance which is usually a consequence of apoptotic deregulation (abnormal survival).

Researchers also have demonstrated that platelets also contain the necessary apoptotic machinery (e.g., Bax, Bak, Bcl-$x_L$, Bcl-2, cytochrome c, caspase-9, caspase-3 and APAF-1) to execute programmed cell death through the intrinsic apoptotic pathway. Although circulating platelet production is a normal physiological process, a number of diseases are caused or exacerbated by excess of, or undesired activation of platelets. The above suggests that therapeutic agents capable of inhibiting anti-apoptotic proteins in platelets and reducing the number of platelets in mammals maybe useful in treating pro-thrombotic conditions and diseases that are characterized by an excess of or undesired activation of, platelets.

Abbott Laboratories Inc. has developed a class of small molecule BH3-only protein mimetics, i.e., ABT-737 and ABT-263, that bind strongly to a subset of anti-apoptotic Bcl-2 proteins including Bcl-2, Bcl-w and Bcl-$x_L$, but only weakly to Mcl-1 and A1, and exhibits mechanism-based cytotoxicity. These compounds were tested in animal studies and demonstrated cytotoxic activity in certain xenograft models as single agents, as well as enhanced the effects of a number of chemotherapeutic agents on other xenograft models when used in combination. See, Tse, C. et al. *Cancer Res* (2008) 68, 3421-3428; and van Delft, M. F. et al. *Cancer Cell* (2006) 10, 389-399. These in vivo studies suggest the potential utility of inhibitors of anti-apoptotic Bcl-2 family proteins for the treatment of diseases that involve a dysregulated apoptotic pathway.

The natural expression levels of anti-apoptotic Bcl-2 family proteins members vary in different cell types. For example, in young platelets, Bcl-$x_L$ protein is highly expressed and plays an important role in regulating cell death (life span) of platelets. Also, in certain cancer cell types, the cancer cell's survival is attributed to the dysregulation of the apoptotic pathway caused by the over-expression of one or more anti-apoptotic Bcl-2 protein family members. In view of the important role for Bcl-2 family of proteins in regulating apoptosis in both cancerous and normal (i.e., non-cancerous) cells, and the recognized inter-cell type variability of Bcl-2 family protein expression, it is advantageous, to have a small molecule inhibitor that selectively targets and preferably binds to one type or a subset of anti-apoptotic Bcl-2 protein(s), for example, to an anti-apoptotic Bcl-2 family member that overexpressed in a certain cancer type. Such a selective compound also may confer certain advantages in the clinical setting, by providing: for example, the flexibility to select a dosing regimen, a reduced on-target toxic effect in normal cells, among others (e.g., lymphopenia has been observed in Bcl-2 deficient mice). See, Nakayama, K. et al. *PNAS* (1994) 91, 3700-3704.

In view of the above, there is a need in the art for small molecules therapeutics that can selectively inhibit the activity of one type or a subset of anti-apoptotic Bcl-2 proteins, for example, of a Bcl-$x_L$ anti-apoptotic protein. The present invention fulfills at least this need.

SUMMARY OF INVENTION

In one aspect, the present invention provides for a compound of Formula I

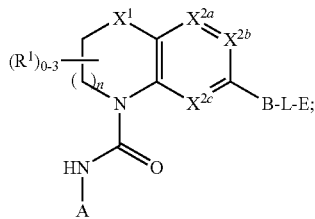

or a pharmaceutically acceptable salt thereof, in which $R^1$ is independently a member selected from the group consisting of $C_{1-6}$ alkyl, $C_{1-6}$ heteroalkyl, $C_{2-6}$ alkenyl, $C_{2-6}$ alkynyl, $C_{1-6}$ haloalkyl and halogen. In Formula I, the subscript n is an integer from 0 to 2, wherein when n is 0 then $X^1$ is —$CH_2$—, —C(H)($R^a$)— or —C($R^a$)$_2$. $X^1$ is a member selected from the group consisting of —$CH_2$—, —C(H)($R^a$)—, —C($R^a$)$_2$, —O—, —N(H)—, —N($R^a$)—, —N(C(O)$R^a$)—, —N(C(O)O$R^a$)—, —N(S(O)$_2R^a$)—, —N(S(O)$R^a$)—, —S—, —S(O)—, —S(O)$_2$—, in which $R^a$ is selected from the group consisting of $C_{1-6}$ alkyl, $C_{2-6}$ alkenyl, $C_{2-6}$ alkynyl, $C_{1-6}$ haloalkyl, $C_{3-6}$ cycloalkyl and halogen. $X^{2a}$, $X^{2b}$ and $X^{2c}$ are each independently selected from the group consisting of C(H), C($R^2$) and N, in which at least one of $X^{2a}$ and $X^{2b}$ is C(H) or C($R^2$); and in which $R^2$ is independently selected from the group consisting of —$OR^b$, —$SR^b$, —C(O)$OR^c$, —C(O)$NR^bR^c$, —$NR^bC(O)R^d$, —S(O)$_2R^d$, —S(O)$R^d$, —S(O)$_2NR^bR^c$, —$R^d$, halogen, —CN and —$NO_2$. For the $R^2$ substituent, $R^b$ and $R^c$ are each independently selected from the group consisting of hydrogen, $C_{1-4}$ alkyl, $C_{2-4}$ alkenyl, $C_{2-4}$ alkynyl, $C_{1-4}$ haloalkyl, or optionally $R^b$ and $R^c$, together with the atom to which each is attached, are combined to form a 3- to 7-membered heterocyclic ring comprising 1 to 2 heteroatoms selected from N, O and S as ring vertices; and $R^d$ is selected from the group consisting of $C_{1-6}$ alkyl, $C_{2-6}$ alkenyl, $C_{2-6}$ alkynyl and $C_{1-6}$ haloalkyl. In Formula I A is a member selected from the group consisting of:

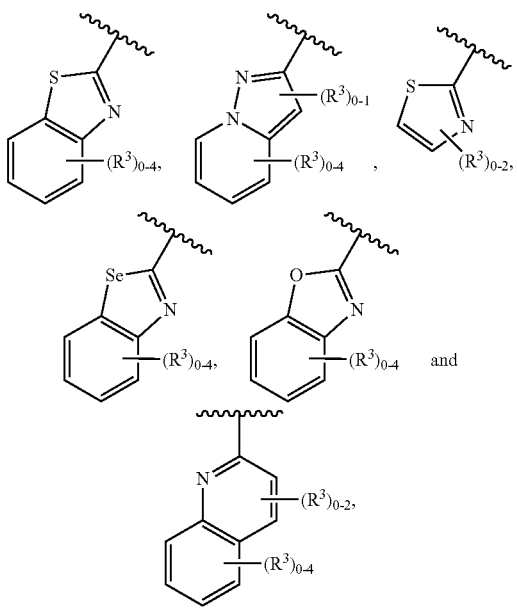

in which $R^3$ is independently selected from the group consisting of —$NR^eR^f$, —$OR^e$, —CN, —$NO_2$, halogen, —C(O)$OR^e$, —C(O)$NR^eR^f$, —$NR^eC(O)R^f$, —$NR^eS(O)_2R^g$, —$NR^eS(O)R^g$, —S(O)$_2R^g$, S(O)$R^g$ and —$R^g$. For the $R^3$ group, $R^e$ and $R^f$ at each occurrence are each independently selected from the group consisting of hydrogen, $C_{1-4}$ alkyl, $C_{2-4}$ alkenyl, $C_{2-4}$ alkynyl, $C_{1-4}$ haloalkyl and —(CH$_2$)$_{1-4}$phenyl, or $R^e$ and $R^f$, or $R^e$ and $R^g$ together with the atom to which each is attached, are optionally combined to form a 3- to 7-membered heterocyclic ring comprising 1 to 2 heteroatoms selected from N, O and S as ring vertices; and $R^g$ is selected from the group consisting of $C_{1-4}$ alkyl, $C_{2-4}$ alkenyl, $C_{2-4}$ alkynyl and $C_{1-4}$ haloalkyl. B is a member selected from the group consisting of

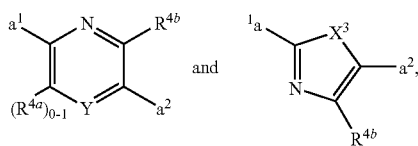

in which Y is N, C(H) or C($R^{4a}$); $X^3$ is —N(H), —N($C_{1-3}$ alkyl), O or S; $R^{4a}$, if present, is independently selected from $C_{1-4}$ alkyl, $C_{1-4}$ haloalkyl, $C_{2-4}$ alkenyl, $C_{2-4}$ alkynyl, halogen and —CN. $R^{4b}$, at each occurrence, is independently selected from the group consisting of —C(O)OR$^j$, —C(O)NR$^h$R$^i$, —C(O)R$^i$, —NR$^h$C(O)R$^i$, —NR$^h$C(O)NR$^h$R$^i$, —OC(O) NR$^h$R$^i$, —NR$^h$C(O)OR$^j$, —C(=NOR$^h$)NR$^h$R$^i$, —NR$^h$C (=NCN)NR$^h$R$^i$, —NR$^h$S(O)$_2$NR$^h$R$^i$, —S(O)$_2$R$^j$, —S(O)$_2$ NR$^h$R$^i$, —N(R$^h$)S(O)$_2$R$^i$, —NR$^h$C(=NR$^i$)NR$^h$R$^i$, —C(=S) NR$^h$R$^i$, —C(=NR$^h$R$^i$, halogen, —NO$_2$, and —CN, in which $R^h$ and $R^i$ at each occurrence are each independently selected from the group consisting of hydrogen, $C_{1-6}$ alkyl, $C_{2-6}$ alkenyl, $C_{2-6}$ alkynyl, $C_{3-6}$ cycloalkyl, $C_{1-6}$ haloalkyl, phenyl and —(CH$_2$)$_{1-4}$-phenyl, or $R^h$ and $R^i$, or $R^h$ and $R^j$, together with the atom to which each is attached are optionally combined to form a 3- to 7-membered heterocyclic ring comprising 1 to 2 heteroatoms selected from N, O and S as ring vertices. $R^j$ is selected from the group consisting of $C_{1-6}$ alkyl, $C_{2-6}$ alkenyl, $C_{2-6}$ alkynyl, $C_{1-6}$ haloalkyl, $C_{3-7}$ cycloalkyl, phenyl and —(CH$_2$)$_{1-4}$ phenyl; or in the alternative, $R^4$ is selected from the group consisting of

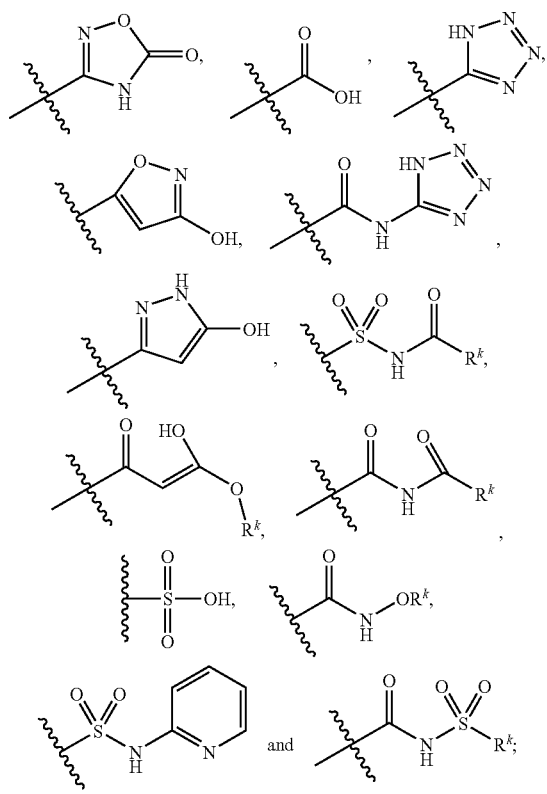

in which $R^k$ is selected from $C_{1-6}$ alkyl, $C_{2-6}$ alkenyl, $C_{2-6}$ alkynyl, $C_{3-7}$ cycloalkyl and $C_{1-6}$ haloalkyl. In Formula I, L is absent or is a member selected from the group consisting of $C_{6-10}$ arylene-$C_{1-6}$ heteroalkylene, $C_{5-9}$ heteroarylene-$C_{1-6}$ heteroalkylene, $C_{1-6}$ heteroalkylene, $C_{1-6}$ alkylene, $C_{1-6}$ haloalkylene, $C_{2-6}$ alkenylene, $C_{2-6}$ alkynylene, —NH—, —S— and —O—, wherein the alkylene, alkenylene, alkynylene or heteroalkylene portions of the L group is substituted with 0 to 4 $R^{5a}$ substituents selected from the group consisting of halogen, —R$^m$ and =O, and the aromatic portions of the L group is substituted with 0 to 4 $R^{5b}$ substituents selected from the group consisting of halogen, —OR$^n$, —NR$^n$R$^o$, —R$^n$, —NO$_2$, and CN; wherein $R^m$ is selected from the group consisting of $C_{1-6}$ alkyl, $C_{2-6}$ alkenyl, $C_{2-6}$ alkynyl, $C_{1-6}$ heteroalkyl and $C_{1-6}$ haloalkyl. Optionally any two $R^{5a}$ substituents attached to the same or different atoms of L can be combined to form a 5- to 7-membered carbocyclic ring or a 5- to 7-membered heterocyclic ring comprising 1 to 2 heteroatoms selected from N, O and S as ring vertices; and wherein $R^n$ and $R^o$, at each occurrence, is selected from the group consisting of hydrogen, $C_{1-6}$ alkyl, $C_{2-6}$ alkenyl, $C_{2-6}$ alkynyl and $C_{1-6}$ haloalkyl, and wherein optionally $R^n$ and $R^o$, together with the atoms to which each is attached, are combined to form a 3- to 7-membered heterocyclic ring comprising 1 to 2 heteroatoms selected from N, O and S as ring vertices. In Formula I, E is hydrogen or halogen; or in the alternative E is selected from the group consisting of phenyl, $C_{5-6}$ heteroaryl, $C_{3-7}$ heterocycloalkyl and $C_{3-7}$ cycloalkyl, and optionally fused to E is 1 or 2 rings independently selected from the group consisting of a 3- to 7-membered carbocyclic ring, a 3- to 7-membered heterocyclic ring, a benzene ring and a 5- to 6-membered heteroaromatic ring, in which E and each ring optionally fused to E is independently substituted with 0 to 5 $R^6$ substituents selected from the group consisting of halogen, —NR$^p$R$^q$, —SR$^p$, —OR$^p$, —C(O) OR$^p$, —C(O)NR$^p$R$^q$, —C(O)R$^p$, —NR$^p$C(O)R$^q$, —OC(O) R$^r$, —NR$^p$C(O)NR$^p$R$^q$, —OC(O)NR$^p$R$^q$, —NR$^p$C(O)OR$^r$, —C(=NOR$^p$)NR$^p$R$^q$, —NR$^p$C(=N—CN)NR$^p$R$^q$, —NR$^p$S (O)$_2$NR$^p$R$^q$, —S(O)$_2$R$^r$, —S(O)$_2$NR$^p$R$^q$, —R$^r$, —R$^s$, —NO$_2$, —N$_3$, =O, —CN, —Z$^1$—NR$^p$R$^q$, —Z$^1$—SR$^p$, —Z$^1$—OR$^p$, —Z$^1$—C(O)OR$^p$, —Z$^1$—C(O)NR$^p$R$^q$, —Z$^1$— C(O)R$^p$, —Z$^1$—NR$^p$C(O)R$^q$, —Z$^1$—OC(O)R$^r$, —Z$^1$— NR$^p$C(O)NR$^p$R$^q$, —Z$^1$—OC(O)NR$^p$R$^q$, —Z$^1$—NR$^p$C(O) OR$^r$, —Z$^1$—C(=NOR$^p$)NR$^p$R$^q$, —Z$^1$—NR$^p$C(=N—CN) NR$^p$R$^q$, —Z$^1$—NR$^p$S(O)$_2$NR$^p$R$^q$, —Z$^1$—S(O)$_2$R$^r$, —Z$^1$—S (O)$_2$NR$^p$R$^q$, —Z$^1$—NO$_2$, —Z$^1$—N$_3$, —Z$^1$—R$^s$ and —Z$^1$— CN. In Formula I, $Z^1$ is selected from the group consisting of $C_{1-6}$ alkylene, $C_{2-6}$ alkenylene, $C_{2-6}$ alkynylene, $C_{1-6}$ heteroalkylene, $C_{3-7}$ cycloalkylene and $C_{3-7}$ heterocycloalkylene; $R^p$ and $R^q$ are each independently selected from hydrogen, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —(CH$_2$)$_{1-4}$-phenyl; $R^r$ is selected from the group consisting of $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —(CH$_2$)$_{1-4}$-phenyl. Optionally within each $R^6$ substituent $R^p$ and $R^q$ or $R^p$ and re, together with the atom to which each is attached, are optionally combined to form a 3- to 7-membered heterocyclic ring optionally comprising 1 to 2 heteroatoms selected from N, O and S as ring vertices. $R^s$ is selected from the group consisting of phenyl, $C_{5-6}$ heteroaryl, $C_{3-7}$ heterocycloalkyl, $C_{3-7}$ cycloalkyl, and optionally fused to $R^s$ is 1 or 2 rings each independently selected from the group consisting of a 5- to 7-membered carbocyclic ring, a 5- to 7-membered heterocyclic ring, a benzene ring and a 5- to 6-membered heteroaromatic ring, and $R^s$ and each ring optionally fused to $R^s$ is each independently substituted with 0 to 5 $R^7$ substituents selected from the group consisting of halogen, —NR$^t$R$^u$, —SR$^t$, —OR$^t$, —C(O)OR$^t$, —C(O)NR$^t$R$^u$, —C(O)R$^t$, —NR$^t$C(O) R$^v$, —OC(O)R$^v$, —NR$^t$C(O)NR$^t$R$^u$, —OC(O)NR$^t$R$^r$, —NR$^t$C(O)OR$^v$, —C(=NOR$^t$)NR$^t$R$^u$, —NR$^t$C(=N—CN) NR$^t$R$^u$, —NR$^t$S(O)$_2$NR$^t$R$^u$, —S(O)$_2$R$^v$, —S(O)$_2$NR$^t$R$^u$, —R$^v$, —NO$_2$, —N$_3$, =O, —CN, —Z$^2$—NR$^t$R$^u$, —Z$^2$—SR$^t$, —Z$^2$—OR$^t$, —Z$^2$—C(O)OR$^t$, —Z$^2$—C(O)NR$^t$R$^u$, —Z$^2$—C (O)R$^v$, —Z$^2$—NR$^t$C(O)R$^u$, —Z$^2$—OC(O)R$^v$, —Z$^2$—NR$^t$C (O)NR$^t$R$^u$, —Z$^2$—OC(O)NR$^t$R$^u$, —Z$^2$—NR$^t$C(O)OR$^v$, —Z$^2$—C(=NOR$^t$)NR$^t$R$^u$, —Z$^2$—NR$^t$C(=N—CN)NR$^t$R$^u$, —Z$^2$—NR$^t$S(O)$_2$NR$^t$R$^u$, —Z$^2$—S(O)$_2$R$^v$, —Z$^2$—S(O)$_2$NR$^t$ R$^u$, —Z$^2$—NO$_2$, —Z$^2$—N$_3$ and —Z$^2$—CN. $Z^2$ is selected from the group consisting of $C_{1-6}$ alkylene, $C_{2-6}$ alkenylene, $C_{2-6}$ alkynylene, $C_{1-6}$ heteroalkylene, $R^t$ and $R^u$ are each independently selected from hydrogen, $C_{1-6}$ alkyl, $C_{1-6}$ haloalkyl, $C_{2-6}$ alkenyl, $C_{2-6}$ alkynyl and —$(CH_2)_{1-4}$-phenyl, $C_{3-7}$ cycloalkyl and $C_{3-7}$ heterocycloalkyl; $R^v$ is selected from $C_{1-4}$ alkyl, $C_{1-4}$ haloalkyl, $C_{2-6}$ alkenyl, $C_{2-6}$ alkynyl, $C_{3-7}$ cycloalkyl, $C_{3-7}$ heterocycloalkyl and —$(CH_2)_{1-4}$-phenyl. Within each $R^7$ substituent, $R^t$ and $R^u$ or IV and $R^v$, together with the atom to which each is attached, optionally are combined to form a 3- to 7-membered heterocyclic ring having 1 to 2 heteroatoms selected from N, O and S as ring vertices.

In another aspect, the present invention provides for pharmaceutical compositions comprising compounds of Formula I as well as methods for using compounds of Formula I for the treatment of diseases and conditions (e.g., cancer, thrombocythemia, etc) characterized by the expression or over-expression of Bcl-2 anti-apoptotic proteins, e.g., of anti-apoptotic Bcl-$x_L$ proteins.

DESCRIPTION OF THE DRAWINGS

FIG. 2A, FIG. 2B, FIG. 2C, FIG. 2D, FIG. 2E and FIG. 2F show certain embodiments of E groups for compounds of Formula I.

DETAILED DESCRIPTION OF THE INVENTION

I. Definitions

Figure 1:
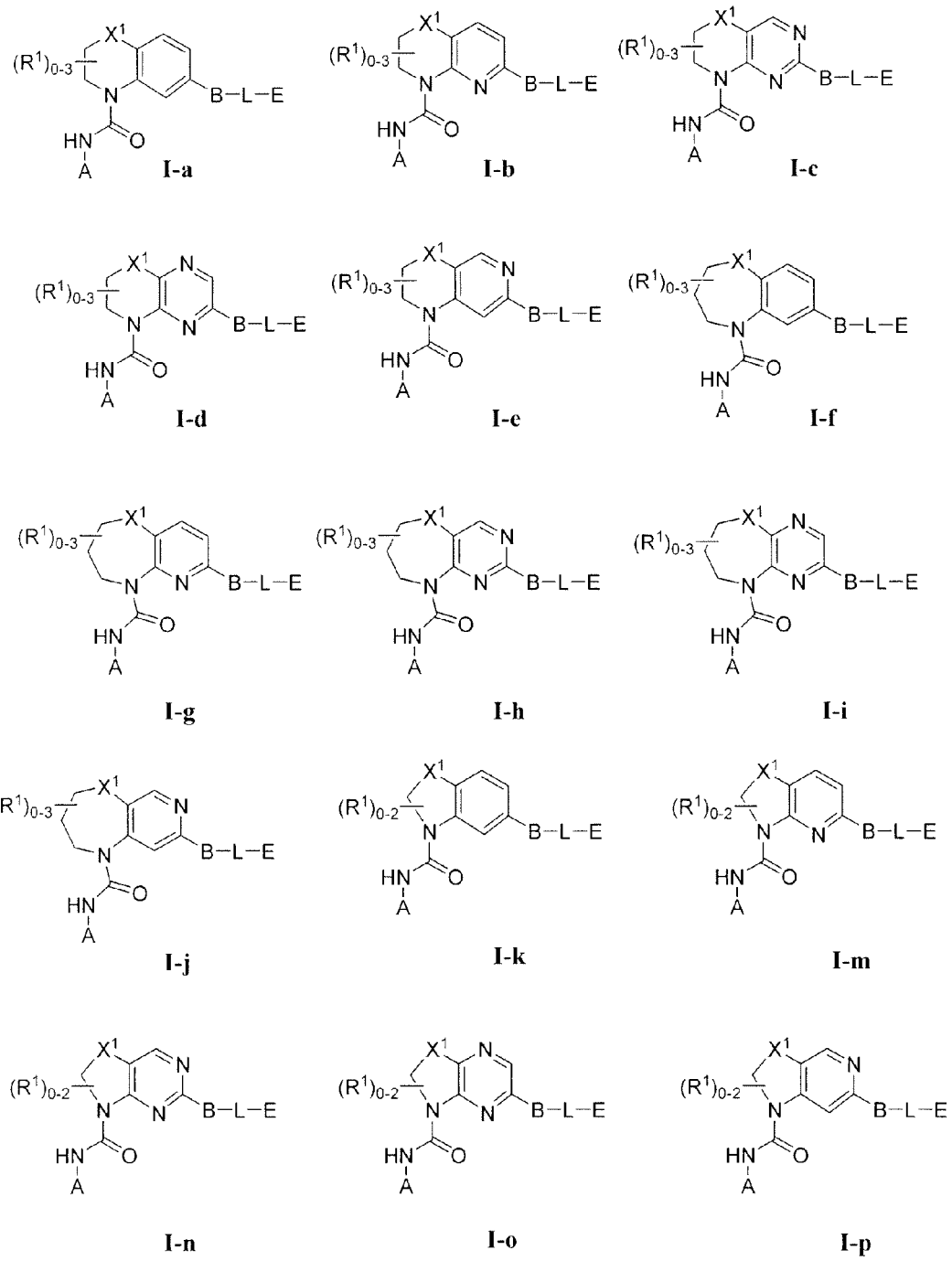
FIG. 1 shows certain subformulae of compounds of the invention, i.e., Subformulae I-a, I-b, I-c, I-d, I-e, I-f, I-g, I-h, I-k, I-m, I-n, I-o and I-p.

As used herein, the term "alkyl", by itself or as part of another substituent, means, unless otherwise stated, a straight or branched chain hydrocarbon radical, having the number of carbon atoms designated (i.e., $C_{1-6}$ means one to eight carbons). Examples of alkyl groups include methyl, ethyl, n-propyl, iso-propyl, n-butyl, t-butyl, iso-butyl, sec-butyl, n-pentyl, n-hexyl, n-heptyl, n-octyl, and the like. The term "alkenyl" refers to an unsaturated alkyl radical having one or more double bonds and is meant to include mono- and poly-halogenated variants. Similarly, the term "alkynyl" refers to an unsaturated alkyl radical having one or more triple bonds and is meant to include mono- and poly-halogenated variants. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The terms "cycloalkyl," "carbocyclic," and "carbocycle," are used interchangeably and when used by itself or as part of another substituent refers to hydrocarbon rings having the indicated number of ring atoms (e.g., $C_{3-6}$ cycloalkyl) and being fully saturated or having no more than one double bond between ring vertices. As used herein, "cycloalkyl," "carbocyclic," or "carbocycle" is also meant to refer to bicyclic, polycyclic and spirocyclic hydrocarbon rings such as, for example, bicyclo [2.2.1]heptane, pinane, bicyclo[2.2.2]octane, adamantane, norborene, spirocyclic $C_{5-12}$ alkane, etc. A "cycloalkyl," "carbocyclic," or "carbocycle" ring can be attached to the remainder of a molecule through a ring carbon atom, or, if stated as such, in the alternative, a "cycloalkyl," "carbocyclic," or "carbocycle" ring can be fused to the remainder of a molecule. Non-limiting examples of a "cycloalkyl," "carbocyclic," or "carbocycle" ring that is fused to, for example, a benzene ring include, 1,2,3,4-tetrahydronaphthalene, 2,3-dihydro-1H-indene, (Z)-6,9-dihydro-5H-benzo[7]annulene, and the like.

The term "heteroalkyl," by itself or in combination with another term, means, unless otherwise stated, a stable straight or branched chain hydrocarbon radical, consisting of the stated number of carbon atoms and from one to three heteroatoms selected from the group consisting of O, N, Si and S, and wherein the nitrogen and sulfur atoms can optionally be oxidized and the nitrogen heteroatom can optionally be quaternized. The heteroatom(s) O, N and S can be placed at any interior position of the heteroalkyl group. The heteroatom Si can be placed at any position of the heteroalkyl group, including the position at which the alkyl group is attached to the remainder of the molecule. A "heteroalkyl" can contain up to three units of unsaturation (e.g., double and triple bonds), and also includes mono- and poly-halogenated variants, or combinations thereof. Examples of "heteroalkyl" include —$CH_2$—$CH_2$—O—$CH_3$, —$CH_2$—$CH_2$—O—$CF_3$, —$CH_2$—$CH_2$—NH—$CH_3$, —$CH_2$—$CH_2$—N($CH_3$)—$CH_3$, —$CH_2$—S—$CH_2$—$CH_3$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Also, for "heteroalkyl" up to two heteroatoms can be consecutive, such as, for example, —$CH_2$—NH—$OCH_3$ and —$CH_2$—O—Si($CH_3$)$_3$.

The terms "heterocycloalkyl," "heterocyclic," and "heterocycle" are used interchangeably and when as used by itself or as part of another substituent refers to a cycloalkyl group that contain from one to five heteroatoms selected from N, O, and S, wherein the nitrogen and sulfur atoms are optionally oxidized, and the nitrogen atom(s) are optionally quaternized. Those skilled in the art will understand, with respect to "heterocycloalkyl," "heterocyclic," and "heterocycle" having a designated number of carbon atoms (e.g., "$C_{3-7}$ heterocycloalkyl"), that at least one, and possibly up to five, if feasible, of the designated carbons are replaced with a heteroatom. For example, "$C_3$ heterocycloalkyl" includes, among other possibilities, oxiranyl, which has two carbon atoms plus one oxygen atom as ring members. Unless otherwise stated, "heterocycloalkyl," "heterocyclic," and "heterocycle" ring can be a monocyclic, a bicyclic, spirocyclic or a polycylic ring system. Non-limiting examples of "heterocycloalkyl," "heterocyclic," and "heterocycle" groups include pyrrolidine, piperidine, imidazolidine, pyrazolidine, butyrolactam, valerolactam, imidazolidinone, hydantoin, dioxolane, phthalimide, piperidine, pyrimidine-2,4(1H,3H)-dione, pyrimidin-4-one, pyrimidin-2-one, 1,4-dioxane, morpholine, thiomorpholine, thiomorpholine-S-oxide, thiomorpholine-S, S-oxide, piperazine, pyran, pyridone, 3-pyrroline, thiopyran, pyrone, tetrahydrofuran, tetrhydrothiophene, quinuclidine, tropane and the like. A "heterocycloalkyl," "heterocyclic," or "heterocycle" group can be attached to the remainder of the molecule through a ring carbon, a heteroatom, or alternatively, if stated as such, a "heterocycloalkyl," "heterocyclic," or "heterocycle" group can be fused to the remainder of a molecule. Non-limiting examples of a "heterocycloalkyl," "heterocyclic," or "heterocycle" ring that is fused to, for example, a benzene ring include, isochroman, 2,3-dihydrobenzofuran, (Z)-4,5-dihydro-1H-benzo[b]azepine, and the like. Unless otherwise stated, "heterocycloalkyl," "heterocyclic," and "heterocycle" rings include mono- and poly-halogenated variants thereof.

The term "alkylene" by itself or as part of another substituent means a divalent radical derived from an alkane or haloalkane, as exemplified by —$CH_2CH_2CH_2CH_2$— and —$CF_2CF_2$—. Typically, an alkyl (or alkylene) group will have from 1 to 24 carbon atoms, with those groups having 10 or fewer carbon atoms being preferred in the present invention. "Alkenylene" and "alkynylene" refer to the unsaturated forms of "alkylene" having double or triple bonds, respectively, including mono and poly halogenated variants.

The term "heteroalkylene" by itself or as part of another substituent means a divalent radical derived from heteroalkyl, as exemplified by —O—CH₂—CH₂—CH₂—CH₂—O—, —O—CH₂, —CH₂—O—, —CH₂—CH₂—S—CH₂CH₂— and —CH₂—S—CH₂—CH₂—NH—CH₂—, —O—CH₂—CH═CH—, —CH₂—CH═C(H)CH₂—O—CH₂—, —CF₂—O—. For heteroalkylene groups, a heteroatom can also occupy either or both of the chain termini (e.g., alkyleneoxy, alkylenedioxy, alkyleneamino, alkylenediamino, and the like). As used herein, the term "heteroalkylene" also refers to mono- and poly-halogenated variants.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^i$R$^{ii}$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group, which can be a single ring or multiple rings (up to three rings) which are fused together. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridinyl, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Optional substituents for each of the above noted aryl and heteroaryl ring systems can be selected from, but are not limited to, the group of acceptable substituents described further below.

As used herein, the term "arylene" generically refers to any aryl that is a divalent radical. For a more specific example, "phenylene" refers to a divalent phenyl ring radical. The terms "1,2-arylene," "1,3-arylene" or "1,4-arylene" refer to geometrical isomers of a particular arylene wherein, two groups attached to an aryl as depicted in a formula are situated in an ortho, meta or para geometrical relationship about the aryl, respectively.

As used herein, the term "heteroarylene" generically refers to any heteroaryl that is a divalent radical. For a more specific example, "pyridylene" refers to a divalent pyridyl ring radical.

Those skilled in the art will understand, with respect to the terms "heteroaryl" and "heteroarylene" having a designated number of carbon atoms (e.g., "$C_{5-6}$ heteroaryl" or "$C_{5-9}$ heteroarylene"), that at least one and, where feasible, up to five of the designated carbon atoms are replaced with a heteroatom. A $C_5$ heteroaryl, for example, can be pyrrolyl or, as another example, be thiazolyl, among other possibilities.

As used herein, the combination term of "arylene-heteroalkylene" generically refers to a divalent radical comprised of aryl group and heteroalkyl group that are covalently attached to each other, and wherein the aryl and alkyl group each comprises an additional radical center to which can be attached another group. Examples of arylene-heteroalkylene include, but are not limited to:

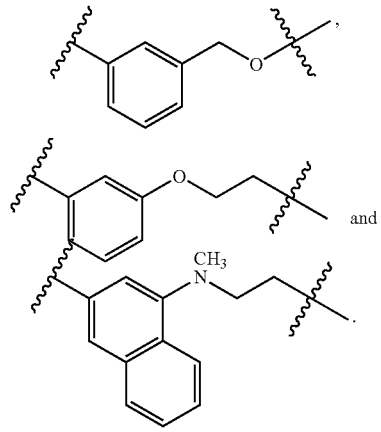

Similarly, the term "heteroarylene-heteroalkylene" refers to a divalent radical comprised of a heteroaryl group and heteroalkyl group that are covalently attached to each other, and wherein and wherein the heteroaryl and heteroalkyl group each comprises an additional radical center to which is attached another group. Examples of heteroarylene-heteroalkylene include, but are not limited to

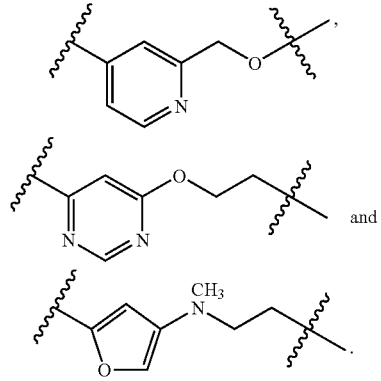

The above terms (e.g., "alkyl," "aryl" and "heteroaryl"), in some embodiments, will include both substituted and unsubstituted forms of the indicated radical. Preferred substituents for each type of radical are provided below.

Substituents for the alkyl radicals (including those groups often referred to as alkylene, alkenyl, alkynyl, heteroalkyl, heterocycloalkyl and cycloalkyl) can be a variety of groups including, but not limited to, -halogen, —OR', —NR'R", —SR', —SiR'R"R''', —OC(O)R', —C(O)R', —CO₂R', —CONR'R", —OC(O)NR'R", —NR"C(O)R', —NR'''C(O) NR'R", —NR"C(O)₂R', —NHC(NH₂)═NH, —NR'C(NH₂) ═NH, —NHC(NH₂)═NR', —NR'''C(NR'R")═N—CN, —NR'''C(NR'R")═NOR', —NHC(NH₂)═NR', —S(O)R', —S(O)₂R', —S(O)₂NR'R", —NR'S(O)₂R", —NR"S(O)₂ NR'R", —CN, ═O, ═S, ═N—OH and —NO₂ in a number ranging from zero to (2 m'+1), where m' is the total number of carbon atoms in such radical. R', R" and R''' each independently refers to groups including, for example, hydrogen, unsubstituted $C_{1-6}$ alkyl, unsubstituted heteroalkyl, unsubstituted aryl, aryl substituted with 1-3 halogens, unsubstituted $C_{1-6}$ alkyl, $C_{1-6}$ alkoxy or $C_{1-6}$ thioalkoxy groups, or unsubstituted aryl-$C_{1-4}$alkyl groups, unsubstituted heteroaryl, substituted heteroaryl, among others. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. Other substituents for alkyl radicals, including heteroalkyl, alkylene, include for example, =O, =NR', =N—OR', =N—CN, =NH, wherein R' include substituents as described above.

Similarly, substituents for the aryl and heteroaryl groups are varied and are generally selected from the group including, but not limited to, -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'C(O)NR"R'", —NHC(NH$_2$)=NH, —NR'C(NH$_2$)=NH, —NHC(NH$_2$)=NR', —S(O)R', —S(O)$_2$R', —S(O)$_2$NR'R", —NR'S(O)$_2$R", —N$_3$, perfluoro-$C_{1-4}$ alkoxy, and perfluoro-$C_{1-4}$ alkyl, in a number ranging from zero to the total number of open valences on the aromatic ring system; and where R', R" and R'" can be independently selected from hydrogen, $C_{1-6}$ alkyl, $C_{1-6}$ haloalkyl, $C_{3-6}$ cycloalkyl, $C_{2-6}$ alkenyl, $C_{2-6}$ alkynyl, unsubstituted aryl and heteroaryl, (unsubstituted aryl)-$C_{1-4}$ alkyl, and unsubstituted aryloxy-$C_{1-4}$ alkyl. Other suitable substituents include each of the above aryl substituents attached to a ring atom by an alkylene tether of from 1-4 carbon atoms.

As used herein, a wavy line, " ~~~ ",, that intersects a single, double or triple bond in any chemical structure depicted herein, represent the point attachment of the single, double, or triple bond to the remainder of the molecule.

As used herein, a "compound of the invention" refers to a compound of Formula I or any specific embodiment thereof; or to any stereoisomer, geometric isomer, tautomer, solvate, metabolites or pharmaceutically acceptable salt or prodrug of a compound of Formula I or an embodiment thereof.

To describe the number of times that a substituent (e.g., $R^{10}$) can be attached to a chemical structure shown in this application, the substituent (e.g., $R^{10}$) is written in parenthesis and the possible number of occurrences is noted as a subscript range. For example, "—$(R^{10})_{0-4}$" means that the $R^{10}$ group can be absent or can be present for up to four occurrences.

As used herein, the term "heteroatom" is meant to include oxygen (O), nitrogen (N), sulfur (S) and silicon (Si).

II. Compounds

In one aspect, the present invention provides for a compound of Formula I

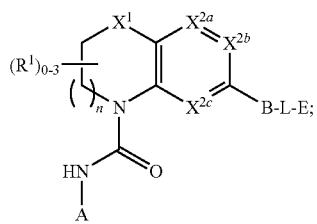

I or a pharmaceutically acceptable salt thereof, in which $R^1$ is independently a member selected from the group consisting of $C_{1-6}$ alkyl, $C_{1-6}$ heteroalkyl, $C_{2-6}$ alkenyl, $C_{2-6}$ alkynyl, $C_{1-6}$ haloalkyl and halogen. In Formula I, the subscript n is an integer from 0 to 2, wherein when n is 0 then $X^1$ is —CH$_2$—, —C(H)($R^a$)— or —C($R^a$)$_2$. $X^1$ is a member selected from the group consisting of —CH$_2$—, —C(H)($R^a$)—, —C($R^a$)$_2$, —O—, —N(H)—, —N($R^a$)—, —N(C(O)$R^a$)—, —N(C(O)OR$^a$)—, —N(S(O)$_2$R$^a$)—, —N(S(O)R$^a$)—, —S—, —S(O)—, —S(O)$_2$—, in which $R^a$ is selected from the group consisting of $C_{1-6}$ alkyl, $C_{2-6}$ alkenyl, 2b $C_{2-6}$ alkynyl, $C_{1-6}$ haloalkyl, $C_{3-6}$ cycloalkyl and halogen. $X^{2a}$, $X^{2b}$ and $X^{2c}$ are each independently selected from the group consisting of C(H), C($R^2$) and N, in which at least one of $X^{2a}$ and $X^{2b}$ is C(H) or C($R^2$); and in which $R^2$ is independently selected from the group consisting of —OR$^b$, —NR$^b$R$^c$, —SR$^b$, —C(O)OR$^c$, —C(O)NR$^b$R$^c$, —NR$^b$C(O)R$^d$, —S(O)$_2$R$^d$, —S(O)R$^d$, —S(O)$_2$NR$^b$R$^c$, —R$^d$, halogen, —CN and —NO$_2$. For the $R^2$ substituent, $R^b$ and $R^c$ are each independently selected from the group consisting of hydrogen, $C_{1-4}$ alkyl, $C_{2-4}$ alkenyl, $C_{2-4}$ alkynyl, $C_{1-4}$ haloalkyl, or optionally $R^b$ and $R^c$, together with the atom to which each is attached, are combined to form a 3- to 7-membered heterocyclic ring comprising 1 to 2 heteroatoms selected from N, O and S as ring vertices; and $R^d$ is selected from the group consisting of $C_{1-6}$ alkyl, $C_{2-6}$ alkenyl, $C_{2-6}$ alkynyl and $C_{1-6}$ haloalkyl. In Formula I A is a member selected from the group consisting of

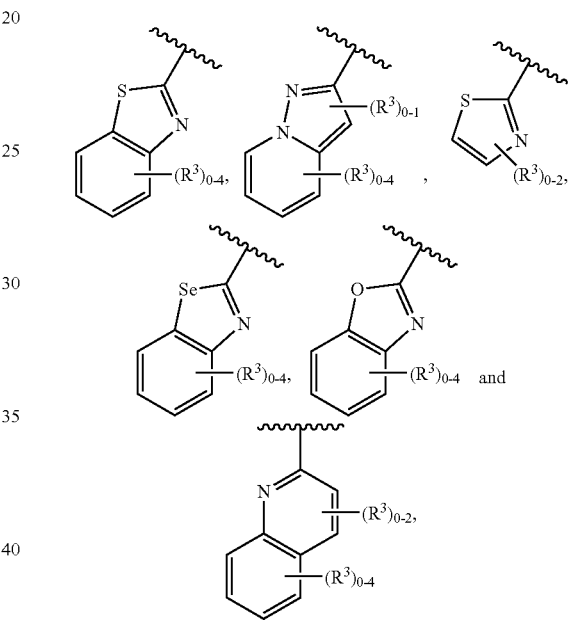

in which $R^3$ is independently selected from the group consisting of —NR$^e$R$^f$, —OR$^e$, —CN, —NO$_2$, halogen, —C(O)OR$^e$, —C(O)NR$^e$R$^f$, —NR$^e$C(O)R$^f$, —NR$^e$S(O)$_2$R$^g$, —NR$^e$S(O)R$^g$, —S(O)$_2$R$^g$, S(O)R$^g$ and —R$^g$. For the $R^3$ group, $R^e$ and $R^f$ at each occurrence are each independently selected from the group consisting of hydrogen, $C_{1-4}$ alkyl, $C_{2-4}$ alkenyl, $C_{2-4}$ alkynyl, $C_{1-4}$ haloalkyl and —(CH$_2$)$_{1-4}$ phenyl, or $R^e$ and $R^f$, or $R^e$ and $R^g$ together with the atom to which each is attached, are optionally combined to form a 3- to 7-membered heterocyclic ring comprising 1 to 2 heteroatoms selected from N, O and S as ring vertices; and $R^g$ is selected from the group consisting of $C_{1-4}$ alkyl, $C_{2-4}$ alkenyl, $C_{2-4}$ alkynyl and $C_{1-4}$ haloalkyl. B is a member selected from the group consisting of:

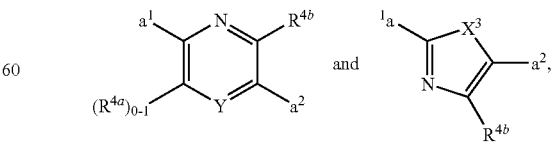

in which Y is N, C(H) or C($R^{4a}$); $X^3$ is —N(H), —N($C_{1-3}$ alkyl), O or S; $R^{4a}$, if present, is independently selected from $C_{1-4}$ alkyl, $C_{1-4}$ haloalkyl, $C_{2-4}$ alkenyl, $C_{2-4}$ alkynyl, halogen and —CN. $R^{4b}$, at each occurrence, is independently selected from the group consisting of —C(O)OR$^j$, —C(O)NR$^h$R$^i$, —C(O)R$^i$, —NR$^h$C(O)R$^i$, —NR$^h$C(O)NR$^h$R$^i$, —OC(O)NR$^h$R$^i$, —NR$^h$C(O)OR$^j$, —C(=NOR$^h$)NR$^h$R$^i$, —NR$^h$C(=NCN)NR$^h$R$^i$, —NR$^h$S(O)$_2$NR$^h$R$^i$, —S(O)$_2$R$^j$, —S(O)$_2$NR$^h$R$^i$, —N(R$^h$)S(O)$_2$R$^i$, —NR$^h$C(=NCN)NR$^h$R$^i$, —C(=S)NR$^h$R$^i$, —C(=NR$^h$)NR$^h$R$^i$, halogen, —NO$_2$, and —CN, in which R$^h$ and R$^i$ at each occurrence are each independently selected from the group consisting of hydrogen, C$_{1-6}$ alkyl, C$_{2-6}$ alkenyl, C$_{2-6}$ alkynyl, C$_{3-6}$ cycloalkyl, C$_{1-6}$ haloalkyl, phenyl and —(CH$_2$)$_{1-4}$-phenyl, or R$^h$ and R$^i$, or R$^h$ and R$^j$, together with the atom to which each is attached are optionally combined to form a 3- to 7-membered heterocyclic ring comprising 1 to 2 heteroatoms selected from N, O and S as ring vertices. R$^j$ is selected from the group consisting of C$_{1-6}$ alkyl, C$_{2-6}$ alkenyl, C$_{2-6}$ alkynyl, C$_{1-6}$ haloalkyl, C$_{3-7}$ cycloalkyl, phenyl and —(CH$_2$)$_{14}$ phenyl; or in the alternative, R$^4$ is selected from the group consisting of

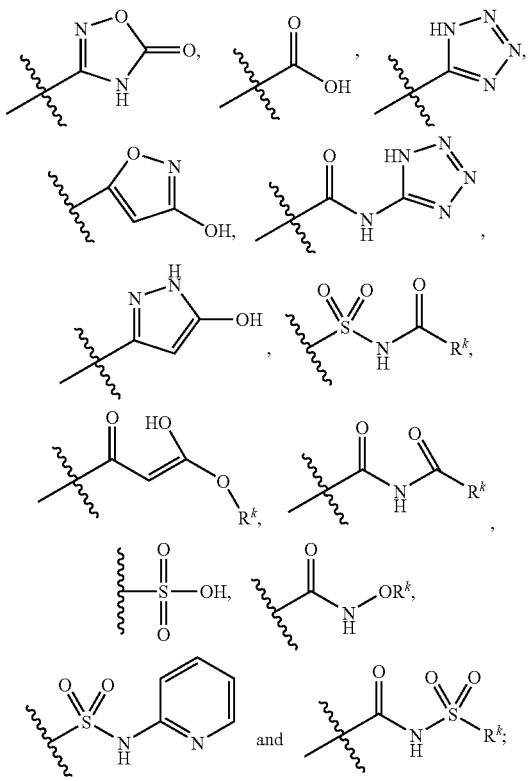

in which R$^k$ is selected from C$_{1-6}$ alkyl, C$_{2-6}$ alkenyl, C$_{2-6}$ alkynyl, C$_{3-7}$ cycloalkyl and C$_{1-6}$ haloalkyl. In Formula I, L is absent or is a member selected from the group consisting of C$_{6-10}$ arylene-C$_{1-6}$ heteroalkylene, C$_{5-9}$ heteroarylene-C$_{1-6}$ heteroalkylene, C$_{1-6}$ heteroalkylene, C$_{1-6}$ alkylene, C$_{1-6}$ haloalkylene, C$_{2-6}$ alkenylene, C$_{2-6}$ alkynylene, —NH—, —S— and —O—, wherein the alkylene, alkenylene, alkynylene or heteroalkylene portions of the L group is substituted with 0 to 4 R$^{5a}$ substituents selected from the group consisting of halogen, —R$^m$ and =O, and the aromatic portions of the L group is substituted with 0 to 4 R$^{5b}$ substituents selected from the group consisting of halogen, —OR$^n$, —NR$^n$R$^o$, —NO$_2$, and CN; wherein R$^m$ is selected from the group consisting of C$_{1-6}$ alkyl, C$_{2-6}$ alkenyl, C$_{2-6}$ alkynyl, C$_{1-6}$ heteroalkyl and C$_{1-6}$ haloalkyl. Optionally any two R$^{sa}$ substituents attached to the same or different atoms of L can be combined to form a 5- to 7-membered carbocyclic ring or a 5- to 7-membered heterocyclic ring comprising 1 to 2 heteroatoms selected from N, O and S as ring vertices; and wherein R$^n$ and R$^o$, at each occurrence, is selected from the group consisting of hydrogen, C$_{1-6}$ alkyl, C$_{2-6}$ alkenyl, C$_{2-6}$ alkynyl and C$_{1-6}$ haloalkyl, and wherein optionally R$^n$ and R$^o$, together with the atoms to which each is attached, are combined to form a 3- to 7-membered heterocyclic ring comprising 1 to 2 heteroatoms selected from N, O and S as ring vertices. In Formula I, E is hydrogen or halogen; or in the alternative E is selected from the group consisting of phenyl, C$_{5-6}$ heteroaryl, C$_{3-7}$ heterocycloalkyl and C$_{3-7}$ cycloalkyl, and optionally fused to E is 1 or 2 rings independently selected from the group consisting of a 3- to 7-membered carbocyclic ring, a 3- to 7-membered heterocyclic ring, a benzene ring and a 5- to 6-membered heteroaromatic ring, in which E and each ring optionally fused to E is independently substituted with 0 to 5 R$^6$ substituents selected from the group consisting of halogen, —NR$^p$R$^q$, —SR$^p$, —OR$^p$, —C(O)OR$^p$, —C(O)NR$^p$R$^q$, —C(O)R$^p$, —NR$^p$C(O)R$^q$, —OC(O)R$^r$, —NR$^p$C(O)NR$^p$R$^q$, —OC(O)NR$^p$R$^q$, —NR$^p$C(O)OR$^r$, —C(=NOR$^p$)NR$^p$R$^q$, —NR$^p$C(=N—CN)NR$^p$R$^q$, —NR$^p$S(O)$_2$NR$^p$R$^q$, —S(O)$_2$R$^r$, —S(O)$_2$NR$^p$R$^q$, —R$^r$, —R$^s$, —NO$_2$, —N$_3$, =O, —CN, —Z$^1$—NR$^p$R$^q$, —Z$^1$—SR$^p$, —Z$^1$—OR$^p$, —Z$^1$—C(O)OR$^p$, —Z$^1$—C(O)NR$^p$R$^q$, —Z$^1$—C(O)R$^p$, —Z$^1$—NR$^p$C(O)R$^q$, —Z$^1$—OC(O)R$^r$, —Z$^1$—NR$^p$C(O)NR$^p$R$^q$, —Z$^1$—OC(O)NR$^p$R$^q$, —Z$^1$NR$^p$C(O)OR$^r$, —Z$^1$—C(=NOR$^p$)NR$^p$R$^q$, —Z$^1$—NR$^p$C(=N—CN)NR$^p$R$^q$, —Z$^1$—NR$^p$S(O)$_2$NR$^p$R$^q$, —Z$^1$—S(O)$_2$R$^r$, —Z$^1$—S(O)$_2$NR$^p$R$^q$, —Z$^1$—NO$_2$, —Z$^1$—N$_3$, —Z$^1$—R$^s$ and —Z$^1$—CN. In Formula I, Z$^1$ is selected from the group consisting of C$_{1-6}$ alkylene, C$_{2-6}$ alkenylene, C$_{2-6}$ alkynylene, C$_{1-6}$ heteroalkylene, C$_{3-7}$ cycloalkylene and C$_{3-7}$ heterocycloalkylene; R$^p$ and WI are each independently selected from hydrogen, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl; R$^r$ is selected from the group consisting of C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl. Optionally within each R$^6$ substituent R$^p$ and 10 or R$^p$ and R$^r$, together with the atom to which each is attached, are optionally combined to form a 3- to 7-membered heterocyclic ring optionally comprising 1 to 2 heteroatoms selected from N, O and S as ring vertices. R$^s$ is selected from the group consisting of phenyl, C$_{5-6}$ heteroaryl, C$_{3-7}$ heterocycloalkyl, C$_{3-7}$ cycloalkyl, and optionally fused to R$^s$ is 1 or 2 rings each independently selected from the group consisting of a 5- to 7-membered carbocyclic ring, a 5- to 7-membered heterocyclic ring, a benzene ring and a 5- to 6-membered heteroaromatic ring, and R$^s$ and each ring optionally fused to R$^s$ is each independently substituted with 0 to 5 R$^7$ substituents selected from the group consisting of halogen, —NR$^t$R$^u$, —SR$^t$, —C(O)OR$^t$, —C(O)NR$^t$R$^u$, —C(O)R$^t$, —NR$^t$C(O)R$^u$, —OC(O)R$^v$, —NR$^t$C(O)NR$^t$R$^u$, —OC(O)NR$^t$R$^t$, —NR$^t$C(O)OR$^v$, —C(=NOR$^t$)NR$^t$R$^u$, —NR$^t$C(=N—CN)NR$^t$R$^u$, —NR$^t$S(O)$_2$NR$^t$R$^u$, —S(O)$_2$R$^v$, —S(O)$_2$NR$^t$R$^u$, —NO$_2$, —N$_3$, =O, —CN, —Z$^2$—NR$^t$R$^u$, —Z$^2$—OR$^t$, —Z$^2$—C(O)OR$^t$, —Z$^2$—C(O)NR$^t$R$^u$, —Z$^2$—C(O)R$^v$, —Z$^2$—NR$^t$C(O)R$^u$, —Z$^2$—OC(O)R$^v$, —Z$^2$—NR$^t$C(O)NR$^t$R$^u$, —Z$^2$—OC(O)NR$^t$R$^u$, —Z$^2$—NR$^t$C(O)OR$^v$, —Z$^2$—C(=NOR$^t$)NR$^t$R$^u$, —Z$^2$—NR$^t$C(=N—CN)NR$^t$R$^u$, —Z$^2$—NR$^t$S(O)$_2$NR$^t$R$^u$, —Z$^2$—S(O)$_2$R$^v$, —Z$^2$—S(O)$_2$NR$^t$R$^u$, —Z$^2$—NO$_2$, —Z$^2$—N$_3$ and —Z$^2$—CN. Z$^2$ is selected from the group consisting of C$_{1-6}$ alkylene, C$_{2-6}$ alkenylene, C$_{2-6}$ alkynylene, C$_{1-6}$ heteroalkylene, R$^t$ and R$^u$ are each independently selected from hydrogen, C$_{1-6}$ alkyl, C$_{1-6}$ haloalkyl, C$_{2-6}$ alkenyl, C$_{2-6}$ alkynyl and —(CH$_2$)$_{14}$-phenyl, C$_{3-7}$ cycloalkyl and C$_{3-7}$ heterocycloalkyl; R$^v$ is selected from C$_{1-4}$ alkyl, C$_{1-4}$ haloalkyl, C$_{2-6}$ alkenyl, C$_{2-6}$ alkynyl, C$_{3-2}$ cycloalkyl, $C_{3-7}$ heterocycloalkyl and —$(CH_2)_{1-4}$-phenyl. Within each $R^7$ substituent, $R^t$ and $R^u$ or $R^t$ and $R^v$, together with the atom to which each is attached, optionally are combined to form a 3- to 7-membered heterocyclic ring having 1 to 2 heteroatoms selected from N, O and S as ring vertices.

In a first embodiment, the compound of Formula I is of a formula selected from the group consisting of Formula I-a, Formula I-b, Formula I-c, Formula I-d, Formula I-e, Formula I-f, Formula I-g, Formula I-h, Formula I-i, Formula I-j, Formula I-k, Formula I-m, Formula I-n. Formula I-o and Formula I-p as set forth in FIG. 1.

In a second embodiment, and within certain aspects of the first embodiment, the compound Formula I is of Formula I-a,

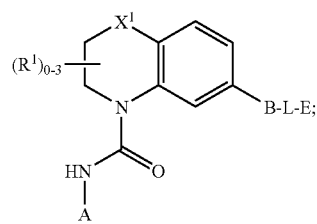

in which $R^1$ is absent. $X^1$ is selected from the group consisting of —$CH_2$—, —$C(H)(R^a)$—, —$C(R^a)_2$—, —O—, —N(H)—, —$N(R^a)$—, —$N(C(O)R^a)$—, —$N(C(O)OR^a)$—, —$N(S(O)_2 R^a)$—, —$N(S(O)R^a)$—, —S—, —$S(O)$—, and —$S(O)_2$—. A is

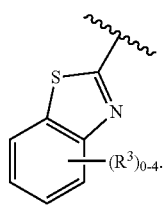

B is a member selected from the group consisting of

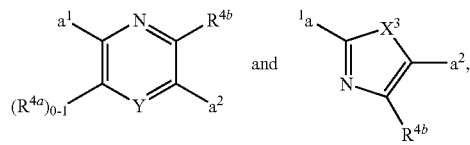

in which $R^{4b}$ is selected from the group consisting of

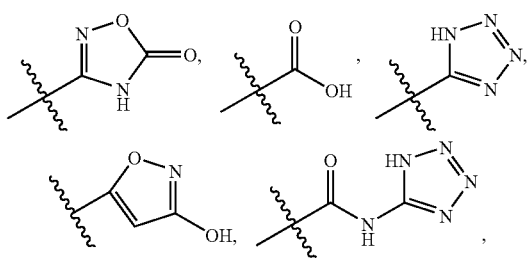

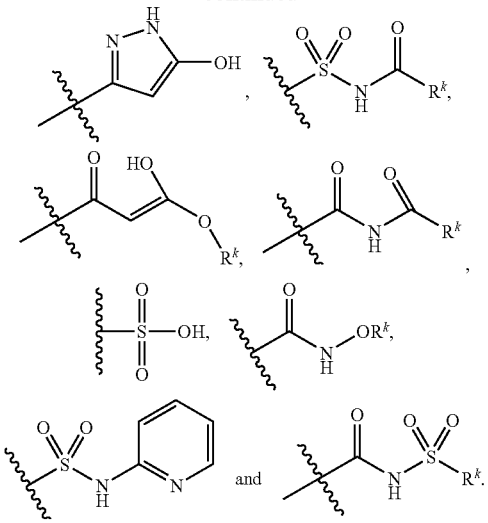

In a third embodiment, within certain aspects of the second embodiment of compounds of the invention, wherein $X^1$ is —$CH_2$— and —O—.

In a fourth embodiment, within certain aspects of the first embodiment of compound of the invention, the compound is of Formula I-a,

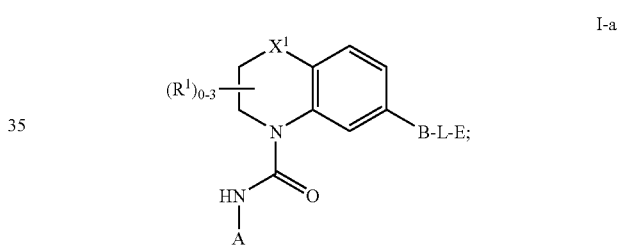

in which $R^1$ is absent. $X^1$ is —$CH_2$—, —$C(H)(R^a)$—, —$C(R^a)_2$—, —O—, —N(H)—, —$N(R^a)$—, —$N(C(O)R^a)$—, —$N(C(O)OR^a)$—, —$N(S(O)_2R^a)$—, —$N(S(O)R^a)$—, —S—, —$S(O)$—, or —$S(O)_2$—. A is

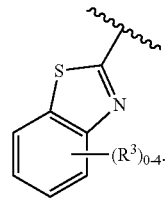

B is a member selected from the group consisting of:

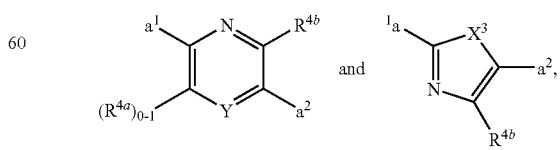

in which $R^{4b}$ is selected from the group consisting of —C(O)O$R^j$, —C(O)N$R^h R^i$, —C(O)$R^i$, —N$R^h$C(O)$R^i$, —N$R^h$C(O)

$NR^hR^i$, —OC(O)$NR^hR^i$, —$NR^hC(O)OR^j$, —C(=$NOR^h$)$NR^hR^i$, —$NR^hC$(=NCN)$NR^hR^i$, —$NR^hS(O)_2NR^hR^i$, —S(O)$_2R^j$, —S(O)$_2NR^hR^i$, —N($R^h$)S(O)$_2R^i$, —$NR^hC$(=$NR^i$)$NR^hR^i$, —C(=S)$NR^hR^i$, —C(=$NR^h$)$NR^hR^i$, halogen, —NO$_2$, and —CN.

In a fifth embodiment, and within certain aspects of the fourth embodiment of compounds of the invention, $X^1$ is —CH$_2$— or —O—, In a sixth embodiment, for compounds of Formula I or the first, second or fourth embodiment thereof, B is

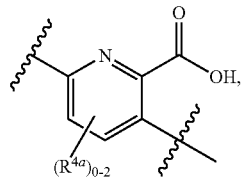

wherein $R^{4a}$, if present, is selected from the group consisting of halogen and C$_{1-4}$ alkyl.

In a seventh embodiment, for compounds of Formula I or the first, second or fourth embodiment thereof, B is

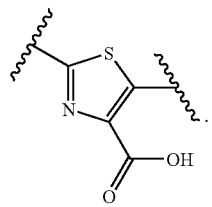

In an eighth embodiment, for compounds of Formula I or the first, second, fourth, sixth or seventh embodiment thereof, L is absent or is an optionally substituted group selected from the group consisting of C$_{6-10}$ arylene-C$_{1-6}$ heteroalkylene, C$_{5-9}$ heteroarylene-C$_{1-6}$ heteroalkylene, C$_{1-6}$ heteroalkylene, C$_{2-6}$ heteroalkenylene, C$_{1-6}$ alkylene, C$_{2-6}$ alkenylene, C$_{2-6}$ alkynylene and —O—. E is a ring selected from the group consisting of phenyl, C$_{5-6}$ heteroaryl, C$_{3-7}$ heterocycloalkyl, C$_{3-7}$ cycloalkyl, and wherein optionally fused to E is a 5- to 7-membered heterocyclic ring, a benzene ring, or a 5- to 6-membered heteroaromatic ring, and in which E and said ring optionally fused to E is substituted with 0 to 5 $R^6$ substituents selected from the group consisting of fluoro, chloro, bromo, —NR$^p$R$^q$, —SR$^p$, —OR$^p$, —C(O)OR$^p$, —C(O)NR$^p$R$^q$, —C(O)R$^p$, —NR$^p$C(O)R$^q$, —OC(O)R$^r$, —NR$^p$C(O)NR$^p$R$^q$, —OC(O)NR$^p$R$^q$, —NR$^p$C(O)OR$^r$, —S(O)$_2$R$^r$, —S(O)$_2$NR$^p$R$^q$, —R$^r$, —R$^s$, —NO$_2$, —N$_3$, —CN, —Z$^1$—NR$^p$R$^q$, —Z$^1$—SR$^p$, —Z$^1$—OR$^p$, —Z$^1$—OC(O)NR$^p$R$^q$, —Z$^1$—NR$^p$C(O)OR$^r$, —Z$^1$—S(O)$_2$R$^r$, —Z$^1$—R$^s$ and —Z$^1$—S(O)$_2$NR$^p$R$^q$. Z$^1$ is selected from the group consisting of C$_{1-6}$ alkylene, C$_{2-6}$ alkenylene, C$_{2-6}$ alkynylene and C$_{1-6}$ heteroalkylene. R$^p$ and R$^q$ are each independently selected from hydrogen, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl. R$^r$ is selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl and —(CH$_2$)$_{1-4}$-phenyl. Optionally within each R$^6$ substituent, R$^p$ and R$^q$, or R$^p$ and R$^r$, together with the atom to which each is attached, are combined to form a 3- to 7-membered heterocyclic ring comprising 1 to 2 heteroatoms selected from N, O and S as ring vertices. R$^s$ is phenyl, a 5- to 6-membered heteroaromatic ring or a 5- to 7 membered heterocyclic ring, in which optionally fused to R$^s$ is a benzene ring, a 5- to 6-membered heteroaromatic ring or a 5- to 7 membered heterocyclic ring. R$^s$ and said ring optionally fused to R$^s$ is substituted with 0 to 3 R$^7$ substituents selected from the group consisting of halogen, —NR$^t$R$^u$, —SR$^t$, —OR$^t$, —OC(O)NR$^t$R$^u$, —NR$^t$C(O)OR$^v$, —R$^v$, —Z$^2$—NR$^t$R$^u$, —Z$^2$—OC(O)NR$^t$R$^u$, —Z$^2$—NR$^t$C(O)OR$^v$ and —CN. Z$^2$ is selected from the group consisting of C$_{1-6}$ alkylene, C$_{2-6}$ alkenylene, C$_{2-6}$ alkynylene and C$_{1-6}$ heteroalkylene, in which R$^t$ and R$^u$ each independently selected from hydrogen, C$_{1-6}$ alkyl, C$_{1-6}$ haloalkyl, C$_{2-6}$ alkenyl, C$_{2-6}$ alkynyl, C$_{3-7}$ cycloalkyl and C$_{3-7}$ heterocycloalkyl. R$^v$ is selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl and —(CH$_2$)$_{1-4}$-phenyl. Optionally within each R$^7$ substitutent, R$^t$ and R$^u$ or R$^t$ and R$^v$, together with the atoms to which each is attached, are combined to form a 3- to 7-membered heterocyclic ring optionally comprising 1 to 2 heteroatoms selected from N, O and S as ring vertices.

In a ninth embodiment, within certain aspects of the sixth embodiment of compounds of the invention, L is absent and E is selected from the group consisting of phenyl and pyridyl, and wherein optionally fused to E is a ring selected from the group consisting of a pyrimidin-4-one ring, a pyrimidin-2-one ring, a benzene ring, a pyridine ring, a pyrrole ring, a pyrazole ring, an imidazole ring, a furan ring and a thiophene ring, wherein E and the ring optionally fused to E are each optionally independently substituted.

In a tenth embodiment, for compounds of Formula I, or the first, second, fourth, sixth, seventh or eighth embodiment thereof, L is C$_{1-4}$ alkylene or C$_{1-4}$ heteroalkylene.

In an eleventh embodiment, for compounds of Formula I or the first, second, fourth, sixth, seventh or eighth embodiment thereof, L is selected from the group consisting of:

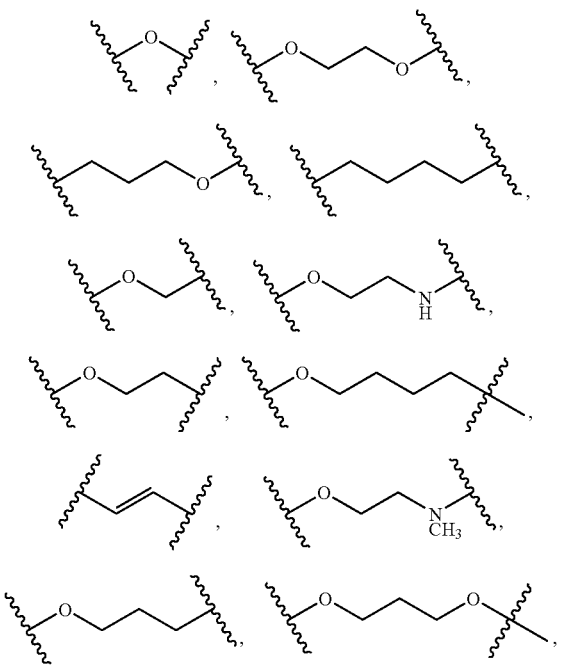

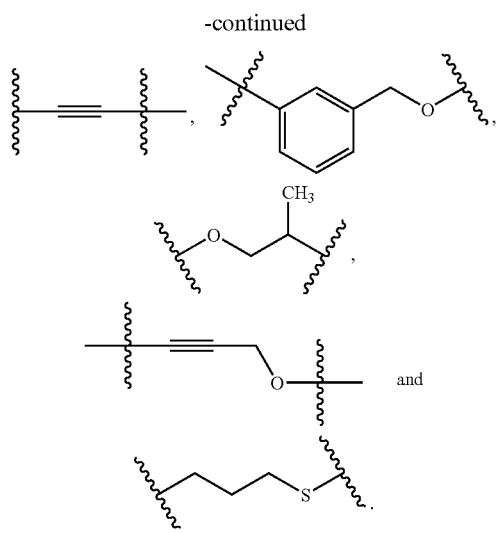

In a twelfth embodiment, within certain aspects of the tenth or eleventh embodiments of compounds of the invention, L is present and E is selected from the group consisting of phenyl, pyridyl, pyrimidinyl, piperidinyl, piperazinyl, morpholino, pyrrolidinyl, pyrrolidonyl and cyclobutyl. Optionally fused to E is a pyridine ring, a benzene ring, pyrimidin-4-one ring, a pyrimidin-2-one ring or a dioxolane ring, and in which E and said ring optionally fused to E is substituted with 0 to 5 $R^6$ substituents selected from the group consisting of fluoro, chloro, —$NR^pR^q$, —$SR^p$, —$S(O)_2R^r$, —$OR^p$, —$NR^pC(O)OR^r$, —$R^r$, —$Z^1$—$NR^pR^q$, —$Z^1$—$NR^pC(O)OR^r$ and —$R^s$. $R^p$ and $R^q$ are each independently selected from hydrogen, $C_{1-6}$ alkyl, $C_{1-6}$ haloalkyl, $C_{2-6}$alkenylene, $C_{2-6}$ alkynylene and $C_{1-6}$ heteroalkylene. $R^r$ is selected from $C_{1-6}$ alkyl, $C_{1-6}$ haloalkyl, $C_{2-6}$ alkenyl, $C_{2-6}$ alkynyl, $C_{3-7}$cycloalkyl, $C_{3-7}$ heterocycloalkyl and —$(CH_2)_{1-4}$-phenyl. Optionally within each $R^6$ substituent $R^p$ and $R^q$ or $R^p$ and $R^r$, are combined to form a 3- to 6-membered heterocyclic ring having 1 to 2 heteroatoms selected from N, O and S as ring vertices.

In a thirteenth embodiment, for compounds of Formula I or the first, second, fourth, sixth, seventh or eighth embodiment thereof, E is phenyl and is meta or para substituted with an optionally substituted $R^s$ group is of a formula selected from the group consisting of

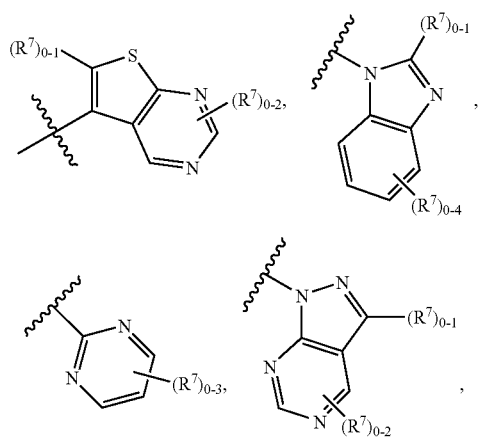

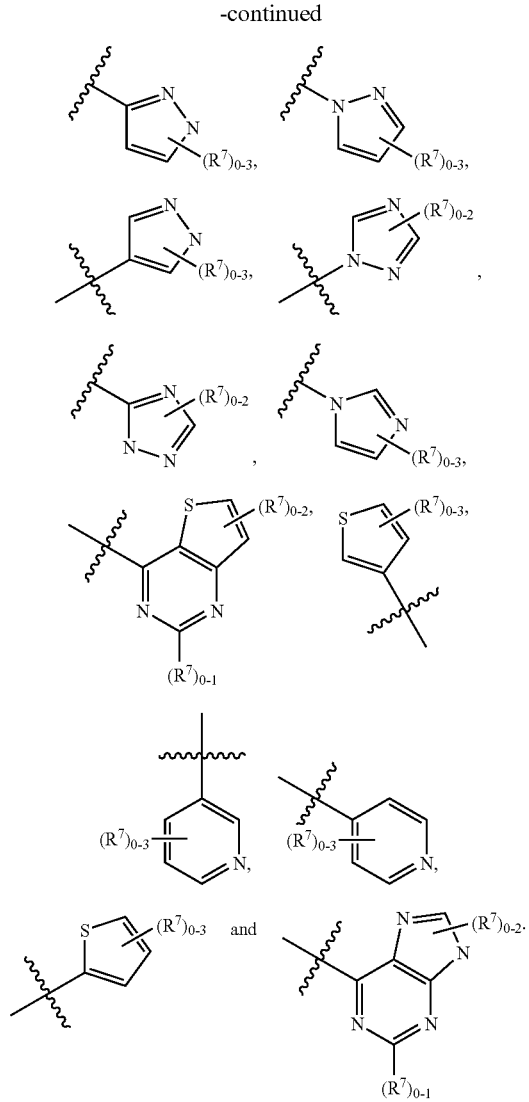

In a fourteenth embodiment, for compounds of Formula I, or the first, second, fourth, sixth, seventh or eighth embodiment thereof, E is selected from the group set forth in FIG. 2-A and FIG. 2-B.

In a fifteenth embodiment, for compounds of Formula I, or the first, second, fourth, sixth, seventh or eighth embodiment thereof, E is selected from the group set forth in FIG. 2-C, FIG. 2-D, FIG. 2-E and FIG. 2-F.

In a sixteenth embodiment, for compounds of Formula I, or the first, second or fourth embodiment thereof, L is absent and E is hydrogen or halogen.

In a seventeenth embodiment, for compounds of Formula I or the first, second or fourth embodiment thereof, L is selected from the group consisting of $C_{1-6}$ heteroalkylene, $C_{1-6}$ alkylene, $C_{2-6}$ alkenylene and $C_{2-6}$ alkynylene, each of which is independently optionally substituted; and E is hydrogen.

In an eighteenth embodiment, within certain aspects of the seventeenth embodiment of compounds of the invention, L is an optionally substituted $C_{1-4}$ heteroalkylene.

In a nineteenth embodiment, compounds of Formula I are selected from the group set forth in Table 1.

TABLE 1

| No | Structure | Name |
|---|---|---|
| 1 | 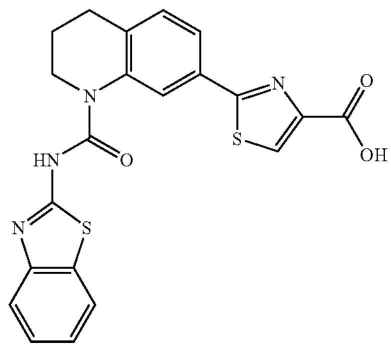 | 2-(1-(benzo[d]thiazol-2-ylcarbamoyl)-1,2,3,4-tetrahydroquinolin-7-yl)thiazole-4-carboxylic acid |
| 2 | 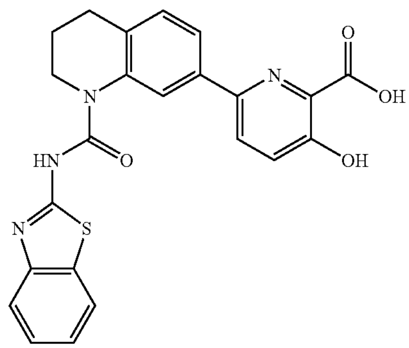 | 6-(1-(benzo[d]thiazol-2-ylcarbamoyl)-1,2,3,4-tetrahydroquinolin-7-yl)-3-hydroxypicolinic acid |
| 3 | 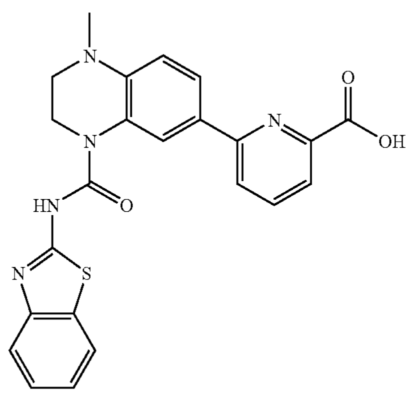 | 6-(4-(benzo[d]thiazol-2-ylcarbamoyl)-1-methyl-1,2,3,4-tetrahydroquinoxalin-6-yl)picolinic acid |
| 4 | 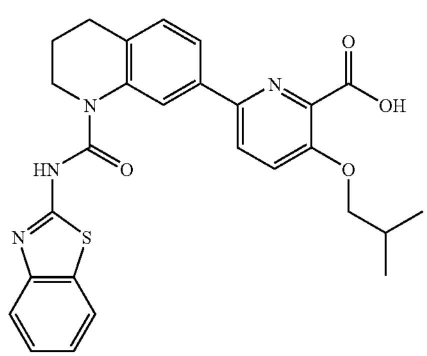 | 6-(1-(benzo[d]thiazol-2-ylcarbamoyl)-1,2,3,4-tetrahydroquinolin-7-yl)-3-isobutoxypicolinic acid |

| No | Structure | Name |
|---|---|---|
| 5 | 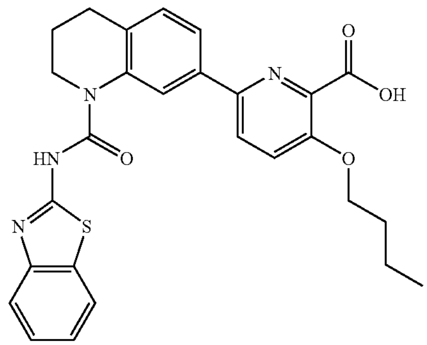 | 6-(1-(benzo[d]thiazol-2-ylcarbamoyl)-1,2,3,4-tetrahydroquinolin-7-yl)-3-butoxypicolinic acid |
| 6 | 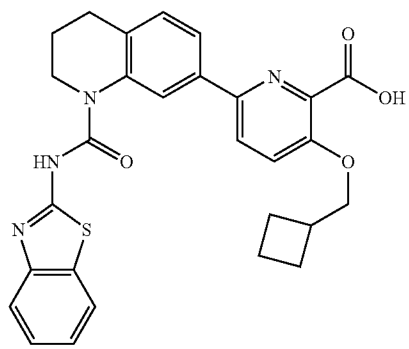 | 6-(1-(benzo[d]thiazol-2-ylcarbamoyl)-1,2,3,4-tetrahydroquinolin-7-yl)-3-(cyclobutylmethoxy)picolinic acid |
| 7 | 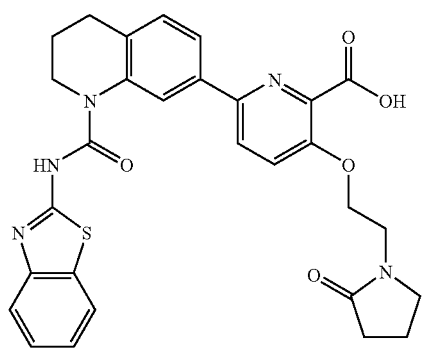 | 6-(1-(benzo[d]thiazol-2-ylcarbamoyl)-1,2,3,4-tetrahydroquinolin-7-yl)-3-(2-(2-oxopyrrolidin-1-yl)ethoxy)picolinic acid |
| 8 | 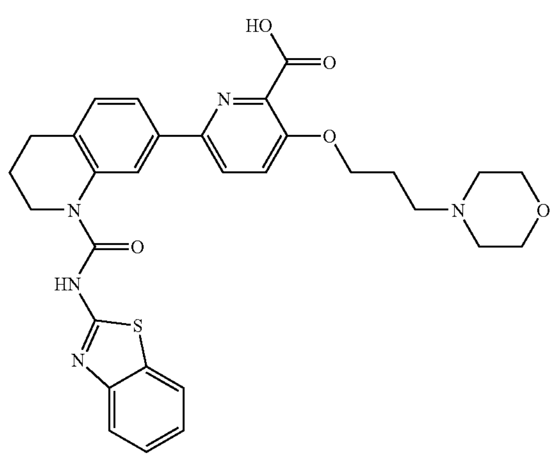 | 6-(1-(benzo[d]thiazol-2-ylcarbamoyl)-1,2,3,4-tetrahydroquinolin-7-yl)-3-(3-morpholinopropoxy)picolinic acid |

TABLE 1-continued

| No | Structure | Name |
|---|---|---|
| 9 | 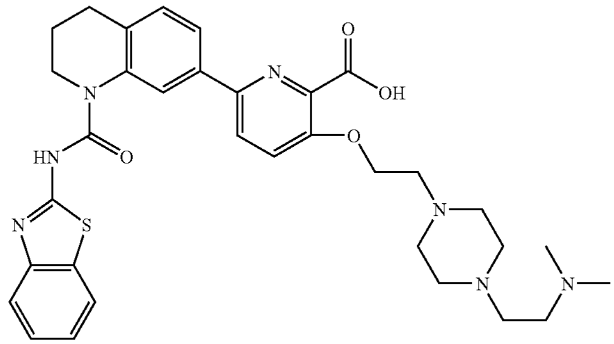 | 6-(1-(benzo[d]thiazol-2-ylcarbamoyl)-1,2,3,4-tetrahydroquinolin-7-yl)-3-(2-(4-(2-(dimethylamino)ethyl)piperazin-1-yl)ethoxy)picolinic acid |
| 10 | 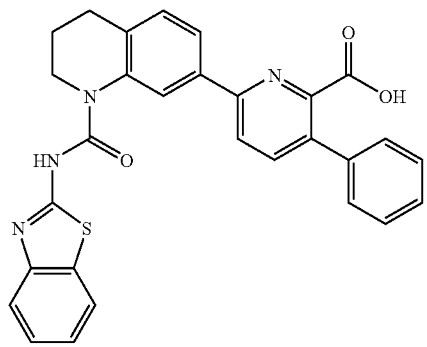 | 6-(1-(benzo[d]thiazol-2-ylcarbamoyl)-1,2,3,4-tetrahydroquinolin-7-yl)-3-phenylpicolinic acid |
| 11 | 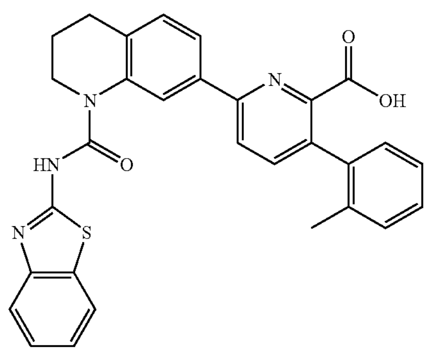 | 6-(1-(benzo[d]thiazol-2-ylcarbamoyl)-1,2,3,4-tetrahydroquinolin-7-yl)-3-o-tolylpicolinic acid |
| 12 | 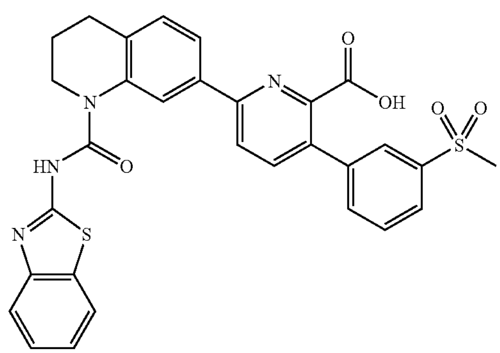 | 6-(1-(benzo[d]thiazol-2-ylcarbamoyl)-1,2,3,4-tetrahydroquinolin-7-yl)-3-(3-(methylsulfonyl)phenyl)picolinic acid |

TABLE 1-continued

| No | Structure | Name |
|---|---|---|
| 13 | 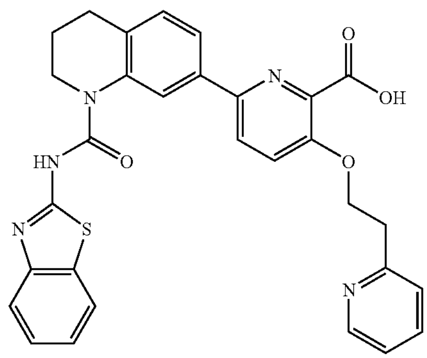 | 6-(1-(benzo[d]thiazol-2-ylcarbamoyl)-1,2,3,4-tetrahydroquinolin-7-yl)-3-(2-(pyridin-2-yl)ethoxy)picolinic acid |
| 14 | 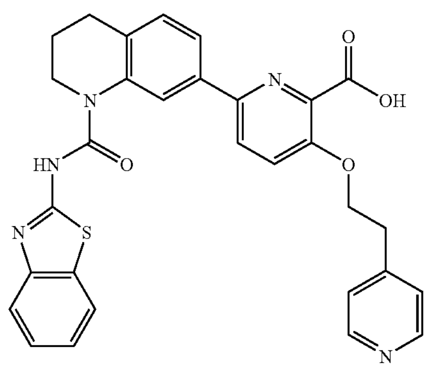 | 6-(1-(benzo[d]thiazol-2-ylcarbamoyl)-1,2,3,4-tetrahydroquinolin-7-yl)-3-(2-(pyridin-4-yl)ethoxy)picolinic acid |
| 15 | 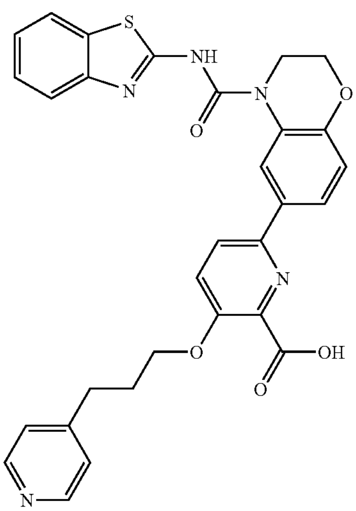 | 6-(4-(benzo[d]thiazol-2-ylcarbamoyl)-3,4-dihydro-2H-benzo[b][1,4]oxazin-6-yl)-3-(3-(pyridin-4-yl)propoxy)picolinic acid |
| 16 | 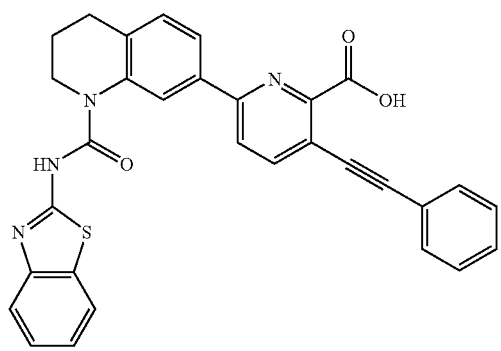 | 6-(1-(benzo[d]thiazol-2-ylcarbamoyl)-1,2,3,4-tetrahydroquinolin-7-yl)-3-(phenylethynyl)picolinic acid |

TABLE 1-continued

| No | Structure | Name |
|---|---|---|
| 17 | 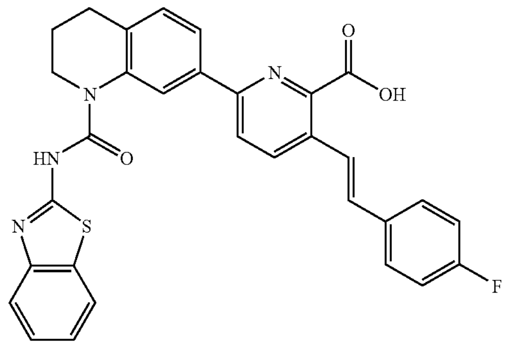 | (E)-6-(1-(benzo[d]thiazol-2-ylcarbamoyl)-1,2,3,4-tetrahydroquinolin-7-yl)-3-(4-fluorostyryl)picolinic acid |
| 18 | 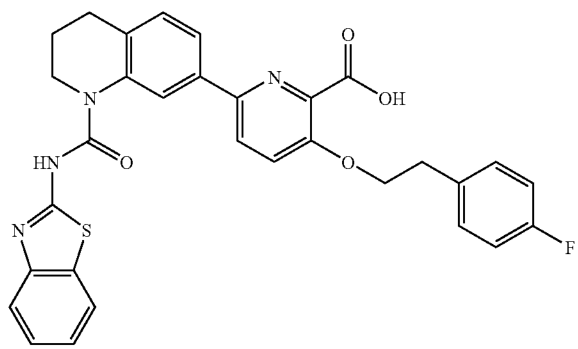 | 6-(1-(benzo[d]thiazol-2-ylcarbamoyl)-1,2,3,4-tetrahydroquinolin-7-yl)-3-(4-fluorophenethoxy)picolinic acid |
| 19 | 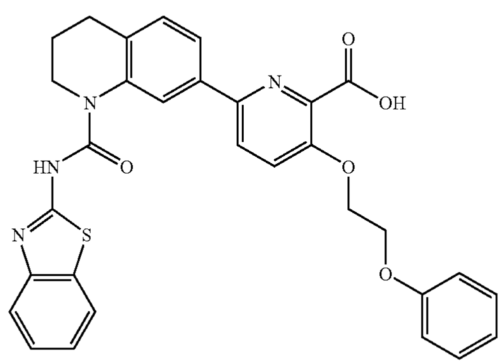 | 6-(1-(benzo[d]thiazol-2-ylcarbamoyl)-1,2,3,4-tetrahydroquinolin-7-yl)-3-(2-phenoxyethoxy)picolinic acid |
| 20 | 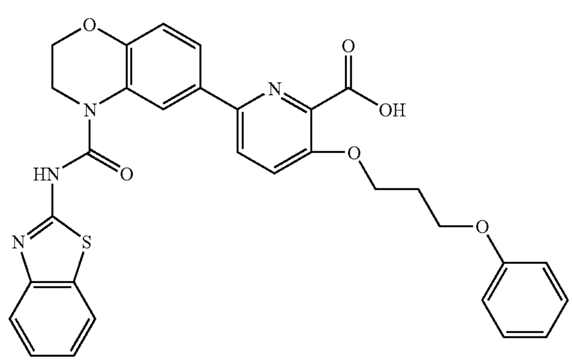 | 6-(4-(benzo[d]thiazol-2-ylcarbamoyl)-3,4-dihydro-2H-benzo[b][1,4]oxazin-6-yl)-3-(3-phenoxypropoxy)picolinic acid |

TABLE 1-continued

| No | Structure | Name |
|----|-----------|------|
| 21 | 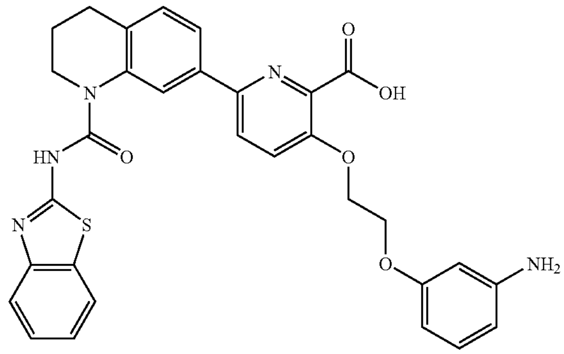 | 3-(2-(3-aminophenoxy)ethoxy)-6-(1-(benzo[d]thiazol-2-ylcarbamoyl)-1,2,3,4-tetrahydroquinolin-7-yl)picolinic acid |
| 22 | 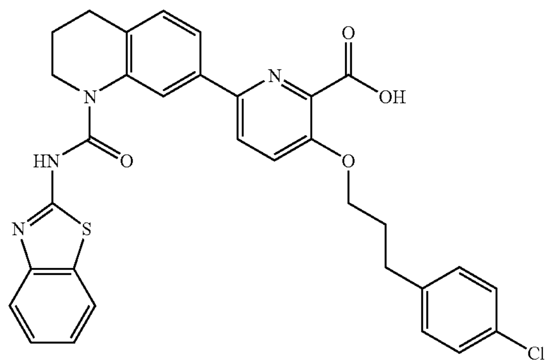 | 6-(1-(benzo[d]thiazol-2-ylcarbamoyl)-1,2,3,4-tetrahydroquinolin-7-yl)-3-(3-(4-chlorophenyl)propoxy)picolinic acid |
| 23 | 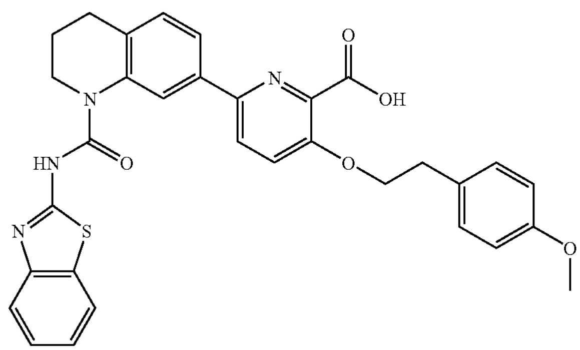 | 6-(1-(benzo[d]thiazol-2-ylcarbamoyl)-1,2,3,4-tetrahydroquinolin-7-yl)-3-(4-methoxyphenethoxy)picolinic acid |
| 24 | 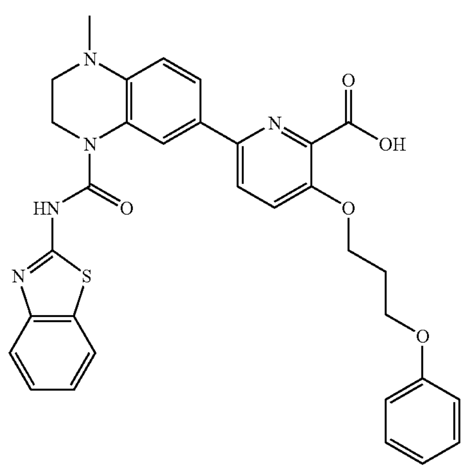 | 6-(4-(benzo[d]thiazol-2-ylcarbamoyl)-1-methyl-1,2,3,4-tetrahydroquinoxalin-6-yl)-3-(3-phenoxypropoxy)picolinic acid |

TABLE 1-continued

| No | Structure | Name |
|---|---|---|
| 25 | 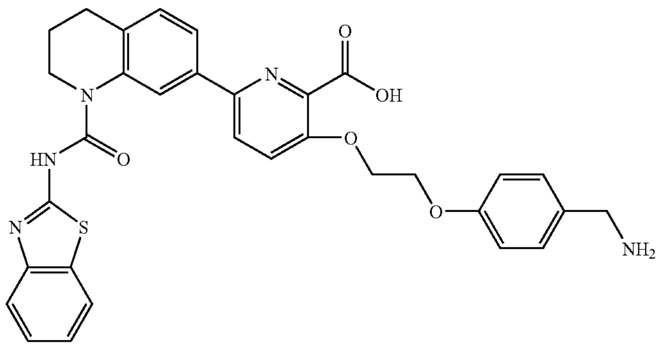 | 3-(2-(4-(aminomethyl)phenoxy)ethoxy)-6-(1-(benzo[d]thiazol-2-ylcarbamoyl)-1,2,3,4-tetrahydroquinolin-7-yl)picolinic acid |
| 26 | 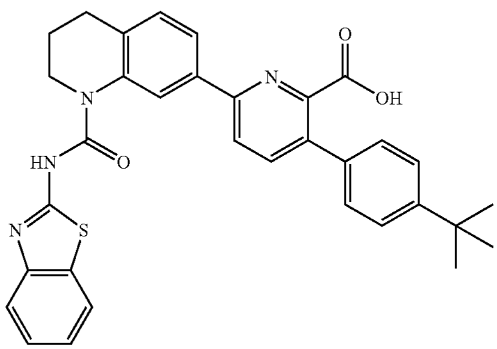 | 6-(1-(benzo[d]thiazol-2-ylcarbamoyl)-1,2,3,4-tetrahydroquinolin-7-yl)-3-(4-tert-butylphenyl)picolinic acid |
| 27 | 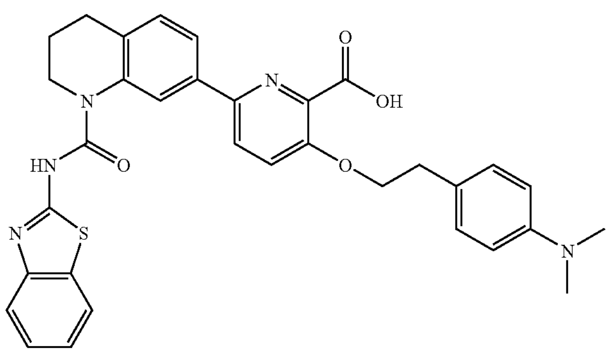 | 6-(1-(benzo[d]thiazol-2-ylcarbamoyl)-1,2,3,4-tetrahydroquinolin-7-yl)-3-(4-(dimethylamino)phenethoxy)picolinic acid |
| 28 | 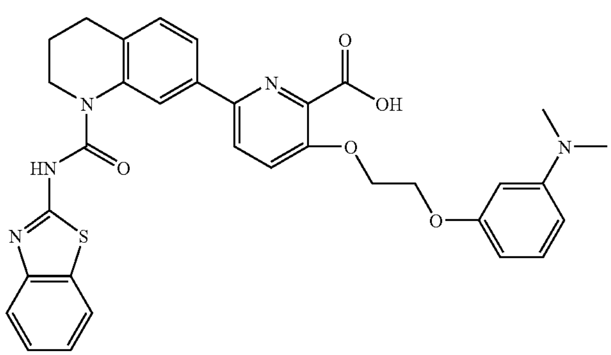 | 6-(1-(benzo[d]thiazol-2-ylcarbamoyl)-1,2,3,4-tetrahydroquinolin-7-yl)-3-(2-(3-(dimethylamino)phenoxy)ethoxy)picolinic acid |

TABLE 1-continued

| No | Structure | Name |
|---|---|---|
| 29 | 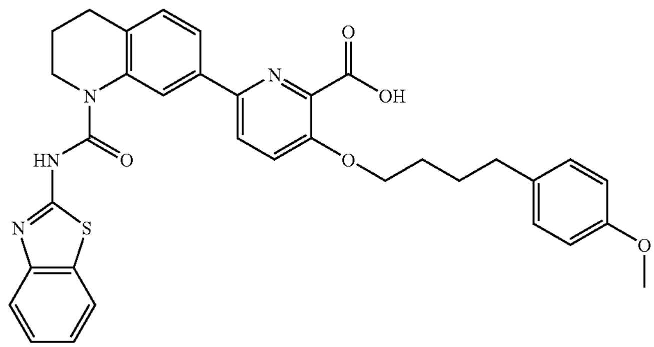 | 6-(1-(benzo[d]thiazol-2-ylcarbamoyl)-1,2,3,4-tetrahydroquinolin-7-yl)-3-(4-(4-methoxyphenyl)butoxy)picolinic acid |
| 30 | 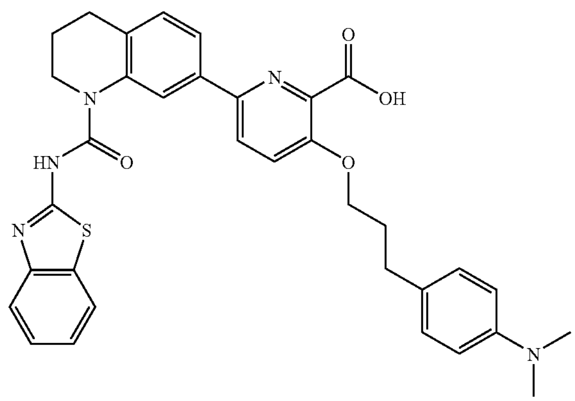 | 6-(1-(benzo[d]thiazol-2-ylcarbamoyl)-1,2,3,4-tetrahydroquinolin-7-yl)-3-(3-(4-(dimethylamino)phenyl)propoxy)picolinic acid |
| 31 | 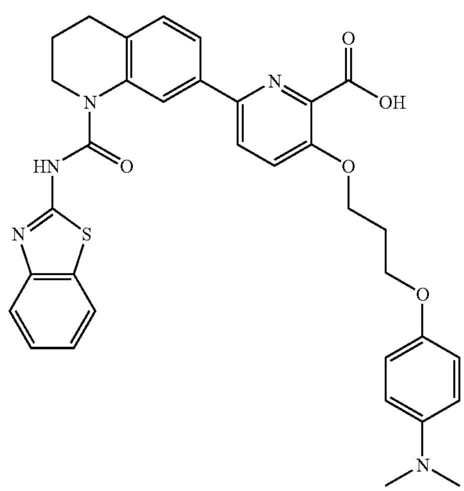 | 6-(1-(benzo[d]thiazol-2-ylcarbamoyl)-1,2,3,4-tetrahydroquinolin-7-yl)-3-(3-(4-(dimethylamino)phenoxy)propoxy)picolinic acid |

TABLE 1-continued

| No | Structure | Name |
|---|---|---|
| 32 | 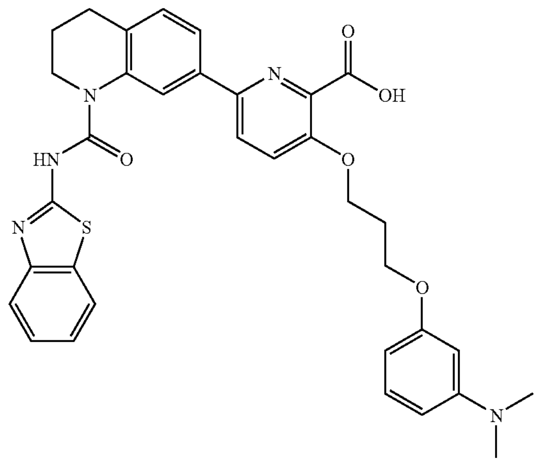 | 6-(1-(benzo[d]thiazol-2-ylcarbamoyl)-1,2,3,4-tetrahydroquinolin-7-yl)-3-(3-(3-(dimethylamino)phenoxy)propoxy)picolinic acid |
| 33 | 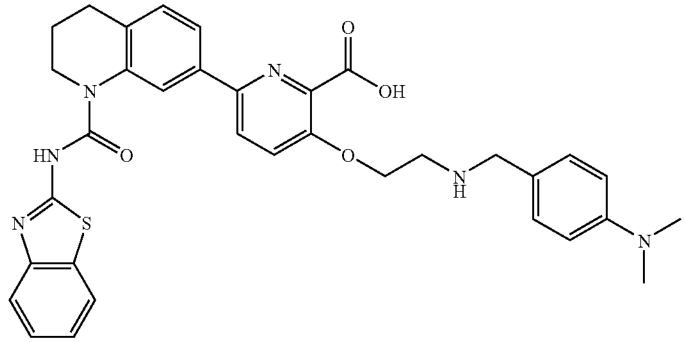 | 6-(1-(benzo[d]thiazol-2-ylcarbamoyl)-1,2,3,4-tetrahydroquinolin-7-yl)-3-(2-(4-(dimethylamino)benzylamino)ethoxy)picolinic acid |
| 34 | 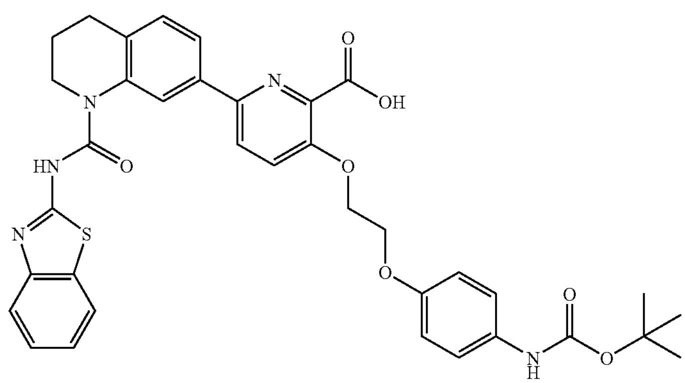 | 6-(1-(benzo[d]thiazol-2-ylcarbamoyl)-1,2,3,4-tetrahydroquinolin-7-yl)-3-(2-(4-(tert-butoxycarbonylamino)phenoxy)ethoxy)picolinic acid |
| 35 | 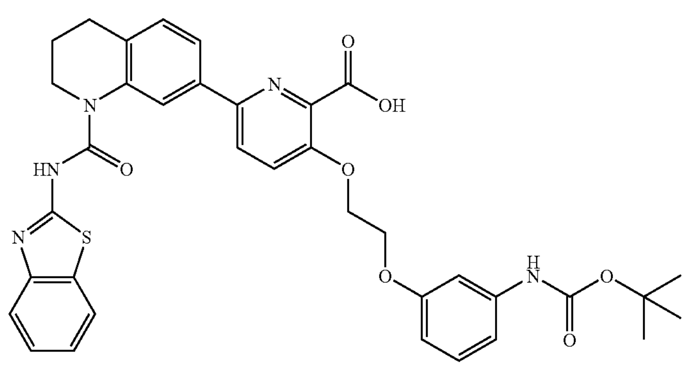 | 6-(1-(benzo[d]thiazol-2-ylcarbamoyl)-1,2,3,4-tetrahydroquinolin-7-yl)-3-(2-(3-(tert-butoxycarbonylamino)phenoxy)ethoxy)picolinic acid |

TABLE 1-continued

| No | Structure | Name |
|---|---|---|
| 36 | 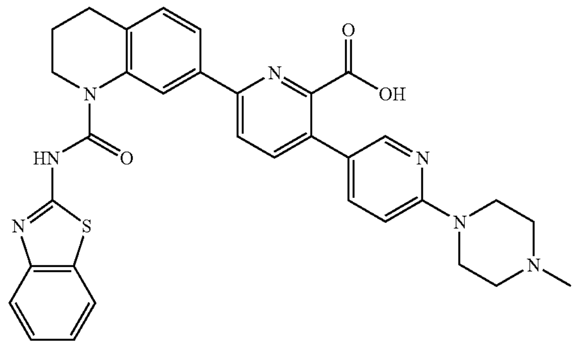 | 6-(1-(benzo[d]thiazol-2-ylcarbamoyl)-1,2,3,4-tetrahydroquinolin-7-yl)-6'-(4-methylpiperazin-1-yl)-3,3'-bipyridine-2-carboxylic acid |
| 37 | 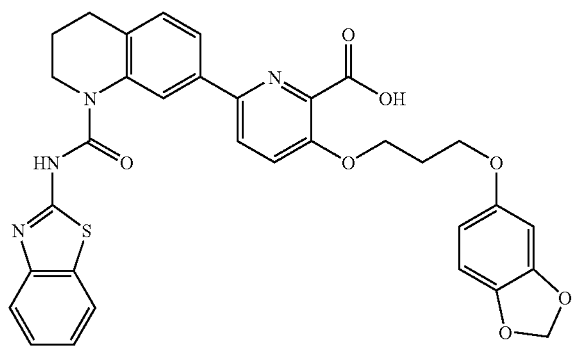 | 3-(3-(benzo[d][1,3]dioxol-5-yloxy)propoxy)-6-(1-(benzo[d]thiazol-2-ylcarbamoyl)-1,2,3,4-tetrahydroquinolin-7-yl)picolinic acid |
| 38 | 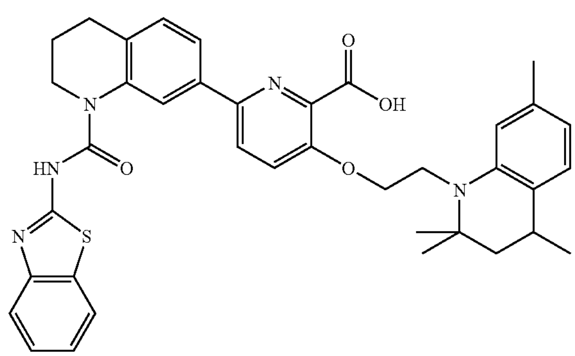 | 6-(1-(benzo[d]thiazol-2-ylcarbamoyl)-1,2,3,4-tetrahydroquinolin-7-yl)-3-(2-(2,2,4,7-tetramethyl-3,4-dihydroquinolin-1(2H)-yl)ethoxy)picolinic acid |
| 39 | 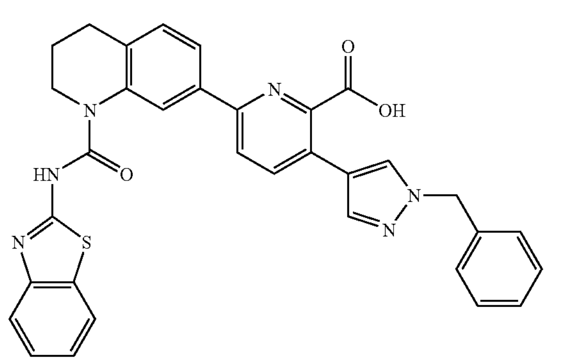 | 6-(1-(benzo[d]thiazol-2-ylcarbamoyl)-1,2,3,4-tetrahydroquinolin-7-yl)-3-(1-benzyl-1H-pyrazol-4-yl)picolinic acid |

TABLE 1-continued

| No | Structure | Name |
|----|-----------|------|
| 40 | 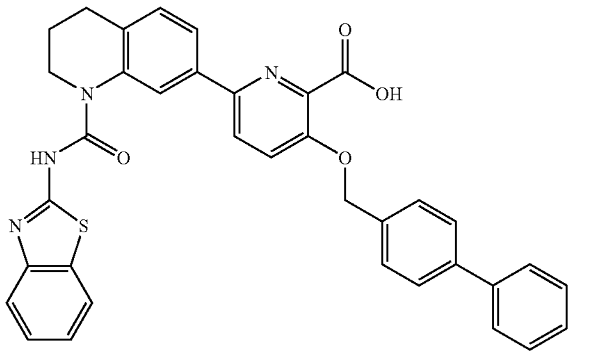 | 6-(1-(benzo[d]thiazol-2-ylcarbamoyl)-1,2,3,4-tetrahydroquinolin-7-yl)-3-(biphenyl-4-ylmethoxy)picolinic acid |
| 41 | 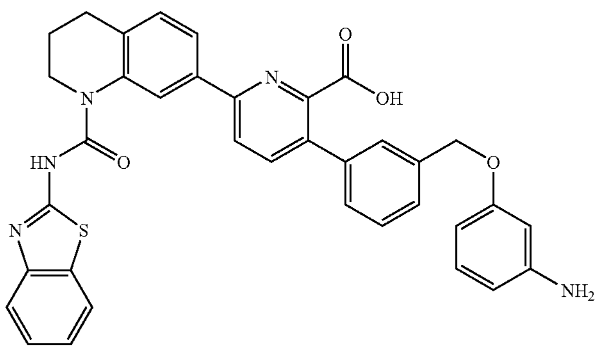 | 3-(3-((3-aminophenoxy)methyl)phenyl)-6-(1-(benzo[d]thiazol-2-ylcarbamoyl)-1,2,3,4-tetrahydroquinolin-7-yl)picolinic acid |
| 42 | 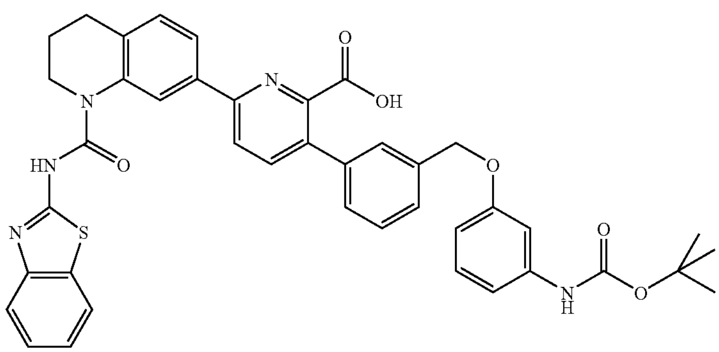 | 6-(1-(benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinic acid |
| 43 | 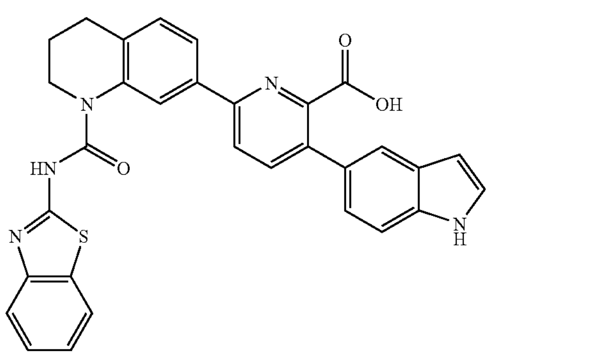 | 6-(1-(benzo[d]thiazol-2-ylcarbamoyl)-1,2,3,4-tetrahydroquinolin-7-yl)-3-(1H-indol-5-yl)picolinic acid |

TABLE 1-continued

| No | Structure | Name |
|---|---|---|
| 44 | 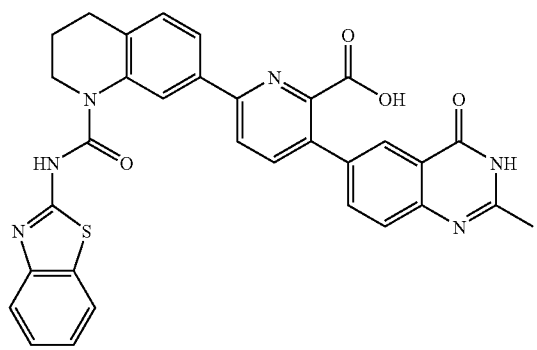 | 6-(1-(benzo[d]thiazol-2-ylcarbamoyl)-1,2,3,4-tetrahydroquinolin-7-yl)-3-(2-methyl-4-oxo-3,4-dihydroquinazolin-6-yl)picolinic acid |
| 45 | 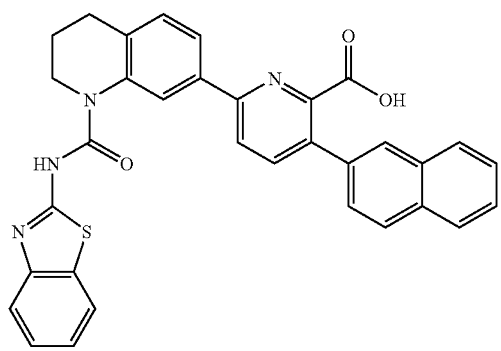 | 6-(1-(benzo[d]thiazol-2-ylcarbamoyl)-1,2,3,4-tetrahydroquinolin-7-yl)-3-(naphthalen-2-yl)picolinic acid |
| 46 | 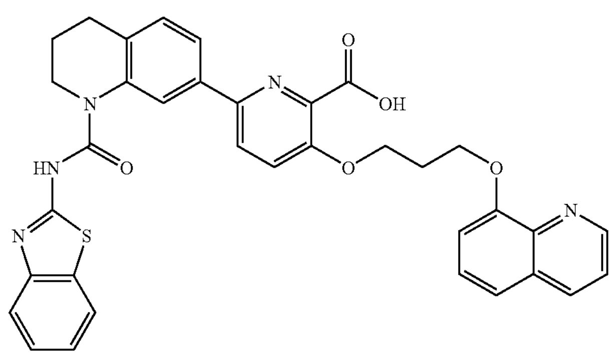 | 6-(1-(benzo[d]thiazol-2-ylcarbamoyl)-1,2,3,4-tetrahydroquinolin-7-yl)-3-(3-(quinolin-8-yloxy)propoxy)picolinic acid |
| 47 | 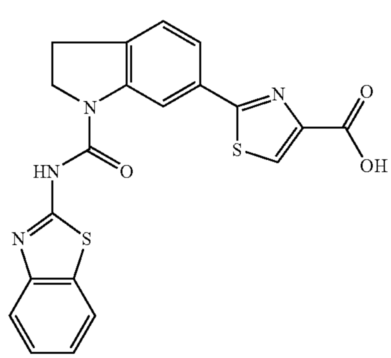 | 2-(1-(benzo[d]thiazol-2-ylcarbamoyl)indolin-6-yl)thiazole-4-carboxylic acid |

TABLE 1-continued

| No | Structure | Name |
|---|---|---|
| 48 | 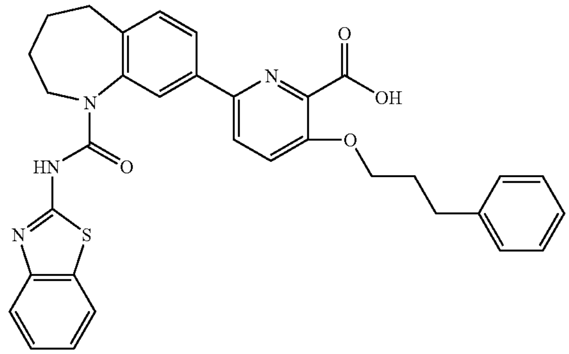 | 6-(1-(benzo[d]thiazol-2-ylcarbamoyl)-2,3,4,5-tetrahydro-1H-benzo[b]azepin-8-yl)-3-(3-phenylpropoxy)picolinic acid |
| 49 | 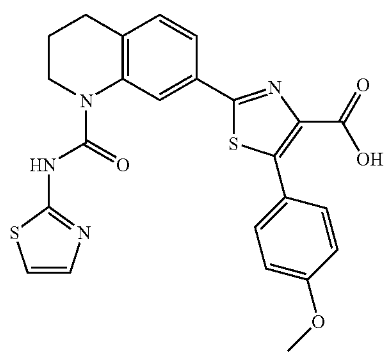 | 5-(4-methoxyphenyl)-2-(1-(thiazol-2-ylcarbamoyl)-1,2,3,4-tetrahydroquinolin-7-yl)thiazole-4-carboxylic acid |
| 50 | 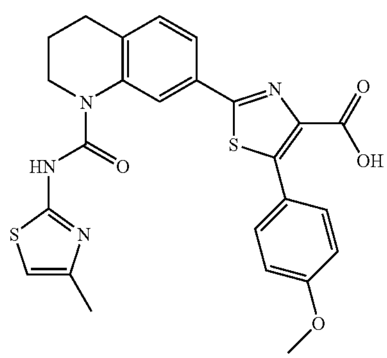 | 5-(4-methoxyphenyl)-2-(1-(4-methylthiazol-2-ylcarbamoyl)-1,2,3,4-tetrahydroquinolin-7-yl)thiazole-4-carboxylic acid |
| 51 | 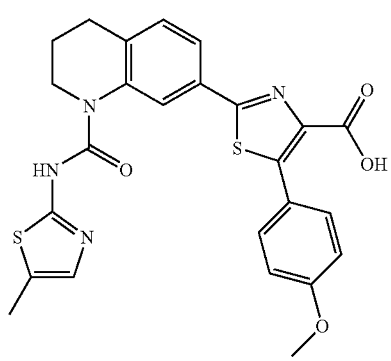 | 5-(4-methoxyphenyl)-2-(1-(5-methylthiazol-2-ylcarbamoyl)-1,2,3,4-tetrahydroquinolin-7-yl)thiazole-4-carboxylic acid |

TABLE 1-continued

| No | Structure | Name |
|----|-----------|------|
| 52 | 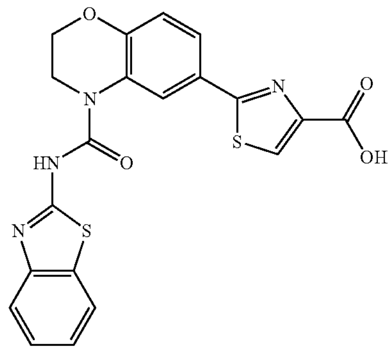 | 2-(4-(benzo[d]thiazol-2-ylcarbamoyl)-3,4-dihydro-2H-benzo[b][1,4]oxazin-6-yl)thiazole-4-carboxylic acid |
| 53 | 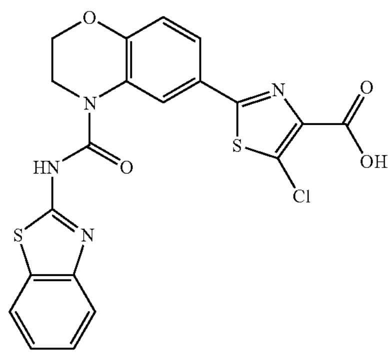 | 2-(4-(benzo[d]thiazol-2-ylcarbamoyl)-3,4-dihydro-2H-benzo[b][1,4]oxazin-6-yl)-5-chlorothiazole-4-carboxylic acid |
| 54 | 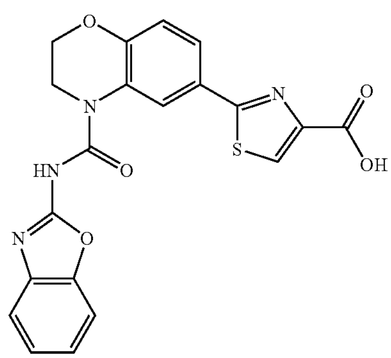 | 2-(4-(benzo[d]oxazol-2-ylcarbamoyl)-3,4-dihydro-2H-benzo[b][1,4]oxazin-6-yl)thiazole-4-carboxylic acid |
| 55 | 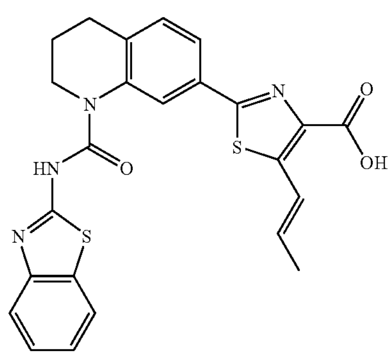 | (E)-2-(1-(benzo[d]thiazol-2-ylcarbamoyl)-1,2,3,4-tetrahydroquinolin-7-yl)-5-(prop-1-enyl)thiazole-4-carboxylic acid |

TABLE 1-continued

| No | Structure | Name |
|---|---|---|
| 56 | 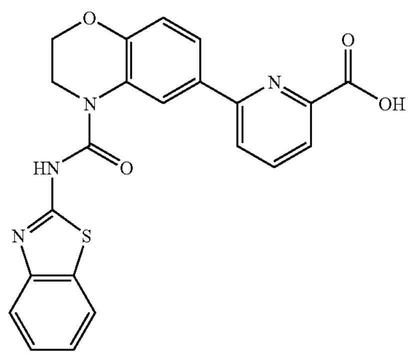 | 6-(4-(benzo[d]thiazol-2-ylcarbamoyl)-3,4-dihydro-2H-benzo[b][1,4]oxazin-6-yl)picolinic acid |
| 57 | 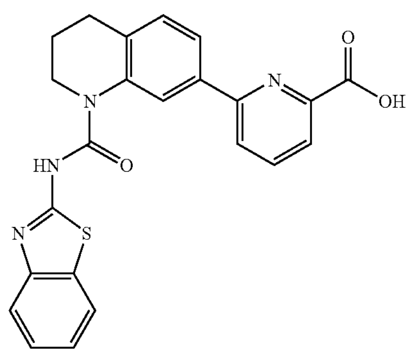 | 6-(1-(benzo[d]thiazol-2-ylcarbamoyl)-1,2,3,4-tetrahydroquinolin-7-yl)picolinic acid |
| 58 | 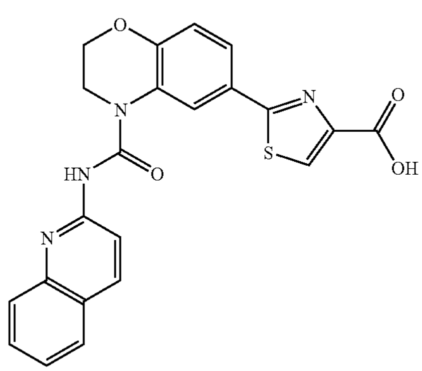 | 2-(4-(quinolin-2-ylcarbamoyl)-3,4-dihydro-2H-benzo[b][1,4]oxazin-6-yl)thiazole-4-carboxylic acid |
| 59 | 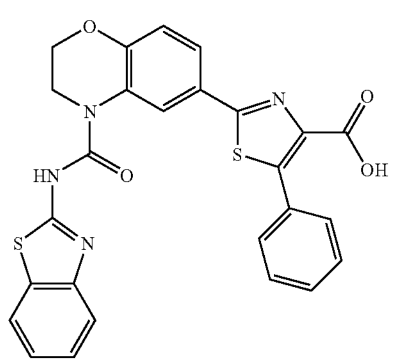 | 2-(4-(benzo[d]thiazol-2-ylcarbamoyl)-3,4-dihydro-2H-benzo[b][1,4]oxazin-6-yl)-5-phenylthiazole-4-carboxylic acid |

TABLE 1-continued

| No | Structure | Name |
|---|---|---|
| 60 | 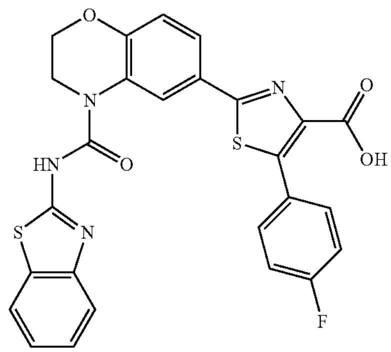 | 2-(4-(benzo[d]thiazol-2-ylcarbamoyl)-3,4-dihydro-2H-benzo[b][1,4]oxazin-6-yl)-5-(4-fluorophenyl)thiazole-4-carboxylic acid |
| 61 | 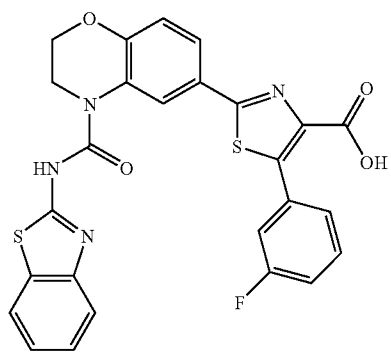 | 2-(4-(benzo[d]thiazol-2-ylcarbamoyl)-3,4-dihydro-2H-benzo[b][1,4]oxazin-6-yl)-5-(3-fluorophenyl)thiazole-4-carboxylic acid |
| 62 | 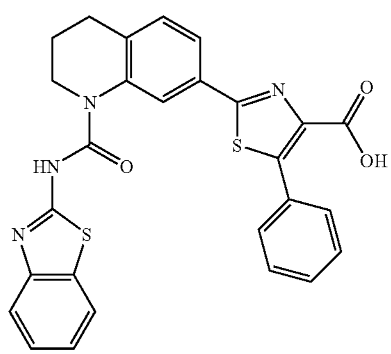 | 2-(1-(benzo[d]thiazol-2-ylcarbamoyl)-1,2,3,4-tetrahydroquinolin-7-yl)-5-phenylthiazole-4-carboxylic acid |
| 63 | 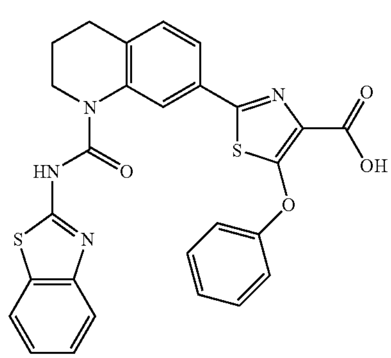 | 2-(1-(benzo[d]thiazol-2-ylcarbamoyl)-1,2,3,4-tetrahydroquinolin-7-yl)-5-phenoxythiazole-4-carboxylic acid |

TABLE 1-continued

| No | Structure | Name |
|---|---|---|
| 64 | 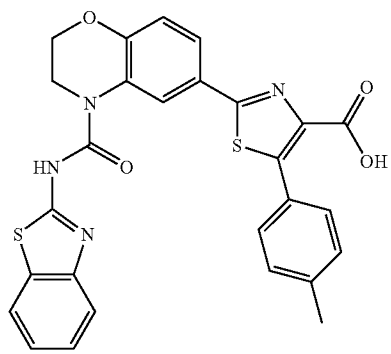 | 2-(4-(benzo[d]thiazol-2-ylcarbamoyl)-3,4-dihydro-2H-benzo[b][1,4]oxazin-6-yl)-5-p-tolylthiazole-4-carboxylic acid |
| 65 | 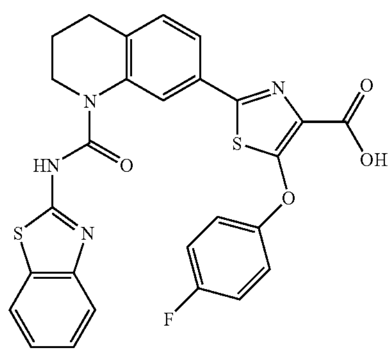 | 2-(1-(benzo[d]thiazol-2-ylcarbamoyl)-1,2,3,4-tetrahydroquinolin-7-yl)-5-(4-fluorophenoxy)thiazole-4-carboxylic acid |
| 66 | 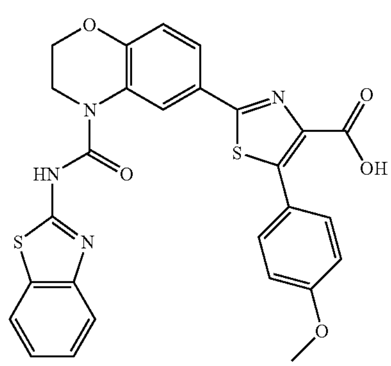 | 2-(4-(benzo[d]thiazol-2-ylcarbamoyl)-3,4-dihydro-2H-benzo[b][1,4]oxazin-6-yl)-5-(4-methoxyphenyl)thiazole-4-carboxylic acid |
| 67 | 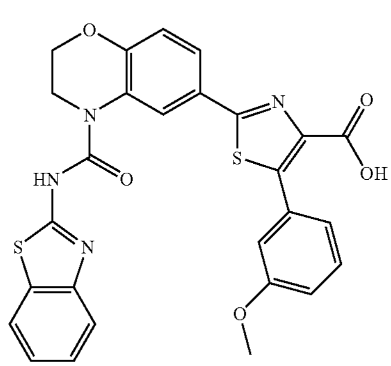 | 2-(4-(benzo[d]thiazol-2-ylcarbamoyl)-3,4-dihydro-2H-benzo[b][1,4]oxazin-6-yl)-5-(3-methoxyphenyl)thiazole-4-carboxylic acid |

TABLE 1-continued

| No | Structure | Name |
|---|---|---|
| 68 | 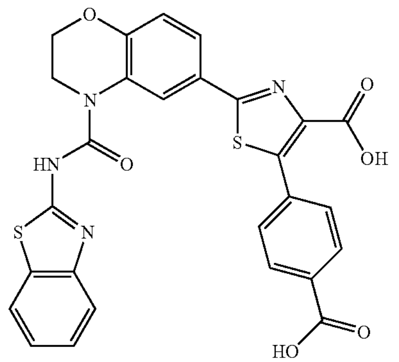 | 2-(4-(benzo[d]thiazol-2-ylcarbamoyl)-3,4-dihydro-2H-benzo[b][1,4]oxazin-6-yl)-5-(4-carboxyphenyl)thiazole-4-carboxylic acid |
| 69 | 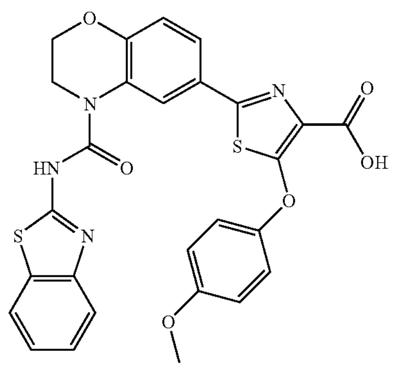 | 2-(4-(benzo[d]thiazol-2-ylcarbamoyl)-3,4-dihydro-2H-benzo[b][1,4]oxazin-6-yl)-5-(4-methoxyphenoxy)thiazole-4-carboxylic acid |
| 70 | 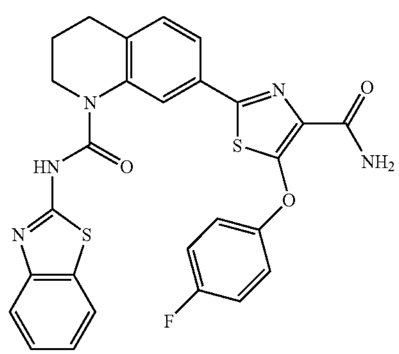 | 2-(1-(benzo[d]thiazol-2-ylcarbamoyl)-1,2,3,4-tetrahydroquinolin-7-yl)-5-(4-fluorophenoxy)thiazole-4-carboxamide |
| 71 | 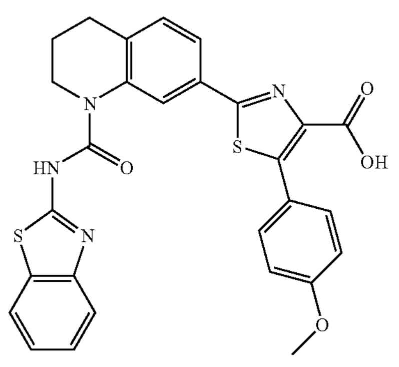 | 2-(1-(benzo[d]thiazol-2-ylcarbamoyl)-1,2,3,4-tetrahydroquinolin-7-yl)-5-(4-methoxyphenyl)thiazole-4-carboxylic acid |

TABLE 1-continued

| No | Structure | Name |
|---|---|---|
| 72 | 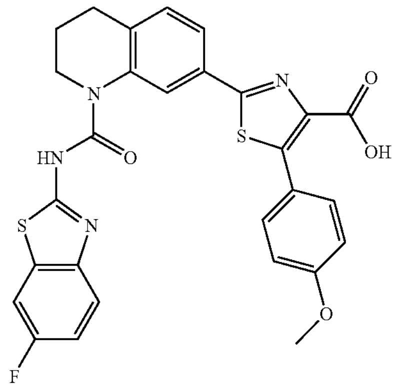 | 2-(1-(6-fluorobenzo[d]thiazol-2-ylcarbamoyl)-1,2,3,4-tetrahydroquinolin-7-yl)-5-(4-methoxyphenyl)thiazole-4-carboxylic acid |
| 73 | 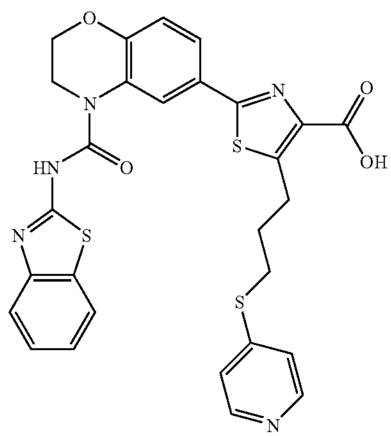 | 2-(4-(benzo[d]thiazol-2-ylcarbamoyl)-3,4-dihydro-2H-benzo[b][1,4]oxazin-6-yl)-5-(3-(pyridin-4-ylthio)propyl)thiazole-4-carboxylic acid |
| 74 | 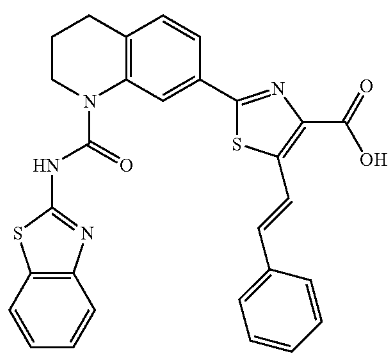 | (E)-2-(1-(benzo[d]thiazol-2-ylcarbamoyl)-1,2,3,4-tetrahydroquinolin-7-yl)-5-styrylthiazole-4-carboxylic acid |
| 75 | 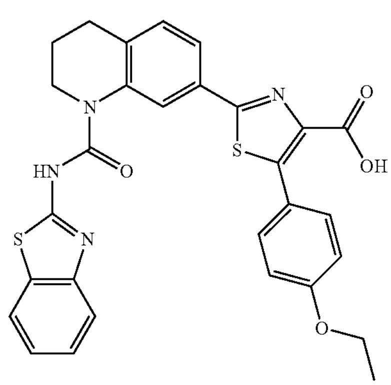 | 2-(1-(benzo[d]thiazol-2-ylcarbamoyl)-1,2,3,4-tetrahydroquinolin-7-yl)-5-(4-ethoxyphenyl)thiazole-4-carboxylic acid |

TABLE 1-continued

| No | Structure | Name |
|---|---|---|
| 76 | 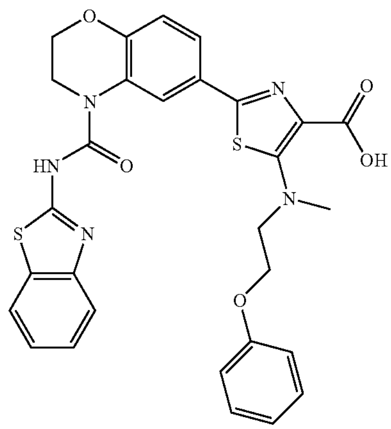 | 2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylic acid |
| 77 | 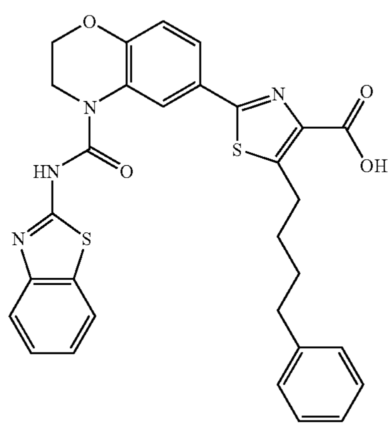 | 2-(4-(benzo[d]thiazol-2-ylcarbamoyl)-3,4-dihydro-2H-benzo[b][1,4]oxazin-6-yl)-5-(4-phenylbutyl)thiazole-4-carboxylic acid |
| 78 | 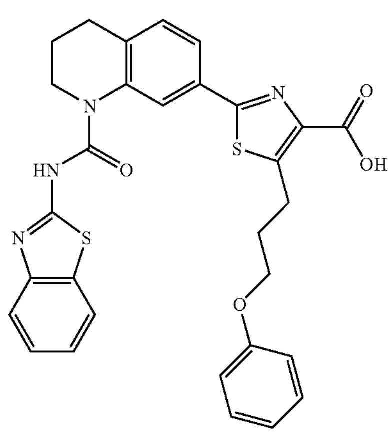 | 2-(1-(benzo[d]thiazol-2-ylcarbamoyl)-1,2,3,4-tetrahydroquinolin-7-yl)-5-(3-phenoxypropyl)thiazole-4-carboxylic acid |

TABLE 1-continued

| No | Structure | Name |
|----|-----------|------|
| 79 | 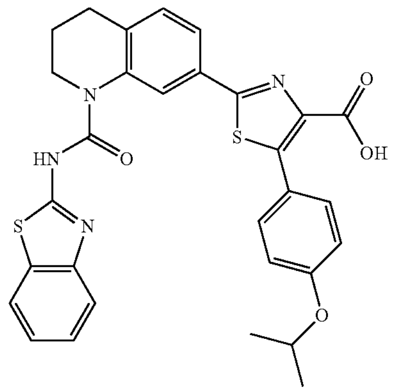 | 2-(1-(benzo[d]thiazol-2-ylcarbamoyl)-1,2,3,4-tetrahydroquinolin-7-yl)-5-(4-isopropoxyphenyl)thiazole-4-carboxylic acid |
| 80 | 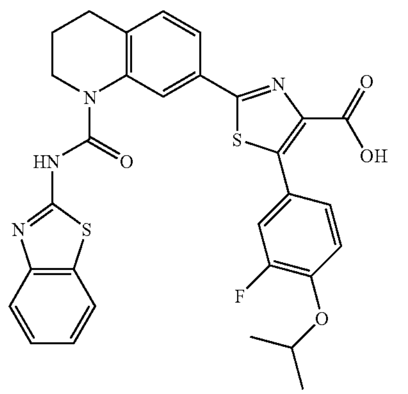 | 2-(1-(benzo[d]thiazol-2-ylcarbamoyl)-1,2,3,4-tetrahydroquinolin-7-yl)-5-(3-fluoro-4-isopropoxyphenyl)thiazole-4-carboxylic acid |
| 81 | 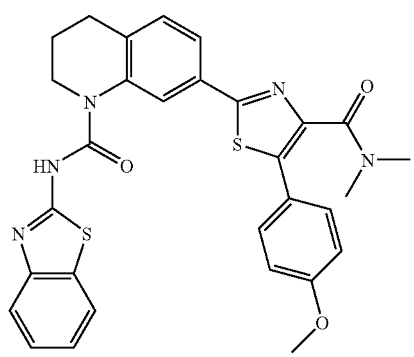 | 2-(1-(benzo[d]thiazol-2-ylcarbamoyl)-1,2,3,4-tetrahydroquinolin-7-yl)-5-(4-methoxyphenyl)-N,N-dimethylthiazole-4-carboxamide |
| 82 | 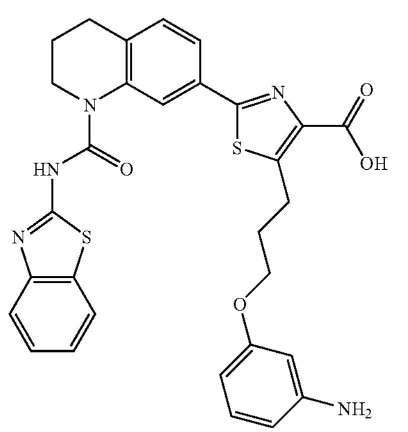 | 5-(3-(3-aminophenoxy)propyl)-2-(1-(benzo[d]thiazol-2-ylcarbamoyl)-1,2,3,4-tetrahydroquinolin-7-yl)thiazole-4-carboxylic acid |

TABLE 1-continued

| No | Structure | Name |
|---|---|---|
| 83 | 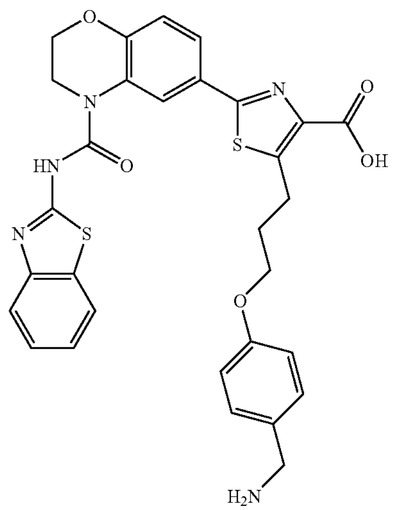 | 5-(3-(4-(aminomethyl)phenoxy)propyl)-2-(4-(benzo[d]thiazol-2-ylcarbamoyl)-3,4-dihydro-2H-benzo[b][1,4]oxazin-6-yl)thiazole-4-carboxylic acid |
| 84 | 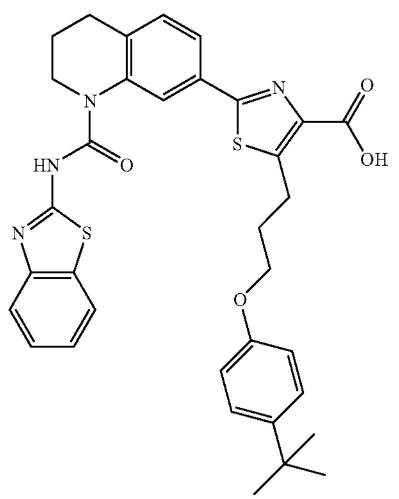 | 2-(1-(benzo[d]thiazol-2-ylcarbamoyl)-1,2,3,4-tetrahydroquinolin-7-yl)-5-(3-(4-tert-butylphenoxy)propyl)thiazole-4-carboxylic acid |
| 85 | 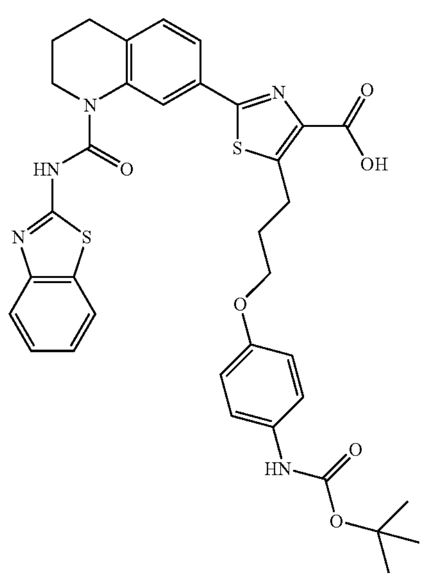 | 2-(1-(benzo[d]thiazol-2-ylcarbamoyl)-1,2,3,4-tetrahydroquinolin-7-yl)-5-(3-(4-(tert-butoxycarbonylamino)phenoxy)propyl)thiazole-4-carboxylic acid |

TABLE 1-continued

| No | Structure | Name |
|---|---|---|
| 86 | 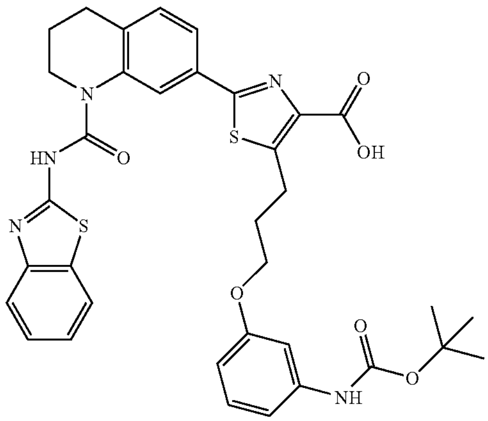 | 2-(1-(benzo[d]thiazol-2-ylcarbamoyl)-1,2,3,4-tetrahydroquinolin-7-yl)-5-(3-(3-(tert-butoxycarbonylamino)phenoxy)propyl)thiazole-4-carboxylic acid |
| 87 | 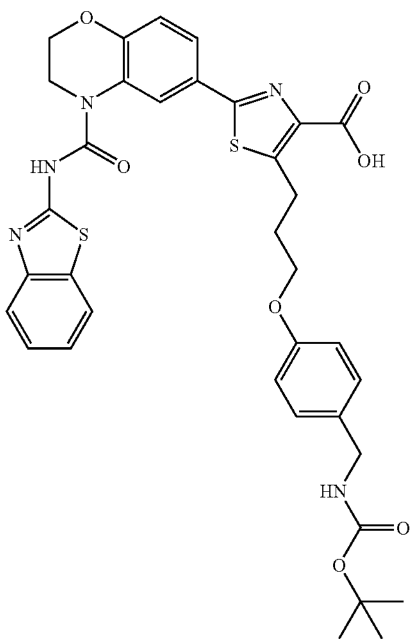 | 2-(4-(benzo[d]thiazol-2-ylcarbamoyl)-3,4-dihydro-2H-benzo[b][1,4]oxazin-6-yl)-5-(3-(4-((tert-butoxycarbonylamino)methyl)phenoxy)propyl)thiazole-4-carboxylic acid |
| 88 | 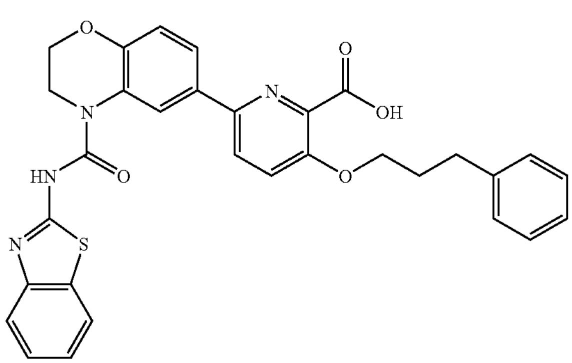 | 6-(4-(benzo[d]thiazol-2-ylcarbamoyl)-3,4-dihydro-2H-benzo[b][1,4]oxazin-6-yl)-3-(3-phenylpropoxy)picolinic acid |

TABLE 1-continued

| No | Structure | Name |
|---|---|---|
| 89 | 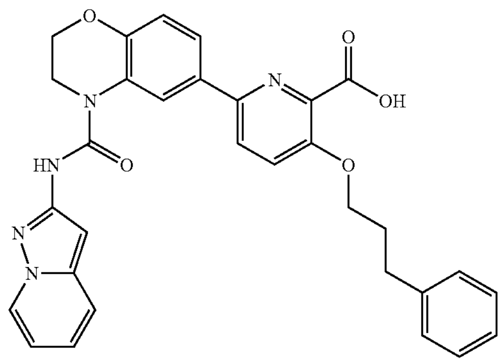 | 3-(3-phenylpropoxy)-6-(4-(pyrazolo[1,5-a]pyridin-2-ylcarbamoyl)-3,4-dihydro-2H-benzo[b][1,4]oxazin-6-yl)picolinic acid |
| 90 | 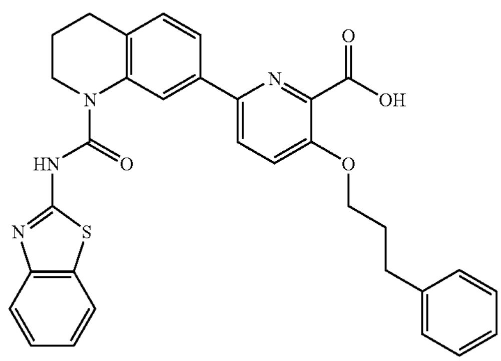 | 6-(1-(benzo[d]thiazol-2-ylcarbamoyl)-1,2,3,4-tetrahydroquinolin-7-yl)-3-(3-phenylpropoxy)picolinic acid |
| 91 | 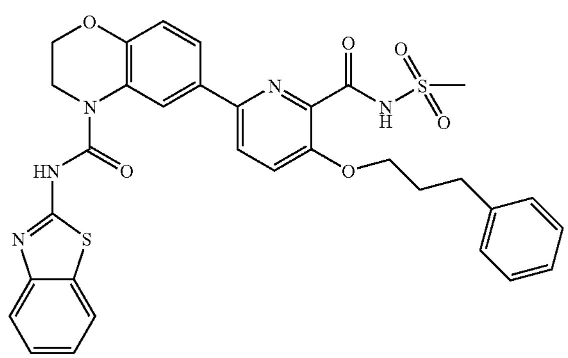 | N-(benzo[d]thiazol-2-yl)-6-(6-(methylsulfonylcarbamoyl)-5-(3-phenylpropoxy)pyridin-2-yl)-2H-benzo[b][1,4]oxazine-4(3H)-carboxamide |
| 92 | 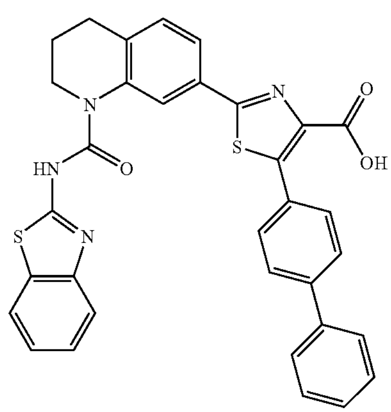 | 2-(1-(benzo[d]thiazol-2-ylcarbamoyl)-1,2,3,4-tetrahydroquinolin-7-yl)-5-(biphenyl-4-yl)thiazole-4-carboxylic acid |

TABLE 1-continued

| No | Structure | Name |
|---|---|---|
| 93 | 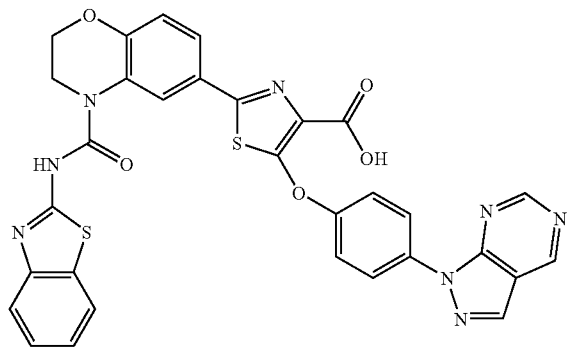 | 5-(4-(1H-pyrazolo[3,4-d]pyrimidin-1-yl)phenoxy)-2-(1-(benzo[d]thiazol-2-ylcarbamoyl)-1,2,3,4-tetrahydroquinolin-7-yl)thiazole-4-carboxylic acid |
| 94 | 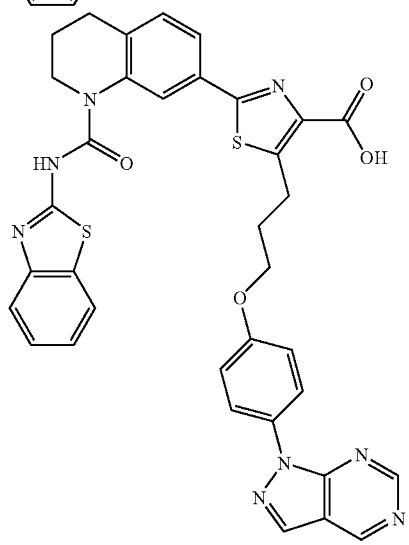 | 5-(3-(4-(1H-pyrazolo[3,4-d]pyrimidin-1-yl)phenoxy)propyl)-2-(1-(benzo[d]thiazol-2-ylcarbamoyl)-1,2,3,4-tetrahydroquinolin-7-yl)thiazole-4-carboxylic acid |

General Synthetic Procedures

Compounds of the invention can be prepared by synthetic methods known in the art, some of which are described below for illustrative purposes. Compounds of Formula I having a tetrahydroquinoline core can be prepared as shown in Scheme I below.

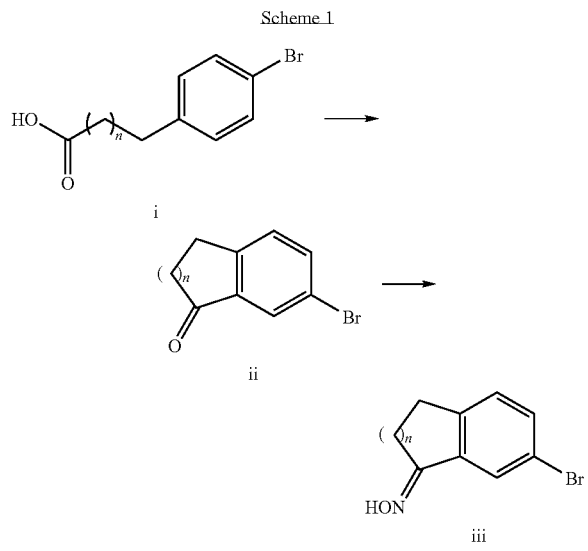

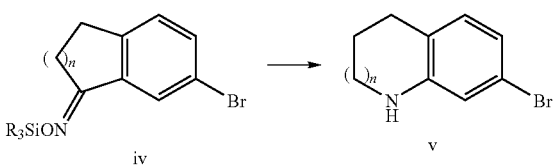

As shown in Scheme 1, intramolecular Friedal-Crafts acylation (e.g., using $AlCl_3$) of a halo-substituted phenylalkanoic acid (i) can provide the ketone product (ii). Conversion of ii to the O-silylated oxime derivative (iii) can be accomplished by combining ii with oxime hydrochloride under basic conditions (e.g., potassium carbonate) followed by silylation of the resultant oxime product, using, for example, a trialkylsilyl chloride ($R_3SiCl$). Lewis acid promoted Beckman rearrangement of iv followed by reduction of the intermediate imminium compound can produce tetrahydroquinoline v. In Scheme 1, the subscript n represents be an integer from 1 to 3.

Preparation of Compounds of Formula I Having a Benzo-Fused Oxazine core can be prepared following the synthetic procedure outlined in Scheme 2 below.

Scheme 2

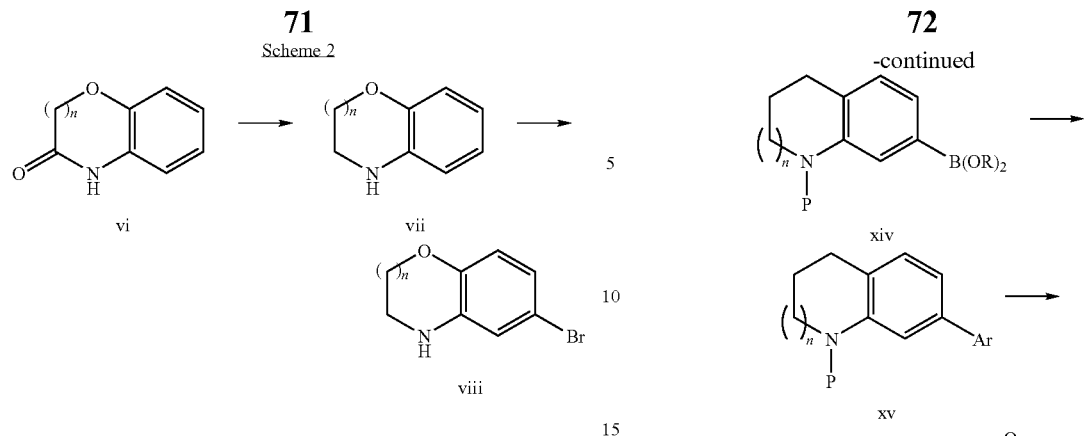

As shown in Scheme 2, hydride reduction of amide compound vi, e.g., using LiAlH₄, can provide the benzo-fused oxazine vii. Bromination of vii, using for example N-bromosuccinimde, can provide the bromide product viii. In Scheme 2, the subscript represents an integer from 1 to 3

Preparation of Certain Aza Derivatives of Compounds of Formula I can be prepared as shown in Scheme 3 below.

Scheme 3

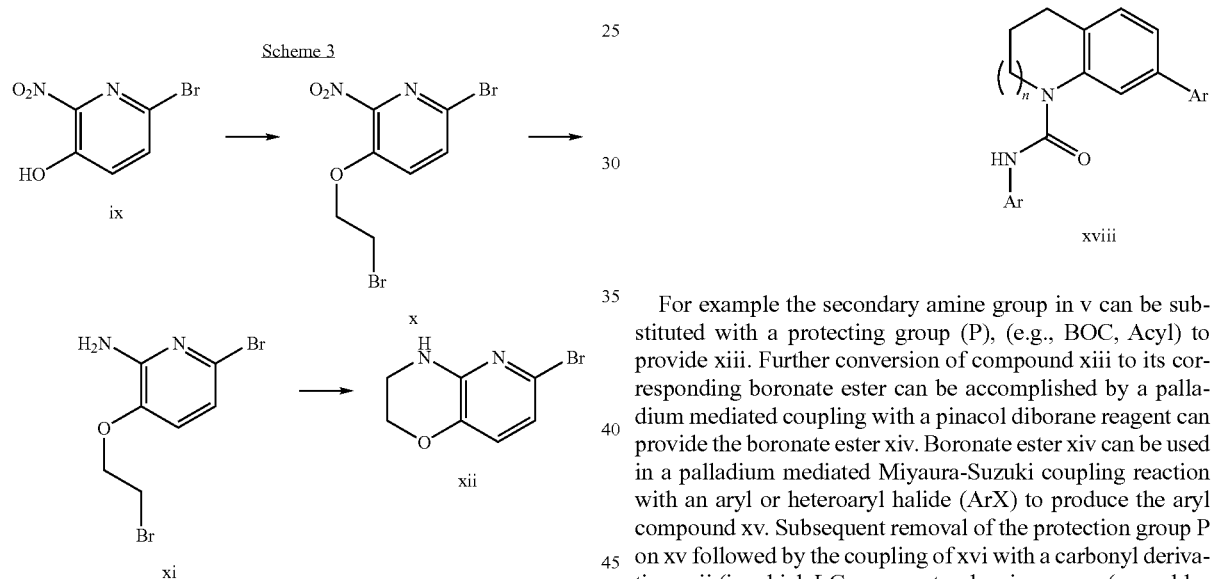

As shown in Scheme 3, alkylation of hydroxynitropyridine ix with a dihaloalkane, e.g., dibromoethane, can provide the alkylated product x. Reduction of the nitro group in x using for example, iron powder in acetic acid, can provide the corresponding amino product xi, which upon heating under basic conditions can provide the cyclized oxazine product xii.

Bromide intermediates v, viii and xii can be further modified as illustrated in Scheme 4 below for compound v.

Scheme 4

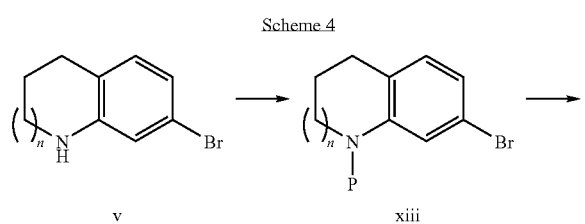

For example the secondary amine group in v can be substituted with a protecting group (P), (e.g., BOC, Acyl) to provide xiii. Further conversion of compound xiii to its corresponding boronate ester can be accomplished by a palladium mediated coupling with a pinacol diborane reagent can provide the boronate ester xiv. Boronate ester xiv can be used in a palladium mediated Miyaura-Suzuki coupling reaction with an aryl or heteroaryl halide (ArX) to produce the aryl compound xv. Subsequent removal of the protection group P on xv followed by the coupling of xvi with a carbonyl derivative xvii (in which LG represents a leaving group (e.g., chloride, imiazole, bromide) can provide the ureido compound xviii.

Additional synthetic transformations that can be used to convert intermediate xviii (and also related compounds viii and xii) to compounds of Formula I are described in detail throughout the Examples section.

III. Compositions

In addition to one or more of the compounds provided above (or stereoisomers, geometric isomers, tautomers, solvates, metabolites or pharmaceutically acceptable salts, or prodrugs thereof), compositions for modulating Bcl-2 protein family activity in humans and animals will typically contain a pharmaceutical carrier or diluent. In one embodiment, the invention provides for a pharmaceutical composition comprising a compound of Formula I and at least one pharmaceutically acceptable diluent, carrier or excipient.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

In order to use a compound of this invention for the therapeutic treatment (including prophylactic treatment) of a patient, it is normally formulated in accordance with standard pharmaceutical practice as a pharmaceutical composition. A typical pharmaceutical composition is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300, etc.) and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations can be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. A compound of the present invention is typically formulated into pharmaceutical dosage forms to provide an easily controllable dosage of the drug and to enable patient compliance with the prescribed regimen.

The pharmaceutical composition (or formulation) for application can be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical compositions of a compound of the present invention can be prepared for various routes and types of administration. For example, a compound of the invention (e.g., a compound of Formula I) having the desired degree of purity can optionally be mixed with pharmaceutically acceptable diluents, carriers, excipients or stabilizers (see, Remington: The Science and Practice of Pharmacy: Remington: The Science and Practice of Pharmacy (2005) 21$^{st}$ Edition, Lippincott Williams & Wilkins, Philadelphia, Pa.), in the form of a lyophilized formulation, milled powder, or an aqueous solution. Compositions can be prepared by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but can range from about 3 to about 8. Formulation in an acetate buffer at pH 5 is a suitable embodiment.

A compound of this invention (e.g., compound of Formula I) for use herein is preferably sterile. In particular, compositions or formulations to be used for in vivo administration must be sterile. Such sterilization is readily accomplished by filtration through sterile filtration membranes.

A compound of the invention ordinarily can be stored as a solid composition, a lyophilized formulation or as an aqueous solution.

A pharmaceutical composition of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat diseases that can by characterized by the expression or overexpression of Bcl-$X_L$ proteins. Such amount is preferably below the amount that is toxic to the host.

As a general proposition, the initial pharmaceutically effective amount of an inhibitor compound of the invention administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). An active pharmaceutical ingredient of the invention (e.g., compound of Formula I) can also be entrapped in microcapsules prepared, for example, by coacervation techniques or by interfacial polymerization, for example, hydroxymethylcellulose or gelatin-microcapsules and poly-(methylmethacylate) microcapsules, respectively; in colloidal drug delivery systems, for example, liposomes, albumin microspheres, microemulsions, nano-particles and nanocapsules; or in macroemulsions. Such techniques are disclosed in Remington:

The Science and Practice of Pharmacy: Remington the Science and Practice of Pharmacy (2005) 21$^{st}$ Edition, Lippincott Williams & Wilkins, Philadelphia, Pa.

Sustained-release compositions of a compound of the invention (e.g., compound of Formula I) can be prepared. Suitable examples of sustained-release compositions include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

Pharmaceutical compositions include those suitable for the administration routes detailed herein. The compositions can conveniently be presented in unit dosage form and can be prepared by any of the methods well known in the art of pharmacy. Techniques and formulations generally are found in Remington: The Science and Practice of Pharmacy: Remington the Science and Practice of Pharmacy (2005) 21$^{st}$ Edition, Lippincott Williams & Wilkins, Philadelphia, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Pharmaceutical compositions of a compound of the invention (e.g., compound of Formula I) suitable for oral administration can be prepared as discrete units such as pills, capsules, cachets or tablets each containing a predetermined amount of a compound of the invention.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets can optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs can be prepared for oral use. Formulations of a compound of the invention (e.g., compound of Formula I) intended for oral use can be prepared according to any method known to the art for the manufacture of pharmaceutical compositions and such compositions can contain one or more agents including sweetening agents, flavoring agents, coloring agents and preserving agents, in order to provide a palatable preparation. Tablets containing the active ingredient in admixture with non-toxic pharmaceutically acceptable excipient, which are suitable for manufacture of tablets, are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredient can be employed with either a paraffinic or a water-miscible ointment base. Alternatively, the active ingredients can be formulated in a cream with an oil-in-water cream base.

If desired, the aqueous phase of the cream base can include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations can desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase can comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include TWEEN® 60, SPAN® 80, cetostearyl alcohol, benzyl alcohol, myristyl alcohol, glyceryl mono-stearate and sodium lauryl sulfate.

Aqueous suspensions of a compound of the invention (e.g., compound of Formula I) contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose or saccharin.

A pharmaceutical composition of a compound of the invention (e.g., compound of Formula I) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable composition can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release composition intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Compositions suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

Compositions suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Compositions suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Compositions for rectal administration can be presented as a suppository with a suitable base comprising for example cocoa butter or a salicylate.

Compositions suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis disorders as described below.

Compositions suitable for vaginal administration can be presented as pessaries, tampons, creams, gels, pastes, foams or spray formulations containing in addition to the active ingredient such carriers as are known in the art to be appropriate.

The pharmaceutical compositions can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient (e.g., compound of Formula I) as above defined together with a veterinary carrier therefore. Veterinary carriers are materials useful for the purpose of administering the composition and can be solid, liquid or gaseous materials which are otherwise inert or acceptable in the veterinary art and are compatible with the active ingredient. These veterinary compositions can be administered parenterally, orally or by any other desired route.

IV. Methods of Use

The compounds of the invention (i.e., compounds of Formula I) (or stereoisomers, geometric isomers, tautomers, solvates, metabolites or pharmaceutically acceptable salts, or prodrugs thereof) bind to and inhibit the activity of anti-apoptotic Bcl-2 family proteins, and in certain aspects, of specifically anti-apoptotic Bcl-$X_L$ proteins; and therefore are useful in the treatment of diseases, conditions and/or disorders including, but not limited to, those diseases characterized by the expression or over-expression of anti-apoptotic Bcl-2 family protein members, and in certain embodiments those diseases characterized by the expression or the over-expression of Bcl-$X_L$ proteins. Accordingly, a certain aspect of this invention includes a method of treating diseases or conditions in a patient that can be characterized by the expression or over-expression of anti-apoptotic Bcl-2 protein family members. Within this aspect, in certain embodiments, the disease or condition is cancer. Compounds of the invention can selectively bind to a subgroup of anti-apoptotic Bcl-2 proteins, for example, of Bcl-$X_L$ over Bcl-2, Bcl-w or Mcl-1 proteins. In certain embodiments, compounds of the invention exhibit at least a 2-fold, 50-fold, 100-fold, 1000-fold, 10000-fold, 20000-fold, or 30000-fold selectivity for binding a Bcl-$x_L$ protein over a Bcl-2 protein. In certain embodiments, compounds of the invention exhibit at least a 2-fold, 50-fold, 100-fold, 1000-fold, 10000-fold, 20000-fold, or 30000-fold selectivity for binding a Bcl-$X_L$ protein over a Mcl-1 protein. In certain embodiments, compounds of the invention exhibit at least a 2-fold, 50-fold, 100-fold, 1000-fold, 10000-fold, 20000-fold, or 30000-fold selectivity for binding a Bcl-$x_L$ protein over a Bcl-w protein. In one embodiment, the method comprises administering to a patient in need thereof, a therapeutically effective amount of a compound of the invention, e.g., compound of Formula I, (or a stereoisomer, geometric isomer, tautomer, solvate, metabolite, or pharmaceutically acceptable salt or prodrug thereof). In another embodiment, the present invention provides for methods of treating diseases and conditions in a patient which is characterized by the expression or over-expression of an anti-apoptotic Bcl-$x_L$ protein, said methods comprising administering to the patient a therapeutically effective amount of a compound of Formula I, or a pharmaceutical composition thereof. In one aspect, said compositions for treating diseases and conditions during which are expressed or over-expressed an antiapoptotic Bcl-$X_L$ protein comprise an excipient and a therapeutically effective amount of the compound of Formula I.

Also provided in the invention is the use of a compound of the invention, e.g., of Formula I, (or stereoisomer, geometric isomer, tautomer, solvate, metabolite, or pharmaceutically acceptable salt, or prodrug thereof), in the preparation of a medicament for the treatment of the diseases and conditions described herein in a patient suffering from such disorder.

The compounds of the invention can be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds can be administered by intralesional administration, including perfusing or otherwise contacting the graft with the inhibitor before transplantation. It will be appreciated that the preferred route can vary with for example the condition of the recipient. Where the compound is administered orally, it can be formulated as a pill, capsule, tablet, etc. with a pharmaceutically acceptable carrier or excipient. Where the compound is administered parenterally, it can be formulated with a pharmaceutically acceptable parenteral vehicle and in a unit dosage injectable form, as detailed below.

A dose to treat human patients can range from about 10 mg to about 1000 mg of a Formula I compound. A typical dose can be about 100 mg to about 300 mg of the compound. A dose can be administered once a day (QID), twice per day (BID), or more frequently, depending on the pharmacokinetic and pharmacodynamic properties, including absorption, distribution, metabolism, and excretion of the particular compound. In addition, toxicity factors can influence the dosage and administration regimen. When administered orally, the pill, capsule, or tablet can be ingested daily or less frequently for a specified period of time. The regimen can be repeated for a number of cycles of therapy.

In another embodiment, the present invention provides for compositions comprising an pharmaceutically acceptable excipient and a therapeutically effective amount of a compound of Formula I for treating diseases or conditions of abnormal cell growth and/or dysregulated apoptosis, such as cancer, mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination thereof In another embodiment, the present invention provides for a method of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, said method comprising administering thereto a therapeutically effective amount of a compound of Formula I.

In yet another embodiment, the present invention provides for methods of treating autoimmune disease in a mammal comprising administering thereto a therapeutically acceptable amount of a compound having Formula I. The involvement of Bcl-2 proteins in immune and autoimmune diseases is described in Puck, J. M. et al., *Current Allergy and Asthma Reports* 2003, 3, 378-384; Shimazaki, K. et al., *British Journal of Haematology* 2000, 110(3), 584-90; Rengan, R. et al., *Blood* 2000, 95(4), 1283-92; and Holzelova, E. et al., *New England Journal of Medicine* 2004, 351(14), 1409-1418.

Autoimmune disorders include acquired immunodeficiency disease syndrome (AIDS), autoimmune lymphoproliferative syndrome, hemolytic anemia, inflammatory diseases, and thrombocytopenia, acute or chronic immune disease associated with organ transplantation, Addison's disease, allergic diseases, alopecia, alopecia areata, atheromatous disease/arteriosclerosis, atherosclerosis, arthritis (including osteoarthritis, juvenile chronic arthritis, septic arthritis, Lyme arthritis, psoriatic arthritis and reactive arthritis), autoimmune bullous disease, abetalipoprotemia, acquired immunodeficiency-related diseases, acute immune disease associated with organ transplantation, acquired acrocyanosis, acute and chronic parasitic or infectious processes, acute pancreatitis, acute renal failure, acute rheumatic fever, acute transverse myelitis, adenocarcinomas, aerial ectopic beats, adult (acute) respiratory distress syndrome, AIDS dementia complex, alcoholic cirrhosis, alcohol-induced liver injury, alcohol-induced hepatitis, allergic conjunctivitis, allergic contact dermatitis, allergic rhinitis, allergy and asthma, allograft rejection, alpha-1-antitrypsin deficiency, Alzheimer's disease, amyotrophic lateral sclerosis, anemia, angina pectoris, ankylosing spondylitis associated lung disease, anterior horn cell degeneration, antibody mediated cytotoxicity, antiphospholipid syndrome, anti-receptor hypersensitivity reactions, aortic and peripheral aneurysms, aortic dissection, arterial hypertension, arteriosclerosis, arteriovenous fistula, arthropathy, asthenia, asthma, ataxia, atopic allergy, atrial fibrillation (sustained or paroxysmal), atrial flutter, atrioventricular block, atrophic autoimmune hypothyroidism, autoimmune haemolytic anaemia, autoimmune hepatitis, type-1 autoimmune hepatitis (classical autoimmune or lupoid hepatitis), autoimmune mediated hypoglycaemia, autoimmune neutropaenia, autoimmune thrombocytopaenia, autoimmune thyroid disease, B cell lymphoma, bone graft rejection, bone marrow transplant (BMT) rejection, bronchiolitis obliterans, bundle branch block, burns, cachexia, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chlamydia, choleosatatis, chronic alcoholism, chronic active hepatitis, chronic fatigue syndrome, chronic immune disease associated with organ transplantation, chronic eosinophilic pneumonia, chronic inflammatory pathologies, chronic mucocutaneous candidiasis, chronic obstructive pulmonary disease (COPD), chronic salicylate intoxication, colorectal common varied immunodeficiency (common variable hypogammaglobulinaemia), conjunctivitis, connective tissue disease associated interstitial lung disease, contact dermatitis, Coombs positive haemolytic anaemia, cor pulmonale, Creutzfeldt-Jakob disease, cryptogenic autoimmune hepatitis, cryptogenic fibrosing alveolitis, culture negative sepsis, cystic fibrosis, cytokine therapy associated disorders, Crohn's disease, dementia pugilistica, demyelinating diseases, dengue hemorrhagic fever, dermatitis, dermatitis scleroderma, dermatologic conditions, dermatomyositis/polymyositis associated lung disease, diabetes, diabetic arteriosclerotic disease, diabetes mellitus, Diffuse Lewy body disease, dilated cardiomyopathy, dilated congestive cardiomyopathy, discoid lupus erythematosus, disorders of the basal ganglia, disseminated intravascular coagulation, Down's Syndrome in middle age, drug-induced interstitial lung disease, drug-induced hepatitis, drug-induced movement disorders induced by drugs which block CNS dopamine, receptors, drug sensitivity, eczema, encephalomyelitis, endocarditis, endocrinopathy, enteropathic synovitis, epiglottitis, Epstein-Barr virus infection, erythromelalgia, extrapyramidal and cerebellar disorders, familial hematophagocytic lymphohistiocytosis, fetal thymus implant rejection, Friedreich's ataxia, functional peripheral arterial disorders, female infertility, fibrosis, fibrotic lung disease, fungal sepsis, gas gangrene, gastric ulcer, giant cell arteritis, glomerular nephritis, glomerulonephritides, Goodpasture's syndrome, goitrous autoimmune hypothyroidism (Hashimoto's disease), gouty arthritis, graft rejection of any organ or tissue, graft versus host disease, gram negative sepsis, gram positive sepsis, granulomas due to intracellular organisms, group B streptococci (GBS) infection, Grave's disease, haemosiderosis associated lung disease, hairy cell leukemia, hairy cell leukemia, Hallervorden-Spatz disease, Hashimoto's thyroiditis, hay fever, heart transplant rejection, hemachromatosis, hematopoietic malignancies (leukemia and lymphoma), hemolytic anemia, hemolytic uremic syndrome/thrombolytic thrombocytopenic purpura, hemorrhage, Henoch-Schoenlein purpurea, Hepatitis A, Hepatitis B, Hepatitis C, HIV infection/HIV neuropathy, Hodgkin's disease, hypoparathyroidism, Huntington's chorea, hyperkinetic movement disorders, hypersensitivity reactions, hypersensitivity pneumonitis, hyperthyroidism, hypokinetic movement disorders, hypothalamic-pituitary-adrenal axis evaluation, idiopathic Addison's disease, idiopathic leucopaenia, idiopathic pulmonary fibrosis, idiopathic thrombocytopaenia, idiosyncratic liver disease, infantile spinal muscular atrophy, infectious diseases, inflammation of the aorta, inflammatory bowel disease, insulin dependent diabetes mellitus, interstitial pneumonitis, iridocyclitis/uveitis/optic neuritis, ischemia-reperfusion injury, ischemic stroke, juvenile pernicious anaemia, juvenile rheumatoid arthritis, juvenile spinal muscular atrophy, Kaposi's sarcoma, Kawasaki's disease, kidney transplant rejection, legionella, leishmaniasis, leprosy, lesions of the corticospinal system, linear IgA disease, lipidema, liver transplant rejection, Lyme disease, lymphederma, lymphocytic infiltrative lung disease, malaria, male infertility idiopathic or NOS, malignant histiocytosis, malignant melanoma, meningitis, meningococcemia, microscopic vasculitis of the kidneys, migraine headache, mitochondrial multi-system disorder, mixed connective tissue disease, mixed connective tissue disease associated lung disease, monoclonal gammopathy, multiple myeloma, multiple systems degenerations (Mencel Dejerine-Thomas Shi-Drager and Machado-Joseph), myalgic encephalitis/Royal Free Disease, myasthenia gravis, microscopic vasculitis of the kidneys, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, nephrotic syndrome, neurodegenerative diseases, neurogenic I muscular atrophies, neutropenic fever, Non-alcoholic Steatohepatitis, occlusion of the abdominal aorta and its branches, occlusive arterial disorders, organ transplant rejection, orchitis/epididymitis, orchitis/vasectomy reversal procedures, organomegaly, osteoarthrosis, osteoporosis, ovarian failure, pancreas transplant rejection, parasitic diseases, parathyroid transplant rejection, Parkinson's disease, pelvic inflammatory disease, pemphigus vulgaris, pemphigus foliaceus, pemphigoid, perennial rhinitis, pericardial disease, peripheral atherlosclerotic disease, peripheral vascular disorders, peritonitis, pernicious anemia, phacogenic uveitis, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, postinfectious interstitial lung disease, premature ovarian failure, primary biliary cirrhosis, primary sclerosing hepatitis, primary myxoedema, primary pulmonary hypertension, primary sclerosing cholangitis, primary vasculitis, Progressive supranucleo Palsy, psoriasis, psoriasis type 1, psoriasis type 2, psoriatic arthropathy, pulmonary hypertension secondary to connective tissue disease, pulmonary manifestation of polyarteritis nodosa, post-inflammatory interstitial lung disease, radiation fibrosis, radiation therapy, Raynaud's phenomenon and disease Refsum's disease, regular narrow QRS tachycardia, Reiter's disease, renal disease NOS, renovascular hypertension, reperfusion injury, restrictive cardiomyopathy, rheumatoid arthritis associated interstitial lung disease, rheumatoid spondylitis, sarcoidosis, Schmidt's syndrome, scleroderma, senile chorea, Senile Dementia of Lewy body type, sepsis syndrome, septic shock, seronegative arthropathies, shock, sickle cell anemia, Sjögren's disease associated lung disease, Sjörgren's syndrome, skin allograft rejection, skin changes syndrome, small bowel transplant rejection, sperm autoimmunity, multiple sclerosis (all subtypes), spinal ataxia, spinocerebellar degenerations, spondyloarthropathy, sporadic, polyglandular deficiency type I sporadic, polyglandular deficiency type II, Still's disease, streptococcal myositis, stroke, structural lesions of the cerebellum, Subacute sclerosing panencephalitis, sympathetic ophthalmia, Syncope, syphilis of the cardiovascular system, systemic anaphylaxis, systemic inflammatory response syndrome, systemic onset juvenile rheumatoid arthritis, systemic lupus erythematosus, systemic lupus erythematosus-associated lung disease, systemic sclerosis, systemic sclerosis-associated interstitial lung disease, T-cell or FAB ALL, Takayasu's disease/arteritis, Telangiectasia, Th2 Type and Th1 Type mediated diseases, thromboangitis obliterans, thrombocytopenia, thyroiditis, toxicity, toxic shock syndrome, transplants, trauma/hemorrhage, type-2 autoimmune hepatitis (anti-LKM antibody hepatitis), type B insulin resistance with acanthosis nigricans, type III hypersensitivity reactions, type IV hypersensitivity, ulcerative colitic arthropathy, ulcerative colitis, unstable angina, uremia, urosepsis, urticaria, uveitis, valvular heart diseases, varicose veins, vasculitis, vasculitic diffuse lung disease, venous diseases, venous thrombosis, ventricular fibrillation, vitiligo acute liver disease, viral and fungal infections, vital encephalitis/aseptic meningitis, vital-associated hemaphagocytic syndrome, Wegener's granulomatosis, Wernicke-Korsakoff syndrome, Wilson's disease, xenograft rejection of any organ or tissue, *yersinia* and *salmonella*-associated arthropathy and the like.

In one embodiment, a compound of the invention (e.g., compound of Formula I), or stereoisomer, geometric isomer, tautomer, solvate, metabolite, or pharmaceutically acceptable salt, prodrug thereof, is used as an anticancer agent or as an adjunct agent for the treatment of cancer in a combination therapy. One of ordinary skill in the art is readily able to determine whether or not a candidate compound treats a cancerous condition for any particular cell type, either alone or in combination. Within certain aspects of this embodiment, compounds of the invention are used in adjunct with other therapies, including conventional surgery, radiotherapy and chemotherapy, for the treatment of cancer.

Such therapies can include one or more of the following categories of anti-cancer agents: alkylating agents, angiogenesis inhibitors, antibodies, antimetabolites, antimitotics, antiproliferatives, aurora kinase inhibitors, apoptosis promoters (for example, Bcl-xL, Bcl-w and Bfl-1 inhibitors), activators of death receptor pathway, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, dual variable domains binding proteins (DVDs), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAPs) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNAs), topoisomerase inhibitors, combinations thereof and the like.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani (1997) J. of Immunology. 158 (12): 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand. For example, siRNAs targeting Mcl-1 have been shown to enhance the activity of ABT-263, (i.e., N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide) or ABT-737 (i.e., N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) in multiple tumor cell lines (Tse et. al (2008) Cancer Research. 68(9): 3421 and references therein).

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2

(MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptupurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Aurora kinase inhibitors include AZD-1152, MLN-8054, VX-680 and the like.

Bcl-2 family protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(41R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Activators of death receptor pathway include TRAIL, antibodies or other agents that target death receptors (e.g., DR4 and DR5) such as Apomab, conatumumab, ETR2-ST01, GDC 0145, lexatumumab, HGS-1029, LBY-135, PRO-1762 and trastuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin), eptaplatin, lobaplatin, nedaplatin, PARAPLATIN® (carboplatin), satraplatin, picoplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzumab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL®

(sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® ($^{90}$Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula I may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotoxi), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The combination therapy can be administered as a simultaneous or sequential regimen. When administered sequentially, the combination can be administered in two or more administrations. The combined administration includes coadministration, using separate formulations or a single pharmaceutical formulation, and consecutive administration in either order, wherein preferably there is a time period while both (or all) active agents simultaneously exert their biological activities.

Accordingly, in another embodiment, the present invention provides for compositions for treating diseases in a patient during which is expressed or overexpressed an anti-apoptotic Bcl-$x_L$ protein, said compositions comprising an excipient and a therapeutically effective amount of the compound of Formula I and a therapeutically effective amount of one additional therapeutic agent or more than one additional therapeutic agent.

In another embodiment, the present invention provides for methods of treating diseases in a patient during which is expressed or overexpressed an anti-apoptotic Bcl-$x_L$ protein, said methods comprising administering to the patient a therapeutically effective amount of a compound of Formula I and a therapeutically effective amount of one additional therapeutic agent or more than one additional therapeutic agent.

In another embodiment, the present invention provides for methods of treating mesothioloma, bladder cancer, pancreatic cancer, skin cancer, cancer of the head or neck, cutaneous or intraocular melanoma, ovarian cancer, breast cancer, uterine cancer, carcinoma of the fallopian tubes, carcinoma of the endometrium, carcinoma of the cervix, carcinoma of the vagina, carcinoma of the vulva, bone cancer, ovarian cancer, cervical cancer, colon cancer, rectal cancer, cancer of the anal region, stomach cancer, gastrointestinal (gastric, colorectal, and duodenal), chronic lymphocytic leukemia, esophageal cancer, cancer of the small intestine, cancer of the endocrine system, cancer of the thyroid gland, cancer of the parathyroid gland, cancer of the adrenal gland, sarcoma of soft tissue, cancer of the urethra, cancer of the penis, testicular cancer, hepatocellular cancer (hepatic and billiary duct), primary or secondary central nervous system tumor, primary or secondary brain tumor, Hodgkin's disease, chronic or acute leukemia, chronic myeloid leukemia, lymphocytic lymphomas, lymphoblastic leukemia, follicular lymphoma, lymphoid malignancies of T-cell or B-cell origin, melanoma, multiple myeloma, oral cancer, ovarian cancer, non-small cell lung cancer, prostate cancer, small cell lung cancer, cancer of the kidney and ureter, renal cell carcinoma, carcinoma of the renal pelvis, neoplasms of the central nervous system, primary central nervous system lymphoma, non Hodgkin's lymphoma, spinal axis tumors, brains stem glioma, pituitary adenoma, adrenocortical cancer, gall bladder cancer, cancer of the spleen, cholangiocarcinoma, fibrosarcoma, neuroblastoma, retinoblasitoma, or a combination of one or more of the above cancers in a patient, said methods comprising administering thereto therapeutically effective amounts of a compound of Formula I, or a pharmaceutical composition thereof and one or more than one of etoposide vincristine CHOP, rituximab, rapamycin, R-CHOP or bortezomib.

Suitable dosages for any of the above co-administered agents are those presently used and can be lowered due to the combined action (synergy) of the newly identified agent and other chemotherapeutic agents or treatments.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

In yet another embodiment, the present invention provides for methods of treating diseases or conditions caused, exacerbated by or resulting from an excess of, or undesired activation of, platelets in a patient comprising administering thereto a compound of Formula I, or a pharmaceutical composition thereof.

Diseases caused or exacerbated by an excess of, or undesired activation of, platelets include, but are not limited to, essential thrombocythemia, polycythemia vera, M7 acute myelogenous leukemia, restenosis, cardiovascular disease, perioperative antiplatelet therapy, device-associated thrombi and complications associated therewith, and the like. The involvement of platelets in essential thrombocythemia is reported in Seminars in Hematology (2005), 42(4), 230-238 and also in New Eng. J. Med., 2005, 353:1, 33-45. The involvement of platelets in polycythemia vera is reported in Seminars in Thrombosis and Hemostatis (2006), 32(3), 267-275. The involvement of platelets in restenosis is reported in Journal of Clinical Pathology (2006), 59(3), 232-239. The involvement of platelets in cardiovascular disease is reported in International Journal of Clinical Practice (2003), 57(10), 898-905. The involvement of platelets in perioperative antiplatelet therapy is reported in Journal of Thrombosis Thrombolysis. Diseases or conditions that result from elevated platelet levels include bleeding, thrombosis or other thromboembolic complication, initiation or worsening of other diseases or disorders of the blood, such as "sticky platelet" syndrome.

In one embodiment, the present invention provides for methods of reducing the number of platelets in a patient and treating pro-thrombotic conditions and diseases that are characterized by an excess of, or undesired activation of platelets, by administering thereto a compound of Formula I.

In another embodiment, the present invention provides for methods of treating essential thrombocythemia in a patient comprising administering thereto a compound of Formula I. Within certain aspects of this embodiment, in one embodiment, the present invention provides for a method of reducing the number of platelets in a patient and treating essential thrombocythemia.

In another embodiment, the present invention provides methods of treating polycythemia vera in a patient comprising administering thereto a compound of Formula I which inhibits the activity of an Bcl-$x_L$ family protein member. Within certain aspects of this embodiment, in one embodiment, the present invention provides methods of reducing the number of platelets in a patient and treating polycythemia vera.

In certain aspects, a compound or pharmaceutical composition used in each of the above described methods of the invention is a compound selected from Table 1, or pharmaceutical composition comprising a compound selected from Table 1.

In certain aspects, the present application provides a use of a compound as described herein (e.g., compound of Formula I), or stereoisomer, geometric isomer, tautomer, solvate, metabolite, or pharmaceutically acceptable salt, prodrug thereof, for treating a disease or condition. Exemplary diseases or conditions include, for example, any of the diseases or conditions caused, exacerbated by or resulting from an excess of, or undesired activation of, platelets discussed above, any of the cancers discussed above, or any of the autoimmune diseases discussed above. In certain embodiments of the uses provided, the compound (e.g., compound of Formula I), or stereoisomer, geometric isomer, tautomer, solvate, metabolite, or pharmaceutically acceptable salt, prodrug thereof, is used alone. In other embodiments, the compound (e.g., compound of Formula I), or stereoisomer, geometric isomer, tautomer, solvate, metabolite, or pharmaceutically acceptable salt, prodrug thereof, is used in as part of a combination therapy as discussed above.

The following examples are provided simply to illustrate the invention. The examples provided should not be construed to limit the claimed invention in any way.

V. Examples

In the Examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Column chromatography was conducted on a Biotage system (Manufacturer: Dyax Corporation) having a silica gel column or on a silica SEP PAK® cartridge (Waters) or on an ISCO chromatography system (Manufacturer: Teledyne ISCO) having a silica gel column, or manually using a glass column as generally following the techniques described by W. C. Still (see, Still, W. C.; Kahn, M.; Mitra, A. *J. Org. Chem.* 1978, 43(14), 2923-2925). $^1$H NMR spectra were recorded on a Varian or similar instrument operating at 300 or 400 MHz. $^1$H NMR spectra were obtained in deuterated $CDCl_3$, $d_6$-DMSO, $CH_3OD$ or $d_6$-acetone solutions (reported in ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz). When possible, product formation in the reaction mixtures can be monitored by LC/MS, performed either on an Agilent 1200 Series LC coupled to a 6140 quadrupole mass spectrometer using a Supelco Ascentis Express C18 column with a linear gradient of 5%-95% acetonitrile/water (with 0.1% trifluoroacetic acid in each mobile phase) within 1.4 minutes and held at 95% for 0.3 minute, or on a PE Sciex API 150 EX using a Phenomenex DNYC monolithic C18 column with a linear gradient of 5%-95% acetonitrile/water (with 0.1% trifluoroacetic acid in each mobile phase) within 5 minutes and held at 95% for 1 minute, or similar system.

All abbreviations used to described reagents, reaction conditions, or equipment used are consistent with the definitions set forth in the "List of standard abbreviations and acronyms" published yearly by the Journal of Organic Chemistry (an American Chemical Society journal). The following abbreviations used herein have the meaning as follows: rt=room temperature, DMAP=2,6-dimethylaminopyridine; DCM=dichloromethane, THF=tetrahydrofuran, TEA=triethylamine, EtOAc=ethyl acetate, TFA=trifluoroacetic acid, LC/MS=liquid chromatography/mass spectrometry, APCI=atmospheric pressure chemical ionization, DCI=desporption chemical ioniziation, MS=mass spectrometry, MeOH=methanol, DMA=N,N-dimethylacetamide, EtOH=ethanol, Hex=hexane(s), ESI=electrospray ionization, PMB=paramethoxybenzyl, PE=petroleum ether, DIAD=diisopropyl azodicarboxylate, DMF=N,N-dimethylformamide, DCE=dichloroethane and $Et_3N$=triethylamine.

Example 1

Synthesis of 2-(1-(benzo[d]thiazol-2-ylcarbamoyl)-1,2,3,4-tetrahydroquinolin-7-yl)-5-(4-methoxyphenyl)thiazole-4-carboxylic acid (1)

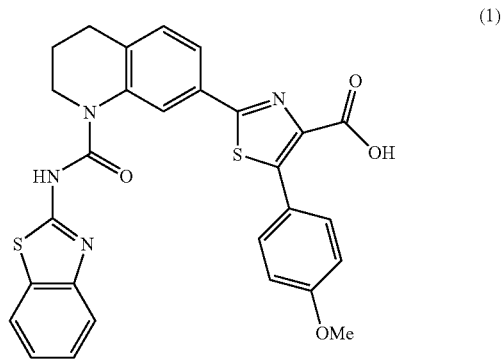

(1)

Step 1: Preparation of 3-(4-bromophenyl)propanoic acid (1A)

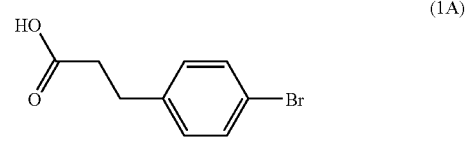

(1A)

2,2-dimethyl-[1,3]dioxane-4,6-dione (120 g, 0.84 mol) and 4-bromo-benzaldehyde (153.4 g, 0.84 mol) were dissolved in 300 mL of TEA and acetic acid. The reaction mixture was refluxed for overnight. At which point, the reaction mixture was diluted with water (4 L) and acidified with 6M HCl (1 L) until pH=2. The precipitated solid was filtered off and washed with diluted HCl, then dissolved in 5% $NaHCO_3$ solution. The aqueous salt solution was washed with ether (4×500 mL), filtered and acidified with diluted HCl. Then filtered and dried under vacuum to provide 100 g (67%) of the desired product 3-(4-bromophenyl)propanoic acid (1A): $^1$H NMR (DMSO-d6, 400 MHz), δ2.5 (m, 2H), 2.8 (m, 2H), 7.2 (m, 2H), 7.5 (m, 2H), 12.2 (s, 1H).

Step 2: Preparation of 6-bromo-2,3-dihydro-1H-inden-1-one (1B)

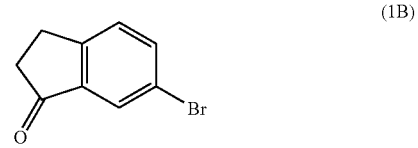

(1B)

3-(4-Bromophenyl)propionic acid (1A) (34.5 g, 0.15 mmol) was dissolved in 40 mL $SOCl_2$ and the mixture were refluxed for 90 minutes. At which point, the solvent was removed under reduced pressure to quantitatively provide 3-(4-bromophenyl)propionyl chloride, which was taken on to the next step immediately.

3-(4-Bromophenyl)propionyl chloride (36.9 g, 0.15 mol) was dissolved in 300 mL DCM and AlCl$_3$ (23.76 g, 0.18 mol) was added slowly. At the completion of the reaction, the mixture was heated to 40° C. and refluxed for 90 minutes and then poured onto ice. Dilute HCl aqueous solution was added and the mixture was extracted with diethyl ether. The organic layer was washed with 2M HCl aqueous solution, water and brine. The product was purified by column chromatography on silica gel eluting with PE:EA (20:1) to obtain a pale brown solid. After removing solvent under vacuum, 23 g (75%) of the desired product 6-bromo-2,3-dihydro-1H-inden-1-one (1B): $^1$H NMR (DMSO-d6, 400 MHz) δ2.6 (m, 2H), 3.1 (m, 2H), 7.55 (m, 1H), 7.1 (m, 1H), 7.85 (m, 1H).

Step 3: Preparation of (Z)-6-bromo-2,3-dihydro-1H-inden-1-one oxime (1C)

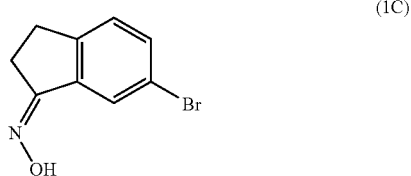

(1C)

To a suspension of hydroxylamine hydrochloride (12.15 g, 142.95 mmol, 1.5 eq) in 200 mL of absolute ethanol was added kalium acetate (14 g, 142.95 mmol, 1.5 eq) followed by 6-bromo-2,3-dihydro-1H-inden-1-one (1B) (20 g, 95.3 mmol). The reaction mixture was heated to reflux for an hour (TLC 6:1 Hexanes/EtOAc shows that the desired compound (1C) is consistent with the starting ketone by TLC). The reaction mixture was then concentrated. Water was added to the residue and the precipitate was collected by filtration. The solids were washed with water and dried to provide 11.5 g (89%) of the desired product (Z)-6-bromo-2,3-dihydro-1H-inden-1-one oxime (1C): $^1$H-NMR (DMSO-d6, 400 MHz): δ2.7 (m, 2H), 2.9 (m, 2H), 7.25 (m, 1H), 7.45 (m, 1H), 7.6 (s, 1H), 11.05 (s, 1H).

Step 4: Preparation of (Z)-6-bromo-2,3-dihydro-1H-inden-1-one O-triisopropylsilyl oxime (1D)

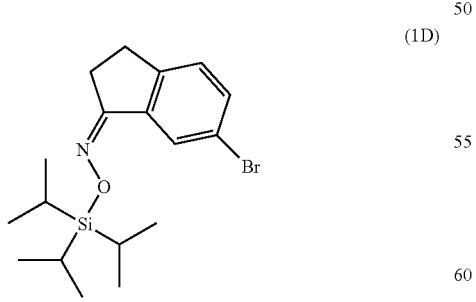

(1D)

A solution of imidazole (11 g, 162 mmol) in 100 mL of dry DCM was added dropwise to a solution of (Z)-6-bromo-2,3-dihydro-1H-inden-1-one oxime (1C) (18.2 g, 81 mmol) and triisopropylsilyl chloride (23.3 g, 121.5 mmol) in solution in 40 mL of dry DCM. The reaction mixture was stirred for 16 hours at rt. It was then filtered to remove the precipitate and the filtrate was concentrated under vacuum. The crude material was purified by column chromatography on silica gel to provide (Z)-6-bromo-2,3-dihydro-1H-inden-1-one O-triisopropylsilyl oxime (10). The crude product was taken on to the next step immediately.

Step 5: Preparation of 7-bromo-1,2,3,4-tetrahydroquinoline (1E)

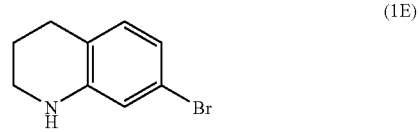

(1E)

BF$_3$.Et$_2$O (49.2 g, 56.7 mL, 346.2 mmol) was added to a solution of (Z)-6-bromo-2,3-dihydro-1H-inden-1-one O-triisopropylsilyl oxime (10) (66 g, 173.1 mmol) in 400 mL of dry Et$_2$O. Me$_2$S.BH$_3$ (31.5 g, 39.48 mL 415.5 mmol) was then added dropwise. The reaction mixture was heated to reflux for 48 hours (followed by TLC 100% petroleum ether until complete disappearance of starting material). The mixture was cooled to 0° C. and dropped to ice/water cautiously, followed by 60 mL of 1:1 solution of water/concentrated HCl. This reaction mixture was heated to 70° C. for 80 minutes and then allowed to cool to rt and stirred for 3.5 hours, washed with Et$_2$O. The pH of the remaining aqueous phase was adjusted to pH>10 with 5M NaOH and extracted three times with Et$_2$O. The combined organic phases were washed with brine and dried over K$_2$CO$_3$. The crude material was purified by column chromatography on silica gel eluting with a gradient of PE:EtOAc (100:1) to provide 11.2 g (31%) of the desired product 7-bromo-1,2,3,4-tetrahydroquinoline (1E): $^1$H-NMR (DMSO-d6, 400 MHz): δ1.7 (m, 2H), 2.6 (m, 2H), 3.15 (m, 2H), 5.9 (s, 1H), 6.45 (m, 1H), 6.55 (m, 1H), 6.75 (m, 1H). LC/MS (APCI): m/z 211.7 (M+H).

Step 6: Preparation of 1-(7-bromo-3,4-dihydroquinolin-1(2H)-yl)ethanone (1F)

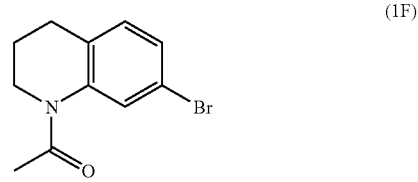

(1F)

To 7-bromo-1,2,3,4-tetrahydroquinoline (1E) (1.0 g, 4.7 mmol) in DCM (30 mL) was added TEA (1.6 mL, 12 mmol), acetic anhydride (1.1 mL, 12 mmol), and pyridine (1.0 mL, 10.0 mmol). The reaction was allowed to stir at rt for 24 hours while monitoring by LCMS. To the reaction mixture was added TEA (1.6 mL, 12 mmol), acetic anhydride (1.1 mL, 12.0 mmol), and pyridine (1.0 mL, 10 mmol). The reaction was allowed to stir at rt for 24 hours. The reaction mixture was concentrated under reduced pressure. The crude residue was purified by column chromatography on silica gel eluting with a gradient of 0 to 100% EtOAc in hexanes to provide 1.09 g (91%) of the desired product 1-(7-bromo-3,4-dihydroquinolin-1(2H)-yl)ethanone (1F): LC/MS (APCI): m/z 255.7 (M+H).

Step 7: Preparation of 1-(7-(4,4,5,5-tetramethyl-1,3, 2-dioxaborolan-2-yl)-3,4-dihydroquinolin-1(2H)-yl) ethanone (1G)

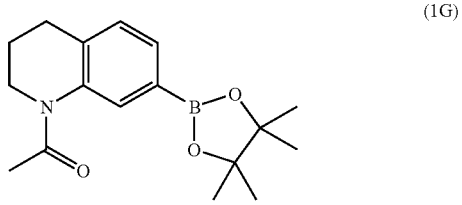

(1G)

To 1-(7-bromo-3,4-dihydroquinolin-1(2H)-yl)ethanone (1F) (6.0 g, 24 mmol), potassium acetate (4.63 g, 47 mmol), bis(triphenylphosphine)palladium(II) chloride (1.66 g, 4.7 mmol), and bispinacol ester boronate (7.79 g, 31 mmol) was added toluene (100 mL). Nitrogen was bubbled through the reaction mixture for 5 minutes. The reaction was heated to 100° C. and stirred overnight. The reaction mixture was cooled to rt, diluted with EtOAc, filtered through Celite, and concentrated under reduced pressure. The crude residue was purified by column chromatography on silica gel eluting with a gradient of 0 to 80% EtOAc in hexanes to provide 7.1 g (100%) of the desired product 1-(7-(4,4,5,5-tetramethyl-1,3, 2-dioxaborolan-2-yl)-3,4-dihydroquinolin-1(2H)-yl)etha-none (1G): LC/MS (APCI): m/z 301.0 (M+H).

Step 8: Preparation of ethyl 2-amino-5-chlorothiazole-4-carboxylate (1H)

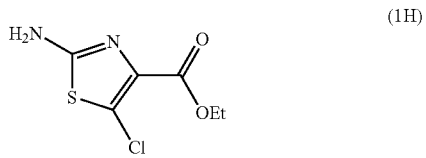

(1H)

Ethyl 2-aminothiazole-4-carboxylate (4.72 g, 27.4 mmol) was combined with N-chlorosuccinimide (4.0 g, 30 mmol) and dissolved in acetonitrile (50 mL). The mixture was heated at mild reflux (>81.5° C.) for 5 hours. Subsequently, the flask was cooled to rt and decolorizing carbon was added to the mixture which was further diluted with EtOAc. The resulting slurry was filtered through a pad of silica and concentrated under reduced pressure to provide 5.57 g (98%) of the desired product ethyl 2-amino-5-chlorothiazole-4-carboxylate (1H). The analytical data on this compound corresponded to that previously reported (see, South, M. S. *J. Heterocyclic Chem.* 1991, 28, 1003.).

Step 9: Preparation of ethyl 2-bromo-5-chlorothiazole-4-carboxylate (1I)

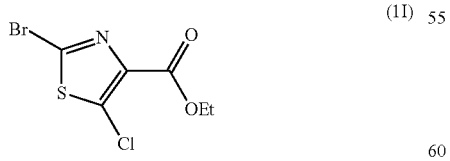

(1I)

Ethyl 2-amino-5-chlorothiazole-4-carboxylate (1H) (14.08 g, 68.1 mmol) was added in portions to a solution of tent-butyl nitrite (12.0 mL, 102 mmol) and copper(II) bromide (22.8 g, 102 mmol) in acetonitrile (351 mL) at rt. The resulting mixture was heated at 80° C. for 2 hours. Subsequently, the mixture was cooled to rt and partitioned between DCM (120 mL), water (75 mL) and concentrated HCl (6 mL). The aqueous layer was extracted with DCM (2×150 mL) and the combined organic extracts were washed sequentially with water and brine and dried over solid MgSO₄. Filtered off the solids and concentrated under reduced pressure. The resulting residue was purified by column chromatography on silica gel eluting with a gradient of 0 to 30% EtOAc in hexanes to provide 8.83 g (47.9%) of the desired product ethyl 2-bromo-5-chlorothiazole-4-carboxylate (H). The analytical report for this compound matched that reported previously (see, Hodgetts, K. J.; Kershaw, M. T. *Org. Lett.* 2002, 4, 1363).

Step 10: Preparation of ethyl 2-(1-acetyl-1,2,3,4-tetrahydroquinolin-7-yl)-5-chlorothiazole-4-carboxylate (1J)

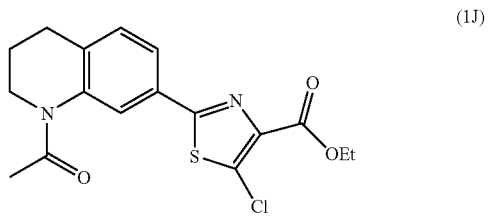

(1J)

To 1-(7-(4,4,5,5-tetramethyl-1,3,2-dioxaborolan-2-yl)-3, 4-dihydroquinolin-1(2H)-yl)ethanone (1G) (1.24 g, 4.12 mmol), ethyl 2-bromo-5-chlorothiazole-4-carboxylate (1I) (1.12 g, 4.12 mmol), lithium chloride (0.52 g, 12.4 mmol), tetrakis(triphenylphosphine)palladium (0.476 g, 0.412 mmol), and cesium carbonate (4.03 g, 12.4 mmol) was added 1,4-dioxane (30 mL) and water (10 mL). Nitrogen was bubbled through the reaction mixture for 5 minutes. The reaction mixture was heated to 100° C. and stirred overnight. The reaction mixture was cooled to rt, diluted with EtOAc, filtered through Celite, and concentrated under reduced pressure. To the crude residue was added EtOAc and water. The layers were separated and the aqueous layer was extracted with EtOAc and the combined organic extracts were washed sequentially with water, brine, dried over MgSO₄, filtered, and concentrated under reduced pressure. The crude residue was purified by column chromatography on silica gel eluting with a gradient of 0 to 80% EtOAc in hexanes to provide 0.505 g (34%) of the desired product ethyl 2-(1-acetyl-1,2,3, 4-tetrahydroquinolin-7-yl)-5-chlorothiazole-4-carboxylate (1J): LC/MS (APCI): m/z 365.3 (M+H).

Step 11: Preparation of ethyl 2-(1-acetyl-1,2,3,4-tetrahydroquinolin-7-yl)-5-(4-methoxyphenyl)thiazole-4-carboxylate (1K)

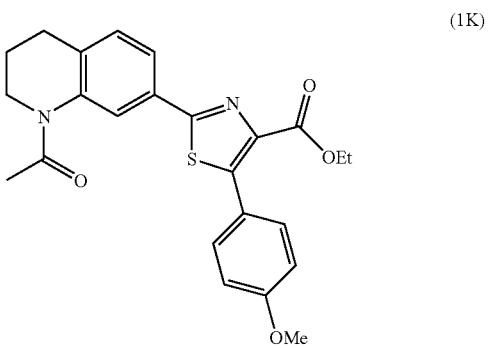

(1K)

To ethyl 2-(1-acetyl-1,2,3,4-tetrahydroquinolin-7-yl)-5-chlorothiazole-4-carboxylate (1J) (0.450 g, 1.23 mmol), 4-methoxyphenylboronic acid (0.281 g, 1.85 mmol), lithium chloride (0.157 g, 3.70 mmol), tetrakis(triphenylphosphine)

palladium (0) (0.142 g, 0.12 mmol), and cesium carbonate (1.2 g, 3.70 mmol) was added 1,4-dioxane (20 mL) and water (10 mL). Nitrogen was bubbled through the reaction mixture for 5 minutes. The reaction mixture was heated to 100° C. and stirred overnight. The reaction mixture was cooled to rt, diluted with EtOAc, filtered through Celite, and concentrated under reduced pressure. The crude residue was purified by column chromatography on silica gel eluting with a gradient of 0 to 80% EtOAc in hexanes to provide 0.483 g (90%) of the desired product ethyl 2-(1-acetyl-1,2,3,4-tetrahydroquinolin-7-yl)-5-(4-methoxyphenyl)thiazole-4-carboxylate (1K): LC/MS (APCI): m/z 436.8 (M+H).

Step 12: Preparation of 5-(4-methoxyphenyl)-2-(1,2,3,4-tetrahydroquinolin-7-yl)thiazole-4-carboxylic acid (1L)

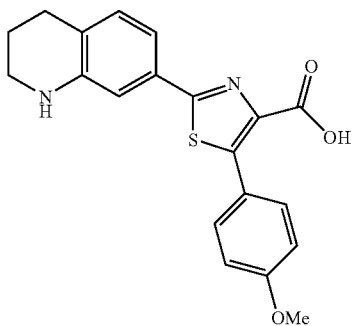

(1L)

To ethyl 2-(1-acetyl-1,2,3,4-tetrahydroquinolin-7-yl)-5-(4-methoxyphenyl)thiazole-4-carboxylate (1K) (0.483 g, 1.11 mmol) and KOH (1.24 g, 22.1 mmol) was added MeOH (10 mL) and water (45 mL). The reaction mixture was allowed to heat to 55° C. and stirred 48 hours. The reaction was monitored by LCMS. To the reaction mixture was added (0.5 g, 8.9 mmol). The reaction mixture was allowed to heat to 55° C. and stirred for 24 hours. The reaction mixture was cooled to rt and concentrated under reduced pressure. To the crude residue was added EtOAc and water. The layers were separated and the aqueous extract was acidified to ~pH6 with 1N HCl and extracted with EtOAc. The combined organic extracts were washed sequentially with water, brine, dried over MgSO$_4$, filtered, and concentrated under reduced pressure to provide 0.350 g (86%) of the desired product 5-(4-methoxyphenyl)-2-(1,2,3,4-tetrahydroquinolin-7-yl)thiazole-4-carboxylic acid (1L): LC/MS (APCI): m/z 367.0 (M+H).

Step 13: Preparation of N-(benzo[d]thiazol-2-yl)-1H-imidazole-1-carboxamide (1M)

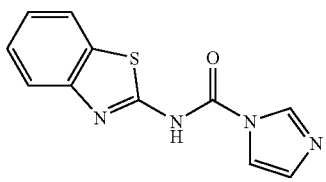

(1M)

To CDI (1.6 g, 10 mmol) in acetonitrile (30 mL) was slowly added 2-aminobenzothiazole (1.0 g, 6.6 mmol) and allowed to stir at rt for 48 hours. The reaction mixture was filtered, washed with acetonitrile, and dried to provide 1.44 g (88%) of the desired product N-(benzo[d]thiazol-2-yl)-1H-imidazole-1-carboxamide (1M): LC/MS (APCI): m/z 245.1 (M+H).

Step 14: Preparation of title compound 2-(1-(benzo[d]thiazol-2-ylcarbamoyl)-1,2,3,4-tetrahydroquinolin-7-yl)-5-(4-methoxyphenyl)thiazole-4-carboxylic acid (1)

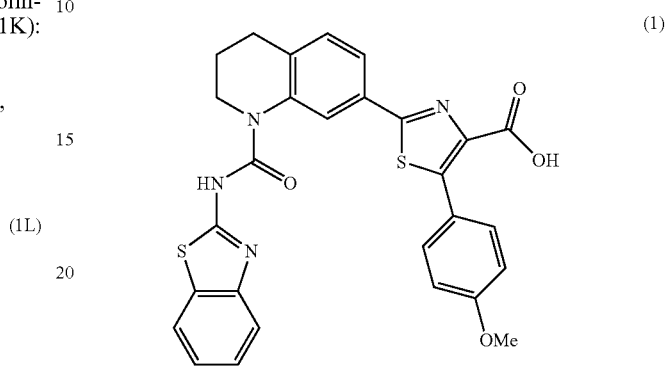

(1)

The title compound 2-(1-(benzo[d]thiazol-2-ylcarbamoyl)-1,2,3,4-tetrahydroquinolin-7-yl)-5-(4-methoxyphenyl)thiazole-4-carboxylic acid (1) was prepared by the following procedure: To 5-(4-methoxyphenyl)-2-(1,2,3,4-tetrahydroquinolin-7-yl)thiazole-4-carboxylic acid (1L) (0.070 g, 0.19 mmol) and N-(benzo[d]thiazol-2-yl)-1H-imidazole-1-carboxamide (1M) (0.051 g, 0.21 mmol) was added DMF (2 mL). The reaction mixture was allowed to stir at rt overnight. To the reaction mixture was added EtOAc and water. The layers were separated and the aqueous layer was extracted with EtOAc. The combined organic extracts were washed sequentially with water, brine, dried over MgSO$_4$, filtered, and concentrated under reduced pressure. The crude residue was purified by reverse phase HPLC to provide 0.028 g (27%) of the desired product 2-(1-(benzo[d]thiazol-2-ylcarbamoyl)-1,2,3,4-tetrahydroquinolin-7-yl)-5-(4-methoxyphenyl)thiazole-4-carboxylic acid (1): LC/MS (APCI): m/z 543.1 (M+H).

Example 2

Synthesis of N-(thiazol-2-yl)-1H-imidazole-1-carboxamide (2)

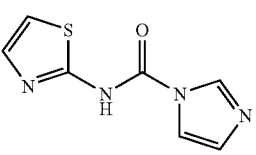

(2)

The title compound N-(thiazol-2-yl)-1H-imidazole-1-carboxamide (2) was prepared by the following procedure: N-(thiazol-2-yl)-1H-imidazole-1-carboxamide (2) was prepared following a similar procedure as that described in example 1, except 2-aminothiazole was used instead of 2-aminobenzothiazole in step 13 of example 1. LC/MS (APCI): m/z 195.0 (M+H).

Example 3

Synthesis of N-(5-methylthiazol-2-yl)-1H-imidazole-1-carboxamide (3)

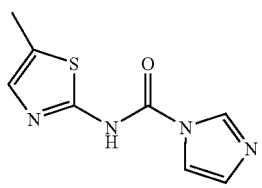
(3)

The title compound N-(5-methylthiazol-2-yl)-1H-imidazole-1-carboxamide (3) was prepared by the following procedure: N-(5-methylthiazol-2-yl)-1H-imidazole-1-carboxamide (3) was prepared following a similar procedure as that described in example 1, except 2-amino-5-methylthiazole was used instead of 2-aminobenzothiazole in step 13 of example 1. LC/MS (APCI): m/z 209.2 (M+H).

Example 4

Synthesis of N-(4-methylthiazol-2-yl)-1H-imidazole-1-carboxamide (4)

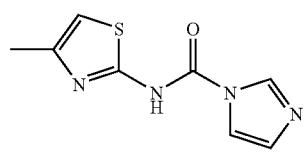
(4)

The title compound N-(4-methylthiazol-2-yl)-1H-imidazole-1-carboxamide (4) was prepared by the following procedure: N-(4-methylthiazol-2-yl)-1H-imidazole-1-carboxamide (4) was prepared following a similar procedure as that described in example 1, except 2-amino-4-methylthiazole was used instead of 2-aminobenzothiazole in step 13 of example 1. LC/MS (APCI): m/z 208.9 (M+H).

Example 5

Synthesis of N-(6-fluorobenzo[d]thiazol-2-yl)-1H-imidazole-1-carboxamide (5)

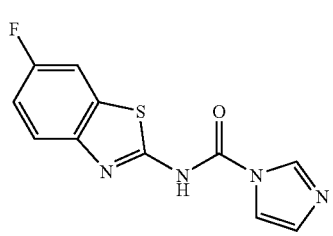
(5)

The title compound N-(6-fluorobenzo[d]thiazol-2-yl)-1H-imidazole-1-carboxamide (5) was prepared by the following procedure: N-(6-fluorobenzo[d]thiazol-2-yl)-1H-imidazole-1-carboxamide (5) was prepared following a similar procedure as that described in example 1, except 2-amino-6-fluorobenzothiazole was used instead of 2-aminobenzothiazole in step 13 of example 1.

Example 6

Synthesis of 2-(1-(benzo[d]thiazol-2-ylcarbamoyl)-1,2,3,4-tetrahydroquinolin-7-yl)thiazole-4-carboxylic acid (6)

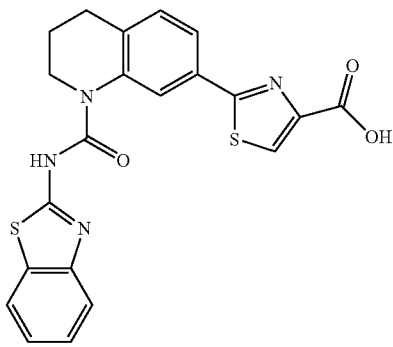
(6)

The title compound 2-(1-(benzo[d]thiazol-2-ylcarbamoyl)-1,2,3,4-tetrahydroquinolin-7-yl)thiazole-4-carboxylic acid (6) was prepared by the following procedure: 2-(1-(Benzo[d]thiazol-2-ylcarbamoyl)-1,2,3,4-tetrahydroquinolin-7-yl)thiazole-4-carboxylic acid (6) was prepared following a similar procedure as that described in example 1, except methyl 2-bromothiazole-4-carboxylate was used instead of ethyl 2-bromo-5-chlorothiazole-4-carboxylate (II) in step 10 of example 1. LC/MS (APCI): m/z 437.51 (M+H).

Example 7

Synthesis of 2-(4-(benzo[d]thiazol-2-ylcarbamoyl)-3,4-dihydro-2H-benzo[b][1,4]oxazin-6-yl)-5-phenylthiazole-4-carboxylic acid (7)

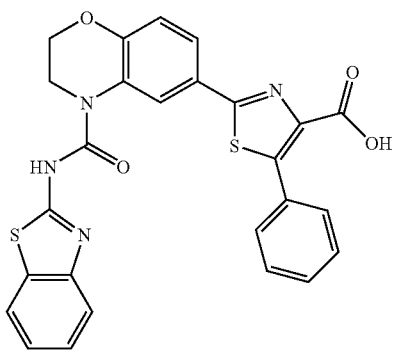
(7)

Step 1: Preparation of 6-bromo-3,4-dihydro-2H-benzo[b][1,4]oxazine (7A)

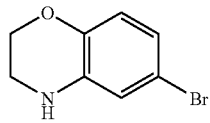

(7A)

2H-benzo[b][1,4]oxazin-3(4H)-one (10.0 g, 43.8 mmol) was dissolved in tetrahydrofuran (180 mL). Lithium tetrahydroaluminate (2.5 g, 66 mmol) was added to the solution at rt. The mixture was then stirred under an atmosphere of nitrogen until TLC indicated that the reaction was completed (ca. 12 h). The reaction mixture was poured into a saturated mixture of Rochelle's salt (Potassium sodium tartarate) and diethyl ether and stirred vigorously until the phases partitioned. Extracted with EtOAc (70 mL) and concentrated under reduced pressure to provide 8.3 g (88%) of the desired product 6-bromo-3,4-dihydro-2H-benzo[b][1,4]oxaxine (7A) which was used without further purification.

Step 2: Preparation of 1-(6-bromo-2H-benzo[b][1,4]oxazin-4(3H)-yl)ethanone (7B)

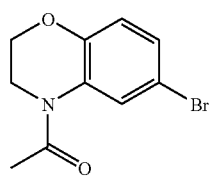

(7B)

6-Bromo-2H-benzo[b][1,4]oxazin-3(4H)-one (7A) (2.5 g, 11.7 mmol) was taken up in DCM (100 mL) and treated with TEA (4.07 mL, 29.2 mmol) followed by Ac$_2$O (2.75 mL, 29.2 mmol). 4-DMAP (0.285 g, 2.34 mmol) was added and the reaction mixture was stirred at rt overnight. The reaction mixture was concentrated under reduced pressure and purified by column chromatography on silica gel eluting with a gradient of 0 to 50% EtOAc in hexanes to provide 2.62 g (87%) of the desired compound 1-(6-bromo-2H-benzo[b][1,4]oxazin-4(3H)-yl)ethanone (7B).

Step 3: Preparation of 1-(6-(4,4,5,5-tetramethyl-1,3,2-dioxaborolan-2-yl)-2H-benzo[b][1,4]oxazin-4(3H)-yl)ethanone (7C)

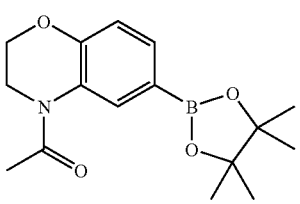

(7C)

1-(6-(4,4,5,5-Tetramethyl-1,3,2-dioxaborolan-2-yl)-2H-benzo[b][1,4]oxazin-4(3H)-yl)ethanone (7C) was prepared following a similar procedure as that described in example 1, except 1-(6-bromo-2H-benzo[b][1,4]oxazin-4(3H)-yl)ethanone (7B) was used instead of 1-(7-bromo-3,4-dihydroquinolin-1(2H)-yl)ethanone (1F) in step 7 of example 1. LC/MS (APCI): m/z 303.1 (M+H).

Step 4: Preparation of ethyl 2-(4-acetyl-3,4-dihydro-2H-benzo[b][1,4]oxazin-6-yl)-5-chlorothiazole-4-carboxylate (7D)

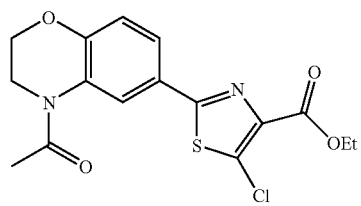

(7D)

Ethyl 2-(4-acetyl-3,4-dihydro-2H-benzo[b][1,4]oxazin-6-yl)-5-chlorothiazole-4-carboxylate (7D) was prepared following a similar procedure as that described in example 1, except 1-(6-(4,4,5,5-tetramethyl-1,3,2-dioxaborolan-2-yl)-2H-benzo[b][1,4]oxazin-4(3H)-yl)ethanone (7C) was used instead of 1-(7-(4,4,5,5-tetramethyl-1,3,2-dioxaborolan-2-yl)-3,4-dihydroquinolin-1(2H)-yl)ethanone (1G) in step 10 of example 1. LC/MS (APCI): m/e 366.1 (M+H).

Step 5: Preparation of ethyl 2-(4-acetyl-3,4-dihydro-2H-benzo[b][1,4]oxazin-6-yl)-5-phenylthiazole-4-carboxylate (7E)

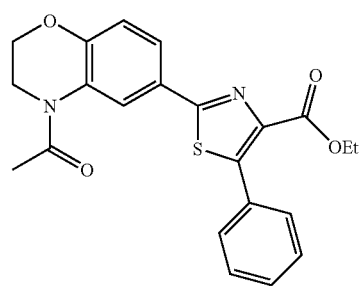

(7E)

Ethyl 2-(4-acetyl-3,4-dihydro-2H-benzo[b][1,4]oxazin-6-yl)-5-phenylthiazole-4-carboxylate (7E) was prepared following a similar procedure as that described in example 1, except ethyl 2-(4-acetyl-3,4-dihydro-2H-benzo[b][1,4]oxazin-6-yl)-5-chlorothiazole-4-carboxylate (7D) was used instead of ethyl 2-(1-acetyl-1,2,3,4-tetrahydroquinolin-7-yl)-5-chlorothiazole-4-carboxylate (1J) and phenylboronic acid was used instead of 4-methoxyphenylboronic acid in step 11 of example 1. LC/MS (APCI): m/z 409.1 (M+H).

Step 6: Preparation of 2-(3,4-dihydro-2H-benzo[b]
[1,4]oxazin-6-yl)-5-phenylthiazole-4-carboxylic acid
(7F)

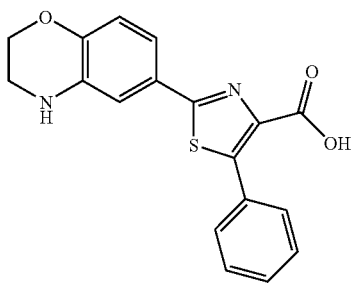

(7F)

2-(3,4-Dihydro-2H-benzo[b][1,4]oxazin-6-yl)-5-phenylthiazole-4-carboxylic acid (7F) was prepared following a similar procedure as that described in example 1, except ethyl 2-(4-acetyl-3,4-dihydro-2H-benzo[b][1,4]oxazin-6-yl)-5-phenylthiazole-4-carboxylate (7E) was used instead of ethyl 2-(1-acetyl-1,2,3,4-tetrahydroquinolin-7-yl)-5-(4-methoxyphenyl)thiazole-4-carboxylate (1K) in step 12 of example 1. LC/MS (APCI): m/z 339.0 (M+H).

Step 7: Preparation of title compound 2-(4-(benzo[d]
thiazol-2-ylcarbamoyl)-3,4-dihydro-2H-benzo[b][1,
4]oxazin-6-yl)-5-phenylthiazole-4-carboxylic acid
(7)

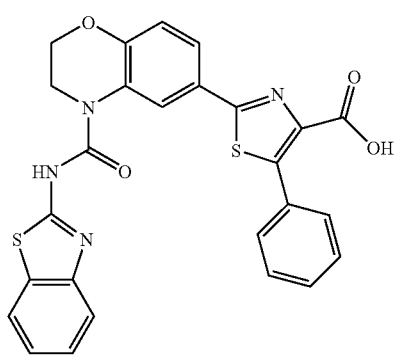

(7)

The title compound 2-(4-(benzo[d]thiazol-2-ylcarbamoyl)-3,4-dihydro-2H-benzo[b][1,4]oxazin-6-yl)-5-phenylthiazole-4-carboxylic acid (7) was prepared by the following procedure: 2-(4-(Benzo[d]thiazol-2-ylcarbamoyl)-3,4-dihydro-2H-benzo[b][1,4]oxazin-6-yl)-5-phenylthiazole-4-carboxylic acid (7) was prepared following a similar procedure as that described in example 1, except 2-(3,4-dihydro-2H-benzo[b][1,4]oxazin-6-yl)-5-phenylthiazole-4-carboxylic acid (7F) was used instead of 5-(4-methoxyphenyl)-2-(1,2,3,4-tetrahydroquinolin-7-yl)thiazole-4-carboxylic acid (1L) in step 14 of example 1. LC/MS (APCI): m/z 515.1 (M+H).

Example 8

Synthesis of 2-(4-(benzo[d]thiazol-2-ylcarbamoyl)-
3,4-dihydro-2H-benzo[b][1,4]oxazin-6-yl)-5-(4-
methoxy phenyl)thiazole-4-carboxylic acid (8)

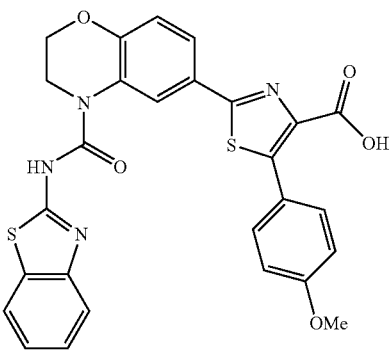

(8)

The title compound 2-(4-(benzo[d]thiazol-2-ylcarbamoyl)-3,4-dihydro-2H-benzo[b][1,4]oxazin-6-yl)-5-(4-methoxyphenyl)thiazole-4-carboxylic acid (8) was prepared by the following procedure: 2-(4-(Benzo[d]thiazol-2-ylcarbamoyl)-3,4-dihydro-2H-benzo[b][1,4]oxazin-6-yl)-5-(4-methoxyphenyl)thiazole-4-carboxylic acid (8) was prepared following a similar procedure as that described in example 7, except 4-methoxyphenylboronic acid was used instead of phenylboronic acid in step 5 of example 7. LC/MS (APCI): m/z 545.1 (M+H).

Example 9

Synthesis of 2-(4-(benzo[d]thiazol-2-ylcarbamoyl)-
3,4-dihydro-2H-benzo[b][1,4]oxazin-6-yl)-5-(3-
methoxyphenyl)thiazole-4-carboxylic acid (9)

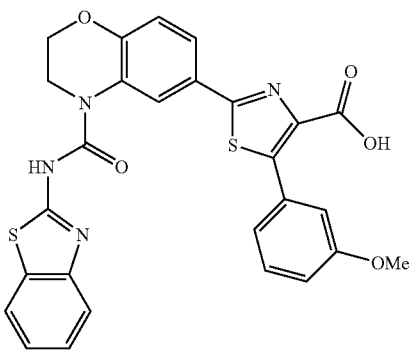

(8)

The title compound 2-(4-(benzo[d]thiazol-2-ylcarbamoyl)-3,4-dihydro-2H-benzo[b][1,4]oxazin-6-yl)-5-(3-methoxyphenyl)thiazole-4-carboxylic acid (9) was prepared by the following procedure: 2-(4-(Benzo[d]thiazol-2-ylcarbamoyl)-3,4-dihydro-2H-benzo[b][1,4]oxazin-6-yl)-5-(3-methoxyphenyl)thiazole-4-carboxylic acid (9) was prepared following a similar procedure as that described in example 7, except 3-methoxyphenylboronic acid was used instead of phenylboronic acid in step 5 of example 7. LC/MS (APCI): m/z 545.1 (M+H).

Example 10

Synthesis of 2-(4-(benzo[d]thiazol-2-ylcarbamoyl)-3,4-dihydro-2H-benzo[b][1,4]oxazin-6-yl)-5-(4-fluorophenyl)thiazole-4-carboxylic acid (10)

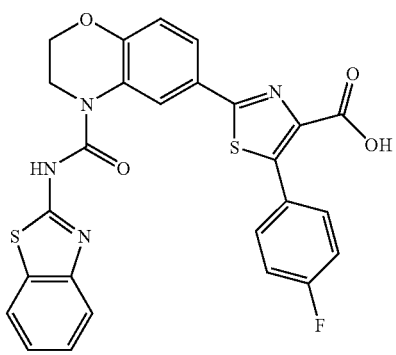

(10)

The title compound 2-(4-(benzo[d]thiazol-2-ylcarbamoyl)-3,4-dihydro-2H-benzo[b][1,4]oxazin-6-yl)-5-(4-fluorophenyl)thiazole-4-carboxylic acid (10) was prepared by the following procedure: 2-(4-(Benzo[d]thiazol-2-ylcarbamoyl)-3,4-dihydro-2H-benzo[b][1,4]oxazin-6-yl)-5-(4-fluorophenyl)thiazole-4-carboxylic acid (10) was prepared following a similar procedure as that described in example 7, except 4-fluorophenylboronic acid was used instead of phenylboronic acid in step 5 of example 7. LC/MS (APCI): m/z 533.1 (M+H).

Example 11

Synthesis of 2-(4-(benzo[d]thiazol-2-ylcarbamoyl)-3,4-dihydro-2H-benzo[b][1,4]oxazin-6-yl)-5-(3-fluorophenyl)thiazole-4-carboxylic acid (11)

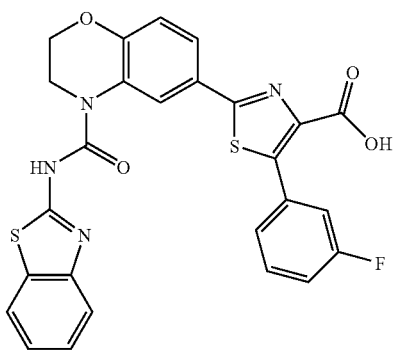

(11)

The title compound 2-(4-(benzo[d]thiazol-2-ylcarbamoyl)-3,4-dihydro-2H-benzo[b][1,4]oxazin-6-yl)-5-(3-fluorophenyl)thiazole-4-carboxylic acid (11) was prepared following procedure: 2-(4-(Benzo[d]thiazol-2-ylcarbamoyl)-3,4-dihydro-2H-benzo[b][1,4]oxazin-6-yl)-5-(3-fluorophenyl)thiazole-4-carboxylic acid (11) was prepared following a similar procedure as that described in example 7, except 3-fluorophenylboronic acid was used instead of phenylboronic acid in step 5 of example 7. LC/MS (APCI): m/z 533.1 (M+H).

Example 12

Synthesis of 2-(1-(benzo[d]thiazol-2-ylcarbamoyl)-1,2,3,4-tetrahydroquinolin-7-yl)-5-(4-isopropoxyphenyl)thiazole-4-carboxylic acid (12)

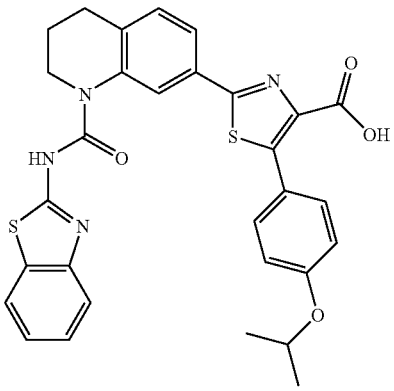

(12)

The title compound 2-(1-(benzo[d]thiazol-2-ylcarbamoyl)-1,2,3,4-tetrahydroquinolin-7-yl)-5-(4-isopropoxyphenyl)thiazole-4-carboxylic acid (12) was prepared by the following procedure: 2-(1-(benzo[d]thiazol-2-ylcarbamoyl)-1,2,3,4-tetrahydroquinolin-7-yl)-5-(4-isopropoxyphenyl)thiazole-4-carboxylic acid (12) was prepared following a similar procedure as that described in example 1, except 4-isopropoxyphenylboronic acid was used instead of 4-methoxyphenylboronic acid in step 11 of example 1. LC/MS (APCI): m/z 571.2 (M+H).

Example 13

Synthesis of 2-(1-(benzo[d]thiazol-2-ylcarbamoyl)-1,2,3,4-tetrahydroquinolin-7-yl)-5-(biphenyl-4-yl)thiazole-4-carboxylic acid (13)

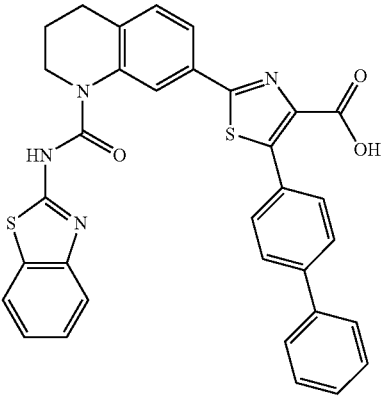

(13)

The title compound 2-(1-(benzo[d]thiazol-2-ylcarbamoyl)-1,2,3,4-tetrahydroquinolin-7-yl)-5-(biphenyl-4-yl)thiazole-4-carboxylic acid (13) was prepared by the following procedure: 2-(1-(Benzo[d]thiazol-2-ylcarbamoyl)-1,2,3,4-tetrahydroquinolin-7-yl)-5-(biphenyl-4-yl)thiazole-4-carboxylic acid (13) was prepared following a similar procedure as that described in example 1, except 4-biphenylboronic acid was used instead of 4-methoxyphenylboronic acid in step 11 of example 1. LC/MS (APCI): m/z 589.1 (M+H).

Example 14

Synthesis of (E)-2-(1-(benzo[d]thiazol-2-ylcarbamoyl)-1,2,3,4-tetrahydroquinolin-7-yl)-5-styrylthiazole-4-carboxylic acid (14)

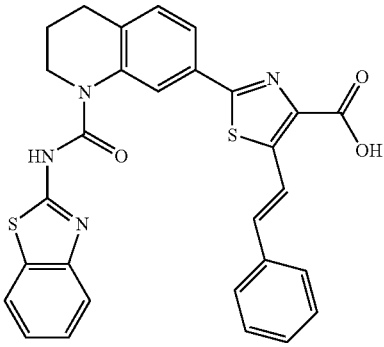

(14)

The title compound (E)-2-(1-(benzo[d]thiazol-2-ylcarbamoyl)-1,2,3,4-tetrahydroquinolin-7-yl)-5-styrylthiazole-4-carboxylic acid (14) was prepared by the following procedure: (E)-2-(1-(benzo[d]thiazol-2-ylcarbamoyl)-1,2,3,4-tetrahydroquinolin-7-yl)-5-styrylthiazole-4-carboxylic acid (14) was prepared following a similar procedure as that described in example 1, except E-phenethylboronic acid was used instead of 4-methoxyphenylboronic acid in step 11 of example 1. LC/MS (APCI): m/z 539.1 (M+H).

Example 15

Synthesis of 5-(4-methoxyphenyl)-2-(1-(thiazol-2-ylcarbamoyl)-1,2,3,4-tetrahydroquinolin-7-yl)thiazole-4-carboxylic acid (15)

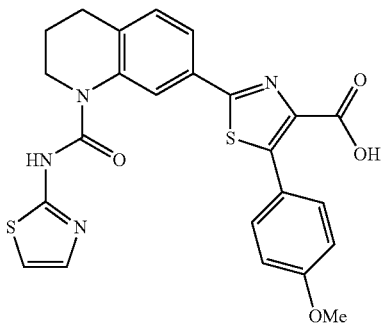

(15)

The title compound 5-(4-methoxyphenyl)-2-(1-(thiazol-2-ylcarbamoyl)-1,2,3,4-tetrahydroquinolin-7-yl)thiazole-4-carboxylic acid (15) was prepared by the following procedure: 5-(4-Methoxyphenyl)-2-(1-(thiazol-2-ylcarbamoyl)-1,2,3,4-tetrahydroquinolin-7-yl)thiazole-4-carboxylic acid (15) was prepared following a similar procedure as that described in example 1, except N-(thiazol-2-yl)-1H-imidazole-1-carboxamide (2) was used instead of N-(benzo[d]thiazol-2-yl)-1H-imidazole-1-carboxamide (1M) in step 14 of example 1. LC/MS (APCI): m/z 493.1 (M+H).

Example 16

Synthesis of 5-(4-methoxyphenyl)-2-(1-(5-methylthiazol-2-ylcarbamoyl)-1,2,3,4-tetrahydroquinolin-7-yl)thiazole-4-carboxylic acid (16)

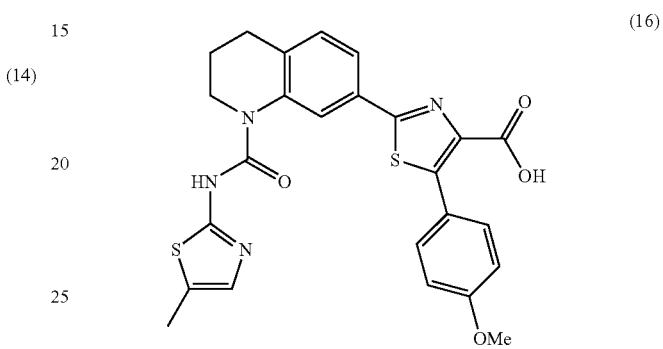

(16)

The title compound 5-(4-methoxyphenyl)-2-(1-(5-methylthiazol-2-ylcarbamoyl)-1,2,3,4-tetrahydroquinolin-7-yl)thiazole-4-carboxylic acid (16) was prepared by the following procedure: 5-(4-Methoxyphenyl)-2-(1-(5-methylthiazol-2-ylcarbamoyl)-1,2,3,4-tetrahydroquinolin-7-yl)thiazole-4-carboxylic acid (16) was prepared following a similar procedure as that described in example 1, except N-(5-methylthiazol-2-yl)-1H-imidazole-1-carboxamide (3) was used instead of N-(benzo[d]thiazol-2-yl)-1H-imidazole-1-carboxamide (1M) in step 14 of example 1. LC/MS (APCI): m/z 507.1 (M+H).

Example 17

Synthesis of 5-(4-methoxyphenyl)-2-(1-(4-methylthiazol-2-ylcarbamoyl)-1,2,3,4-tetrahydroquinolin-7-yl)thiazole-4-carboxylic acid (17)

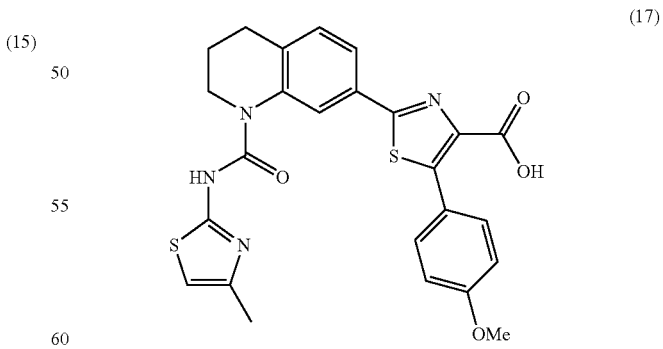

(17)

The title compound 5-(4-methoxyphenyl)-2-(1-(4-methylthiazol-2-ylcarbamoyl)-1,2,3,4-tetrahydroquinolin-7-yl)thiazole-4-carboxylic acid (17) was prepared by the following procedure: 5-(4-Methoxyphenyl)-2-(1-(4-methylthiazol-2-ylcarbamoyl)-1,2,3,4-tetrahydroquinolin-7-yl)thiazole-4-carboxylic acid (17) was prepared following a similar procedure as that described in example 1, except N-(4-methylthiazol-2-yl)-1H-imidazole-1-carboxamide (4) was used instead of N-(benzo[d]thiazol-2-yl)-1H-imidazole-1-carboxamide (1M) in step 14 of example 1. LC/MS (APCI): m/z 507.1 (M+H).

Example 18

Synthesis of 2-(1-(6-fluorobenzo[d]thiazol-2-ylcarbamoyl)-1,2,3,4-tetrahydroquinolin-7-yl)-5-(4-methoxyphenyl)thiazole-4-carboxylic acid (18)

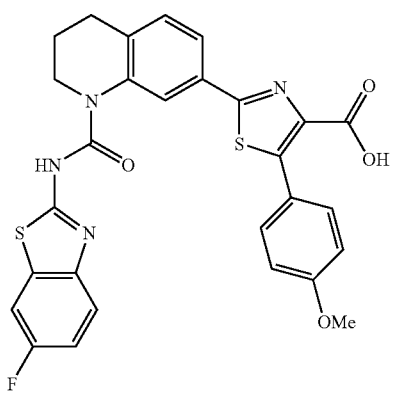

(18)

The title compound 2-(1-(6-fluorobenzo[d]thiazol-2-ylcarbamoyl)-1,2,3,4-tetrahydroquinolin-7-yl)-5-(4-methoxyphenyl)thiazole-4-carboxylic acid (18) was prepared by the following procedure: 2-(1-(6-Fluorobenzo[d]thiazol-2-ylcarbamoyl)-1,2,3,4-tetrahydroquinolin-7-yl)-5-(4-methoxyphenyl)thiazole-4-carboxylic acid (18) was prepared following a similar procedure as that described in example 1, except N-(6-fluorobenzo[d]thiazol-2-yl)-1H-imidazole-1-carboxamide (5) was used instead of N-(benzo[d]thiazol-2-yl)-1H-imidazole-1-carboxamide (1M) in step 14 of example 1. LC/MS (APCI): m/z 561.1 (M+H).

Example 19

Synthesis of 4-nitrophenyl benzo[d]thiazol-2-ylcarbamate (19)

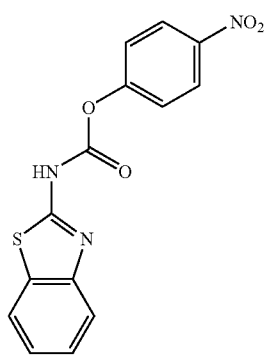

(19)

The title compound 4-nitrophenyl benzo[d]thiazol-2-ylcarbamate (19) was prepared by the following procedure: To 2-aminobenzothiazole (5.0 g, 30 mmol) was added DCM (36 mL) and the reaction mixture was stirred at 0° C. for 15 minutes. Then, p-nitrophenyl chloroformate (6.64 g, 33 mmol) in DCM (60 mL) was added, followed by pyridine (2.66 mL, 33 mmol) in DCM (36 mL). The reaction mixture was stirred and allowed to warm to rt overnight. The reaction mixture was filtered, washed with DCM, and dried to provide 9.22 g (90%) of the desired product 4-nitrophenyl benzo[d]thiazol-2-ylcarbamate (19): LC/MS (APCI): m/z 316.0 (M+H).

Example 20

Synthesis of 2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylic acid (20)

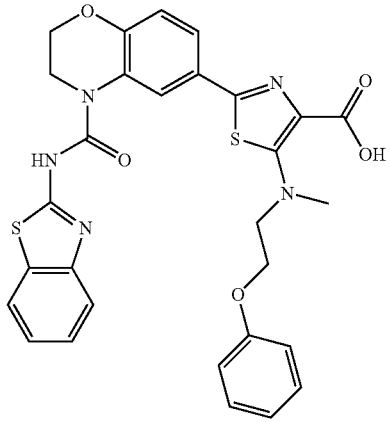

(20)

Step 1: Preparation of ethyl 2-(4-acetyl-3,4-dihydro-2H-benzo[b][1,4]oxazin-6-yl)-5-(methyl(2-phenoxyethyl)amino)thiazole-4-carboxylate (20A)

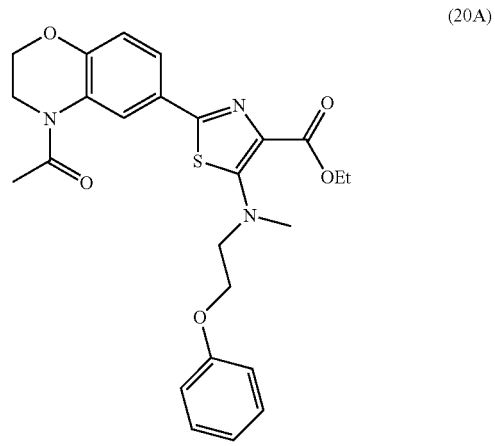

(20A)

To ethyl 2-(4-acetyl-3,4-dihydro-2H-benzo[b][1,4]oxazin-6-yl)-5-chlorothiazole-4-carboxylate (7D) (0.15 g, 0.41 mmol) and methyl-(2-phenoxy-ethyl)-amine (1.24 g, 8.1 mmol) was added DMF (10 mL). The reaction mixture was allowed to heat to 70° C. for 48 hours. The reaction mixture was cooled to rt and concentrated under reduced pressure. The crude residue was purified by column chromatography on silica gel eluting with a gradient of 0 to 80% EtOAc in hexanes to provide 0.102 g (52%) of the desired product ethyl 2-(4-acetyl-3,4-dihydro-2H-benzo[b][1,4]oxazin-6-yl)-5-(methyl(2-phenoxyethyl)amino)thiazole-4-carboxylate (20A): LC/MS (APCI): m/z 482.1 (M+H).

Step 2: Preparation of ethyl 2-(3,4-dihydro-2H-benzo[b][1,4]oxazin-6-yl)-5-(methyl(2-phenoxyethyl)amino)thiazole-4-carboxylate (20B)

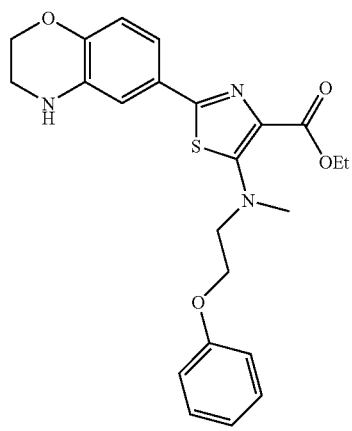

(20B)

To ethyl 2-(4-acetyl-3,4-dihydro-2H-benzo[b][1,4]oxazin-6-yl)-5-(methyl(2-phenoxyethyl)amino)thiazole-4-carboxylate (20A) (0.102 g, 0.212 mmol) was added ethanol (4 mL) and 6N HCl (6 mL). The reaction mixture was allowed to heat to 60° C. and stir for 8 hours. The reaction was allowed to cool to rt. To the reaction mixture was added EtOAc and saturated sodium bicarbonate. The layers were separated and extracted with EtOAc and the combined organic extracts were washed sequentially with water, brine, dried over MgSO$_4$, filtered, and concentrated under reduced pressure to provide 0.079 g (85%) of the desired product ethyl 2-(3,4-dihydro-2H-benzo[b][1,4]oxazin-6-yl)-5-(methyl(2-phenoxyethyl)amino)thiazole-4-carboxylate (20B): LC/MS (APCI): m/z 440.1 (M+H).

Step 3: Preparation of ethyl 2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylate (20C)

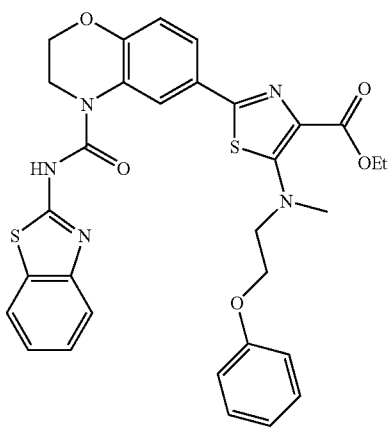

(20C)

To ethyl 2-(3,4-dihydro-2H-benzo[b][1,4]oxazin-6-yl)-5-(methyl(2-phenoxyethyl)amino)thiazole-4-carboxylate (20B) (0.150 g, 0.34 mmol) and 4-nitrophenyl benzo[d]thiazol-2-ylcarbamate (19) (0.349 g, 0.11 mmol) was added acetonitrile (10 mL). The reaction mixture was allowed to heat to 85° C. and stirred for 8 hours. Then the reaction mixture was allowed to heat at 70° C. and stirred overnight. The reaction mixture was allowed to cool to rt and concentrated under reduced pressure. To the concentrate was added EtOAc and water and filtered. The layers of the filtrate were separated and extracted with EtOAc. The combined organic extracts were washed sequentially with water, brine, dried over MgSO$_4$, filtered, and concentrated under reduced pressure to provide 0.21 g (quantitative) ethyl 2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylate (20C): LC/MS (APCI): m/z 616.3 (M+H).

Step 4: Preparation of title compound 2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylic acid (20)

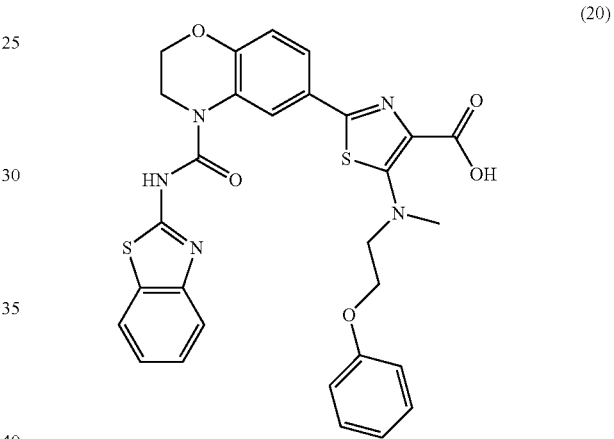

(20)

The title compound 2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylic acid (20) was prepared by the following procedure: To ethyl 2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylate (20C) (0.210 g, 0.34 mmol) and KOH (0.1 g, 1.8 mmol) was added MeOH (2 mL) and water (5 mL). The reaction mixture was allowed to heat to 55° C. and stirred 24 hours. The reaction was monitored by LCMS. To the reaction mixture was added (0.1 g, 1.8 mmol). The reaction mixture was allowed to heat to 55° C. and stirred for 24 hours. The reaction mixture was cooled to rt and concentrated under reduced pressure. To the crude residue was added EtOAc and water. The layers were separated and extracted with EtOAc and the combined organic extracts were washed sequentially with water, brine, dried over MgSO$_4$, filtered, and concentrated under reduced pressure. The crude residue was purified by reverse phase HPLC to provide 0.015 g (8%) of the desired product 2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylic acid (20): LC/MS (APCI): m/z 588.1 (M+H).

Example 21

Synthesis of 2-(1-(benzo[d]thiazol-2-ylcarbamoyl)-1,2,3,4-tetrahydroquinolin-7-yl)-5-phenoxythiazole-4-carboxylic acid (21)

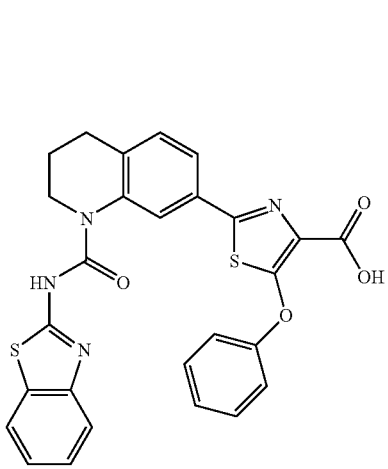

(21)

Step 1: Preparation of ethyl 2-(1-acetyl-1,2,3,4-tetrahydroquinolin-7-yl)-5-phenoxythiazole-4-carboxylate (21A)

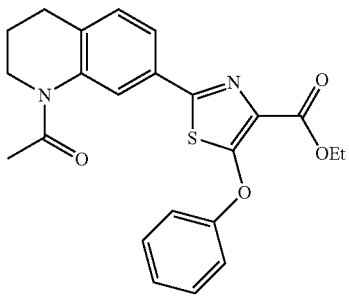

(21A)

To ethyl 2-(1-acetyl-1,2,3,4-tetrahydroquinolin-7-yl)-5-chlorothiazole-4-carboxylate (1J) (0.250 g, 0.69 mmol), phenol (0.129 g, 1.4 mmol), and KOH (0.284 g, 2.1 mmol) was added DMF (10 mL). The reaction mixture was allowed to heat to 70° C. for 72 hours. The reaction mixture was cooled to rt and diluted with EtOAc and water. The layers were separated and the aqueous layer was extracted with EtOAc. The combined organic extracts were washed sequentially with water, brine, dried over MgSO$_4$, filtered, and concentrated under reduced pressure. The crude residue was purified by column chromatography on silica gel eluting with a gradient of 0 to 80% EtOAc in hexanes to provide 0.208 g (72%) ethyl 2-(1-acetyl-1,2,3,4-tetrahydroquinolin-7-yl)-5-phenoxythiazole-4-carboxylate (21A): LC/MS (APCI): m/z 424.0 (M+H).

Step 2: Preparation of title compound 2-(1-(benzo[d]thiazol-2-ylcarbamoyl)-1,2,3,4-tetrahydroquinolin-7-yl)-5-phenoxythiazole-4-carboxylic acid (21)

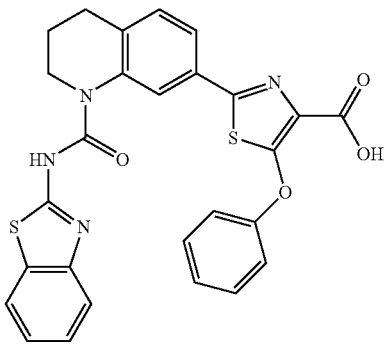

(21)

The title compound 2-(1-(benzo[d]thiazol-2-ylcarbamoyl)-1,2,3,4-tetrahydroquinolin-7-yl)-5-phenoxythiazole-4-carboxylic acid (21) was prepared by the following procedure: 2-(1-(Benzo[d]thiazol-2-ylcarbamoyl)-1,2,3,4-tetrahydroquinolin-7-yl)-5-phenoxythiazole-4-carboxylic acid (21) was prepared following a similar procedure as that described in step 12 and step 14 of example 1. LC/MS (APCI): m/z 529.1 (M+H).

Example 22

Synthesis of 4-(1H-pyrazolo[3,4-d]pyrimidin-1-yl)phenol (22)

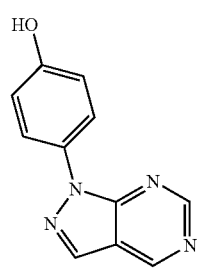

(22)

Step 1: Preparation of 5-amino-1-(4-bromophenyl)-1H-pyrazole-4-carboxylic acid (22A)

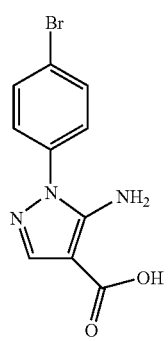

(22A)

A mixture of (Z)-ethyl 2-cyano-3-ethoxyacrylate (2.099 g, 12.41 mmol), 4-bromophenylhydrazine hydrochloride (2.76 g, 12.41 mmol) and Na$_2$CO$_3$ (0.789 g, 7.44 mmol) in ethanol (30 mL) was refluxed for 5 hours and slightly concentrated under reduced pressure. The precipitate was collected by filtration, rinsed with ether, and dried to provide the ester. The ester was dissolved in THF (5 mL) and MeOH (25 mL). To the reaction mixture was added 10% NaOH (154 mL). The resulting mixture was stirred at 50° C. overnight and concentrated. A small amount of water was added and the resulting solution was neutralized with HCl to pH 6. The white precipitate was collected, washed with water, and dried to provide the desired compound 5-amino-1-(4-bromophenyl)-1H-pyrazole-4-carboxylic acid (22A): $^1$H NMR (400 MHz, DMSO-D$_6$) ppm 12.09 (1H, s), 7.72 (2H, d), 7.52 (2H, d), 6.35 (2H, s).

Step 2: Preparation of
1-(4-bromophenyl)-1H-pyrazolo[3,4-d]pyrimidine (22B)

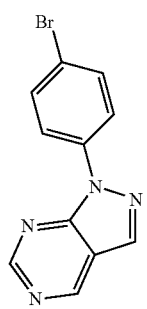

(22B)

To a solution of 1,3,5-triazine (0.575 g, 7.09 mmol) and 5-amino-1-(4-bromophenyl)-1H-pyrazole-4-carboxylic acid (22A) (2 g, 7.09 mmol) in DMSO (30 mL) was added boron trifluoride etherate (1.08 mL, 8.51 mmol). The resulting mixture was heated at 120° C. for 20 hours, cooled, diluted with EtOAc and washed with 1% NaOH and brine. The organic layer was dried over Na$_2$SO$_4$ and concentrated under reduced pressure. The residue was triturated with small amount of EtOAc and the precipitate was collected to provide the desired product 1-(4-bromophenyl)-1H-pyrazolo[3,4-d]pyrimidine (22B): $^1$H NMR (400 MHz, DMSO-D$_6$) δ ppm 9.47 (1H, s), 9.16 (1H, s), 8.68 (1H, s), 8.22 (2H, d), 7.80 (2H, d).

Step 3: Preparation of 1-(4-(4,4,5,5-tetramethyl-1,3,2-dioxaborolan-2-yl)phenyl)-1H-pyrazolo[3,4-d]-pyrimidine (22C)

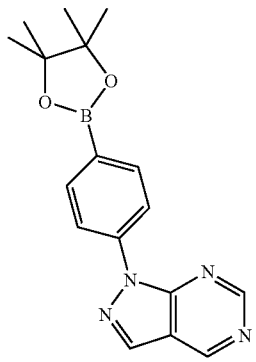

(22C)

A mixture of 1-(4-bromophenyl)-1H-pyrazolo[3,4-d]-pyrimidine (22B) (500 mg, 1.817 mmol), 4,4,4',4',5,5,5',5'-octamethyl-2,2'-bi(1,3,2-dioxaborolane) (508 mg, 1.999 mmol), PdCl$_2$(dppf)-CH$_2$Cl$_2$ adduct (74.2 mg, 0.091 mmol) and potassium acetate (535 mg, 5.45 mmol) in DMSO (15 ml) was purged with nitrogen and then heated at 80° C. overnight. The reaction was diluted with EtOAc and washed with brine. The organic layer was dried over Na$_2$SO$_4$ and concentrated under reduced pressure. The residue was purified column chromatography on silica gel eluting with a gradient of 0 to 20% EtOAc in DCM to provide the desired compound 1-(4,4,5,5-tetramethyl-1,3,2-dioxaborolan-2-yl)phenyl)-1H-pyrazolo[3,4-d]-pyrimidine (22C). $^1$H NMR (400 MHz, DMSO-D$_6$) δ ppm 9.49 (1H, s), 9.20 (1H, s), 8.70 (1H, s), 8.33 (2H, d), 7.90 (2H, d), 1.33 (12H, s).

Step 4: Preparation of title compound
4-(1H-pyrazolo[3,4-d]pyrimidin-1-yl)phenol (22)

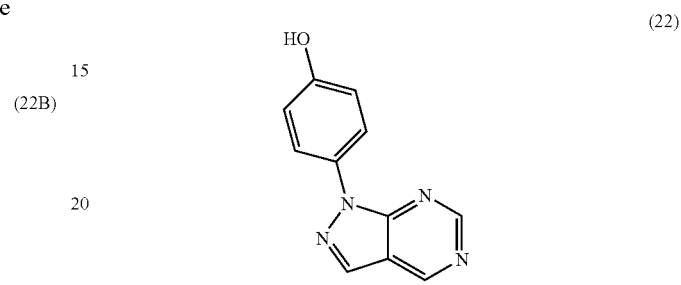

(22)

The title compound 4-(1H-pyrazolo[3,4-d]-pyrimidin-1-yl)phenol (22) was prepared by the following procedure: To a solution of 1-(4-(4,4,5,5-tetramethyl-1,3,2-dioxaborolan-2-yl)phenyl)-1H-pyrazolo[3,4-d]pyrimidine (22C) (100 mg, 0.31 mmol) in THF (5 mL) was added NaOH (0.248 mL, 0.621 mmol) and hydrogen peroxide (0.048 mL, 0.466 mmol). The mixture was stirred at 0° C. for 30 minutes The reaction mixture was concentrated and the residue was dissolved water (8 mL). The aqueous solution was acidified with diluted HCl. The white precipitate was collected, washed with water and dried to provide the title compound 4-(1H-pyrazolo[3,4-d]pyrimidin-1-yl)phenol (22): $^1$H NMR (400 MHz, DMSO-D$_6$) δ ppm 9.75 (1H, s), 9.44 (1H, s), 9.09 (1H, s), 8.59 (1H, s), 7.82-7.99 (2H, m), 6.83-7.05 (2H, m).

Example 23

Synthesis of 5-(3-(4-(1H-pyrazolo[3,4-d]pyrimidin-1-yl)phenoxy)propyl)-2-(1-(benzo[d]thiazol-2-ylcarbamoyl)-1,2,3,4-tetrahydroquinolin-7-yl)thiazole-4-carboxylic acid (23)

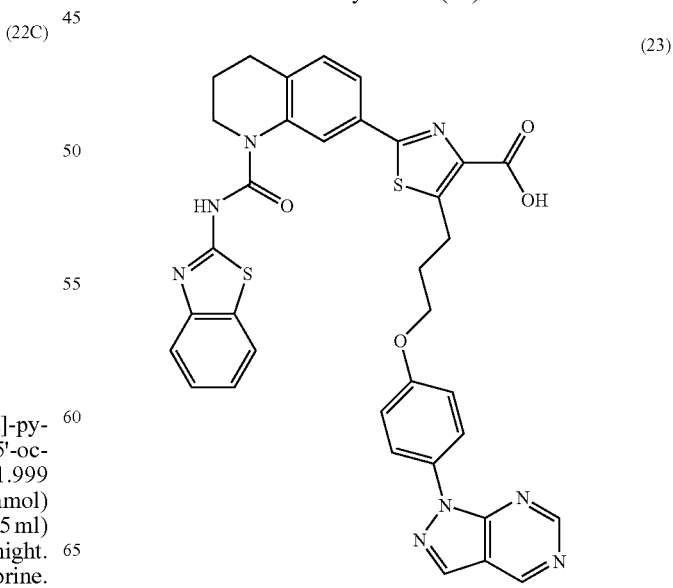

(23)

Step 1: Preparation of ethyl 3-bromo-6-chloro-2-oxohexanoate (23A)

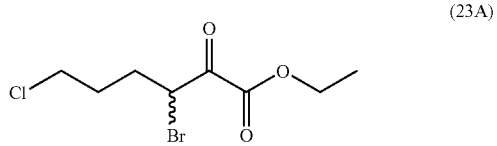

Ethyl 6-chloro-2-oxohexanoate (2.9 g, 15 mmol) in carbon tetrachloride (30 mL) was treated with bromine (0.85 mL, 16.5 mmol) and stirred at ambient temperature for 1 hour. The reaction mixture was diluted with EtOAc, washed with Na$_2$S$_2$O$_3$ solution, water and brine, dried (MgSO$_4$), filtered and concentrated under reduced pressure. The concentrate was purified by column chromatography on silica gel eluting with a gradient of 0 to 10% EtOAc in hexanes to provide (95%) of the desired product ethyl 3-bromo-6-chloro-2-oxo-hexanoate (23A) as a pale yellow oil: $^1$H NMR (300 MHz, DMSO-d$_6$) δ ppm 5.25 (1H, dd), 4.29 (2H, q), 3.71 (2H, t), 2.16 (1H, m), 1.91 (1H, m), 1.29 (3H, t).

Step 2: Preparation of ethyl 2-amino-5-(3-chloropropyl)thiazole-4-carboxylate (23B)

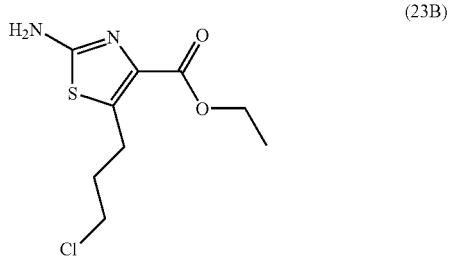

To a solution of ethyl 3-bromo-6-chloro-2-oxohexanoate (23A) (0.845 g, 3.11 mmol) in acetone (6 mL) was added thiourea (0.284 g, 3.73 mmol) and refluxed overnight. The reaction mixture was concentrated under reduced pressure. EtOAc and hexanes in a ratio of 1:9 was added and stirred for 1 hour. Added acetone to dissolve material and concentrated under reduced pressure to give 0.718 g (93%) of the desired product ethyl 2-amino-5-(3-chloropropyl)thiazole-4-carboxylate (23B): LC/MS (APCI): m/z 249.5 (M+H).

Step 3: Preparation of ethyl 2-bromo-5-(3-chloropropyl)thiazole-4-carboxylate (23C)

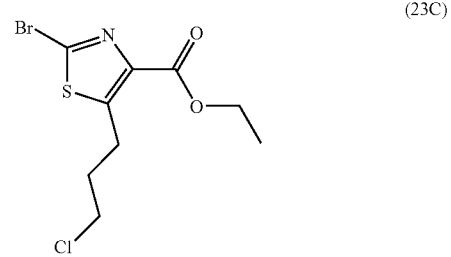

Ethyl 2-amino-5-(3-chloropropyl)thiazole-4-carboxylate (23B) (3.3 g, 13 mmol) in acetonitrile (15 mL) was heated slightly in order to dissolve the starting material. Tert-butyl nitrite (2.05 g, 19.9 mmol) was added and the reaction was stirred for 10 minutes Then copper(II) bromide (5.04 g, 22.6 mmol;) was added to the reaction mixture. The reaction was heated at 80° C. and stirred for 2 hours. DCM and 1N HCl were added, layers were separated, and the aqueous layer was extracted 3× with DCM. The organic extracts were extracted with brine, dried over MgSO$_4$, filtered, and concentrated under reduced pressure. The crude residue was purified by column chromatography on silica gel eluting with a gradient of 0 to 60% EtOAc in hexane to give 1.45 g (35%) of the desired product ethyl 2-bromo-5-(3-chloropropyl)thiazole-4-carboxylate (23C): LC/MS (APCI): m/z 313.8 (M+H).

Step 4: Preparation of tert-butyl 7-bromo-3,4-dihydroquinoline-1(2H)-carboxylate (23D)

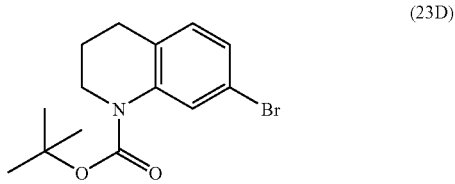

7-bromo-1,2,3,4-tetrahydroquinoline (1E) (1.0 g, 4.7 mmol), di-tert-butyldicarbonate (3.1 g, 14 mmol) were combined and heated to 100° C. for 1 h. Cooled to rt and purified by column chromatography on silica gel eluting with a gradient of 0 to 25% EtOAc in hexanes to provide 1.46 g (99%) of the desired compound tert-butyl 7-bromo-3,4-dihydro-quinoline-1(2H)-carboxylate (23D).

Step 5: Preparation of tert-butyl 7-(4,4,5,5-tetramethyl-1,3,2-dioxaborolan-2-yl)-3,4-dihydroquinoline-1(2H)-carboxylate (23E)

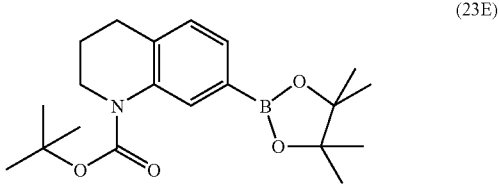

Tert-butyl 7-(4,4,5,5-tetramethyl-1,3,2-dioxaborolan-2-yl)-3,4-dihydroquinoline-1(2H)-carboxylate (23E) was prepared following a similar procedure as that described in example 1, except tert-butyl 7-bromo-3,4-dihydroquinoline-1(2H)-carboxylate (23D) was used instead of 1-(7-bromo-3,4-dihydroquinolin-1(2H)-yl)ethanone (1F) in step 7 example 1.

Step 6: Preparation of ethyl 2-(1-(tert-butoxycarbonyl)-1,2,3,4-tetrahydroquinolin-7-yl)-5-(3-chloropropyl)thiazole-4-carboxylate (23F)

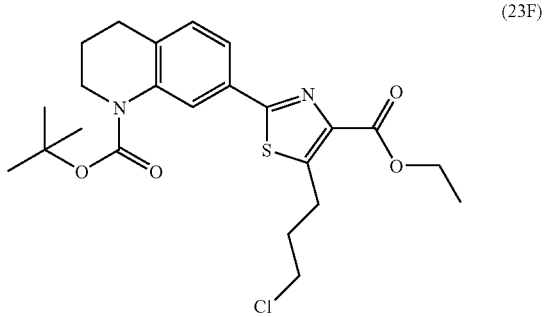

(23F)

Ethyl 2-bromo-5-(3-chloropropyl)thiazole-4-carboxylate (23C) (0.790 g, 2.5 mmol) was dissolved in dioxane, the tent-butyl 7-(4,4,5,5-tetramethyl-1,3,2-dioxaborolan-2-yl)-3,4-dihydroquinoline-1(2H)-carboxylate (23E) (0.910 g, 2.5 mmol) was added followed by lithium chloride (0.320 g, 7.6 mmol), tetrakis(triphenylphosphine)palladium(0) (0.290 g, 0.25 mmol), cesium carbonate (2.5 g, 7.6 mmol) and water. This was transferred to a sealed tube, the reaction was evacuated, flushed with nitrogen and heated at 100° C. overnight. The reaction was filtered through Celite, eluted with EtOAc, concentrated under reduced pressure, and dry loaded onto silica. The crude material was purified by column chromatography on silica gel eluting with a gradient of 0 to 50% EtOAc in hexanes to provide 0.943 g (80%) of the desired product ethyl 2-(1-(tert-butoxycarbonyl)-1,2,3,4-tetrahydroquinolin-7-yl)-5-(3-chloropropyl)thiazole-4-carboxylate (23F): LC/MS (APCI): m/z 466.1 (M+H).

Step 7: Preparation of ethyl 2-(1-(tert-butoxycarbonyl)-1,2,3,4-tetrahydroquinolin-7-yl)-5-(3-iodopropyl)thiazole-4-carboxylate (23G)

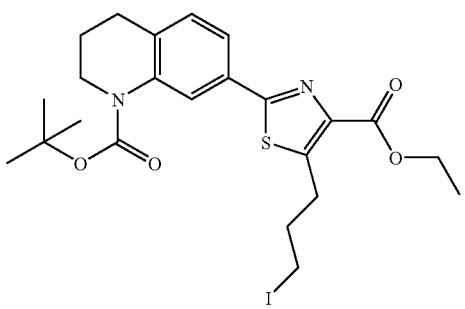

(23G)

Ethyl 2-(1-(tert-butoxycarbonyl)-1,2,3,4-tetrahydroquinolin-7-yl)-5-(3-chloropropyl)thiazole-4-carboxylate (23F) (0.943 g, 2.02 mmol) was dissolved in Acetonitrile (10 mL). To this reaction mixture was added NaI (0.309 g, 2.06 mmol) and heated to 80° C. The reaction was stirred for 48 hours. The reaction was filtered and concentrated under reduced pressure. The crude material was dissolved in EtOAc, washed with water, brine, dried over MgSO$_4$, filtered, and concentrated under reduced pressure to provide 0.370 g (97%) of the desired product ethyl 2-(1-(tert-butoxycarbonyl)-1,2,3,4-tetrahydroquinolin-7-yl)-5-(3-iodopropyl)thiazole-4-carboxylate (23G): LC/MS (APCI): m/z 557.2 (M+H).

Step 8: Preparation of ethyl 5-(3-(4-(1H-pyrazolo[3,4-d]pyrimidin-1-yl)phenoxy)propyl)-2-(1,2,3,4-tetrahydroquinolin-7-yl)thiazole-4-carboxylate (23H)

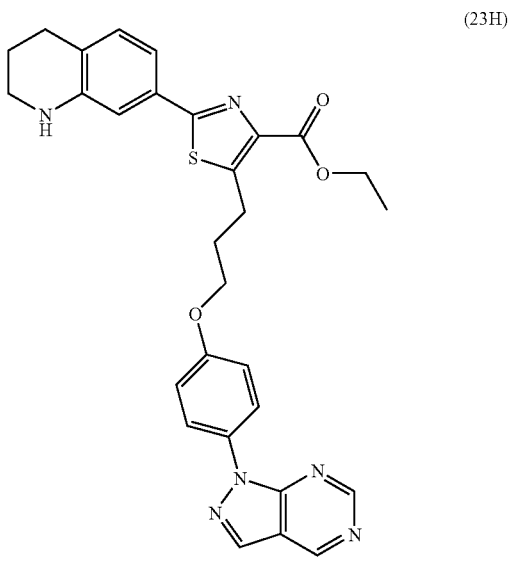

(23H)

To NaH (10 mg, 0.43 mmol) and 4-(1H-pyrazolo[3,4-d]pyrimidin-1-yl)phenol (22) (100 mg, 0.47 mmol) was added DMF (1 mL) and stirred under nitrogen for 10 minutes. Ethyl 2-(1-(tert-butoxycarbonyl)-1,2,3,4-tetrahydroquinolin-7-yl)-5-(3-iodopropyl)thiazole-4-carboxylate (23G) (240 mg, 0.43 mmol) in DMF (2 mL) was added to the reaction mixture and then stirred at rt overnight. The reaction mixture was diluted with EtOAc, washed sequentially with NaHCO$_3$, water, brine, dried over MgSO$_4$, filtered, and concentrated under reduced pressure. LC/MS (APCI): m/z 641.3 (M+H).

The material was dissolved in 1:1 DCM:TFA and stirred for 90 minutes. The reaction mixture was concentrated under reduced pressure, dissolved in EtOAc, washed with saturated NaHCO$_3$, brine, dried over MgSO$_4$, filtered, and concentrated under reduced pressure. The crude material was dry loaded onto silica and purified on by column chromatography on silica gel eluting with a gradient of 0 to 70% EtOAc in hexanes to provide 93 mg (40%) of the desired product ethyl 5-(3-(4-(1H-pyrazolo[3,4-d]-pyrimidin-1-yl)phenoxy)propyl)-2-(1,2,3,4-tetrahydroquinolin-7-yl)thiazole-4-carboxylate (23H): LC/MS (APCI): m/z 541.2 (M+H).

Step 9: Preparation of ethyl 5-(3-(4-(1H-pyrazolo[3,4-d]pyrimidin-1-yl)phenoxy)propyl)-2-(1-(benzo[d]thiazol-2-ylcarbamoyl)-1,2,3,4-tetrahydroquinolin-7-yl)thiazole-4-carboxylate (23I)

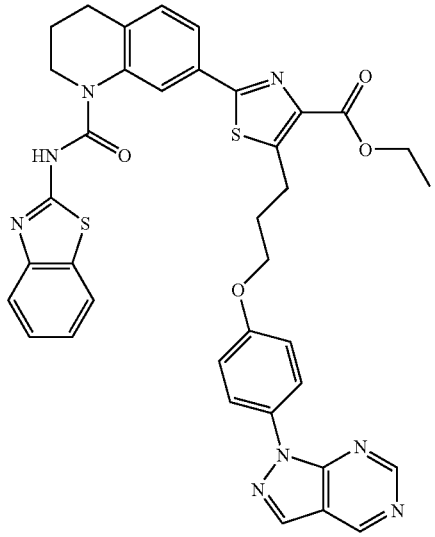

(23I)

Ethyl 5-(3-(4-(1H-pyrazolo[3,4-d]pyrimidin-1-yl)phenoxy)propyl)-2-(1-(benzo[d]thiazol-2-ylcarbamoyl)-1,2,3,4-tetrahydroquinolin-7-yl)thiazole-4-carboxylate (23I) was prepared following a similar procedure as that described in example 1, except ethyl 5-(3-(4-(1H-pyrazolo[3,4-d]-pyrimidin-1-yl)phenoxy)propyl)-2-(1,2,3,4-tetrahydroquinolin-7-yl)thiazole-4-carboxylate (23H) was used instead of 5-(4-methoxyphenyl)-2-(1,2,3,4-tetrahydroquinolin-7-yl)thiazole-4-carboxylic acid (1L) in step 14 example 1. The reaction mixture was filtered and washed with water and MeOH to provide the desired product ethyl 5-(3-(4-(1H-pyrazolo[3,4-d]pyrimidin-1-yl)phenoxy)propyl)-2-(1-(benzo[d]thiazol-2-ylcarbamoyl)-1,2,3,4-tetrahydroquinolin-7-yl)thiazole-4-carboxylate (23I) which was taken on without further purification. LC/MS (APCI): m/z 717.6 (M+H).

Step 10: Preparation of title compound 5-(3-(4-(1H-pyrazolo[3,4d]-pyrimidin-1-yl)phenoxy)propyl)-2-(1-(benzo[d]thiazol-2-ylcarbamoyl)-1,2,3,4-tetrahydroquinolin-7-yl)thiazole-4-carboxylic acid (23)

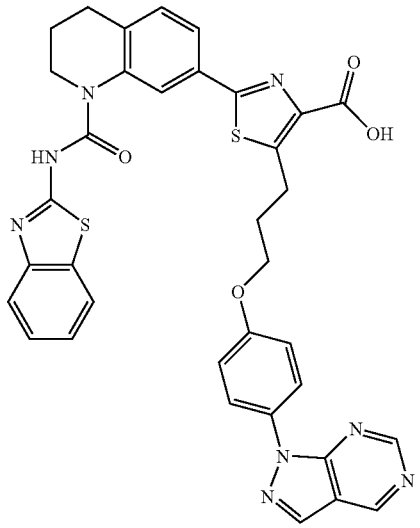

(23)

The title compound 5-(3-(4-(1H-pyrazolo[3,4-d]pyrimidin-1-yl)phenoxy)propyl)-2-(1-(benzo[d]thiazol-2-ylcarbamoyl)-1,2,3,4-tetrahydroquinolin-7-yl)thiazole-4-carboxylic acid (23) was prepared by the following procedure: To ethyl 5-(3-(4-(1H-pyrazolo[3,4-d]pyrimidin-1-yl)phenoxy)propyl)-2-(1-(benzo[d]thiazol-2-ylcarbamoyl)-1,2,3,4-tetrahydroquinolin-7-yl)thiazole-4-carboxylate (23I) (120 mg, 0.17 mmol) was added MeOH and THF. LiOH (20 mg, 0.85 mmol) was dissolved in water and added to the reaction mixture. The reaction mixture was stirred and heated at 60° C. for two hours. The reaction was cooled and put in refrigerator overnight. The precipitate was transferred to a centrifuge tube and centrifuged down at 17,000 RPM. The precipitate was washed water. Then the precipitate was added to acetonitrile and water and lyophilized to give 69 mg (59%) of the desired product 5-(3-(4-(1H-pyrazolo[3,4-t]pyrimidin-1-yl)phenoxy)propyl)-2-(1-(benzo[d]thiazol-2-ylcarbamoyl)-1,2,3,4-tetrahydroquinolin-7-yl)thiazole-4-carboxylic acid (23): $^1$H NMR (400 MHz, DMSO) δ 9.44 (s, 1H), 9.10 (s, 1H), 8.61 (s, 1H), 8.04 (d, J=8.7, 2H), 7.66 (s, 1H), 7.45 (d, J=34.2, 2H), 7.20 (t, J=18.3, 5H), 4.12 (s, 3H), 3.95 (s, 3H), 2.79 (s, 2H), 2.16 (s, 3H), 1.89 (s, 2H), −0.00 (s, 3H).

Example 24

Synthesis of 2-(1-(benzo[d]thiazol-2-ylcarbamoyl)-1,2,3,4-tetrahydroquinolin-7-yl)-5-(3-phenoxypropyl)thiazole-4-carboxylic acid (24)

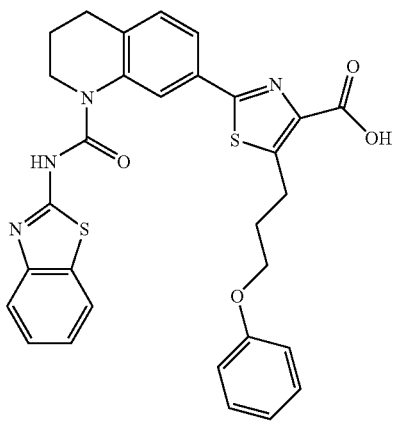

(24)

Step 1: Preparation of ethyl 5-(3-phenoxypropyl)-2-(1,2,3,4-tetrahydroquinolin-7-yl)thiazole-4-carboxylate (24A)

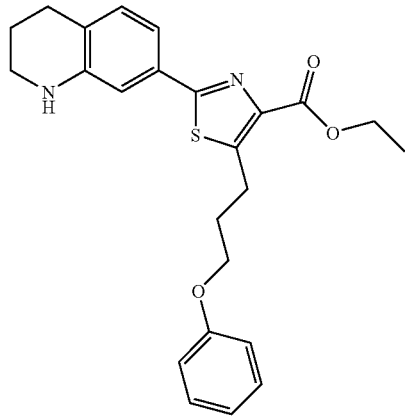

(24A)

To K$_2$CO$_3$ (32 mg, 0.23 mmol), phenol (28 mg, 0.30 mmol) and 18-crown-6 (180 mg, 0.70 mmol) was added DMF (1 mL). After 5 minutes ethyl 2-(1-(tert-butoxycarbonyl)-1,2,3,4-tetrahydroquinolin-7-yl)-5-(3-iodopropyl)thiazole-4-carboxylate (23G) (129 mg, 0.23 mmol) in DMF (1 mL) was added to the reaction mixture and stirred at rt for 72 hours. The reaction was monitored by LCMS and starting material remained. To the reaction mixture was added K$_2$CO$_3$ (32 mg, 0.23 mmol) and phenol (28 mg, 0.30 mmol) and stirred at rt overnight. The reaction mixture was diluted with EtOAc, washed with saturated NaHCO$_3$, water, brine, dried over MgSO$_4$ and concentrated under reduced pressure. The crude material was purified by column chromatography on silica gel to provide 50 mg as a mixture of starting material and product. To DMF (1 mL) was added NaH (4 mg) and phenol (13 mg) and stirred for 10 minutes. To the reaction mixture was added the isolated material (50 mg) as a mixture of starting material and product and allowed to stir at rt overnight. The reaction mixture was diluted with EtOAc, washed with saturated NaHCO$_3$, water, brine, dried with MgSO$_4$ and concentrated under reduced pressure. The crude material was purified by column chromatography on silica gel to provide 22 mg of the desired product.

The material was dissolved in 1:1 DCM:TFA and stirred for 90 minutes. The reaction mixture was concentrated under reduced pressure to provide the desired product ethyl 5-(3-phenoxypropyl)-2-(1,2,3,4-tetrahydroquinolin-7-yl)thiazole-4-carboxylate (24A): LC/MS (APCI): m/z 423.2 (M+H).

Step 2: Preparation of title compound 2-(1-(benzo[d]thiazol-2-ylcarbamoyl)-1,2,3,4-tetrahydroquinolin-7-yl)-5-(3-phenoxypropyl)thiazole-4-carboxylic acid (24)

(24)

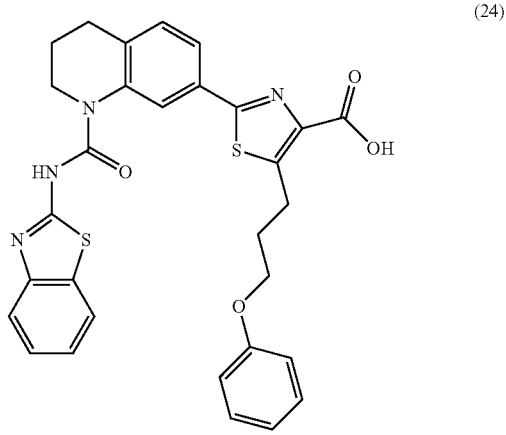

The title compound 2-(1-(benzo[d]thiazol-2-ylcarbamoyl)-1,2,3,4-tetrahydroquinolin-7-yl)-5-(3-phenoxypropyl)thiazole-4-carboxylic acid (24) was prepared by the following procedure: To ethyl 5-(3-phenoxypropyl)-2-(1,2,3,4-tetrahydroquinolin-7-yl)thiazole-4-carboxylate (24A) (18 mg, 0.0.42 mmol) and N-(benzo[d]thiazol-2-yl)-1H-imidazole-1-carboxamide (1M) (10 mg, 0.042 mmol) was added DMF (2 mL) and stirred at rt overnight. The reaction mixture was diluted with EtOAc, washed sequentially with NaHCO$_3$, water, brine, dried over MgSO$_4$, filtered, and concentrated under reduced pressure to provide ethyl 2-(1-(benzo[d]thiazol-2-ylcarbamoyl)-1,2,3,4-tetrahydroquinolin-7-yl)-5-(3-phenoxypropyl)thiazole-4-carboxylate. LC/MS (APCI): m/z 599.5 (M+H).

To ethyl 2-(1-(benzo[d]thiazol-2-ylcarbamoyl)-1,2,3,4-tetrahydroquinolin-7-yl)-5-(3-phenoxypropyl)thiazole-4-carboxylate in 1:1 MeOH and THF (2 mL) was added LiOH (5 mg, 0.21 mmol) dissolved in water (2 mL). The reaction mixture was stirred at 60° C. for 1 hour. The reaction mixture was concentrated under reduced pressure. To this crude material was added water and MeOH and allowed to sit overnight. The resulting precipitate was filtered and washed with water. To this solid was added water and acetonitrile and lyophilized to give 12 mg of the desired product 2-(1-(benzo[d]thiazol-2-ylcarbamoyl)-1,2,3,4-tetrahydroquinolin-7-yl)-5-(3-phenoxypropyl)thiazole-4-carboxylic acid (24). $^1$H NMR (400 MHz, DMSO) δ 8.62 (s, 1H), 7.60 (s, 2H), 7.51-7.33 (m, 3H), 7.27 (t, J=8.0, 3H), 7.17 (t, J=7.7, 2H), 6.92 (dd, J=7.5, 14.2, 5H), 4.03 (t, J=6.4, 3H), 3.95 (s, 2H), 3.42 (d, J=7.8, 4H), 2.78 (s, 2H), 2.10 (s, 3H), 1.88 (d, J=9.5, 3H).

Example 25

Synthesis of 6-(4-(benzo[d]thiazol-2-ylcarbamoyl)-1-methyl-1,2,3,4-tetrahydroquinoxalin-6-yl)picolinic acid (25)

(25)

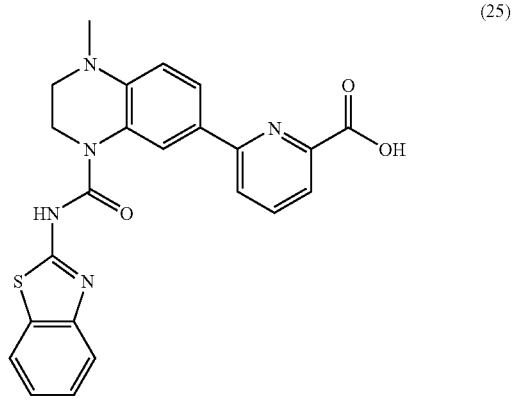

Step 1: Preparation of tert-butyl 6-bromopicolinate (25A)

(25A)

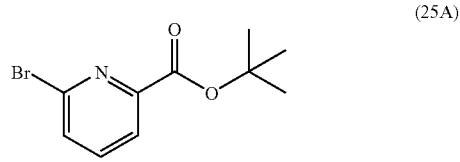

p-Toluenesulfonyl chloride (9.0 g, 47.2 mmol) was added portionwise to a mixture of 2-bromo-picolinic acid (4.02 g, 19.9 mmol) in tert-butanol (36 mL) and pyridine (10.8 mL, 134 mmol) at 0° C. and the mixture was stirred at rt for 14 hours. An aqueous solution of sodium bicarbonate was slowly added. The precipitate was filtered, washed with water and dried in vacuo to provide 4.04 g (79%) of the desired product tert-butyl 6-bromopicolinate (25A): $^1$H NMR (300 MHz, CDCl$_3$) δ 7.97 (1H, dd), 7.64 (2H, m), 1.62 (9H, s).

Step 2: Preparation of 2-((4-bromo-2-nitrophenyl)(methyl)amino)ethanol (25B)

(25B)

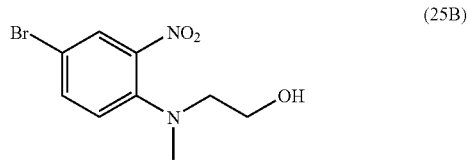

5-bromo-2-fluoronitrobenzene (5.0 g, 22.7 mmol), 2-(methylamino)ethanol (4.26 g, 56.8 mmol) and K$_2$CO$_3$ (9.4 g, 68.1 mmol) in DMF (20 mL) was heated to 60° C. for 1.5 hours, cooled to rt, diluted with water and extracted with EtOAc. The organic phases were washed with water, brine, dried over Na$_2$SO$_4$, filtered, and concentrated under reduced pressure to provide 6.98 g (100%) of the desired product 2-((4-bromo-2-nitrophenyl)(methyl)amino)ethanol (25B): $^1$H NMR (300 MHz, CDCl$_3$) δ 7.87 (1H, d), 7.51 (1H, dd), 7.10 (1H, d), 3.77 (2H, t), 3.39 (2H, t), 2.83 (3H, s).

Step 3: Preparation of 2-((2-amino-4-bromophenyl)(methyl)amino)ethanol (25C)

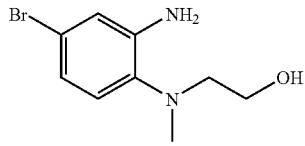

(25C)

Iron (1.5 g, 26.2 mmol) and ammonium chloride (0.39 g, 1.0 eq) in water (8 mL) was heated to reflux for 0.5 hours. 2-((4-bromo-2-nitrophenyl)(methyl)amino)ethanol (25B) (2.0 g, 7.27 mmol) was slowly added. The reaction mixture was heated to reflux for 14 hours, cooled to rt, diluted with water and EtOAc and filtered through Celite. The aqueous phase was extracted with EtOAc. The combined organic phases were washed with brine, dried over Na$_2$SO$_4$, filtered, and concentrated under reduced pressure. The crude material was purified by column chromatography on silica gel eluting with a gradient of PE:EtOAc 60:40-40:60, to provide 1.36 g (76%) of the desired product 2-((2-amino-4-bromophenyl)(methyl)amino)ethanol (25C): $^1$H NMR (300 MHz, CDCl$_3$) δ 6.92-6.82 (3H, m), 3.68 (2H, t), 3.04 (2H, t), 2.70 (3H, s).

Step 4: Preparation of 4-bromo-N$^1$-(2-chloroethyl)-N$^1$-methylbenzene-1,2-diamine (25D)

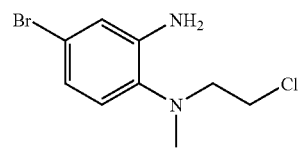

(25D)

Thionylchloride (0.78 g, 6.74 mmol) was added dropwise to a solution of 2-((2-amino-4-bromophenyl)(methyl)amino)ethanol (25C) (1.376 g, 5.62 mmol) in DCM (50 mL) and DMF (10 drops) at 0° C. The mixture was allowed to warm up to rt and stirred for 1 hour. Then, the mixture was heated to 35° C. for 2.5 hours, concentrated, diluted with 1N NaOH, and extracted with DCM. The organic phases were washed with brine, dried over Na$_2$SO$_4$, filtered, and concentrated under reduced pressure. The crude material was purified by flash column chromatography on silica gel eluting with a gradient of PE:EtOAc 100:0-85:15, to provide 0.611 g (41%) of the desired product 4-bromo-N$^1$-(2-chloroethyl)-N$^1$-methylbenzene-1,2-diamine (25D): $^1$H NMR (300 MHz, CDCl$_3$) δ 6.88-6.79 (3H, m), 4.20 (2H, bs), 3.56 (2H, t), 3.17 (2H, t), 2.67 (3H, s).

Step 5: Preparation of 6-bromo-1-methyl-1,2,3,4-tetrahydroquinoxaline (25E)

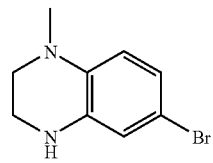

(25E)

A solution of 4-bromo-N$^1$-(2-chloroethyl)-N$^1$-methylbenzene-1,2-diamine (25D) (0.611 g, 2.3 mmol) and K$_2$CO$_3$ (0.634 g, 4.6 mmol) in DMF (7 mL) was heated to 80° C. for 1 hour and then at 100° C. for 1.5 hours, cooled to rt, diluted with water and extracted with EtOAc. The organic phases were washed with brine, dried over Na$_2$SO$_4$, filtered, and concentrated under reduced pressure to provide 0.528 g (100%) of the desired product 6-bromo-1-methyl-1,2,3,4-tetrahydroquinoxaline (25E): $^1$H NMR (300 MHz, CDCl$_3$) δ 6.72 (1H, dd), 6.56 (1H, d), 6.38 (1H, d), 3.74 (1H, bs), 3.47 (2H, t), 3.22 (2H, t), 2.82 (3H, s).

Step 6: Preparation of 1-methyl-6-(4,4,5,5-tetramethyl-1,3,2-dioxaborolan-2-yl)-1,2,3,4-tetrahydroquinoxaline (25F)

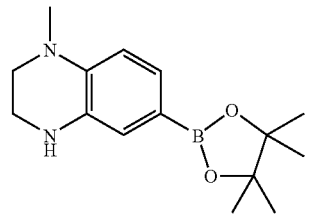

(25F)

A solution of 6-bromo-1-methyl-1,2,3,4-tetrahydroquinoxaline (25E) (200 mg, 0.88 mmol), bis(pinacolato)diboron (304 mg, 1.20 mmol), potassium acetate (204 mg, 2.08 mmol), tris(dibenzylideneacetone)-dipalladium(0) (20 mg, 0.022 mmol), and 2-dicyclohexylphosphino-2',4',6'-tri-isopropyl-1,1'-biphenyl (42 mg, 0.09 mmol) in anhydrous dioxane (3.5 mL) was heated at 100° C. for 45 minutes, cooled to rt, diluted with water and extracted with EtOAc. The organic phases were washed with brine, dried over Na$_2$SO$_4$, filtered, and concentrated under reduced pressure. The crude material was purified by flash column chromatography on silica gel eluting with a gradient of PE:EtOAc 100:0-85:15, to provide 247 mg (100%) of the desired product 1-methyl-6-(4,4,5,5-tetramethyl-1,3,2-dioxaborolan-2-yl)-1,2,3,4-tetrahydroquinoxaline (25F): $^1$H NMR (300 MHz, DMSO-d6) δ 6.81 (1H, dd), 6.71 (1H, d), 6.38 (1H, d), 5.38 (1H, bs), 3.29 (2H, t), 3.18 (2H, t), 2.78 (3H, s), 1.22 (12H, 5).

Step 7: Preparation of tert-butyl 6-(1-methyl-1,2,3,4-tetrahydroquinoxalin-6-yl)picolinate (25G)

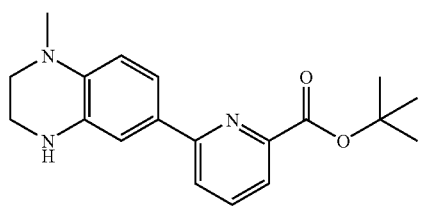

(25G)

Tert-butyl 6-bromopicolinate (25A) (157 mg, 0.61 mmol) in 1,4-dioxane (1.0 mL) was added dropwise to 1-methyl-6-(4,4,5,5-tetramethyl-1,3,2-dioxaborolan-2-yl)-1,2,3,4-tetrahydroquinoxaline (25F) (167 mg, 0.61 mmol), K$_2$CO$_3$ (207 mg, 1.52 mmol), tetrabutylammonium bromide (19.5 mg, 0.061 mmol), and dichlorobis(triphenylphosphine)palladium (II) (17.9 mg, 0.024 mmol) in 1,4-dioxane (2.0 mL) and water (1.0 mL) at rt. The mixture was microwave (150W) heated to 100° C. for 50 minutes, cooled to 20° C., diluted with water and extracted with EtOAc. The organic phases were washed with brine, dried over $Na_2SO_4$, filtered, and concentrated under reduced pressure. The crude material was purified by flash column chromatography on silica gel eluting with a gradient of PE:EtOAc 100:0-70:30, to provide 76 mg (38%) of the desired product tert-butyl 6-(1-methyl-1,2,3,4-tetrahydroquinoxalin-6-yl)picolinate (25G): $^1$H NMR (300 MHz, MeOD) δ 7.84-7.78 (3H, m), 7.35 (1H, d), 7.30 (1H, d), 6.62 (1H, d), 3.41 (2H, t), 3.31 (2H, t), 2.92 (3H, bs), 1.64 (9H, s).

Step 8: Preparation of tert-butyl 6-(4-(benzo[d]thiazol-2-ylcarbamoyl)-1-methyl-1,2,3,4-tetrahydroquinoxalin-6-yl)picolinate (25H)

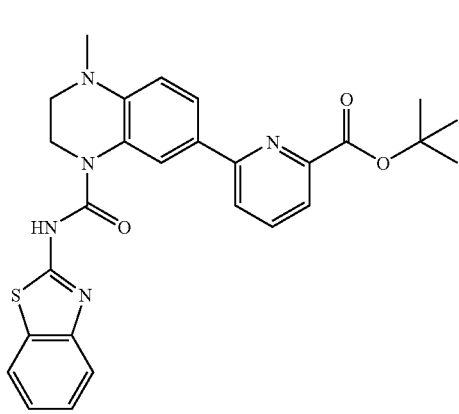

(25H)

A mixture of tert-butyl 6-(1-methyl-1,2,3,4-tetrahydroquinoxalin-6-yl)picolinate (25G) (36 mg, 0.11 mmol) and 4-nitrophenyl benzo[d]thiazol-2-ylcarbamate (19) (42 mg, 0.13 mmol) in anhydrous acetonitrile (1.0 mL) was heated to reflux for 3 hours, cooled to rt, concentrated under reduced pressure, and the crude material was purified by flash column chromatography on silica gel eluting with a gradient of PE:EtOAc 100:0-70:30, to provide 47 mg (85%) of the desired product tert-butyl 6-(4-(benzo[d]thiazol-2-ylcarbamoyl)-1-methyl-1,2,3,4-tetrahydroquinoxalin-6-yl)picolinate (25H): $^1$H NMR (300 MHz, CDCl$_3$) δ 8.14 (1H, s), 7.88-7.77 (2H, m), 7.74 (2H, d), 7.54 (1H, d), 7.34 (1H, t), 7.22 (1H, t), 6.71 (1H, d), 3.97 (2H, t), 3.49 (2H, t), 3.02 (3H, s), 1.56 (9H, s).

Step 9: Preparation of title compound 6-(4-(benzo[d]thiazol-2-ylcarbamoyl)-1-methyl-1,2,3,4-tetrahydroquinoxalin-6-yl)picolinic acid (25)

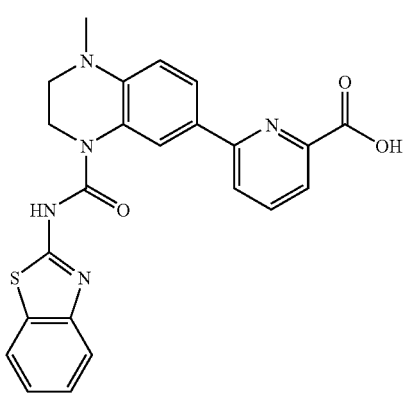

(25)

The title compound 6-(4-(benzo[d]thiazol-2-ylcarbamoyl)-1-methyl-1,2,3,4-tetrahydroquinoxalin-6-yl)picolinic acid (25) was prepared by the following procedure: Trifluoroacetic acid (2.0 mL) was added dropwise to tert-butyl 6-(4-(benzo[d]thiazol-2-ylcarbamoyl)-1-methyl-1,2,3,4-tetrahydroquinoxalin-6-yl)picolinate (25H) (79 mg, 0.16 mmol) in DCM (2.0 mL) at 0° C. The mixture was allowed to warm up to rt and stirred for 72 hours. The mixture was concentrated, triturated with diethylether, filtered, and dried in vacuo to provide 62 mg (70%) of the desired product 6-(4-(benzo[d]thiazol-2-ylcarbamoyl)-1-methyl-1,2,3,4-tetrahydroquinoxalin-6-yl)picolinic acid (25): $^1$H NMR (300 MHz, DMSO-d6) δ 8.28 (1H, s), 8.01-7.72 (5H, m), 7.45-7.30 (2H, m), 7.21 (1H, t), 6.82 (1H, d), 4.03 (2H, t), 3.45 (2H, t), 3.00 (3H, s). MS (ESI(+)): m/z 446.0 (M+H).

Example 26

Synthesis of 6-(4-(benzo[d]thiazol-2-ylcarbamoyl)-1-methyl-1,2,3,4-tetrahydroquinoxalin-6-yl)-3-(3-phenoxypropoxy)picolinic acid (26)

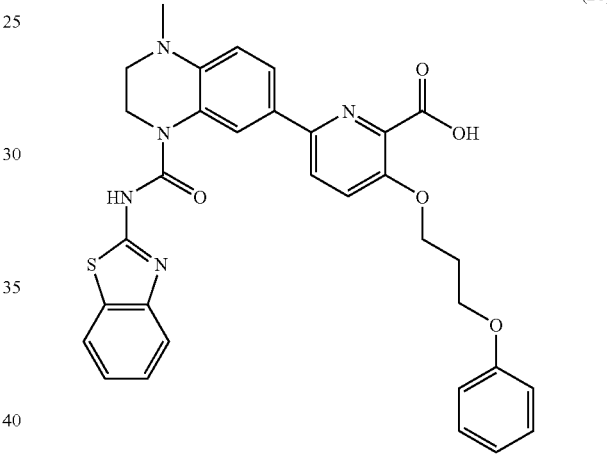

(26)

Step 1: Preparation of methyl 3-hydroxypicolinate (26A)

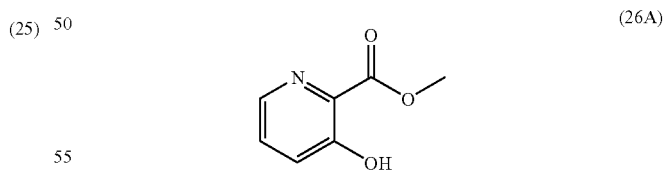

(26A)

Concentrated sulphuric acid (19 mL) was added dropwise to a mixture of 3-hydroxy picolinic acid (23.0 g, 165 mmol) in methanol (700 mL) at rt. The mixture was heated to reflux for 72 hours, cooled and concentrated. The mixture was neutralized with bicarbonate and extracted with EtOAc. The organic phases were washed with brine, dried over $Na_2SO_4$, and concentrated under reduced pressure to provide 21.7 g (85%) of the desired product methyl 3-hydroxypicolinate (26A): $^1$H NMR (300 MHz, CDCl$_3$) δ 10.63 (1H, s), 8.28 (1H, dd), 7.39 (2H, m), 4.06 (3H, s).

Step 2: Preparation of methyl 6-bromo-3-hydroxypicolinate (26B)

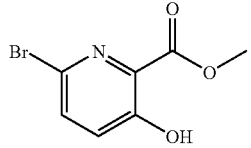

Bromine (5.02 g, 31.4 mmol) was added dropwise to a mixture of methyl 3-hydroxypicolinate (26A) (3.67 g, 26.4 mmol) in water (75 mL) at rt and the mixture was stirred for 2.5 hours. The precipitate was filtered, washed with water and dried in vacuo to provide 4.18 g (75%) of the desired product methyl 6-bromo-3-hydroxypicolinate (26B): $^1$H NMR (300 MHz, DMSO-d6) δ 10.67 (1H, s), 7.69 (1H, d), 7.42 (1H, d), 3.88 (3H, s).

Step 3: Preparation of methyl 6-bromo-3-(3-phenoxypropoxy)picolinate (26C)

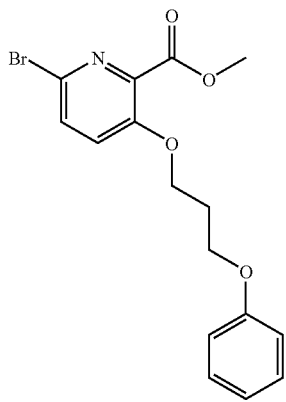

Sodium hydride (60% in mineral oil, 172 mg, 4.53 mmol) was added to a mixture of methyl 6-bromo-3-hydroxypicolinate (26B) (1.0 g, 4.31 mmol) and 3-phenoxypropyl bromide (927 mg, 4.31 mmol) in DMA (20 mL) at rt. The mixture was heated to 100° C. for 1.75 hours, cooled, diluted with 10% citric acid and extracted with EtOAc. The organic phases were washed with brine, dried over Na$_2$SO$_4$, and concentrated under reduced pressure. The crude material was purified by flash column chromatography on silica gel eluting with a gradient of PE:EtOAc 100:0-75:25, to provide 1.35 g (86%) of the desired product methyl 6-bromo-3-(3-phenoxypropoxy)picolinate (26C): $^1$H NMR (300 MHz, CDCl$_3$) δ 7.52 (1H, d), 7.27 (2H, m), 6.92 (2H, m), 4.25 (2H, t), 4.19 (2H, t), 3.92 (3H, s), 2.30 (2H, t).

Step 4: Preparation of methyl 6-(1-methyl-1,2,3,4-tetrahydroquinoxalin-6-yl)-3-(3-phenoxypropoxy)picolinate (26D)

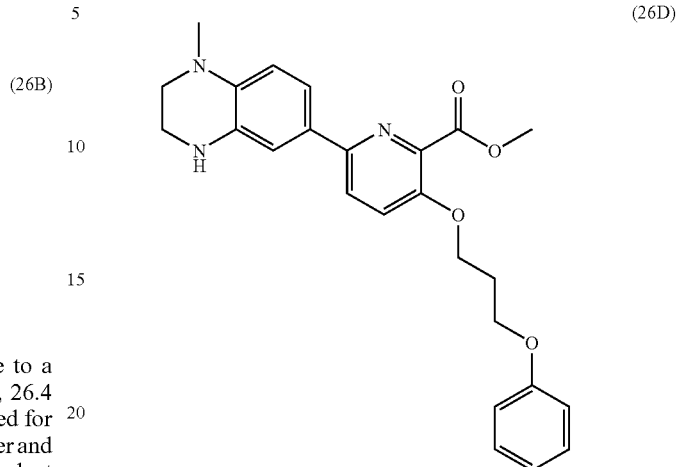

Methyl 6-bromo-3-(3-phenoxypropoxy)picolinate (26C) (141 mg, 0.38 mmol) in 1,4-dioxane (1.0 mL) was added dropwise to a mixture of 1-methyl-6-(4,4,5,5-tetramethyl-1,3,2-dioxaborolan-2-yl)-1,2,3,4-tetrahydroquinoxaline (25F) (105 mg, 0.38 mmol), K$_2$CO$_3$ (207 mg, 1.52 mmol), tetrabutylammonium bromide (12.1 mg, 0.038 mmol), and dichlorobis(triphenylphosphine)palladium(II) (11.3 mg, 0.015 mmol) in 1,4-dioxane (2.5 mL) and water (1.3 mL) at rt. The mixture was microwave (150W) heated to 100° C. for 5 min, cooled, diluted with water and extracted with EtOAc. The organic phases were washed with brine, dried over Na$_2$SO$_4$, filtered, and concentrated under reduced pressure. The crude material was purified by flash column chromatography on silica gel eluting with a gradient of PE:EtOAc 100:0-70:30, to provide 27 mg (16%) of the desired product methyl 6-(1-methyl-1,2,3,4-tetrahydroquinoxalin-6-yl)-3-(3-phenoxypropoxy)picolinate (26D): $^1$H NMR (300 MHz, CDCl$_3$) δ 7.71-7.23 (6H, m), 6.92 (3H, m), 6.58 (1H, d), 4.31-4.13 (6H, m), 3.98 (2H, t), 3.92 (3H, s), 2.30 (2H, t).

Step 5: Preparation of methyl 6-(4-(benzo[d]thiazol-2-ylcarbamoyl)-1-methyl-1,2,3,4-tetrahydroquinoxalin-6-yl)-3-(3-phenoxypropoxy)picolinate (26E)

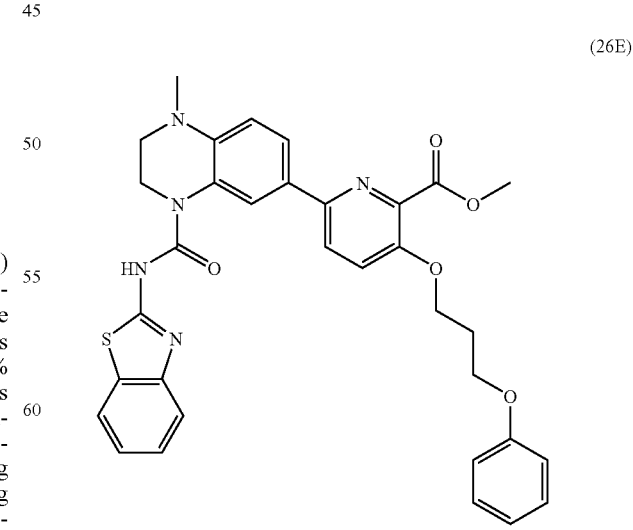

Methyl 6-(4-(benzo[d]thiazol-2-ylcarbamoyl)-1-methyl-1,2,3,4-tetrahydroquinoxalin-6-yl)-3-(3-phenoxypropoxy)

picolinate (26E) (24 mg, 64%) was prepared following a similar procedure as that described in example 25, except methyl 6-(1-methyl-1,2,3,4-tetrahydroquinoxalin-6-yl)-3-(3-phenoxypropoxy)picolinate (26D) was used instead of tert-butyl 6-(1-methyl-1,2,3,4-tetrahydroquinoxalin-6-yl)picolinate (25G) in step 8 of example 25. ¹H NMR (300 MHz, CDCl₃) δ 7.98 (1H, s), 7.78 (1H, d), 7.72 (1H, d), 7.48 (1H, d), 7.39 (2H, d), 7.30-7.17 (4H, m), 6.97-6.90 (3H, m), 6.50 (1H, d), 4.29 (2H, t), 4.22 (2H, t), 3.90 (2H, t), 3.79 (3H, s), 3.38 (2H, t), 2.94 (3H, s), 2.32 (2H, t).

Step 6: Preparation of title compound 6-(4-(benzo[d]thiazol-2-ylcarbamoyl)-1-methyl-1,2,3,4-tetrahydroquinoxalin-6-yl)-3-(3-phenoxypropoxy)picolinic acid (26)

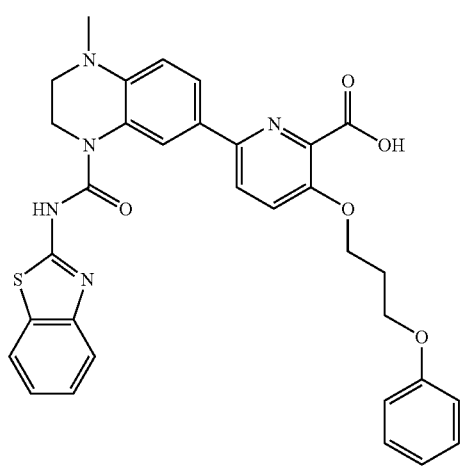

(26)

The title compound 6-(4-(benzo[d]thiazol-2-ylcarbamoyl)-1-methyl-1,2,3,4-tetrahydroquinoxalin-6-yl)-3-(3-phenoxypropoxy)picolinic acid (26) was prepared by the following procedure: LiOH (12 mg, 10 eq) was added to a mixture of Methyl 6-(4-(benzo[d]thiazol-2-ylcarbamoyl)-1-methyl-1,2,3,4-tetrahydroquinoxalin-6-yl)-3-(3-phenoxypropoxy)picolinate (26E) (25 mg, 0.041 mmol) in MeOH (0.5 mL) and water (0.25 mL) at rt. The mixture was heated to 55° C. for 14 hours, cooled to 0° C. and acidified with 1N HCl to pH~4. The resulting precipitate was filtered, washed with water and dried in vacuo to provide 15 mg (61%) of the desired product 6-(4-(benzo[d]thiazol-2-ylcarbamoyl)-1-methyl-1,2,3,4-tetrahydroquinoxalin-6-yl)-3-(3-phenoxypropoxy)picolinic acid (26): ¹H NMR (300 MHz, DMSO-d6) δ 8.13 (1H, bs), 7.83 (1H, d), 7.80 (1H, d), 7.65 (2H, m), 7.37 (1H, t), 7.32-7.18 (4H, m), 6.94 (3H, m), 6.79 (1H, d), 4.26 (2H, t), 4.15 (2H, t), 4.02 (2H, t), 3.41 (2H, t), 2.97 (3H, s), 2.17 (2H, t). MS (ESI(+)): m/z 596.1 (M+H).

Example 27

Synthesis of 6-(1-(benzo[d]thiazol-2-ylcarbamoyl)-1,2,3,4-tetrahydroquinolin-7-yl)-3-(2-phenoxyethoxy)picolinic acid (27)

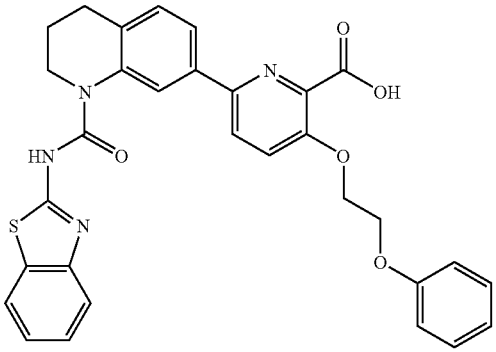

(27)

Step 1: Preparation of methyl 6-bromo-3-(2-phenoxyethoxy)picolinate (27A)

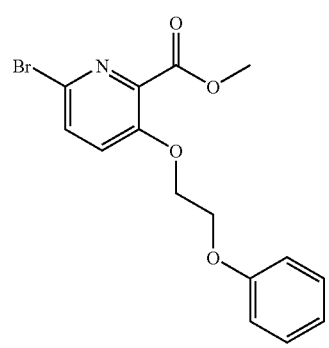

(27A)

A mixture of methyl 6-bromo-3-hydroxypicolinate (26B) (308 mg, 1.33 mmol) and 2-phenoxyethanol (183 mg, 1.33 mmol) were stirred in dry DCM (10 mL). PPh₃-polystyrene bound (665 mg, 2.0 mmol) was added, followed by the dropwise addition of DIAD (0.387 mL, 2.0 mmol). The mixture was stirred for 48 hours, then filtered through Celite and concentrated under reduced pressure. The crude material was purified by flash column chromatography on silica gel eluting with a gradient of PE/EtOAc 9:1-7:3 to provide 334 mg (72%) of the desired compound methyl 6-bromo-3-(2-phenoxyethoxy)picolinate (27A): ¹H NMR (300 MHz, CDCl₃) δ7.58-6.90 (7H, m), 4.43 (2H, m), 4.34 (2H, m), 3.91 (3H, s).

Step 2: Preparation of 7-(4,4,5,5-tetramethyl-1,3,2-dioxaborolan-2-yl)-1,2,3,4-tetrahydroquinoline (27B)

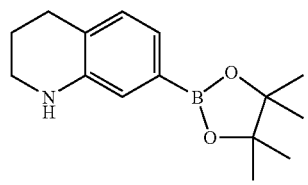

(27B)

7-bromo-1,2,3,4-tetrahydroquinoline (1E) (375 mg, 1.77 mmol) in anhydrous 1,4-dioxane (3 mL) was added dropwise to a mixture of bis(pinacolato)diboron (628 mg, 2.48 mmol), potassium acetate (416 mg, 4.24 mmol), tris(dibenzylideneacetone)-dipalladium(0) (40 mg, 0.044 mmol), and 2-dicyclohexylphosphino-2',4',6'-tri-iso-propyl-1,1'-biphenyl (84 mg, 0.18 mmol) in anhydrous 1,4-dioxane (4 mL) at 95° C. The reaction mixture was stirred at 95° C. for 3.5 hours, cooled to rt, diluted with EtOAc, washed with water, brine, dried over MgSO$_4$, filtered, and concentrated under reduced pressure. The crude material was precipitated from EtOAc/PE to provide 7-(4,4,5,5-tetramethyl-1,3,2-dioxaborolan-2-yl)-1,2,3,4-tetrahydroquinoline (27B): $^1$H NMR (300 MHz, CDCl$_3$) δ 7.08 (1H, dd), 6.97-6.95 (2H, m), 3.31 (2H, t), 2.78 (2H, t), 1.93 (2H, m), 1.32 (12H, s).

Step 3: Preparation of methyl 3-(2-phenoxyethoxy)-6-(1,2,3,4-tetrahydroquinolin-7-yl)picolinate (27C)

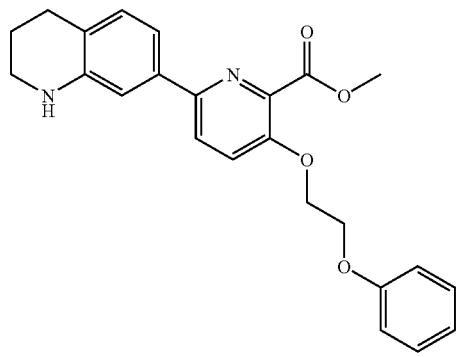

(27C)

Methyl 6-bromo-3-(2-phenoxyethoxy)picolinate (27A) (327 mg, 0.93 mmol), 7-(4,4,5,5-tetramethyl-1,3,2-dioxaborolan-2-yl)-1,2,3,4-tetrahydroquinoline (27B) (181 mg, 0.7 mmol), tetrabutylammonium bromide (30 mg, 0.09 mmol), dichlorobis(triphenylphosphine)palladium(II) (26 mg, 0.04 mmol) and K$_2$CO$_3$ (322 mg, 2.33 mmol) were stirred in 1,4-dioxane (2 mL) and water (1 mL) at 90° C. for 45 minutes. The reaction mixture was allowed to cool to rt and diluted with EtOAc (5 ml), washed with H$_2$O, dried over MgSO$_4$, filtered, and concentrated under reduced pressure. The crude material was purified by column chromatography on silica gel eluting with a gradient of PE/EtOAc 9:1-7:3, to provide 205 mg (72%) of the desired product methyl 3-(2-phenoxyethoxy)-6-(1,2,3,4-tetrahydroquinolin-7-yl)picolinate (27C): $^1$H NMR (300 MHz, CDCl$_3$) δ7.69 (1H, m), 7.44 (1H, m), 7.27 (2H, m), 7.13 (2H, s), 6.94 (4H, m), 4.40 (2H, m), 4.34 (2H, m), 3.90 (3H, s), 3.27 (2H, t), 2.76 (2H, t), 1.92 (2H, m).

Step 4: Preparation of methyl 6-(1-(benzo[d]thiazol-2-ylcarbamoyl)-1,2,3,4-tetrahydroquinolin-7-yl)-3-(2-phenoxyethoxy)picolinate (27D)

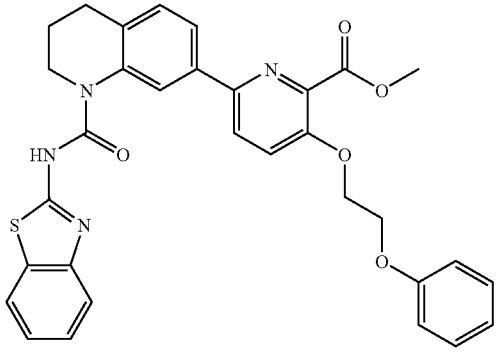

(27D)

Methyl 3-(2-phenoxyethoxy)-6-(1,2,3,4-tetrahydroquinolin-7-yl)picolinate (27C) (81 mg, 0.2 mmol) and 4-nitrophenyl benzo[d]thiazol-2-ylcarbamate (19) (127 mg, 0.4 mmol) were heated to reflux in acetonitrile (5 mL) for 24 hours. After cooling, the mixture was concentrated under reduced pressure and purified by column chromatography on silica gel eluting with a gradient of PE (100%) to PE/EtOAc (4:6), to provide 114 mg (97%) of the desired product methyl 641-(benzo[d]thiazol-2-ylcarbamoyl)-1,2,3,4-tetrahydroquinolin-7-yl)-3-(2-phenoxyethoxy)picolinate (27D). $^1$H NMR (300 MHz, CDCl$_3$) δ8.12 (1H, s), 7.85 (1H, d), 7.73 (1H, m), 7.44 (3H, m), 7.29 (4H, m), 7.09 (1H, m), 6.94 (3H, m), 4.44 (2H, m), 4.37 (2H, m), 3.88 (2H, m), 3.78 (3H, m), 2.74 (2H, m), 2.00 (2H, m).

Step 5: Preparation of title compound 6-(1-(benzo[d]thiazol-2-ylcarbamoyl)-1,2,3,4-tetrahydroquinolin-7-yl)-3-(2-phenoxyethoxy)picolinic acid (27)

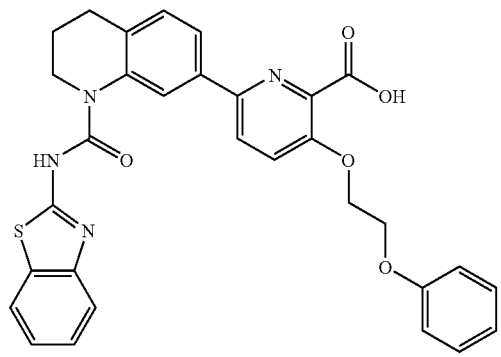

(27)

The title compound 6-(1-(benzo[d]thiazol-2-ylcarbamoyl)-1,2,3,4-tetrahydroquinolin-7-yl)-3-(2-phenoxyethoxy) picolinic acid (27) was prepared by the following procedure: A mixture of methyl 6-(1-(benzo[d]thiazol-2-ylcarbamoyl)-1,2,3,4-tetrahydroquinolin-7-yl)-3-(2-phenoxyethoxy)picolinate (27D) (114 mg, 0.20 mmol) and LiOH (18 mg, 0.75 mmol) was stirred in MeOH (3 mL) and water (1 mL) for 20 hours. The mixture was diluted with diethyl ether (2 mL) and the aqueous layer was separated and acidified with 1M HCl. The precipitate was filtered, washed with EtOAc, and dried to provide 83 mg (75%) of the desired product 6-(1-(benzo[d]thiazol-2-ylcarbamoyl)-1,2,3,4-tetrahydroquinolin-7-yl)-3-(2-phenoxyethoxy)picolinic acid (27): $^1$H NMR (300 MHz, DMSO-d$^6$) δ 7.98 (1H, d), 7.77 (2H, d), 7.65 (1H, m), 7.38-

7.18 (6H, m), 6.99-6.91 (4H, m), 4.46 (2H, m), 4.31 (2H, m), 3.93 (2H, m), 2.79 (2H, m), 1.90 (2H, m). LC/MS (APCI): m/z 567.2 (M+H).

Example 28

Synthesis of 2-(1-(benzo[d]thiazol-2-ylcarbamoyl)indolin-6-yl)thiazole-4-carboxylic acid (28)

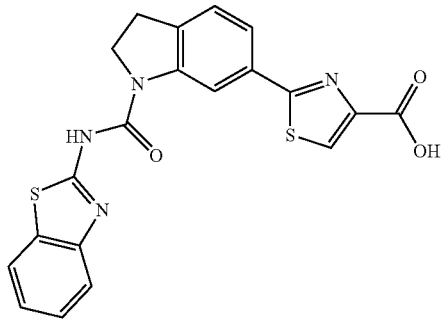

(28)

Step 1: Preparation of tert-butyl 6-bromoindoline-1-carboxylate (28A)

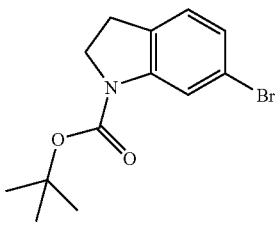

(28A)

6-Bromo-indoline hydrochloride (118 mg, 0.5 mmol), (Boc)₂O (137 mg, 0.63 mmol) and K₂CO₃ (76 mg, 0.55 mmol) were stirred in MeOH (5 mL) for 72 hours. The mixture was diluted with DCM (10 mL), washed with water, the organic layer was dried over MgSO₄, filtered, and concentrated under reduced pressure to provide 156 mg (96%) of the desired product tert-butyl 6-bromoindoline-1-carboxylate (28A): ¹H NMR (300 MHz, CDCl₃) δ 7.02 (3H, m), 3.97 (2H, t), 3.02 (2H, t), 1.53 (9H, s).

Step 2: Preparation of tert-butyl 6-(4,4,5,5-tetramethyl-1,3,2-dioxaborolan-2-yl)indoline-1-carboxylate (28B)

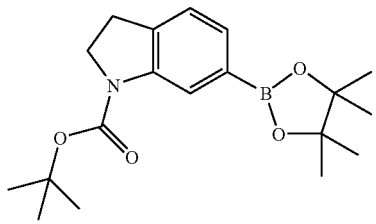

(28B)

A mixture of tert-butyl 6-bromoindoline-1-carboxylate (28A) (156 mg, 0.52 mmol), bis(pinacolato)diboron (173 mg, 0.68 mmol), Pd(dppf)₂Cl₂ (9 mg, 0.012 mmol, 2.2 mol %) and potassium acetate (154 mg, 1.57 mmol) in toluene (3 mL) was heated to 150° C. in a microwave reactor for 40 min. After cooling, the mixture was diluted with DCM (5 mL), washed with water, dried over MgSO₄, filtered, and concentrated under reduced pressure. The crude material was purified by column chromatography on silica gel eluting with a gradient of PE/EtOAc (9:1), to provide 69 mg (38%) of the desired product tert-butyl 6-(4,4,5,5-tetramethyl-1,3,2-dioxaborolan-2-yl)indoline-1-carboxylate (28B): ¹H NMR (300 MHz, CDCl₃) δ 7.41 (2H, m), 7.12 (1H, m), 3.96 (2H, t), 3.09 (2H, t), 1.57 (9H, s), 1.30 (12H, s).

Step 3: Preparation of ethyl 2-(1-(tert-butoxycarbonyl)indolin-6-yl)thiazole-4-carboxylate (28C)

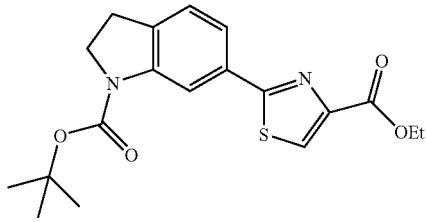

(28C)

A mixture of tert-butyl 6-(4,4,5,5-tetramethyl-1,3,2-dioxaborolan-2-yl)indoline-1-carboxylate (28B) (69 mg, 0.2 mmol), ethyl 2-bromothiazole-4-carboxylate (43 mg, 0.2 mmol), K₂CO₃ (69 mg, 0.5 mmol), tetrabutylammonium bromide (6.0 mg, 0.02 mmol) and dichlorobis(triphenylphosphine)palladium(II) (6.0 mg, 0.003 mmol) in 1,4-dioxane (6 mL) and water (1 mL) was heated to 90° C. for 24 hours. After cooling the mixture was extracted into DCM, washed with H₂O, dried over MgSO₄, filtered, and concentrated under reduced pressure. The crude material was purified by column chromatography on silica gel eluting with a gradient of PE/EtOAc (9:1), to provide 46 mg (61%) of the desired product ethyl 2-O-(tert-butoxycarbonyl)indolin-6-yl)thiazole-4-carboxylate (28C): ¹H NMR (300 MHz, CDCl₃) δ 8.13 (1H, s), 7.18 (1H, dd), 6.95 (1H, dd), 6.43 (1H, dd), 4.44 (2H, m), 3.99 (2H, m), 3.11 (1H, t), 2.97 (1H, t), 1.54 (9H, s), 1.45 (3H, t). LC/MS (APCI): m/z 375.0 (M+H).

Step 4: Preparation of ethyl 2-(indolin-6-yl)thiazole-4-carboxylate (28D)

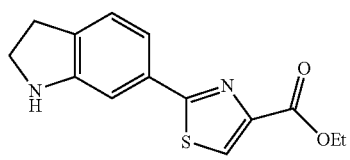

(28D)

To ethyl 2-(1-(tert-butoxycarbonyl)indolin-6-yl)thiazole-4-carboxylate (28C) (46 mg, 0.12 mmol) was added DCM (5 ml) and TFA (1 ml) and stirred for 2.5 hours. The mixture was concentrated under reduced pressure to provide 56 mg of the desired product ethyl 2-(indolin-6-yl)thiazole-4-carboxylate (28D): LC/MS (APCI): m/z 275.0 (M+H).

137

Step 5: Preparation of ethyl 2-(1-(benzo[d]thiazol-2-ylcarbamoyl)indolin-6-yl)thiazole-4-carboxylate (28E)

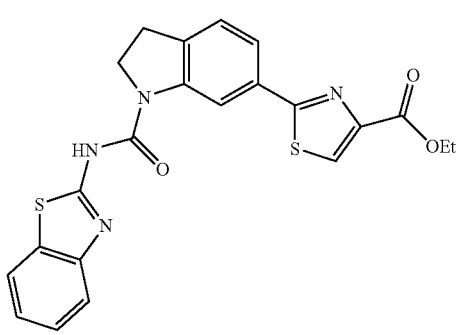

(28E)

A mixture of ethyl 2-(indolin-6-yl)thiazole-4-carboxylate (28D) (56 mg, 0.14 mmol), K$_2$CO$_3$ (22 mg, 0.16 mmol), and 4-nitrophenyl benzo[d]thiazol-2-ylcarbamate (19) (48 mg, 0.15 mmol) was heated to reflux in acetonitrile (3 mL) for 5.5 hours. The reaction mixture was cooled to rt and diluted in EtOAc (5 mL), washed with water, dried over MgSO$_4$, filtered, and concentrated under reduced pressure. The crude material was purified by column chromatography on silica gel eluting with a gradient of PE/EtOAc (1:1), to provide 22 mg (34%) of the desired product ethyl 2-(1-(benzo[d]thiazol-2-ylcarbamoyl)indolin-6-yl)thiazole-4-carboxylate (28E): $^1$H NMR (300 MHz, CDCl$_3$) δ 8.67 (1H, s), 8.12 (1H, s), 7.68 (2H, m), 7.52 (1H, m), 7.38 (1H, m), 7.25 (2H, m), 4.43 (2H, q), 4.22 (2H, m), 3.18 (2H, m) 1.45 (3H, t). LC/MS (APCI): m/z 451.1 (M+H).

Step 6: Preparation of title compound 2-(1-(benzo[d]thiazol-2-ylcarbamoyl)indolin-6-yl)thiazole-4-carboxylic acid (28).

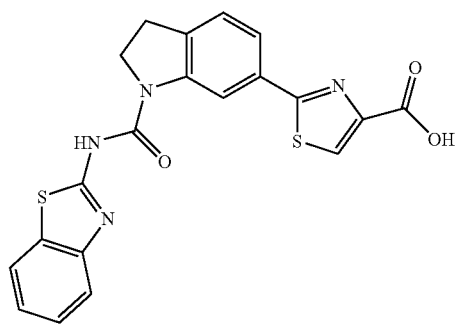

(28)

The title compound 2-(1-(benzo[d]thiazol-2-ylcarbamoyl) indolin-6-yl)thiazole-4-carboxylic acid (28) was prepared by the following procedure: A mixture of ethyl 2-(1-(benzo[d] thiazol-2-ylcarbamoyl)indolin-6-yl)thiazole-4-carboxylate (28E) (22 mg, 0.05 mmol) and LiOH (12 mg, 0.49 mmol) was stirred in MeOH (2 mL) and water (1 mL) for 20 h. The mixture was diluted with EtOAc (5 mL) and acidified with 1M HCl. The organic layer was isolated, washed with H$_2$O, dried over MgSO$_4$, filtered and concentrated under reduced pressure. The crude material was purified by HPLC, to provide 3.0 mg (14%) of the desired product 2-(1-(benzo[d] thiazol-2-ylcarbamoyl)indolin-6-yl)thiazole-4-carboxylic acid (28). LC/MS (APCI): m/z 423.1 (M+H), 844.8 (2M+1).

138

Example 29

Synthesis of 6-(1-(benzo[d]thiazol-2-ylcarbamoyl)-1,2,3,4-tetrahydroquinolin-7-yl)-3-phenylpicolinic acid (29)

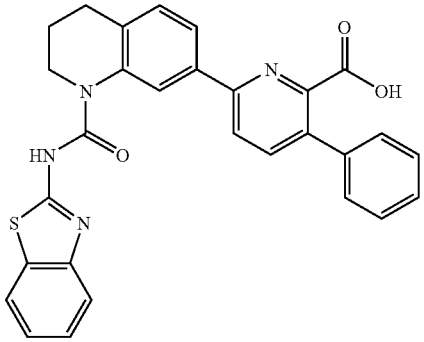

(29)

Step 1: Preparation of methyl 3-(benzyloxy)-6-bromopicolinate (29A)

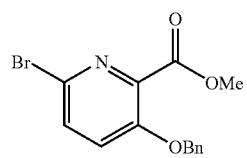

(29A)

Benzyl bromide (3.87 g, 22.6 mmol), was added to a suspension of methyl 6-bromo-3-hydroxypicolinate (5.00 g, 21.6 mmol) and K$_2$CO$_3$ (5.96 g, 43.1 mmol) in anhydrous DMF (40 mL). The reaction mixture was heated at 60° C. for 18 hours, cooled to rt, and poured into an ice/water mixture. After stirring for 2.5 hours, the precipitate was collected by filtration, washed with water, and dried to provide the desired product methyl 3-(benzyloxy)-6-bromopicolinate (29A).

Step 2: Preparation of methyl 3-(benzyloxy)-6-(1,2,3,4-tetrahydroquinolin-7-yl)picolinate (29B)

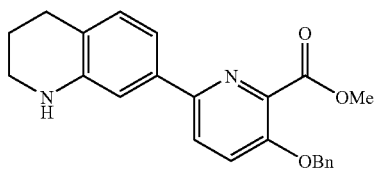

(29B)

To 7-(4,4,5,5-tetramethyl-1,3,2-dioxaborolan-2-yl)-1,2,3,4-tetrahydroquinoline (27B) (1.16 g, 4.48 mmol), methyl 3-(benzyloxy)-6-bromopicolinate (29A) (1.44 g, 4.48 mmol), K$_2$CO$_3$ (1.546 g, 11.2 mmol), tetrabutylammonium bromide (0.144 g, 0.45 mmol), and dichlorobis(triphenylphosphine)palladium(II) (126 mg, 0.18 mmol) was added 1,4-dioxane (30 mL) and water (15 mL). The reaction mixture was heated to 90° C. for 1.5 hours, cooled to rt, concentrated, diluted with EtOAc, washed sequentially with water, brine, dried over MgSO₄, filtered, and concentrated under reduced pressure. The crude material was precipitated from EtOAc/PE to provide the product methyl 3-(benzyloxy)-6-(1,2,3,4-tetrahydroquinolin-7-yl)picolinate (29B). Additional material was isolated from the filtrate by column chromatography on silica gel eluting with a gradient of PE:EtOAc 73:27-63:37, to provide the desired product (29B): ¹H NMR (300 MHz, CDCl₃) δ 7.67 (1H, d), 7.48-7.44 (2H, m), 7.43-7.31 (4H, m), 7.21 (1H, d), 7.16 (1H, dd), 7.01 (1H, d) 5.21 (2H, s), 3.98 (3H, s), 3.34 (2H, m), 2.79 (2H, t), 1.96 (2H, m).

Step 3: Preparation of tert-butyl 7-(5-(benzyloxy)-6-(methoxycarbonyl)pyridin-2-yl)-3,4-dihydroquinoline-1(2H)-carboxylate (29C)

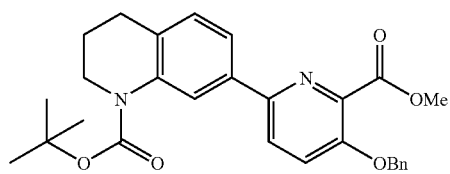

(29C)

A mixture of methyl 3-(benzyloxy)-6-(1,2,3,4-tetrahydroquinolin-7-yl)picolinate (29B) (3.41 g, 9.10 mmol) and di-tert-butyl dicarbonate (5.96 g, 27.3 mmol) was heated to 100° C. for 17 hours, cooled to rt, diluted with DCM, washed with water, dried over MgSO₄, filtered, and concentrated under reduced pressure. The crude material was purified by column chromatography on silica gel eluting with a gradient of PE:EtOAc 83:17-65:35 to provide the desired product tert-butyl 745-(benzyloxy)-6-(methoxycarbonyl)pyridin-2-yl)-3,4-dihydroquinoline-1(2H)-carboxylate (29C): ¹H NMR (300 MHz, CDCl₃) δ 8.27 (1H, d), 7.75 (1H, d), 7.58 (1H, dd), 7.49-7.30 (6H, m), 7.13 (1H, d), 5.23 (2H, s), 3.99 (3H, s), 3.73 (2H, m), 2.79 (2H, t), 1.94 (2H, m), 1.55 (9H, s).

Step 4: Preparation of tert-butyl 7-(5-hydroxy-6-(methoxycarbonyl)pyridin-2-yl)-3,4-dihydroquinoline-1(2H)-carboxylate (29D)

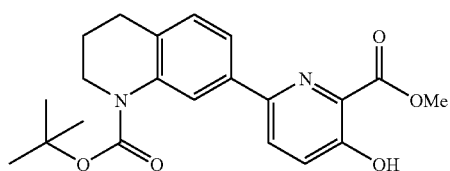

(29D)

To a solution of tert-butyl 7-(5-(benzyloxy)-6-(methoxycarbonyl)pyridin-2-yl)-3,4-dihydroquinoline-1(2H)-carboxylate (29C) (2.72 g, 5.74 mmol) in EtOAc (80 mL) and EtOH (80 mL) and glacial acetic acid (~30 drops) was added 10% Pd—C (420 mg). The reaction mixture was stirred under an atmosphere of hydrogen for 24 hrs, filtered through a bed of Celite, and concentrated to provide the desired product tert-butyl 7-(5-hydroxy-6-(methoxycarbonyl)pyridin-2-yl)-3,4-dihydroquinoline-1(2H)-carboxylate (29D): ¹H NMR (300 MHz, CDCl₃) δ 10.67 (1H, s), 8.30 (1H, d), 7.86 (1H, d), 7.56 (1H, dd), 7.42 (1H, d), 7.15 (1H, d), 4.05 (3H, s), 3.74 (2H, m), 2.80 (2H, t), 1.95 (2H, m), 1.56 (9H, s).

Step 5: Preparation of tert-butyl 7-(6-(methoxycarbonyl)-5-(trifluoromethylsulfonyloxy)pyridin-2-yl)-3,4-dihydroquinoline-1(2H)-carboxylate (29E)

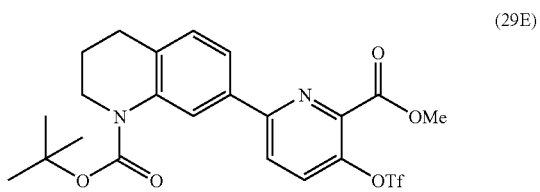

(29E)

Trifluoromethanesulfonic anhydride (1.93 g, 6.86 mmol) was added dropwise to tert-butyl 7-(5-hydroxy-6-(methoxycarbonyl)pyridin-2-yl)-3,4-dihydroquinoline-1(2H)-carboxylate (29D) (2.40 g, 6.23 mmol) and TEA (0.95 g, 9.35 mmol) in anhydrous DCM (25 mL) at 0° C. The reaction mixture was stirred at 0° C. for 1.5 hours, diluted with DCM, washed with 10% citric acid, dried over MgSO₄, filtered, and concentrated under reduced pressure. The crude material was purified by column chromatography on silica gel eluting with a gradient of PE:EtOAc 88:12-82:18 to provide tert-butyl 7-(6-(methoxycarbonyl)-5-(trifluoromethylsulfonyloxy)pyridin-2-yl)-3,4-dihydroquinoline-1(2H)-carboxylate (29E): ¹H NMR (300 MHz, CDCl₃) δ 8.40 (1H d), 7.95 (1H, d), 7.71 (1H, d), 7.66 (1H, dd), 7.19 (1H, d), 4.04 (3H, s), 3.75 (2H, m), 2.82 (2H, t), 1.96 (2H, m), 1.56 (9H, s).

Step 6: Preparation of methyl 6-(1,2,3,4-tetrahydroquinolin-7-yl)-3-(trifluoromethylsulfonyloxy)picolinate (29F)

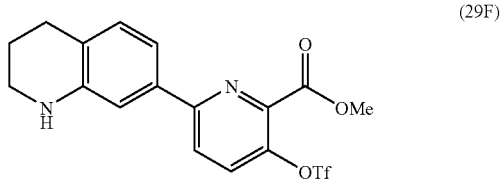

(29F)

Trifluoroacetic acid (18 mL) was added to tert-butyl 7-(6-(methoxycarbonyl)-5-(trifluoromethylsulfonyloxy)pyridin-2-yl)-3,4-dihydroquinoline-1(2H)-carboxylate (29E) (2.00 g, 3.9 mmol) in anhydrous DCM (25 mL). The reaction mixture was stirred at rt for 1.5 hours, concentrated under reduced pressure, diluted with DCM, and washed with saturated NaHCO₃. The aqueous phase was extracted with DCM. The combined organic phases were dried over MgSO₄, filtered, and concentrated under reduced pressure to provide the desired product methyl 6-(1,2,3,4-tetrahydroquinolin-7-yl)-3-(trifluoromethylsulfonyloxy)picolinate (29F) in sufficient purity for subsequent use. ¹H NMR (300 MHz, CDCl₃) δ 7.88 (1H d), 7.66 (1H, d), 7.39 (1H, d), 7.29 (1H, dd), 7.08 (1H, d), 4.03 (3H, s), 3.39 (2H, m), 2.83 (2H, t), 2.02 (2H, m).

Step 7: Preparation of tert-butyl 7-(6-(methoxycarbonyl)-5-phenylpyridin-2-yl)-3,4-dihydroquinoline-1(2H)-carboxylate (29G)

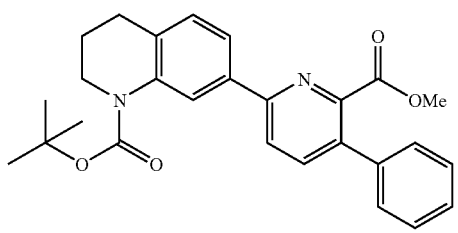
(29G)

Tert-butyl 7-(6-(methoxycarbonyl)-5-(trifluoromethylsulfonyloxy)pyridin-2-yl)-3,4-dihydroquinoline-1(2H)-carboxylate (29E) (40 mg, 0.077 mmol), phenylboronic acid (11 mg, 0.093 mmol, 1.2 eq), $K_2CO_3$ (27 mg, 0.19 mmol), tetrabutylammonium bromide (2.5 mg, 0.0077 mmol), and dichlorobis(triphenylphosphine)palladium(II) (2.2 mg, 0.003 mmol) in 1,4-dioxane (0.5 mL) and water (0.25 mL) was heated to 90° C. for 75 minutes, cooled to rt, diluted with EtOAc, washed with water, brine, dried over $MgSO_4$, filtered, and concentrated under reduced pressure. The crude material was purified by column chromatography on silica gel eluting with a gradient of PE:EtOAc 88:12-82:18, to provide the desired product tert-butyl 7-(6-(methoxycarbonyl)-5-phenylpyridin-2-yl)-3,4-dihydroquinoline-1(2H)-carboxylate (29G): $^1$H NMR (300 MHz, $CDCl_3$) δ 8.41 (1H, d), 7.88 (1H, d), 7.80 (1H, d), 7.71 (1H, dd), 7.48-7.37 (5H, m), 7.19 (1H, d), 3.80-3.70 (5H, m), 2.82 (2H, t), 1.96 (2H, m), 1.57 (9H, s).

Step 8: Preparation of methyl 3-phenyl-6-(1,2,3,4-tetrahydroquinolin-7-yl)picolinate (29H)

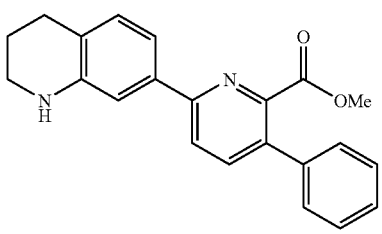
(29H)

Methyl 3-phenyl-6-(1,2,3,4-tetrahydroquinolin-7-yl)picolinate (29H) was prepared following a similar procedure as that described in example 29, except tert-butyl 7-(6-(methoxycarbonyl)-5-phenylpyridin-2-yl)-3,4-dihydroquinoline-1(2H)-carboxylate (29G) was used instead of tert-butyl 7-(6-(methoxycarbonyl)-5-(trifluoromethylsulfonyloxy)pyridin-2-yl)-3,4-dihydroquinoline-1(2H)-carboxylate (29E) in step 6 of example 29.

Step 9: Preparation of methyl 6-(1-(benzo[d]thiazol-2-ylcarbamoyl)-1,2,3,4-tetrahydroquinolin-7-yl)-3-phenylpicolinate (29I)

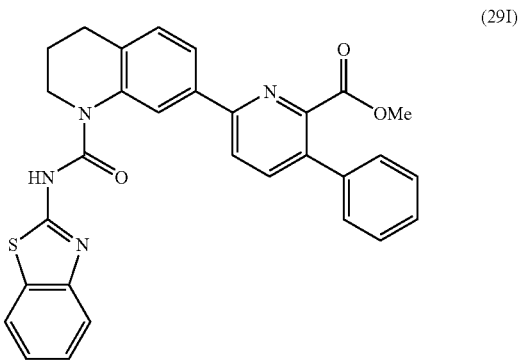
(29I)

A mixture of methyl 3-phenyl-6-(1,2,3,4-tetrahydroquinolin-7-yl)picolinate (29H) (17 mg, 0.049 mmol) and 4-nitrophenyl benzo[d]thiazol-2-ylcarbamate (19) (15.5 mg, 0.049 mmol) in anhydrous $CH_3CN$ (0.8 mL) was heated to reflux for 6 hours, cooled to rt, concentrated under reduced pressure, and the crude material was purified by column chromatography on silica gel eluting with a gradient of PE:EtOAc 72:28-55:45, to provide the desired product methyl 6-(1-(benzo[d]thiazol-2-ylcarbamoyl)-1,2,3,4-tetrahydroquinolin-7-yl)-3-phenylpicolinate (29I): $^1$H NMR (300 MHz, $CDCl_3$) δ 8.23 (1H, d), 8.13 (1H, d), 7.85-7.76 (3H, m), 7.66 (1H, d), 7.48-7.35 (4H, m), 7.34-7.28 (2H, m), 6.89 (1H, d), 3.98 (2H, t), 3.71 (3H, s), 2.85 (2H, t), 2.09 (2H, m).

Step 10: Preparation of title compound 6-(1-(benzo[d]thiazol-2-ylcarbamoyl)-1,2,3,4-tetrahydroquinolin-7-yl)-3-phenylpicolinic acid (29)

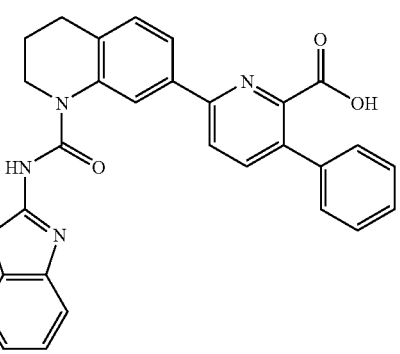
(29)

The title compound 6-(1-(benzo[d]thiazol-2-ylcarbamoyl)-1,2,3,4-tetrahydroquinolin-7-yl)-3-phenylpicolinic acid (29) was prepared by the following procedure: To methyl 6-(1-(benzo[d]thiazol-2-ylcarbamoyl)-1,2,3,4-tetrahydroquinolin-7-yl)-3-phenylpicolinate (29I) (23 mg, 0.044 mmol) in MeOH (0.55 mL) and water (0.11 mL) was added an aqueous solution of LiOH (0.066 mL of 2.0 M, 0.13 mmol). The reaction mixture was stirred at rt for 15 hours, concentrated under reduced pressure to remove MeOH and diluted with water. The pH was adjusted to ~4 with 2 M HCl, and the resulting precipitate was isolated by filtration and washed with water. The crude material was purified by column chromatography on silica gel eluting with a gradient of DCM:MeOH 98:2-92:8, to provide the desired product 6-(1-(benzo[d]thiazol-2-ylcarbamoyl)-1,2,3,4-tetrahydroquinolin-7-yl)-3-phenylpicolinic acid (29): MS (ESI(+)): m/z 507.1 (M+H).

Example 30

Synthesis of: 6-(1-(benzo[d]thiazol-2-ylcarbamoyl)-1,2,3,4-tetrahydroquinolin-7-yl)-3-(4-tert-butylphenyl)picolinic acid (30)

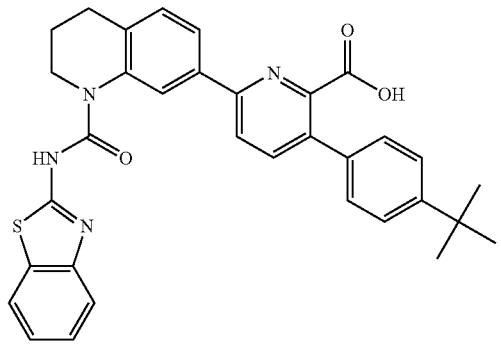

(30)

The title compound 6-(1-(benzo[d]thiazol-2-ylcarbamoyl)-1,2,3,4-tetrahydroquinolin-7-yl)-3-(4-tert-butylphenyl)picolinic acid (30) was prepared by the following procedure: 6-(1-(benzo[d]thiazol-2-ylcarbamoyl)-1,2,3,4-tetrahydroquinolin-7-yl)-3-(4-tert-butylphenyl)picolinic acid (30) was prepared following a similar procedure as that described in example 29, except 4-tert-butylphenylboronic acid was used instead of phenylboronic acid in step 7 of example 29. $^1$H NMR (300 MHz, DMSO) δ 8.43 (1H, s), 7.94-7.85 (2H, m), 7.81 (1H, d), 7.76 (1H, dd), 7.55-7.42 (5H, m), 7.37 (1H, dt), 7.28 (1H, d), 7.19 (1H, dt), 3.96 (2H, t), 2.83 (2H, t), 1.94 (2H, m), 1.32 (9H, s). MS (ESI(+)): m/z 563.2 (M+H).

Example 31

Synthesis of: 6-(1-(benzo[d]thiazol-2-ylcarbamoyl)-1,2,3,4-tetrahydroquinolin-7-yl)-3-(naphthalen-2-yl)picolinic acid (31)

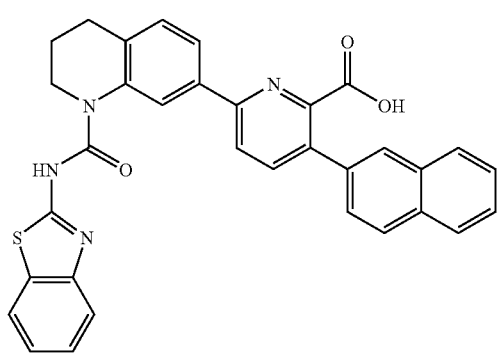

(31)

The title compound 6-(1-(benzo[d]thiazol-2-ylcarbamoyl)-1,2,3,4-tetrahydroquinolin-7-yl)-3-(naphthalen-2-yl)picolinic acid (31) was prepared by the following procedure: 6-(1-(benzo[d]thiazol-2-ylcarbamoyl)-1,2,3,4-tetrahydroquinolin-7-yl)-3-(naphthalen-2-yl)picolinic acid (31) was prepared following a similar procedure as that described in example 29, except 2-naphthaleneboronic acid was used instead of phenylboronic acid in step 7 of example 29. $^1$H NMR (300 MHz, DMSO) δ 8.47 (1H, s), 8.15-7.95 (5H, m), 7.82 (2H, m), 7.65-7.55 (3H, m), 7.48 (1H, d), 7.40-7.27 (2H, m), 7.26-7.17 (2H, m), 3.98 (2H, t), 2.85 (2H, t), 1.96 (2H, m). MS (ESI(+)) m/z 557.0 (M+H).

Example 32

Synthesis of: 6-(1-(benzo[d]thiazol-2-ylcarbamoyl)-1,2,3,4-tetrahydroquinolin-7-yl)-6'44-methylpiperazin-1-yl)-3,3'-bipyridine-2-carboxylic acid (32)

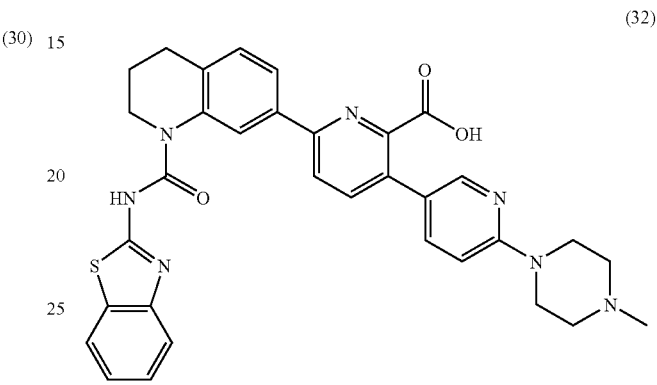

(32)

The title compound 6-(1-(benzo[d]thiazol-2-ylcarbamoyl)-1,2,3,4-tetrahydroquinolin-7-yl)-6'-(4-methylpiperazin-1-yl)-3,3'-bipyridine-2-carboxylic acid (32) was prepared by the following procedure: 6-(1-(benzo[d]thiazol-2-ylcarbamoyl)-1,2,3,4-tetrahydroquinolin-7-yl)-6'-(4-methylpiperazin-1-yl)-3,3'-bipyridine-2-carboxylic acid (32) was prepared following a similar procedure as that described in example 29, except 2-(4-methylpiperazin-1-yl)pyridine-5-boronic acid pinacol ester was used instead of phenylboronic acid in step 7 of example 29. $^1$H NMR (300 MHz, DMSO) δ 8.52 (1H, s), 8.37 (1H, d), 7.86 (1H, dd), 7.76-7.62 (4H, m), 7.46 (1H, d), 7.30 (1H, dt), 7.21 (1H, d), 7.12 (1H, dt), 6.82 (1H, d), 3.96 (2H, t), 3.60-3.40 (8H, m), 2.81 (2H, t), 2.22 (3H, s), 1.92 (2H, m). MS (ESI(+)): m/z 606.0 (M+H).

Example 33

Synthesis of: 6-(1-(benzo[d]thiazol-2-ylcarbamoyl)-1,2,3,4-tetrahydroquinolin-7-yl)-3-(1H-indol-5-yl)picolinic acid (33)

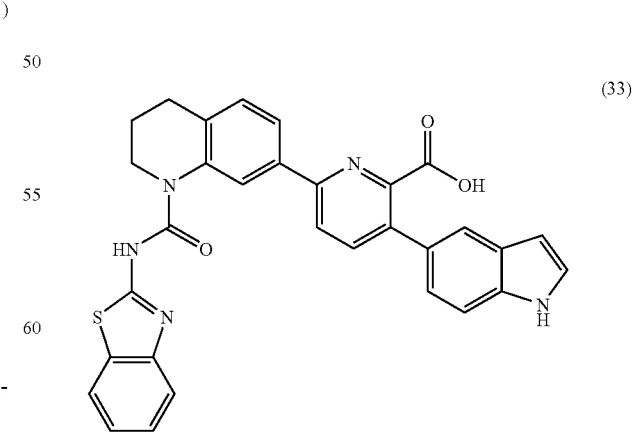

(33)

The title compound 6-(1-(benzo[d]thiazol-2-ylcarbamoyl)-1,2,3,4-tetrahydroquinolin-7-yl)-3-(1H-indol-5-yl)picolinic acid (33) was prepared by the following procedure: 6-(1-(benzo[d]thiazol-2-ylcarbamoyl)-1,2,3,4-tetrahydroquinolin-7-yl)-3-(1H-indol-5-yl)picolinic acid (33) was prepared following a similar procedure as that described in example 29, except 1-tert-butoxycarbonylindole-5-boronic acid pinacol ester was used instead of phenylboronic acid in step 7 of example 29. $^1$H NMR (300 MHz, DMSO) δ 11.15 (1H, s), 8.45 (1H, s), 7.90-7.71 (5H, m), 7.50-7.16 (7H, m), 6.46 (1H, s), 3.96 (2H, m), 2.83 (2H, t), 1.95 (2H, m). MS (ESI(+)): m/z 546.0 (M+H).

Example 34

Synthesis of 3-(3-((3-aminophenoxy)methyl)phenyl)-6-(1-(benzo[d]thiazol-2-ylcarbamoyl)-1,2,3,4-tetrahydroquinolin-7-yl)picolinic acid (34)

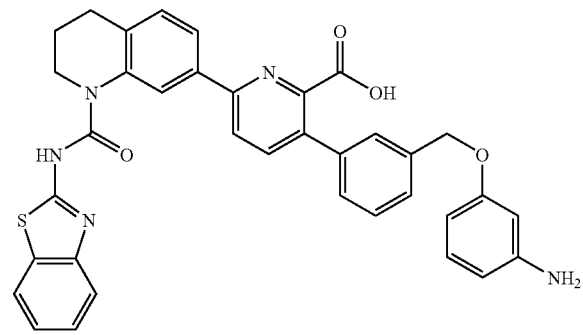

(34)

Step 1: Preparation of tert-butyl 3-(3-bromobenzyloxy)phenylcarbamate (34A)

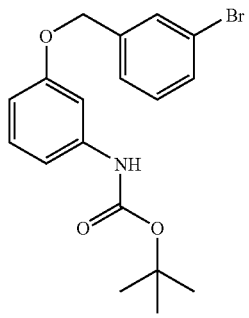

(34A)

To tert-butyl 3-hydroxyphenylcarbamate (0.245 g, 1.17 mmol), K$_2$CO$_3$ (404 mg, 2.93 mmol), and 3-bromobenzyl bromide (322 mg, 1.29 mmol) was added anhydrous DMF (5 mL). The reaction mixture was heated to 60° C. for 18 hours. The reaction mixture was cooled to rt, poured into water and the resulting precipitate was collected by filtration and washed with water to provide the desired product tert-butyl 3-(3-bromobenzyloxy)phenylcarbamate (34A) with sufficient purity for subsequent use.

Step 2: Preparation of tert-butyl 3-(3-(4,4,5,5-tetramethyl-1,3,2-dioxaborolan-2-yl)benzyloxy)phenylcarbamate (34B)

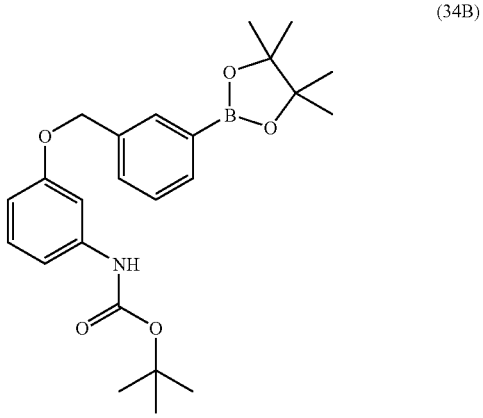

(34B)

Tert-butyl 3-(3-(4,4,5,5-tetramethyl-1,3,2-dioxaborolan-2-yl)benzyloxy)phenylcarbamate (348) was prepared following a similar procedure as that described in example 29, except tent-butyl 3-(3-bromobenzyloxy)phenylcarbamate (34A) was used instead of 7-bromo-1,2,3,4-tetrahydroquinoline (1E) in step 2 of example 27.

Step 3: Preparation of methyl 3-(3-((3-(tert-butoxycarbonylamino)phenoxy)methyl)phenyl)-6-(1,2,3,4-tetrahydroquinolin-7-yl)picolinate (34C)

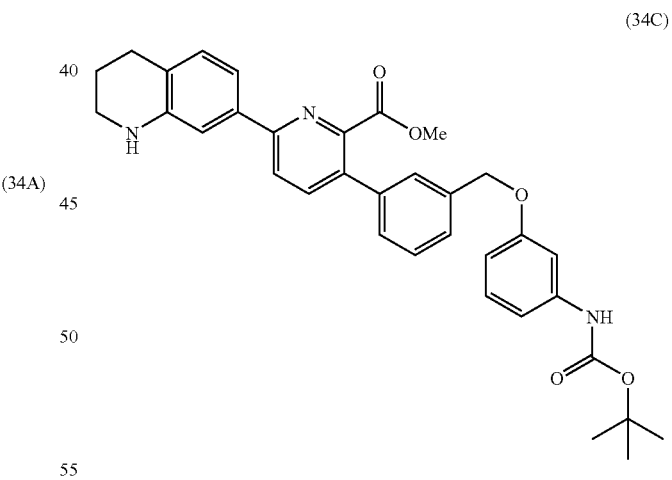

(34C)

3-(3-((3-(Tert-butoxycarbonylamino)phenoxy)methyl) phenyl)-6-(1,2,3,4-tetrahydroquinolin-7-yl)picolinate (34C) was prepared following a similar procedure as that described in example 29, except methyl 6-(1,2,3,4-tetrahydroquinolin-7-yl)-3-(trifluoromethylsulfonyloxy)picolinate (29F) was used instead of tert-butyl 7-(6-(methoxycarbonyl)-5-(trifluoromethylsulfonyloxy)pyridin-2-yl)-3,4-dihydroquinoline-1(2H)-carboxylate (29E), and tert-butyl 3-(3-(4,4,5,5-tetramethyl-1,3,2-dioxaborolan-2-yl)benzyloxy)phenylcarbamate (34B) was used instead of phenylboronic acid in step 7 of example 29.

Step 4: Preparation of methyl 6-(1-(benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinate (34D)

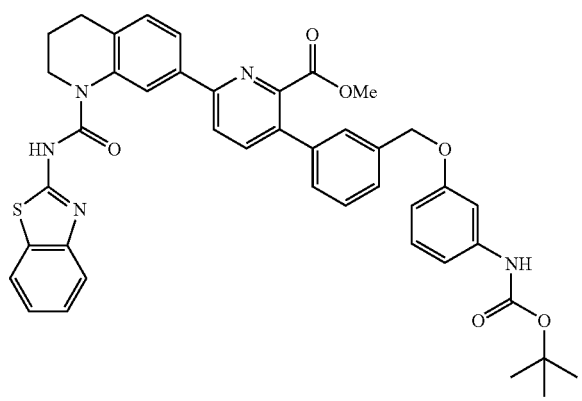

(34D)

Methyl 6-(1-(benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinate (34D) was prepared following a similar procedure as that described in example 29, except methyl 3-(3-((3-(tert-butoxycarbonylamino)phenoxy)methyl)phenyl)-6-(1,2,3,4-tetrahydroquinolin-7-yl)picolinate (34C) was used instead of methyl 3-phenyl-6-(1,2,3,4-tetrahydroquinolin-7-yl)picolinate (29H) in step 9 of example 29.

Step 5: Preparation of 6-(1-(benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinic acid (34E)

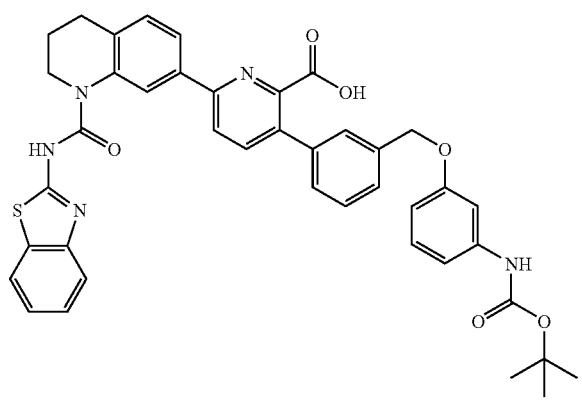

(34E)

6-(1-(Benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinic acid (34E) was prepared following a similar procedure as that described in example 29, except methyl 6-(1-(benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinate (34D) was used instead of methyl 6-(1-(benzo[d]thiazol-2-ylcarbamoyl)-1,2,3,4-tetrahydroquinolin-7-yl)-3-phenylpicolinate (29I) in step 10 of example 29.

Step 6: Preparation of title compound 3-(3-((3-aminophenoxy)methyl)phenyl)-6-(1-(benzo[d]thiazol-2-ylcarbamoyl)-1,2,3,4-tetrahydroquinolin-7-yl)picolinic acid (34)

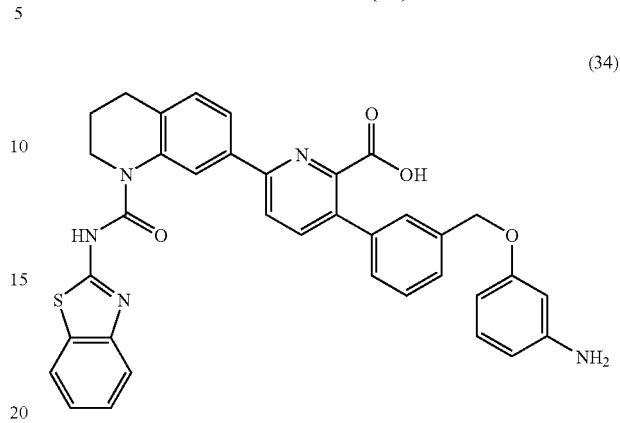

(34)

The title compound 3-(3-((3-aminophenoxy)methyl)phenyl)-6-(1-(benzo[d]thiazol-2-ylcarbamoyl)-1,2,3,4-tetrahydroquinolin-7-yl)picolinic acid (34) was prepared by the following procedure: Trifluoroacetic acid (0.5 mL) was added to a solution of 6-(1-(benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinic acid (34E) (0.016 g, 0.022 mmol) in anhydrous DCM (0.75 mL). The reaction mixture was stirred at rt for 1.5 hours, concentrated under reduced pressure, and the crude material triturated in diethyl ether to provide the desired product 3-(3-((3-aminophenoxy)methyl)phenyl)-6-(1-(benzo[d]thiazol-2-ylcarbamoyl)-1,2,3,4-tetrahydroquinolin-7-yl)picolinic acid (34): $^1$H NMR (300 MHz, DMSO) δ 8.43 (1H, s, br), 8.08 (1H, d), 7.99 (1H, d), 7.85-7.77 (2H, m), 7.67 (1H, s), 7.55-7.41 (4H, m), 7.37 (1H, t), 7.31 (1H, d), 7.22 (1H, t), 7.12 (1H, t), 6.59-7.50 (2H, m), 6.47 (1H, d), 5.11 (2H, s), 3.97 (2H, t), 2.84 (2H, t), 1.96 (2H, m). MS (ESI(+)) m/z 628.1 (M+H).

Example 35

Synthesis of: 6-(1-(benzo[d]thiazol-2-ylcarbamoyl)-1,2,3,4-tetrahydroquinolin-7-yl)-3-(1-benzyl-1H-pyrazol-4-yl)picolinic acid (35)

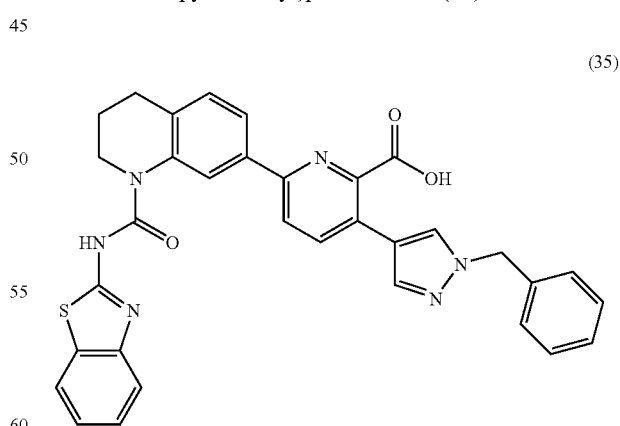

(35)

The title compound 6-(1-(benzo[d]thiazol-2-ylcarbamoyl)-1,2,3,4-tetrahydroquinolin-7-yl)-3-(1-benzyl-1H-pyrazol-4-yl)picolinic acid (35) was prepared by the following procedure: 6-(1-(benzo[d]thiazol-2-ylcarbamoyl)-1,2,3,4-tetrahydroquinolin-7-yl)-3-(1-benzyl-1H-pyrazol-4-yl)picolinic acid (35) was prepared following a similar procedure as that described in example 29, except methyl 6-(1,2,3,4- tetrahydroquinolin-7-yl)-3-(trifluoromethylsulfonyloxy)picolinate (29F) was used instead of tert-butyl 7-(6-(methoxycarbonyl)-5-(trifluoromethylsulfonyloxy)pyridin-2-yl)-3,4-dihydroquinoline-1(2H)-carboxylate (29E), and 1-benzyl-1H-pyrazole-4-boronic acid pinacol ester was used instead of phenylboronic acid in step 7 of example 29. $^1$H NMR (300 MHz, DMSO) δ 8.38 (1H, s, br), 8.19 (1H, s), 8.04 (1H, d), 7.95 (1H, d), 7.85-7.78 (2H, m), 7.75 (1H, dd), 7.47 (1H, d, br), 7.40-7.18 (8H, m), 5.38 (2H, s), 3.95 (2H, t), 2.82 (2H, t), 1.94 (2H, m). MS (ESI(+)): m/z 587.1 (M+H).

Example 36

Synthesis of: 6-(1-(benzo[d]thiazol-2-ylcarbamoyl)-1,2,3,4-tetrahydroquinolin-7-yl)-3-o-tolylpicolinic acid (36)

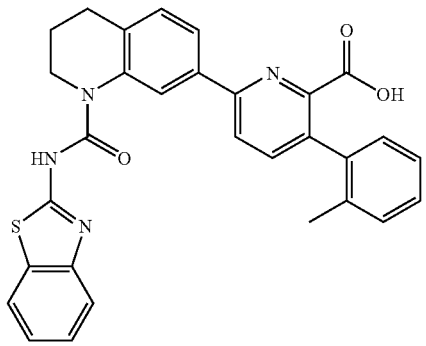

(36)

The title compound 6-(1-(benzo[d]thiazol-2-ylcarbamoyl)-1,2,3,4-tetrahydroquinolin-7-yl)-3-o-tolylpicolinic acid (36) was prepared by the following procedure: 6-(1-(benzo[d]thiazol-2-ylcarbamoyl)-1,2,3,4-tetrahydroquinolin-7-yl)-3-o-tolylpicolinic acid (36) was prepared following a similar procedure as that described in example 29, except methyl 6-(1,2,3,4-tetrahydroquinolin-7-yl)-3-(trifluoromethylsulfonyloxy)picolinate (29F) was used instead of tert-butyl 7-(6-(methoxycarbonyl)-5-(trifluoromethylsulfonyloxy)pyridin-2-yl)-3,4-dihydroquinoline-1(2H)-carboxylate (29E), and 2-methylphenylboronic acid was used instead of phenylboronic acid in step 7 of example 29. $^1$H NMR (300 MHz, DMSO) δ 8.45 (1H, s, br), 8.05 (1H, d), 7.86-7.78 (3H, m), 7.47 (1H, d, br), 7.37 (1H, dt), 7.33-7.18 (5H, m), 7.14 (1H, d), 3.98 (2H, t), 2.85 (2H, t), 2.13 (3H, s), 1.96 (2H, m). MS (ESI(+)): m/z 521.1 (M+H).

Example 37

Synthesis of 6-(1-(benzo[d]thiazol-2-ylcarbamoyl)-1,2,3,4-tetrahydroquinolin-7-yl)-3-(2-methyl-4-oxo-3,4-dihydroquinazolin-6-yl)picolinic acid (37)

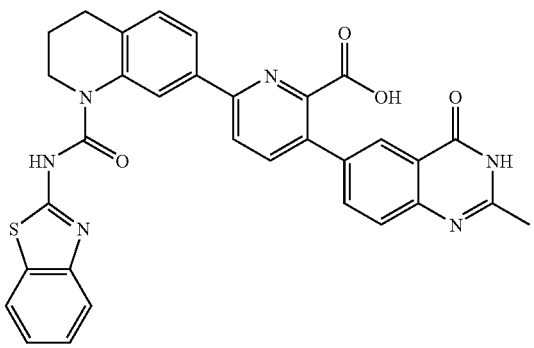

(37)

Step 1: Preparation of N-acetyl-N-(4-bromo-2-cyanophenyl)acetamide (37A)

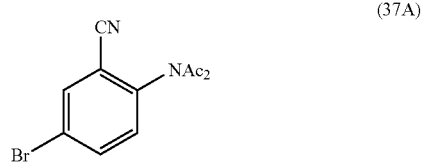

(37A)

4-Dimethylaminopyridine (6.2 mg, 0.05 mmol) was added to a solution of 2-amino-5-bromobenzonitrile (50 mg, 0.25 mmol) in pyridine (1 mL) and acetic anhydride (0.26 mL). The reaction mixture was stirred at rt for 16 hours, concentrated, diluted with EtOAc, washed with 1 M HCl, saturated NaHCO$_3$, dried over MgSO$_4$, filtered, and concentrated under reduced pressure. The crude material was purified by column chromatography on silica gel eluting with PE:EtOAc 3:1 to provide the desired product N-acetyl-N-(4-bromo-2-cyanophenyl)acetamide (37A).

Step 2: Preparation of N-(2-cyano-4-(4,4,5,5-tetramethyl-1,3,2-dioxaborolan-2-yl)phenyl)acetamide (37B)

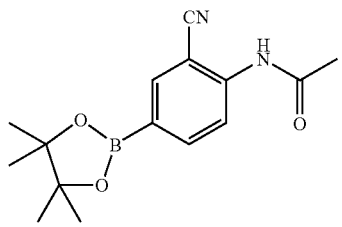

(37B)

N-(2-cyano-4-(4,4,5,5-tetramethyl-1,3,2-dioxaborolan-2-yl)phenyl)acetamide (37B) was prepared following a similar procedure as that described in example 29, except N-acetyl-N-(4-bromo-2-cyanophenyl)acetamide (37A) was used instead of 7-bromo-1,2,3,4-tetrahydroquinoline (1E) in step 2 of example 27.

Step 3: Preparation of methyl 3-(4-acetamido-3-cyanophenyl)-6-(1,2,3,4-tetrahydroquinolin-7-yl)picolinate (37C)

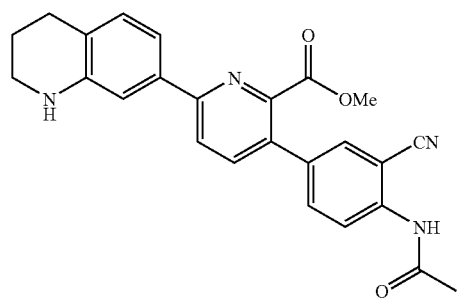

(37C)

Methyl 3-(4-acetamido-3-cyanophenyl)-6-(1,2,3,4-tetrahydroquinolin-7-yl)picolinate (37C) was prepared following a similar procedure as that described in example 29, except methyl 6-(1,2,3,4-tetrahydroquinolin-7-yl)-3-(trifluoromethylsulfonyloxy)picolinate (29F) was used instead of tert-butyl 7-(6-(methoxycarbonyl)-5-(trifluoromethylsulfonyloxy)pyridin-2-yl)-3,4-dihydroquinoline-1(2H)-carboxylate (29E), and N-(2-cyano-4-(4,4,5,5-tetramethyl-1,3,2-dioxaborolan-2-yl)phenyl)acetamide (37B) was used instead of phenylboronic acid in step 7 of example 29.

Step 4: Preparation of methyl 3-(4-acetamido-3-cyanophenyl)-6-(1-(benzo[d]thiazol-2-ylcarbamoyl)-1,2,3,4-tetrahydroquinolin-7-yl)picolinate (37D)

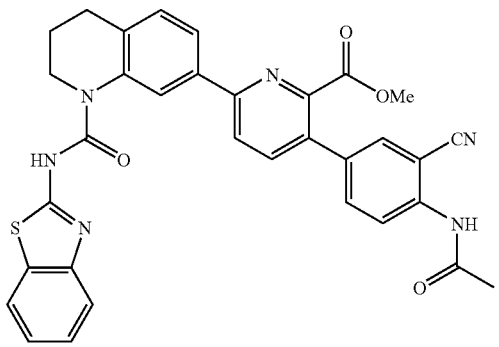
(37D)

Methyl 3-(4-acetamido-3-cyanophenyl)-6-(1-(benzo[d]thiazol-2-ylcarbamoyl)-1,2,3,4-tetrahydroquinolin-7-yl)picolinate (37D) was prepared following a similar procedure as that described in example 29, except methyl 3-(4-acetamido-3-cyanophenyl)-6-(1,2,3,4-tetrahydroquinolin-7-yl)picolinate (37C) was used instead of methyl 3-phenyl-6-(1,2,3,4-tetrahydroquinolin-7-yl)picolinate (29H) in step 9 of example 29.

Step 5: Preparation of title compound 6-(1-(benzo[d]thiazol-2-ylcarbamoyl)-1,2,3,4-tetrahydroquinolin-7-yl)-3-(2-methyl-4-oxo-3,4-dihydroquinazolin-6-yl)picolinic acid (37)

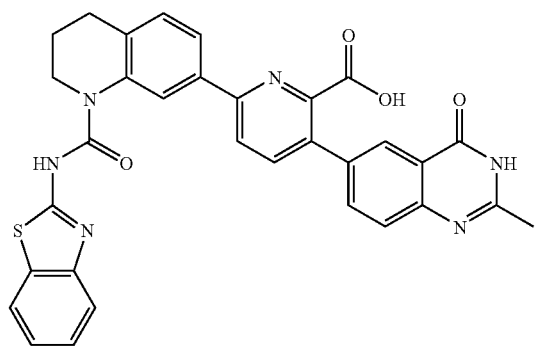
(37)

The title compound 6-(1-(benzo[d]thiazol-2-ylcarbamoyl)-1,2,3,4-tetrahydroquinolin-7-yl)-3-(2-methyl-4-oxo-3,4-dihydroquinazolin-6-yl)picolinic acid (37) was prepared by the following procedure: 6-(1-(benzo[d]thiazol-2-ylcarbamoyl)-1,2,3,4-tetrahydroquinolin-7-yl)-3-(2-methyl-4-oxo-3,4-dihydroquinazolin-6-yl)picolinic acid (37) was prepared following a similar procedure as that described in example 29, except methyl 3-(4-acetamido-3-cyanophenyl)-6-(1-(benzo[d]thiazol-2-ylcarbamoyl)-1,2,3,4-tetrahydroquinolin-7-yl)picolinate (37d) was used instead of methyl 6-(1-(benzo[d]thiazol-2-ylcarbamoyl)-1,2,3,4-tetrahydroquinolin-7-yl)-3-phenylpicolinate (29I) in step 10 of example 29 and the reaction mixture was heated to 50° C. for 4 days. MS (ESI(+)): m/z 589.0 (M+H).

Example 38

Synthesis of: 6-(1-(benzo[d]thiazol-2-ylcarbamoyl)-1,2,3,4-tetrahydroquinolin-7-yl)-3-(3-(methylsulfonyl)phenyl)picolinic acid (38)

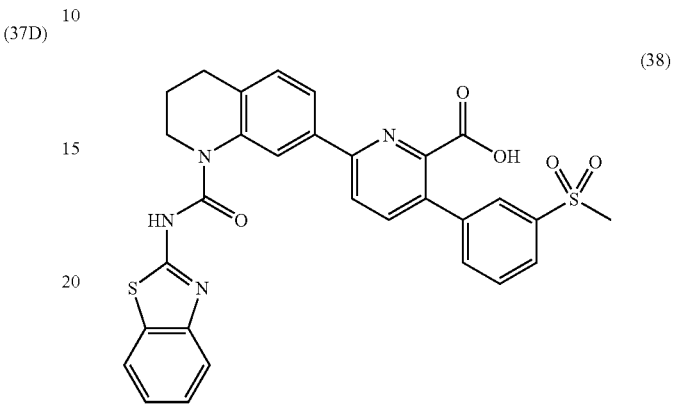
(38)

The title compound 6-(1-(benzo[d]thiazol-2-ylcarbamoyl)-1,2,3,4-tetrahydroquinolin-7-yl)-3-(3-(methylsulfonyl)phenyl)picolinic acid (38) was prepared by the following procedure: 6-(1-(benzo[d]thiazol-2-ylcarbamoyl)-1,2,3,4-tetrahydroquinolin-7-yl)-3-(3-(methylsulfonyl)phenyl)picolinic acid (38) was prepared following a similar procedure as that described in example 29, except methyl 6-(1,2,3,4-tetrahydroquinolin-7-yl)-3-(trifluoromethylsulfonyloxy)picolinate (29F) was used instead of tent-butyl 7-(6-(methoxycarbonyl)-5-(trifluoromethylsulfonyloxy)pyridin-2-yl)-3,4-dihydroquinoline-1(2H)-carboxylate (29E), and 3-(methylsulfonyl)phenylboronic acid was used instead of phenylboronic acid in step 7 of example 29. $^1$H NMR (300 MHz, DMSO) δ 8.47 (1H, s), 8.07-8.00 (3H, m), 7.95 (1H, dt), 7.89 (1H, d), 7.84-7.79 (2H, m), 7.74 (1H, t), 7.48 (1H, d), 7.37 (1H, dt), 7.30 (1H, d), 7.22 (1H, dt), 3.97 (2H, t), 3.26 (3H, s), 2.84 (2H, t), 1.95 (2H, m). MS (ESI(+)): m/z 585.0 (M+H).

Example 39

Synthesis of: 6-(1-(benzo[d]thiazol-2-ylcarbamoyl)-1,2,3,4-tetrahydroquinolin-7-yl)-3-(2-(3-(dimethylamino)phenoxy)ethoxy)picolinic acid (39)

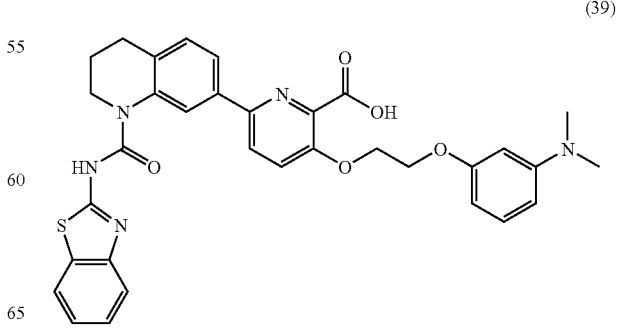
(39)

Step 1: Preparation of 2-(3-(dimethylamino)phenoxy)ethyl acetate (39A)

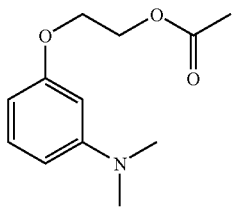

(39A)

2-Bromoethyl acetate (1.34 g, 4.01 mmol) was added to a suspension of 3-(dimethylamino)phenol (0.50 g, 3.64 mmol) and K$_2$CO$_3$ (1.5 g, 10.8 mmol) in anhydrous DMF (3 mL). The reaction mixture was heated to 80° C. for 18 hours, cooled to rt, diluted with water, extracted with DCM. The organic phases were washed with brine, dried over MgSO$_4$, filtered, and concentrated under reduced pressure. The crude material was purified by column chromatography on silica gel eluting with a gradient of PE:EtOAc 90:10-80:20, to provide the desired compound 2-(3-(dimethylamino)phenoxy)ethyl acetate (39A).

Step 2: Preparation of 2-(3-(dimethylamino)phenoxy)ethanol (39B)

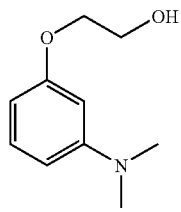

(39B)

A catalytic amount of sodium methoxide (enough to insure a basic solution) was added to a solution of 2-(3-(dimethylamino)phenoxy)ethyl acetate (39A) (0.545 g, 2.44 mmol) in anhydrous MeOH (7 mL). The reaction mixture was stirred at rt for 2.5 hours before a small amount of acidic resin (Dowex 50WX8-200) was added. The reaction mixture was filtered, concentrated under reduced pressure and the crude material was purified by column chromatography on silica gel eluting with a gradient of PE:EtOAc 66:34-50:50, to provide the desired compound 2-(3-(dimethylamino)phenoxy)ethanol (39B).

Step 3: Preparation of methyl 6-bromo-3-(2-(3-(dimethylamino)phenoxy)ethoxy)picolinate (39C)

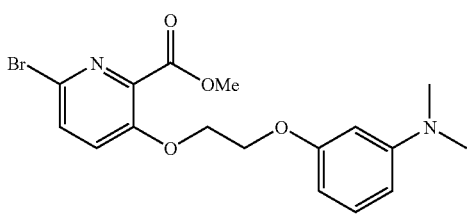

(39C)

Polystyrene bound PPh$_3$ (0.77 g at 1 mmol/g, 0.77 mmol, 1.5 eq) was added to a solution of methyl 6-bromo-3-hydroxypicolinate (0.119 g, 0.51 mmol) and 2-(3-(dimethylamino)phenoxy)ethanol (39B) (0.093 g, 0.51 mmol) in dry DCM (5 mL). To this was added diethyl azodicarboxylate (0.134 mg, 0.77 mmol) dropwise, and the reaction mixture was stirred at rt for 4 hours, filtered to remove the resin, and concentrated under reduced pressure. The crude material was purified by column chromatography on silica gel eluting with a gradient of PE:EtOAc 75:25-60:40, to provide the desired product methyl 6-bromo-3-(2-(3-(dimethylamino)phenoxy)ethoxy)picolinate (39C).

Step 4: Preparation of methyl 3-(2-(3-(dimethylamino)phenoxy)ethoxy)-6-(1,2,3,4-tetrahydroquinolin-7-yl)picolinate (39D)

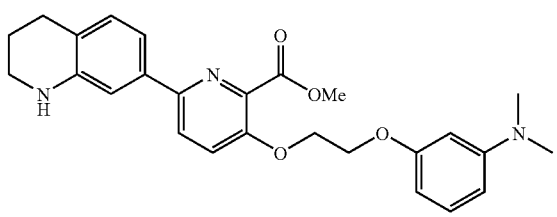

(39D)

Methyl 3-(2-(3-(dimethylamino)phenoxy)ethoxy)-6-(1,2,3,4-tetrahydroquinolin-7-yl)picolinate (39D) was prepared following a similar procedure as that described in example 29, except methyl 6-bromo-3-(2-(3-(dimethylamino)phenoxy)ethoxy)picolinate (39C) was used instead of 3-(benzyloxy)-6-bromopicolinate (29A) in step 2 of example 29.

Step 5: Preparation of methyl 6-(1-(benzo[d]thiazol-2-ylcarbamoyl)-1,2,3,4-tetrahydroquinolin-7-yl)-3-(2-(3-(dimethylamino)phenoxy)ethoxy)picolinate (39E)

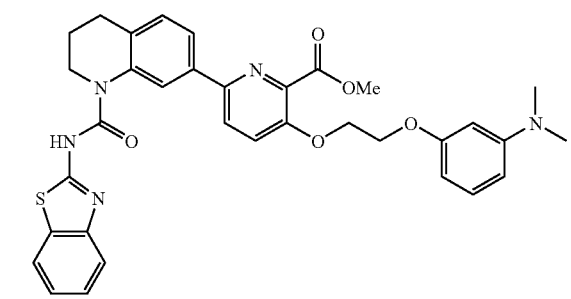

(39E)

Methyl 6-(1-(benzo[d]thiazol-2-ylcarbamoyl)-1,2,3,4-tetrahydroquinolin-7-yl)-3-(2-(3-(dimethylamino)phenoxy)ethoxy)picolinate (39E) was prepared following a similar procedure as that described in example 29, except methyl 3-(2-(3-(dimethylamino)phenoxy)ethoxy)-6-(1,2,3,4-tetrahydroquinolin-7-yl)picolinate (39D) was used instead of methyl 3-phenyl-6-(1,2,3,4-tetrahydroquinolin-7-yl)picolinate (29H) in step 9 of example 29.

Step 6: Preparation of title compound 6-(1-(benzo[d]thiazol-2-ylcarbamoyl)-1,2,3,4-tetrahydroquinolin-7-yl)-3-(2-(3-(dimethylamino)phenoxy)ethoxy)picolinic acid (39)

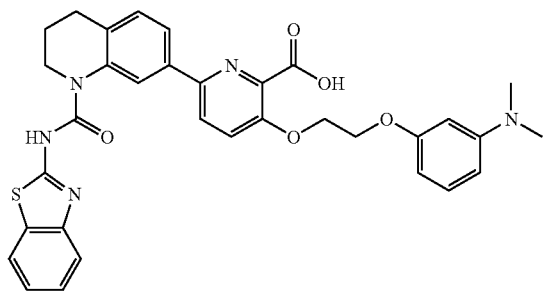

(39)

The title compound 6-(1-(benzo[d]thiazol-2-ylcarbamoyl)-1,2,3,4-tetrahydroquinolin-7-yl)-3-(2-(3-(dimethylamino)phenoxy)ethoxy)picolinic acid (39) was prepared by the following procedure: 6-(1-(benzo[d]thiazol-2-ylcarbamoyl)-1,2,3,4-tetrahydroquinolin-7-yl)-3-(2-(3-(dimethylamino)phenoxy)ethoxy)picolinic acid (39) was prepared following a similar procedure as that described in example 29, except Methyl 6-(1-(benzo[d]thiazol-2-ylcarbamoyl)-1,2,3,4-tetrahydroquinolin-7-yl)-3-(2-(3-(dimethylamino)phenoxy)ethoxy)picolinate (39E) was used instead of methyl 6-(1-(benzo[d]thiazol-2-ylcarbamoyl)-1,2,3,4-tetrahydroquinolin-7-yl)-3-phenylpicolinate (29I) in step 10 of example 29. $^1$H NMR (300 MHz, CDCl$_3$) δ 8.20 (1H, s), 7.84 (1H, d), 7.69 (1H, d), 7.40-7.10 (5H, m), 6.92 (1H, s, br), 6.40-6.28 (3 H, m), 4.53 (2H, t), 4.42 (2H, t), 3.82 (2H, s, br), 2.92 (6H, s), 2.69 (2H, t), 1.96 (2H, m). MS (ESI(+)) m/z 610.0 (M+H).

Example 40

Synthesis of 6-(1-(benzo[d]thiazol-2-ylcarbamoyl)-1,2,3,4-tetrahydroquinolin-7-yl)-3-(3-(3-(dimethylamino)phenoxy)propoxy)picolinic acid (40)

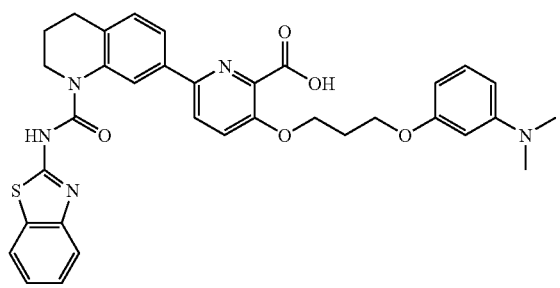

(40)

Step 1: Preparation of methyl 6-bromo-3-(4-methoxybenzyloxy)picolinate (40A)

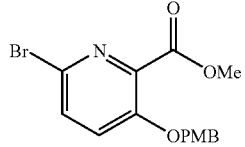

(40A)

4-Methoxybenzyl bromide (0.095 g, 0.47 mmol) was added dropwise to a suspension of methyl 6-bromo-3-hydroxypicolinate (26B) (0.100 g, 0.43 mmol) and K$_2$CO$_3$ (0.089 g, 0.65 mmol) in anhydrous acetone (2.5 mL). The reaction mixture was heated at reflux for 3.5 hours, cooled to rt, and concentrated under reduced pressure. Water was added and the mixture extracted with DCM. The organic phases were washed with 1 M NaOH, brine, dried over MgSO$_4$, filtered, and concentrated under reduced pressure. The concentrate was purified by column chromatography on silica gel eluting with a gradient of PE:EtOAc 84:16 to 72:28, to provide the desired product methyl 6-bromo-3-(4-methoxybenzyloxy)picolinate (40A).

Step 2: Preparation of methyl 3-(4-methoxybenzyloxy)-6-(1,2,3,4-tetrahydroquinolin-7-yl)picolinate (40B)

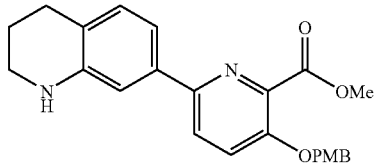

(40B)

Methyl 3-(4-methoxybenzyloxy)-6-(1,2,3,4-tetrahydroquinolin-7-yl)picolinate (40B) was prepared following a similar procedure as that described in example 29, except methyl 6-bromo-3-(4-methoxybenzyloxy)picolinate (40A) was used instead of methyl 3-(benzyloxy)-6-bromopicolinate (29A) in step 2 of example 29.

Step 3: Preparation of methyl 3-hydroxy-6-(1,2,3,4-tetrahydroquinolin-7-yl)picolinate (40C)

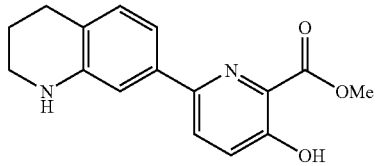

(40C)

Methyl 3-hydroxy-6-(1,2,3,4-tetrahydroquinolin-7-yl)picolinate (40C) was prepared following a similar procedure as that described in example 29, except Methyl 3-(4-methoxybenzyloxy)-6-(1,2,3,4-tetrahydroquinolin-7-yl)picolinate (40B) was used instead of tert-butyl 7-(6-(methoxycarbonyl)-5-(trifluoromethylsulfonyloxy)pyridin-2-yl)-3,4-dihydroquinoline-1(2H)-carboxylate (29E) in step 6 of example 29.

Step 4: Preparation of tert-butyl 7-(5-hydroxy-6-(methoxycarbonyl)pyridin-2-yl)-3,4-dihydroquinoline-1(2H)-carboxylate (29D)

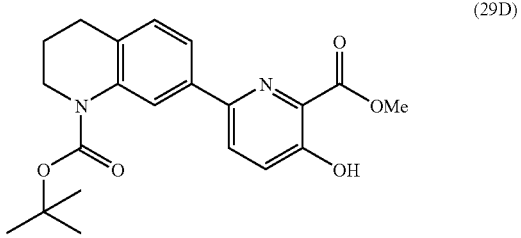

(29D)

A solution of di-tert-butyl dicarbonate (0.057 g, 0.26 mmol) and methyl 3-hydroxy-6-(1,2,3,4-tetrahydroquinolin-7-yl)picolinate (40C) (0.067 g, 0.24 mmol) in dry THF (3 mL) was heated at reflux for 17 hours, cooled to rt, diluted with EtOAc, and washed with saturated $NaHCO_3$. The aqueous phase was extracted with EtOAc, and the combined organic phases were dried over $MgSO_4$, filtered, and concentrated under reduced pressure. The crude material was purified by column chromatography on silica gel eluting with a gradient of PE:EtOAc 88:12 to 75:25, to provide the desired product tert-butyl 7-(5-hydroxy-6-(methoxycarbonyl)pyridin-2-yl)-3,4-dihydroquinoline-1(2H)-carboxylate (29D).

Step 5: Preparation of 3-(3-(dimethylamino)phenoxy)propyl acetate (40D)

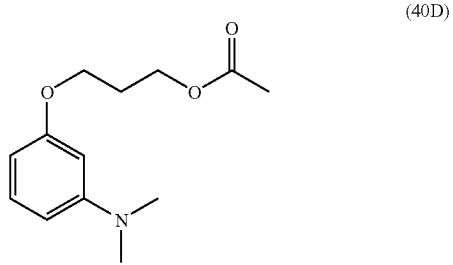

(40D)

3-(3-(Dimethylamino)phenoxy)propyl acetate (40D) was prepared following a similar procedure as that described in example 39, except 2-bromopropyl acetate was used instead of 2-bromoethyl acetate in step 1 of example 39.

Step 6: Preparation of 3-(3-(dimethylamino)phenoxy)propan-1-ol (40E)

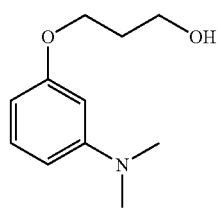

(40E)

3-(3-(Dimethylamino)phenoxy)propan-1-ol (40E) was prepared following a similar procedure as that described in example 39, except 3-(3-(dimethylamino)phenoxy)propyl acetate (40D) was used instead of 2-(3-(dimethylamino)phenoxy)ethyl acetate (39A) in step 2 of example 39.

Step 7: Preparation of title compound 6-(1-(benzo[d]thiazol-2-ylcarbamoyl)-1,2,3,4-tetrahydroquinolin-7-yl)-3-(3-(3-(dimethylamino)phenoxy)propoxy)picolinic acid (40)

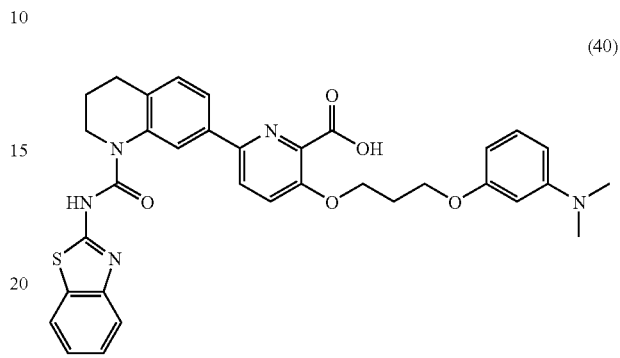

(40)

The title compound 6-(1-(benzo[d]thiazol-2-ylcarbamoyl)-1,2,3,4-tetrahydroquinolin-7-yl)-3-(3-(3-(dimethylamino)phenoxy)propoxy)picolinic acid (40) was prepared by the following procedure: 6-(1-(Benzo[d]thiazol-2-ylcarbamoyl)-1,2,3,4-tetrahydroquinolin-7-yl)-3-(3-(3-(dimethylamino)phenoxy)propoxy)picolinic acid (40) was prepared following a similar procedure as that described in example 39, except tert-butyl 7-(5-hydroxy-6-(methoxycarbonyl)pyridin-2-yl)-3,4-dihydroquinoline-1(2H)-carboxylate (29D) was used instead of methyl 6-bromo-3-hydroxypicolinate (26B) and 3-(3-(dimethylamino)phenoxy)propan-1-ol (40E) was used instead of 2-(3-(dimethylamino)phenoxy)ethanol (39B) in step 3 of example 39. $^1$H NMR (300 MHz, $CDCl_3$) δ 8.12 (1H, s), 7.82 (1H, d), 7.71 (1H, d), 7.50 (1H, d), 7.40-7.30 (2H, m), 7.26-7.09 (3H, m), 6.97 (1H, s, br), 6.38-6.29 (3H, m), 4.35 (2H, t), 4.27 (2H, t), 3.79 (2H, s, br), 2.92 (6H, s), 2.68 (2H, t), 2.36 (2H, m), 1.92 (2H, m). MS (ESI(+)): m/z 624.1 (M+H).

Example 41

Synthesis of 6-(1-(benzo[d]thiazol-2-ylcarbamoyl)-1,2,3,4-tetrahydroquinolin-7-yl)-3-(2-(2,2,4-trimethyl-3,4-dihydroquinolin-1(2H)-yl)ethoxy)picolinic acid (41)

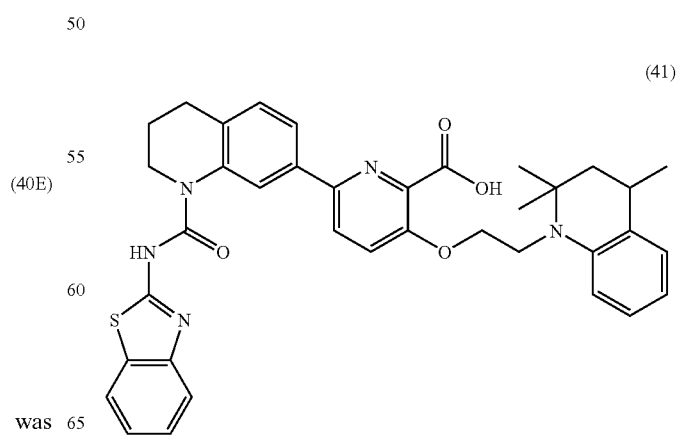

(41)

Step 1: Preparation of 6-bromo-3-(2-(2,2,4-trimethyl-3,4-dihydroquinolin-1(2H)-yl)ethoxy)picolinic acid (41A)

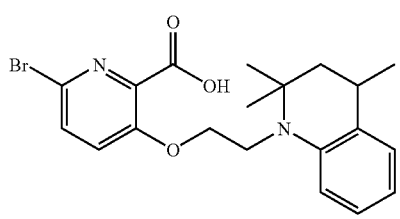

(41A)

6-bromo-3-(2-(2,2,4-trimethyl-3,4-dihydroquinolin-1(2H)-yl)ethoxy)picolinic acid (41A) was prepared following a similar procedure as that described in example 39, except 1-(2-hydroxyethyl)-1,2,3,4-tetrahydro-2,2,4,7-tetramethylquinoline was used instead of 2-(3-(dimethylamino)phenoxy)ethanol (39B) in step 3 of example 39.

Step 2: Preparation of title compound 6-(1-(benzo[d]thiazol-2-ylcarbamoyl)-1,2,3,4-tetrahydroquinolin-7-yl)-3-(2-(2,2,4-trimethyl-3,4-dihydroquinolin-1(2H)-yl)ethoxy)picolinic acid (41)

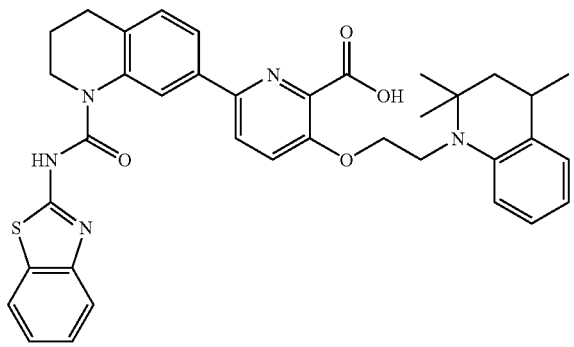

(41)

The title compound 6-(1-(benzo[d]thiazol-2-ylcarbamoyl)-1,2,3,4-tetrahydroquinolin-7-yl)-3-(2-(2,2,4-trimethyl-3,4-dihydroquinolin-1(2H)-yl)ethoxy)picolinic acid (41) was prepared by the following procedure: 6-(1-(Benzo[d]thiazol-2-ylcarbamoyl)-1,2,3,4-tetrahydroquinolin-7-yl)-3-(2-(2,2,4-trimethyl-3,4-dihydroquinolin-1(2H)-yl)ethoxy) picolinic acid (41) was prepared following a similar procedure as that described in example 39, except 6-bromo-3-(2-(2,2,4-trimethyl-3,4-dihydroquinolin-1(2H)-yl)ethoxy) picolinic acid (41A) was used instead of 2-(3-(dimethylamino)phenoxy)ethanol (39B) in step 3 of example 39. $^1$H NMR (300 MHz, DMSO) δ 8.31 (1H, s), 7.79 (1H, d), 7.74 (1H, d), 7.62 (1H, dd), 7.55-7.45 (2H, m), 7.35 (1H, dt), 7.22-7.16 (2H, m), 6.96 (1H, d), 6.42-6.38 (2H, m), 4.12 (2H, m), 3.93 (2H, t), 3.74 (2H, m), 3.41 (2H, m), 2.79 (2H, t), 2.18 (3H, s), 1.90 (2H, m), 1.76 (1H, m), 1.30 (3H, s), 1.22 (3H, d), 1.12 (3H, s).

Example 42

Synthesis of 3-(2-(3-aminophenoxy)ethoxy)-6-(1-(benzo[d]thiazol-2-ylcarbamoyl)-1,2,3,4-tetrahydroquinolin-7-yl)picolinic acid (42)

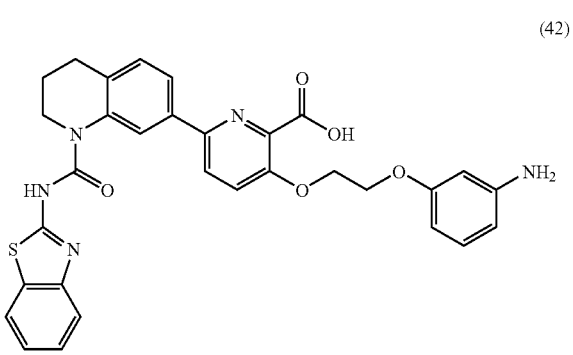

(42)

Step 1: Preparation of tert-butyl 3-hydroxyphenylcarbamate (42A)

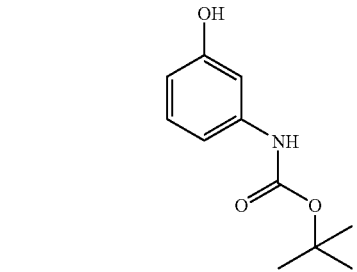

(42A)

tert-Butyl 3-hydroxyphenylcarbamate (42A) was prepared following a similar procedure as that described in example 40, except 3-aminophenol was used instead of methyl 3-hydroxy-6-(1,2,3,4-tetrahydroquinolin-7-yl)picolinate (40C) in step 4 of example 40.

Step 2: Preparation of 2-(3-(tert-butoxycarbonylamino)phenoxy)ethyl benzoate (42B)

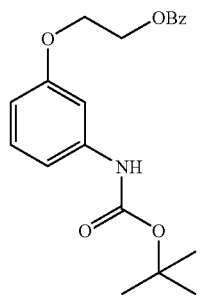

(42B)

2-(3-(tert-Butoxycarbonylamino)phenoxy)ethyl benzoate (42B) was prepared following a similar procedure as that described in example 39, except tert-Butyl 3-hydroxyphenylcarbamate (42A) was used instead of 3-(dimethylamino)phenol and 2-bromoethyl benzoate was used instead of 2-bromoethyl acetate in step 1 of example 39.

Step 3: Preparation of tert-butyl 3-(2-hydroxyethoxy)phenylcarbamate (42C)

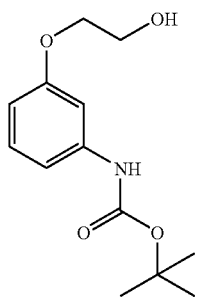

(42C)

tert-Butyl 3-(2-hydroxyethoxy)phenylcarbamate (42C) was prepared following a similar procedure as that described in example 39, except 2-(3-(tert-butoxycarbonylamino)phenoxy)ethyl benzoate (42B) was used instead of 2-(3-(dimethylamino)phenoxy)ethyl acetate (39A) in step 2 of example 39.

Step 4: Preparation of methyl 6-bromo-3-(2-(3-(tert-butoxycarbonylamino)phenoxy)ethoxy)picolinate (42D)

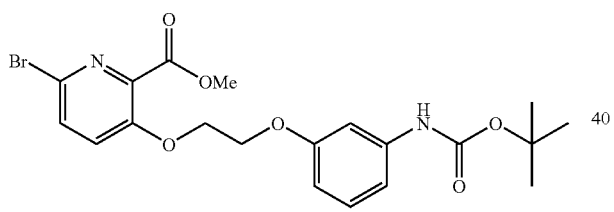

(42D)

6-Bromo-3-(2-(3-(tert-butoxycarbonylamino)phenoxy)ethoxy)picolinate (42D) was prepared following a similar procedure as that described in example 39, except tent-butyl 3-(2-hydroxyethoxy)phenylcarbamate (42C) was used instead of 2-(3-(dimethylamino)phenoxy)ethanol (39B) in step 3 of example 39.

Step 5: Preparation of methyl 3-(2-(3-(tert-butoxycarbonylamino)phenoxy)ethoxy)-6-(1,2,3,4-tetrahydroquinolin-7-yl)picolinate (42E)

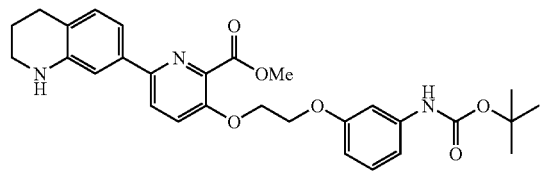

(42E)

Methyl 3-(2-(3-(tert-butoxycarbonylamino)phenoxy)ethoxy)-6-(1,2,3,4-tetrahydroquinolin-7-yl)picolinate (42E) was prepared following a similar procedure as that described in example 29, except 6-bromo-3-(2-(3-(tert-butoxycarbonylamino)phenoxy)ethoxy)picolinate (42D) was used instead of methyl 3-(benzyloxy)-6-bromopicolinate (29A) in step 2 of example 29.

Step 6: Preparation of methyl 6-(1-(benzo[d]thiazol-2-ylcarbamoyl)-1,2,3,4-tetrahydroquinolin-7-yl)-3-(2-(3-(tert-butoxycarbonylamino)phenoxy)ethoxy)picolinate (42F)

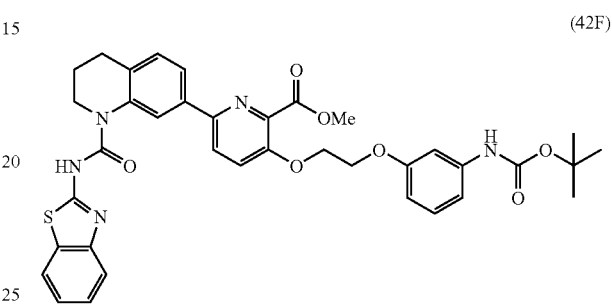

(42F)

Methyl 6-(1-(benzo[d]thiazol-2-ylcarbamoyl)-1,2,3,4-tetrahydroquinolin-7-yl)-3-(2-(3-(tert-butoxycarbonylamino)phenoxy)ethoxy)picolinate (42F) was prepared following a similar procedure as that described in example 29, except methyl 3-(2-(3-(tert-butoxycarbonylamino)phenoxy)ethoxy)-6-(1,2,3,4-tetrahydroquinolin-7-yl)picolinate (42E) was used instead of methyl 3-phenyl-6-(1,2,3,4-tetrahydroquinolin-7-yl)picolinate (29H) in step 9 of example 29.

Step 7: Preparation of 6-(1-(benzo[d]thiazol-2-ylcarbamoyl)-1,2,3,4-tetrahydroquinolin-7-yl)-3-(2-(3-(tert-butoxycarbonylamino)phenoxy)ethoxy)picolinic acid (42G)

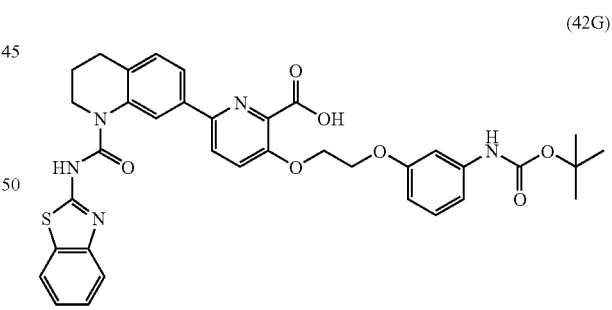

(42G)

6-(1-(Benzo[d]thiazol-2-ylcarbamoyl)-1,2,3,4-tetrahydroquinolin-7-yl)-3-(2-(3-(tert-butoxycarbonylamino)phenoxy)ethoxy)picolinic acid (42G) was prepared following a similar procedure as that described in example 29, except methyl 6-(1-(benzo[d]thiazol-2-ylcarbamoyl)-1,2,3,4-tetrahydroquinolin-7-yl)-3-(2-(3-(tert-butoxycarbonylamino)phenoxy)ethoxy)picolinate (42F) was used instead of methyl 6-(1-(benzo[d]thiazol-2-ylcarbamoyl)-1,2,3,4-tetrahydroquinolin-7-yl)-3-phenylpicolinate (29I) in step 10 of example 29. $^1$H NMR (300 MHz, CDCl$_3$) δ 8.19 (1H, s), 7.85 (1H, d), 7.70 (1H, dd), 7.60 (1H, d), 7.35-7.13 (5H, m), 6.97-6.85 (3H, m), 6.62 (1H, dd), 4.52 (2H, t), 4.44 (2H, t), 3.81 (2H, s, br), 2.68 (2H, t), 1.96 (2H, m), 1.48 (9H, s).

Step 8: Preparation of title compound 3-(2-(3-aminophenoxy)ethoxy)-6-(1-(benzo[d]thiazol-2-ylcarbamoyl)-1,2,3,4-tetrahydroquinolin-7-yl)picolinic acid (42)

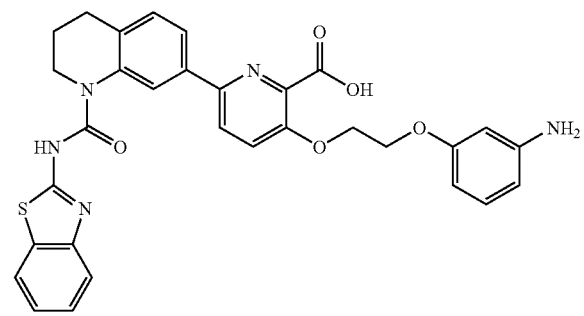
(42)

The title compound 3-(2-(3-aminophenoxy)ethoxy)-6-(1-(benzo[d]thiazol-2-ylcarbamoyl)-1,2,3,4-tetrahydroquinolin-7-yl)picolinic acid (42) was prepared by the following procedure: compound 3-(2-(3-aminophenoxy)ethoxy)-6-(1-(benzo[d]thiazol-2-ylcarbamoyl)-1,2,3,4-tetrahydroquinolin-7-yl)picolinic acid (42) was prepared following a similar procedure as that described in example 34, except 6-(1-(Benzo[d]thiazol-2-ylcarbamoyl)-1,2,3,4-tetrahydroquinolin-7-yl)-3-(2-(3-(tert-butoxycarbonylamino)phenoxy)ethoxy)picolinic acid (42G) was used instead of 6-(1-(Benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinic acid (34E) in step 6 of example 34. $^1$H NMR (300 MHz, DMSO) δ 8.29 (1H, s), 7.97 (1H, d), 7.81 (1H, d), 7.77 (1H, d), 7.68 (1H, dd), 7.46 (1H, m, br), 7.37 (1H, dt), 7.29-7.12 (3H, m), 6.61-6.50 (3H, m), 4.47 (2H, t), 4.28 (2H, t), 3.94 (2H, t), 2.81 (2H, t), 1.94 (2H, m). MS (ESI(+)): m/z 582.1 (M+H).

Example 43

Synthesis of 3-(3-(benzo[d][1,3]dioxol-5-yloxy)propoxy)-6-(1-(benzo[d]thiazol-2-ylcarbamoyl)-1,2,3,4-tetrahydroquinolin-7-yl)picolinic acid (43)

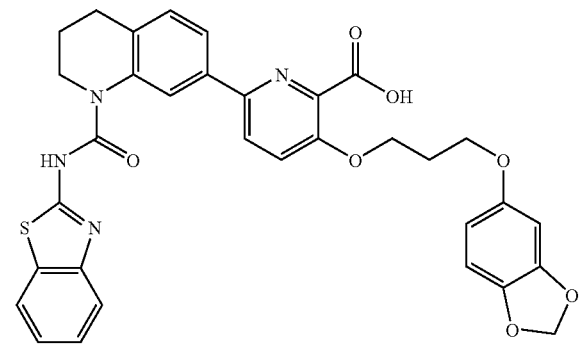
(43)

Step 1: Preparation of 3-(benzo[d][1,3]dioxol-5-yloxy)propyl acetate (43A)

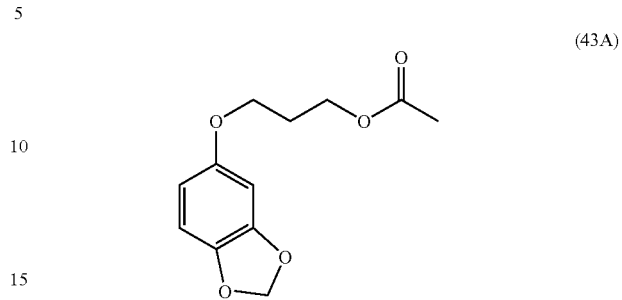
(43A)

3-(Benzo[d][1,3]dioxol-5-yloxy)propyl acetate (43A) was prepared following a similar procedure as that described in example 39, except sesamol was used instead of 3-(dimethylamino)phenol and 2-bromopropyl acetate was used instead of 2-bromoethyl acetate in step 1 of example 39.

Step 2: Preparation of 3-(benzo[d][1,3]dioxol-5-yloxy)propan-1-ol (43B)

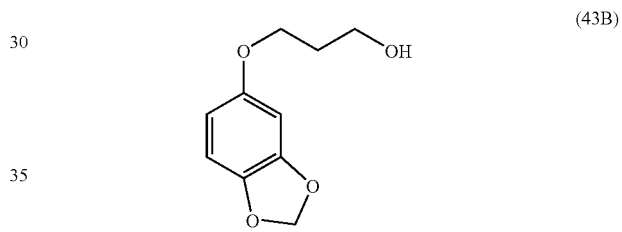
(43B)

3-(Benzo[d][1,3]dioxol-5-yloxy)propan-1-ol (43B) was prepared following a similar procedure as that described in example 39, except 3-(Benzo[d][1,3]dioxol-5-yloxy)propyl acetate (43A) was used instead of 2-(3-(dimethylamino)phenoxy)ethyl acetate (39A) in step 2 of example 39.

Step 3: Preparation of methyl 3-(3-(benzo[d][1,3]dioxol-5-yloxy)propoxy)-6-bromopicolinate (43C)

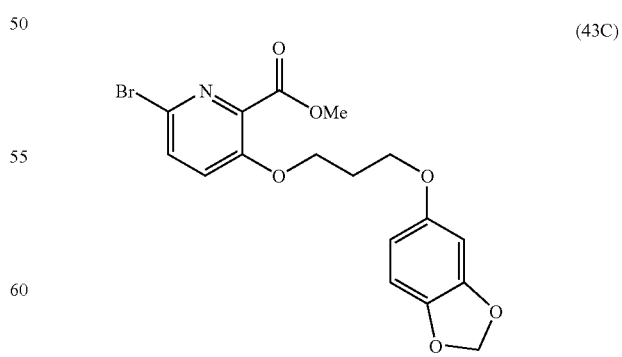
(43C)

Methyl 3-(3-(benzo[d][1,3]dioxol-5-yloxy)propoxy)-6-bromopicolinate (43C) was prepared following a similar procedure as that described in example 39, except 3-(benzo[d]

[1,3]dioxol-5-yloxy)propan-1-ol (43B) was used instead of 2-(3-(dimethylamino)phenoxy)ethanol (39B) in step 3 of example 39.

Step 4: Preparation of title compound 3-(3-(benzo[d][1,3]dioxol-5-yloxy)propoxy)-6-(1-(benzo[d]thiazol-2-ylcarbamoyl)-1,2,3,4-tetrahydroquinolin-7-yl)picolinic acid (43)

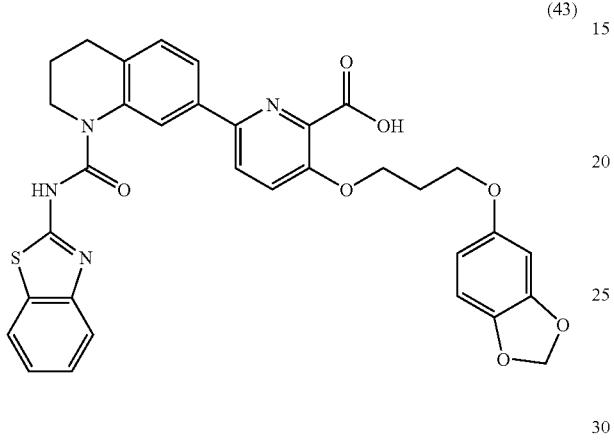

(43)

The title compound 3-(3-(benzo[d][1,3]dioxol-5-yloxy)propoxy)-6-(1-(benzo[d]thiazol-2-ylcarbamoyl)-1,2,3,4-tetrahydroquinolin-7-yl)picolinic acid (43) was prepared by the following procedure: 3-(3-(Benzo[d][1,3]dioxol-5-yloxy)propoxy)-6-(1-(benzo[d]thiazol-2-ylcarbamoyl)-1,2,3,4-tetrahydroquinolin-7-yl)picolinic acid (43) was prepared following a similar procedure as that described in example 29, except methyl 3-(3-(benzo[d][1,3]dioxol-5-yloxy)propoxy)-6-bromopicolinate (43C) was used instead of methyl 3-(benzyloxy)-6-bromopicolinate (29A) in step 2 of example 29.

Example 44

Synthesis of 6-(1-(benzo[d]thiazol-2-ylcarbamoyl)-1,2,3,4-tetrahydroquinolin-7-yl)-3-(3-(quinolin-8-yloxy)propoxy)picolinic acid (44)

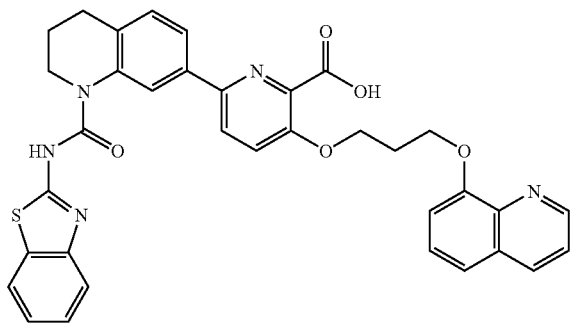

(44)

Step 1: Preparation of 3-(quinolin-8-yloxy)propyl acetate (44A)

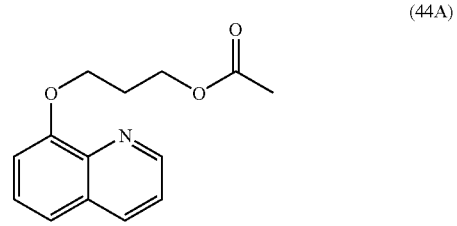

(44A)

3-(Quinolin-8-yloxy)propyl acetate (44A) was prepared following a similar procedure as that described in example 39, except 2-bromopropyl acetate for 2-bromoethyl acetate and 8-hydroxyquinoline was used instead of 3-(dimethylamino)phenol in step 1 of example 39.

Step 2: Preparation of 3-(quinolin-8-yloxy)propan-1-ol (44B)

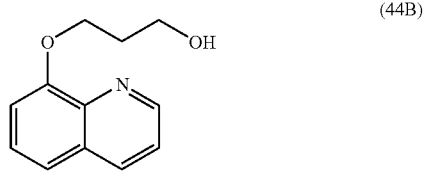

(44B)

3-(Quinolin-8-yloxy)propan-1-ol (44B) was prepared following a similar procedure as that described in example 39, except 3-(quinolin-8-yloxy)propyl acetate (44A) was used instead of 2-(3-(dimethylamino)phenoxy)ethyl acetate (39A) in step 2 of example 39.

Step 3: Preparation of methyl 6-bromo-3-(3-(quinolin-8-yloxy)propoxy)picolinate (44C)

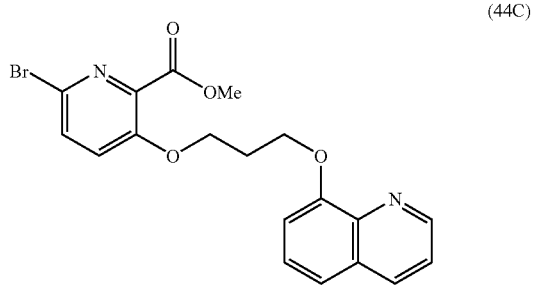

(44C)

Methyl 6-bromo-3-(3-(quinolin-8-yloxy)propoxy)picolinate (44C) was prepared following a similar procedure as that described in example 39, except 3-(Quinolin-8-yloxy)propan-1-ol (44B) was used instead of 2-(3-(dimethylamino)phenoxy)ethanol (39B) in step 3 of example 39.

Step 4: Preparation of title compound 6-O-(benzo[d]thiazol-2-ylcarbamoyl)-1,2,3,4-tetrahydroquinolin-7-yl)-3-(3-(quinolin-8-yloxy)propoxy)picolinic acid (44)

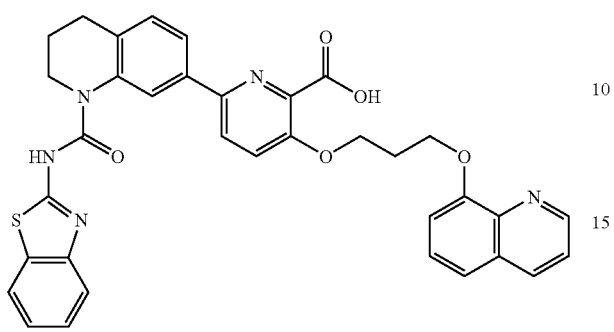

(44)

The title compound 6-(1-(benzo[d]thiazol-2-ylcarbamoyl)-1,2,3,4-tetrahydroquinolin-7-yl)-3-(3-(quinolin-8-yloxy)propoxy)picolinic acid (44) was prepared by the following procedure: 6-(1-(benzo[d]thiazol-2-ylcarbamoyl)-1,2,3,4-tetrahydroquinolin-7-yl)-3-(3-(quinolin-8-yloxy)propoxy)picolinic acid (44) was prepared following a similar procedure as that described in example 29, except methyl 6-bromo-3-(3-(quinolin-8-yloxy)propoxy)picolinate (44C) was used instead of methyl 3-(benzyloxy)-6-bromopicolinate (29A) in step 2 of example 29.

Example 45

Synthesis of 3-(2-(4-(aminomethyl)phenoxy)ethoxy)-6-(1-(benzo[d]thiazol-2-ylcarbamoyl)-1,2,3,4-tetrahydroquinolin-7-yl)picolinic acid (45)

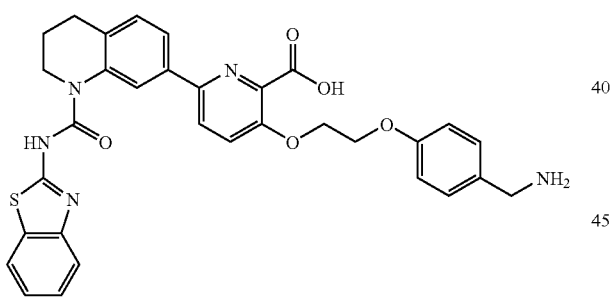

(45)

Step 1: Preparation of tert-butyl 4-(benzyloxy)benzylcarbamate (45A)

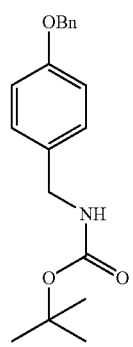

(45A)

Di-tert-butyl dicarbonate (0.934 g, 4.3 mmol) was added to a solution of 4-benzyloxybenzylamine (0.83 g, 3.89 mmol) and NaOH (0.171 g, 4.3 mmol) in water (15 mL) and THF (5 mL). The reaction mixture was stirred at rt for 4 hours, concentrated under reduced pressure to remove THF, and extracted with DCM. The organic phases were dried over MgSO₄, filtered, and concentrated under reduced pressure. The crude material was purified by column chromatography on silica gel eluting with a gradient of PE:EtOAc 92:8 to 87:13 to provide the desired product tert-butyl 4-(benzyloxy)benzylcarbamate (45A).

Step 2: Preparation of tert-butyl 4-hydroxybenzylcarbamate (45B)

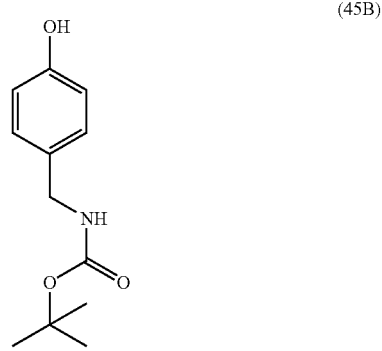

(45B)

tert-Butyl 4-hydroxybenzylcarbamate (45B) was prepared following a similar procedure as that described in example 29, except tert-butyl 4-(benzyloxy)benzylcarbamate (45A) was used instead of tert-butyl 7-(5-(benzyloxy)-6-(methoxycarbonyl)pyridin-2-yl)-3,4-dihydroquinoline-1(2H)-carboxylate (29C) in step 4 of example 29.

Step 3: Preparation of 2-(4-((tert-butoxycarbonylamino)methyl)phenoxy)ethyl acetate (45C)

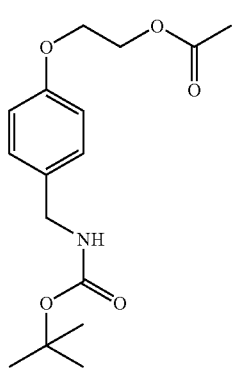

(45C)

2-(4-((tert-Butoxycarbonylamino)methyl)phenoxy)ethyl acetate (45C) was prepared following a similar procedure as that described in example 39, except tert-butyl 4-hydroxybenzylcarbamate (45B) was used instead of 3-(dimethylamino)phenol in step 1 of example 39.

Step 4: Preparation of tert-butyl 4-(2-hydroxyethoxy)benzylcarbamate (45D)

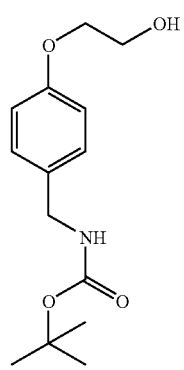

(45D)

tert-Butyl 4-(2-hydroxyethoxy)benzylcarbamate (45D) was prepared following a similar procedure as that described in example 39, except 2-(4-((tert-butoxycarbonylamino)methyl)phenoxy)ethyl acetate (45C) was used instead of 2-(3-(dimethylamino)phenoxy)ethyl acetate (39A) in step 2 of example 39.

Step 5: Preparation of methyl 6-bromo-3-(2-(4-((tert-butoxycarbonylamino)methyl)phenoxy)ethoxy)picolinate (45E)

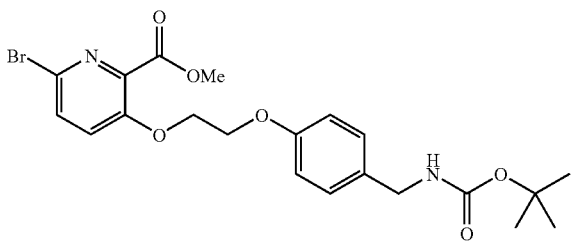

(45E)

Methyl 6-bromo-3-(2-(4-((tert-butoxycarbonylamino)methyl)phenoxy)ethoxy)picolinate (45E) was prepared following a similar procedure as that described in example 39, except tert-Butyl 4-(2-hydroxyethoxy)benzylcarbamate (45D) was used instead of 2-(3-(dimethylamino)phenoxy)ethanol (39B) in step 3 of example 39.

Step 6: Preparation of methyl 3-(2-(4-((tert-butoxycarbonylamino)methyl)phenoxy)ethoxy)-6-(1,2,3,4-tetrahydroquinolin-7-yl)picolinate (45F)

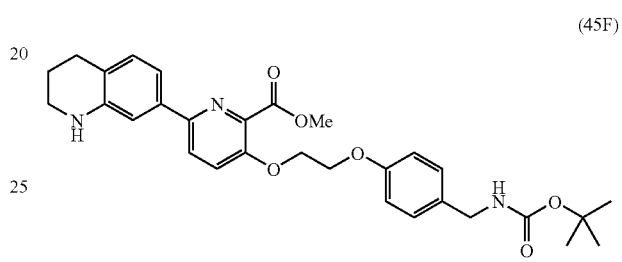

(45F)

Methyl 3-(2-(4-((tert-butoxycarbonylamino)methyl)phenoxy)ethoxy)-6-(1,2,3,4-tetrahydroquinolin-7-yl)picolinate (45F) was prepared following a similar procedure as that described in example 29, except Methyl 6-bromo-3-(2-(4-((tert-butoxycarbonylamino)methyl)phenoxy)ethoxy)picolinate (45E) was used instead of methyl 3-(benzyloxy)-6-bromopicolinate (29A) in step 2 of example 29.

Step 7: Preparation of methyl 6-(1-(benzo[d]thiazol-2-ylcarbamoyl)-1,2,3,4-tetrahydroquinolin-7-yl)-3-(2-(4-((tert-butoxycarbonylamino)methyl)phenoxy)ethoxy)picolinate (45G)

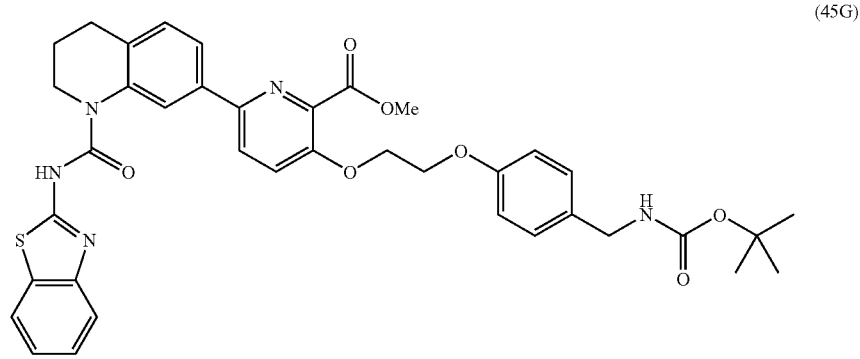

(45G)

Methyl 6-(1-(benzo[d]thiazol-2-ylcarbamoyl)-1,2,3,4-tetrahydroquinolin-7-yl)-3-(2-(4-((tert-butoxycarbonylamino)methyl)phenoxy)ethoxy)picolinate (45G) was prepared following a similar procedure as that described in example 29, except methyl 3-(2-(4-((tert-butoxycarbonylamino)methyl)phenoxy)ethoxy)-6-(1,2,3,4-tetrahydroquinolin-7-yl)picolinate (45F) was used instead of methyl 3-phenyl-6-(1,2,3,4-tetrahydroquinolin-7-yl)picolinate (29H) in step 9 of example 29.

Step 8: Preparation of 6-(1-(benzo[d]thiazol-2-ylcarbamoyl)-1,2,3,4-tetrahydroquinolin-7-yl)-3-(2-(4-((tert-butoxycarbonylamino)methyl)phenoxy)ethoxy)picolinic acid (45H)

4-tetrahydroquinolin-7-yl)picolinic acid (45) was prepared following a similar procedure as that described in example 34, except 6-(1-(benzo[d]thiazol-2-ylcarbamoyl)-1,2,3,4-tetrahydroquinolin-7-yl)-3-(2-(4-((tert-butoxycarbonylamino)methyl)phenoxy)ethoxy)picolinic acid (45H) was used instead of 6-(1-(Benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinic acid (34E) in step 6 of example 34. $^1$H NMR (300 MHz, DMSO) δ 8.29 (1H, s, br), 8.04 (1H, s, v br), 7.98 (1H, d), 7.81 (1H, d), 7.77 (1H, d), 7.68 (1H, dd), 7.45 (1H, s, br), 7.41-7.35 (3H, m), 7.28-7.19 (2H, m), 7.04 (2H, d), 4.48 (2H, m), 4.35 (2H, m), 3.96 (4H, m), 2.81 (2H, t), 1.92 (2H, m). MS (ESI(+)): m/z 596.1 (M+H).

(45H)

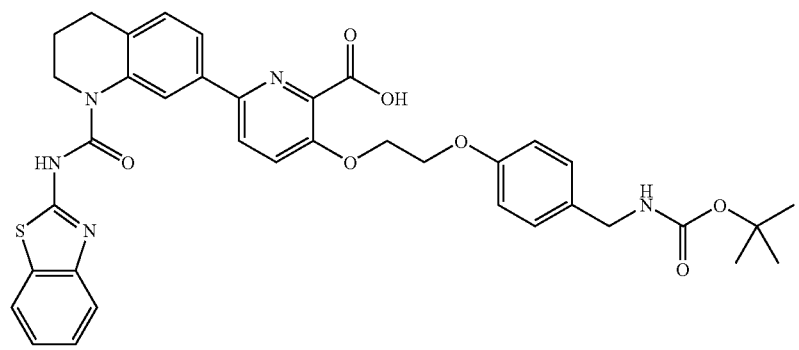

6-(1-(Benzo[d]thiazol-2-ylcarbamoyl)-1,2,3,4-tetrahydroquinolin-7-yl)-3-(2-(4-((tert-butoxycarbonylamino)methyl)phenoxy)ethoxy)picolinic acid (45H) was prepared following a similar procedure as that described in example 29, except Methyl 6-(1-(benzo[d]thiazol-2-ylcarbamoyl)-1,2,3,4-tetrahydroquinolin-7-yl)-3-(2-(4-((tert-butoxycarbonylamino)methyl)phenoxy)ethoxy)picolinate (45G) was used instead of methyl 6-(1-(benzo[d]thiazol-2-ylcarbamoyl)-1,2,3,4-tetrahydroquinolin-7-yl)-3-phenylpicolinate (29I) in step 10 of example 29.

Step 9: Preparation of title compound 3-(2-(4-(aminomethyl)phenoxy)ethoxy)-6-(1-(benzo[d]thiazol-2-ylcarbamoyl)-1,2,3,4-tetrahydroquinolin-7-yl)picolinic acid (45)

(45)

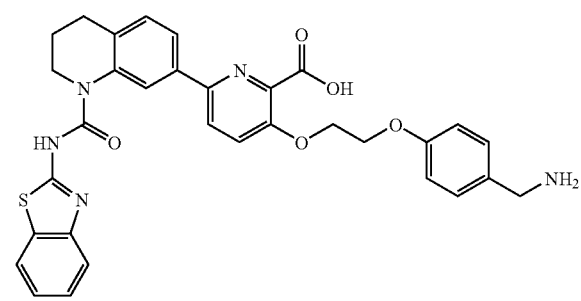

The title compound 3-(2-(4-(aminomethyl)phenoxy)ethoxy)-6-(1-(benzo[d]thiazol-2-ylcarbamoyl)-1,2,3,4-tetrahydroquinolin-7-yl)picolinic acid (45) was prepared by the following procedure: Compound 3-(2-(4-(aminomethyl)phenoxy)ethoxy)-6-(1-(benzo[d]thiazol-2-ylcarbamoyl)-1,2,3, Example 46

Synthesis of 6-(1-(benzo[d]thiazol-2-ylcarbamoyl)-1,2,3,4-tetrahydroquinolin-7-yl)-3-(biphenyl-4-ylmethoxy)picolinic acid (46)

(46)

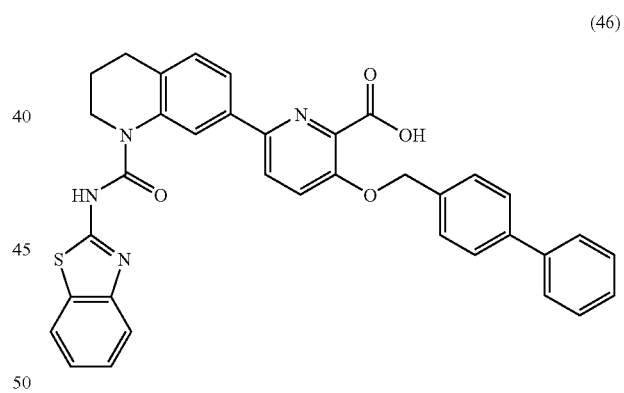

Step 1: Preparation of methyl 3-(biphenyl-4-ylmethoxy)-6-bromopicolinate (46A)

(46A)

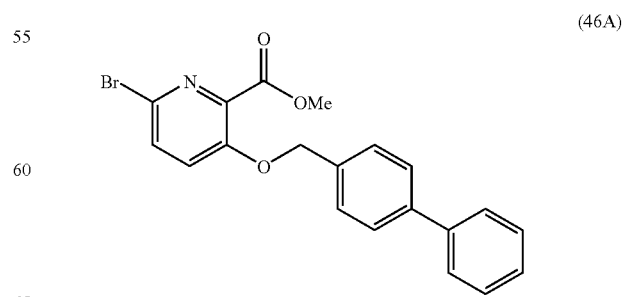

Methyl 3-(biphenyl-4-ylmethoxy)-6-bromopicolinate (46A) was prepared following a similar procedure as that described in example 39, except 4-biphenylmethanol was used instead of 2-(3-(dimethylamino)phenoxy)ethanol (39B) in step 3 of example 39.

Step 2: Preparation of title compound 6-O-(benzo[d]thiazol-2-ylcarbamoyl)-1,2,3,4-tetrahydroquinolin-7-yl)-3-(biphenyl-4-ylmethoxy)picolinic acid (46)

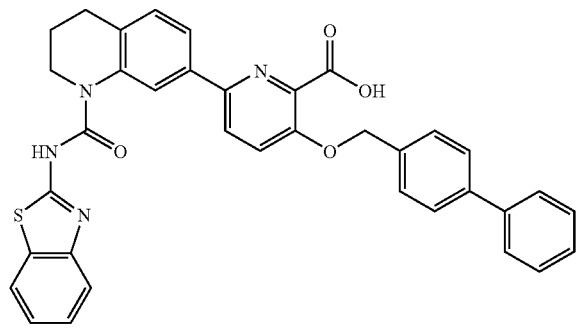

(46)

The title compound 6-(1-(benzo[d]thiazol-2-ylcarbamoyl)-1,2,3,4-tetrahydroquinolin-7-yl)-3-(biphenyl-4-ylmethoxy)picolinic acid (46) was prepared by the following procedure: 6-(1-(Benzo[d]thiazol-2-ylcarbamoyl)-1,2,3,4-tetrahydroquinolin-7-yl)-3-(biphenyl-4-ylmethoxy)picolinic acid (46) was prepared following a similar procedure as that described in example 29, except methyl 3-(biphenyl-4-ylmethoxy)-6-bromopicolinate (46A) was used instead of methyl 3-(benzyloxy)-6-bromopicolinate (29A) in step 2 of example 29.

Example 47

Synthesis of 6-(1-(benzo[d]thiazol-2-ylcarbamoyl)-1,2,3,4-tetrahydroquinolin-7-yl)-3-(3-(4-(dimethylamino)phenoxy)propoxy)picolinic acid (47)

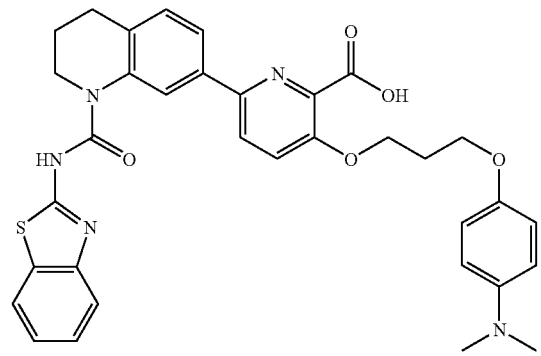

(47)

Step 1: Preparation of 3-(4-(dimethylamino)phenoxy)propyl acetate (47A)

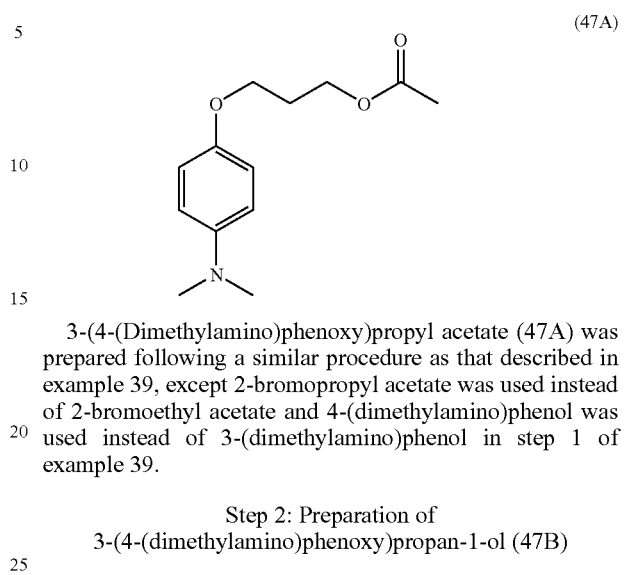

(47A)

3-(4-(Dimethylamino)phenoxy)propyl acetate (47A) was prepared following a similar procedure as that described in example 39, except 2-bromopropyl acetate was used instead of 2-bromoethyl acetate and 4-(dimethylamino)phenol was used instead of 3-(dimethylamino)phenol in step 1 of example 39.

Step 2: Preparation of 3-(4-(dimethylamino)phenoxy)propan-1-ol (47B)

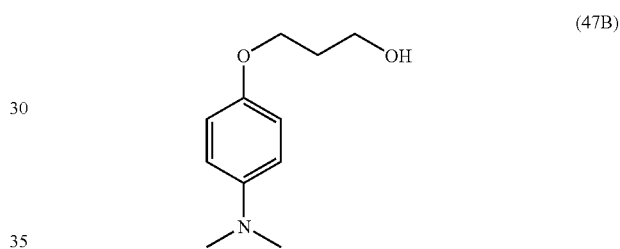

(47B)

3-(4-(Dimethylamino)phenoxy)propan-1-ol (47B) was prepared following a similar procedure as that described in example 39, except 3-(4-(dimethylamino)phenoxy)propyl acetate (47A) was used instead of 2-(3-(dimethylamino)phenoxy)ethyl acetate (39A) in step 2 of example 39.

Step 3: Preparation of title compound 6-(1-(benzo[d]thiazol-2-ylcarbamoyl)-1,2,3,4-tetrahydroquinolin-7-yl)-3-(3-(4-(dimethylamino)phenoxy)propoxy)picolinic acid (47)

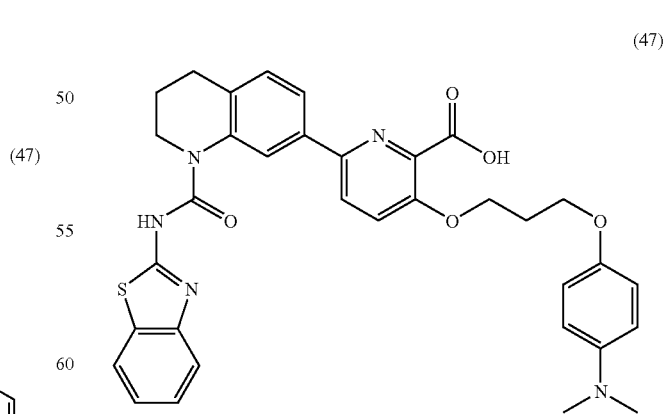

(47)

The title compound 6-(1-(benzo[d]thiazol-2-ylcarbamoyl)-1,2,3,4-tetrahydroquinolin-7-yl)-3-(3-(4-(dimethylamino)phenoxy)propoxy)picolinic acid (47) was prepared by the following procedure: 6-(1-(Benzo[d]thiazol-2-ylcarbamoyl)-1,2,3,4-tetrahydroquinolin-7-yl)-3-(3-(4-(dimethylamino)phenoxy)propoxy)picolinic acid (47) was prepared following a similar procedure as that described in example 39, except tert-butyl 7-(5-hydroxy-6-(methoxycarbonyl)pyridin-2-yl)-3,4-dihydroquinoline-1(2H)-carboxylate (29D) was used instead of methyl 6-bromo-3-hydroxypicolinate (26B) and 3-(4-(dimethylamino)phenoxy)propan-1-ol (47B) was used instead of 2-(3-(dimethylamino)phenoxy)ethanol (39B) in step 3 of example 39. $^1$H NMR (300 MHz, DMSO) δ 8.28 (1H, s), 7.95 (1H, d), 7.81 (1H, d), 7.71 (1H, d), 7.67 (1H, dd), 7.47 (1H, d, br), 7.37 (1H, dt), 7.28-7.19 (2H, m), 6.90-6.75 (4H, m), 4.26 (2H, t), 4.08 (2H, t), 3.94 (2H, t), 2.84-2.77 (8H, m), 2.14 (2H, m), 1.93 (2H, m). MS (ESI(+)): m/z 624.1 (M+H).

Example 48

Synthesis of 6-(1-(benzo[d]thiazol-2-ylcarbamoyl)-1,2,3,4-tetrahydroquinolin-7-yl)-3-(3-(4-(dimethylamino)phenyl)propoxy)picolinic acid (48)

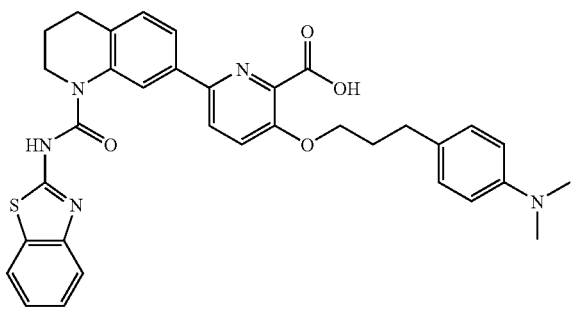
(48)

Step 1: Preparation of 3-(4-(dimethylamino)phenyl)propan-1-ol (48A)

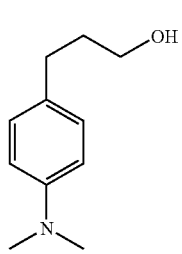
(48A)

LiAlH$_4$ (0.066 g, 1.71 mmol) was added to a solution of 4-(dimethylamino)cinnamaldehyde (0.10 g, 0.57 mmol) in anhydrous THF (2 mL). The reaction mixture was heated at reflux for 2 hours and cooled to rt. To the reaction mixture was added 1M HCl dropwise. The reaction mixture was stirred for 5 minutes before saturated NaHCO$_3$ was added and the mixture was extracted with DCM. The organic phases were dried over MgSO$_4$, filtered, and concentrated under reduced pressure. The crude material was purified by column chromatography on silica gel eluting with a gradient of PE:EtOAc 2:1 to provide the desired product 3-(4-(dimethylamino)phenyl) propan-1-ol (48A).

Step 2: Preparation of title compound 6-(1-(benzo[d]thiazol-2-ylcarbamoyl)-1,2,3,4-tetrahydroquinolin-7-yl)-3-(3-(4-(dimethylamino)phenyl)propoxy)picolinic acid (48)

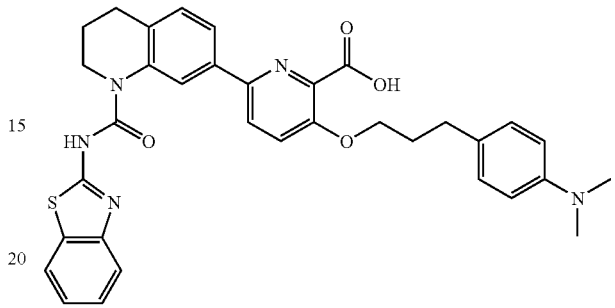
(48)

The title compound 6-(1-(benzo[d]thiazol-2-ylcarbamoyl)-1,2,3,4-tetrahydroquinolin-7-yl)-3-(3-(4-(dimethylamino)phenyl)propoxy)picolinic acid (48) was prepared by the following procedure: 6-(1-(benzo[d]thiazol-2-ylcarbamoyl)-1,2,3,4-tetrahydroquinolin-7-yl)-3-(3-(4-(dimethylamino)phenyl)propoxy)picolinic acid (48) was prepared following a similar procedure as that described in example 39, except tert-butyl 7-(5-hydroxy-6-(methoxycarbonyl)pyridin-2-yl)-3,4-dihydroquinoline-1(2H)-carboxylate (29D) was used instead of methyl 6-bromo-3-hydroxypicolinate (26B) and 3-(4-(dimethylamino)phenyl)propan-1-ol (48A) was used instead of 2-(3-(dimethylamino)phenoxy)ethanol (39B) in step 3 of example 39. $^1$H NMR (300 MHz, DMSO) δ 8.28 (1H, s), 7.93 (1H, d), 7.81 (1H, d), 7.70-7.62 (2H, m), 7.48 (1H, d, br), 7.37 (1H, dt), 7.27-7.12 (6H, m), 4.08 (2H, t), 3.94 (2H, t), 2.93 (6H, s), 2.81 (2H, t), 2.71 (2H, t), 2.02-1.90 (4H, m). MS (ESI(+)): m/z 608.1 (M+H).

Example 49

Synthesis of 6-(1-(benzo[d]thiazol-2-ylcarbamoyl)-1,2,3,4-tetrahydroquinolin-7-yl)-3-(2-(4-(tert-butoxycarbonylamino)phenoxy)ethoxy)picolinic acid (49)

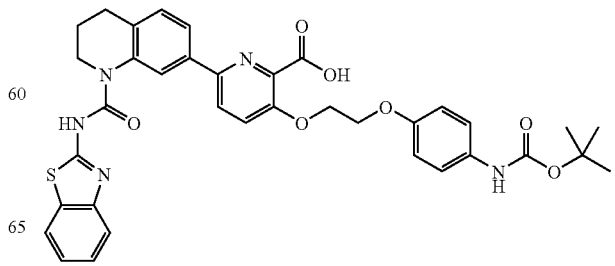
(49)

Step 1: Preparation of methyl 6-bromo-3-(2-(4-(tert-butoxycarbonylamino)phenoxy)ethoxy)picolinate (49A)

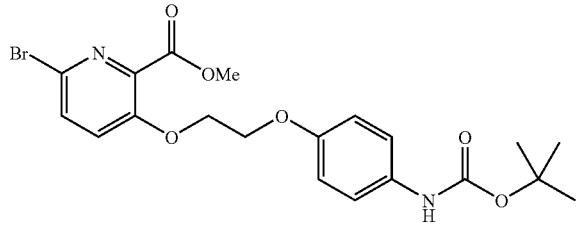

Methyl 6-bromo-3-(2-(4-(tert-butoxycarbonylamino)phenoxy)ethoxy)picolinate (49A) was prepared following a similar procedure as that described in example 39, except tert-butyl 4-(2-hydroxyethoxy)phenylcarbamate was used instead of 2-(3-(dimethylamino)phenoxy)ethanol (39B) in step 3 of example 39.

Step 4: Preparation of title compound 6-(1-(benzo[d]thiazol-2-ylcarbamoyl)-1,2,3,4-tetrahydroquinolin-7-yl)-3-(2-(4-(tert-butoxycarbonylamino)phenoxy)ethoxy)picolinic acid (49)

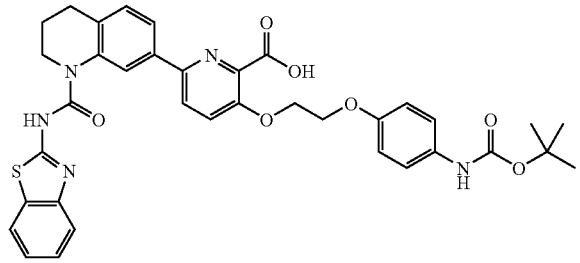

The title compound 6-(1-(benzo[d]thiazol-2-ylcarbamoyl)-1,2,3,4-tetrahydroquinolin-7-yl)-3-(2-(4-(tert-butoxycarbonylamino)phenoxy)ethoxy)picolinic acid (49) was prepared by the following procedure: 6-(1-(Benzo[d]thiazol-2-ylcarbamoyl)-1,2,3,4-tetrahydroquinolin-7-yl)-3-(2-(4-(tert-butoxycarbonylamino)phenoxy)ethoxy)picolinic acid (49) was prepared following a similar procedure as that described in example 29, except methyl 6-bromo-3-(2-(4-(tert-butoxycarbonylamino)phenoxy)ethoxy)picolinate (49A) was used instead of methyl 3-(benzyloxy)-6-bromopicolinate (29A) in step 2 of example 29. $^1$H NMR (300 MHz, CDCl$_3$) δ 8.18 (1H, s), 7.97 (1H, d), 7.80 (1H, d), 7.68-7.60 (2H, m), 7.48 (1H, t), 7.39 (1H, t), 7.26 (1H, m), 7.20-7.15 (2H, m), 6.89 (2H, d), 6.37 (1H, s), 4.53 (2H, m), 4.01 (2H, m), 4.02 (2H, t), 2.83 (2H, t), 2.08 (2H, m), 1.50 (9H, s).

Example 50

Synthesis of (E)-6-(1-(benzo[d]thiazol-2-ylcarbamoyl)-1,2,3,4-tetrahydroquinolin-7-yl)-3-(4-fluorostyryl)picolinic acid (50)

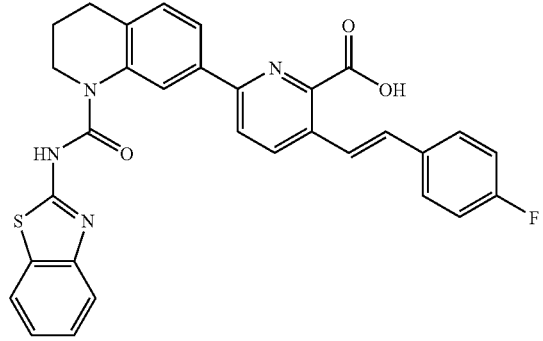

The title compound (E)-6-(1-(benzo[d]thiazol-2-ylcarbamoyl)-1,2,3,4-tetrahydroquinolin-7-yl)-3-(4-fluorostyryl)picolinic acid (50) was prepared by the following procedure: (E)-6-(1-(benzo[d]thiazol-2-ylcarbamoyl)-1,2,3,4-tetrahydroquinolin-7-yl)-3-(4-fluorostyryl)picolinic acid (50) was prepared following a similar procedure as that described in example 29, except trans-2-(4-fluorophenyl)vinylboronic acid was used instead of phenylboronic acid in step 7 of example 29. $^1$H NMR (300 MHz, DMSO) δ 8.64 (1H, s), 8.14 (1H, d), 7.78 (1H, d), 7.69 (1H, d), 7.63-7.52 (4H, m), 7.41 (1H, d), 7.27-7.13 (5H, m), 6.97 (1H, t), 3.96 (1H, t), 2.80 (2H, t), 1.88 (2H, m). MS (ESI(+)): m/z 551.0 (M+H).

Example 51

Synthesis of 6-(1-(benzo[d]thiazol-2-ylcarbamoyl)-1,2,3,4-tetrahydroquinolin-7-yl)-3-(2-(4-(dimethylamino)benzylamino)ethoxy)picolinic acid (51)

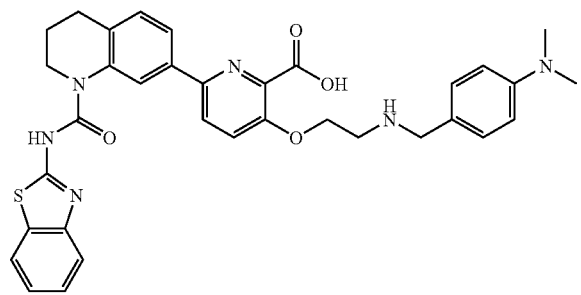

Step 1: Preparation of 2-(4-(dimethylamino)benzylamino)ethanol (51A)

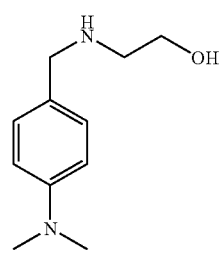

A solution of 2-(dimethylamino)benzaldehyde (0.50 g, 3.35 mmol) and ethanolamine (0.409 g, 6.7 mmol) in anhydrous EtOH (13 mL) was stirred at rt for 17 hours before sodium triacetoxyborohydride (1.42 g, 6.7 mmol) was added. The reaction mixture was stirred for 4.5 hours, added water, and the pH was adjusted to 12 with 5 M NaOH. The mixture was extracted with EtOAc, and the organic phases were dried over MgSO$_4$, filtered, and concentrated under reduced pressure. The crude material was purified by column chromatography on silica gel eluting with a gradient of DCM:MeOH 9:1 to 1:1, to provide the desired product 2-(4-(dimethylamino)benzylamino)ethanol (51A).

Step 2: Preparation of tert-butyl 4-(dimethylamino)benzyl(2-hydroxyethyl)carbamate (MB)

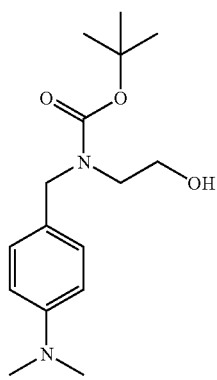

(51B)

tert-Butyl 4-(dimethylamino)benzyl(2-hydroxyethyl)carbamate (51B) was prepared following a similar procedure as that described in example 40, except 2-(4-(dimethylamino)benzylamino)ethanol (51A) was used instead of methyl 3-hydroxy-6-(1,2,3,4-tetrahydroquinolin-7-yl)picolinate (40C) in step 4 of example 40.

Step 3: Preparation of 6-(1-(benzo[d]thiazol-2-ylcarbamoyl)-1,2,3,4-tetrahydroquinolin-7-yl)-3-(2-(4-(dimethylamino)benzylamino)ethoxy)picolinic acid (51)

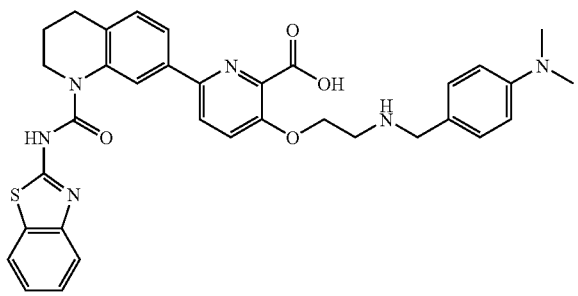

(51)

The title compound 6-(1-(benzo[d]thiazol-2-ylcarbamoyl)-1,2,3,4-tetrahydroquinolin-7-yl)-3-(2-(4-(dimethylamino)benzylamino)ethoxy)picolinic acid (51) was prepared by the following procedure: 6-(1-(Benzo[d]thiazol-2-ylcarbamoyl)-1,2,3,4-tetrahydroquinolin-7-yl)-3-(2-(4-(dimethylamino)benzylamino)ethoxy)picolinic acid (51) was prepared following a similar procedure as that described in example 45, except tert-butyl 4-(dimethylamino)benzyl(2-hydroxyethyl)carbamate (51B) was used instead of tert-butyl 4-(2-hydroxyethoxy)benzylcarbamate (45D) in step 5 of example 45. $^1$H NMR (300 MHz, DMSO) δ 8.82 (2H, s, br), 8.31 (1H, s, br), 8.04 (1H, d), 7.81 (1H, d), 7.77 (1H, d), 7.71 (1H, dd), 7.47 (1H, s, br), 7.41-7.20 (4H, m), 6.75 (2H, d), 4.43 (2H, t), 4.19 (1H, s, br), 3.95 (2H, t, br), 3.37 (2H, s, br), 2.91 (6H, s), 2.82 (2H, t), 1.94 (2H, m). MS (ESI(+)): m/z 623.0 (M+H).

Example 52

Synthesis of 6-(1-(benzo[d]thiazol-2-ylcarbamoyl)-1,2,3,4-tetrahydroquinolin-7-yl)-3-(2-(4-(2-(dimethylamino)ethyl)piperazin-1-yl)ethoxy)picolinic acid (52)

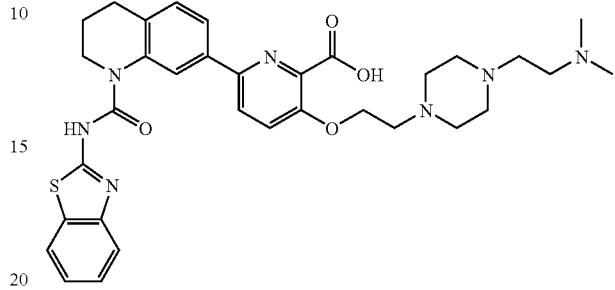

(52)

Step 1: Preparation of 2-(4-(2-(dimethylamino)ethyl)piperazin-1-yl)ethyl acetate (52A)

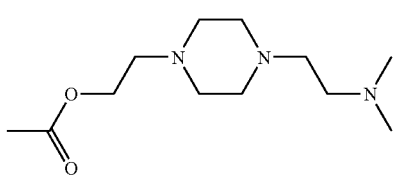

(52A)

2-(4-(2-(Dimethylamino)ethyl)piperazin-1-yl)ethyl acetate (52A) was prepared following a similar procedure as that described in example 39, except 1-(2-dimethylaminoethyl)-piperazine was used instead of 3-(dimethylamino)phenol in step 1 of example 39.

Step 2: Preparation of title compound 6-(1-(benzo[d]thiazol-2-ylcarbamoyl)-1,2,3,4-tetrahydroquinolin-7-yl)-3-(2-(4-(2-(dimethylamino)ethyl)piperazin-1-yl)ethoxy)picolinic acid (52)

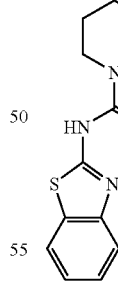

(52)

The title compound 6-(1-(benzo[d]thiazol-2-ylcarbamoyl)-1,2,3,4-tetrahydroquinolin-7-yl)-3-(2-(4-(2-(dimethylamino)ethyl)piperazin-1-yl)ethoxy)picolinic acid (52) was prepared by the following procedure: 6-(1-(benzo[d]thiazol-2-ylcarbamoyl)-1,2,3,4-tetrahydroquinolin-7-yl)-3-(2-(4-(2-(dimethylamino)ethyl)piperazin-1-yl)ethoxy)picolinic acid (52) was prepared following a similar procedure as that described in example 39, except 2-(4-(2-(dimethylamino)ethyl)piperazin-1-yl)ethyl acetate (52A) was used instead of 2-(3-(dimethylamino)phenoxy)ethyl acetate (39A) in step 2 of example 39. $^1$H NMR (300 MHz, DMSO) δ 8.31 (1H, s), 8.23 (1H, s), 7.83-7.74 (2H, m), 7.63 (1H, dd), 7.58 (1H, d), 7.48 (1H, d), 7.36 (1H, t), 7.24-7.16 (2H, m), 4.24 (4H, m), 3.93 (4H, m), 2.80 (4H, m), 2.64 (4H, s), 2.47 (4H, s), 2.25 (6H, s), 1.94 (2H, m). MS (ESI(+)): m/z 630.1 (M+H).

Example 53

Synthesis of 6-(4-(benzo[d]thiazol-2-ylcarbamoyl)-3,4-dihydro-2H-benzo[b][1,4]oxazin-6-yl)-3-(3-phenoxypropoxy)picolinic acid (53)

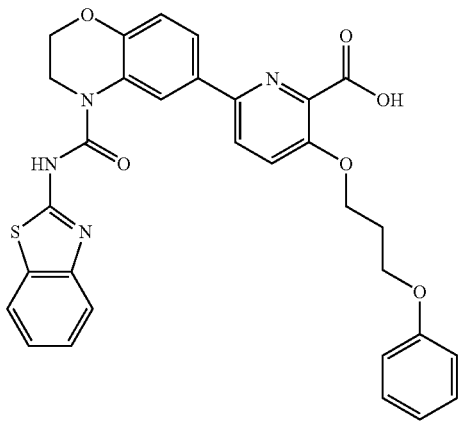
(53)

Step 1: Preparation of tert-butyl 6-bromo-2H-benzo[b][1,4]oxazine-4(3H)-carboxylate (53A)

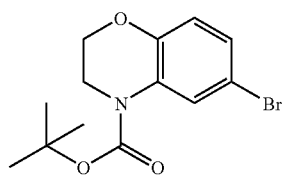
(53A)

Sttert-Butyl 6-bromo-2H-benzo[1)][1,4]oxazine-4(3H)—carboxylate (53A) was prepared following a similar procedure as that described in example 23, except 6-bromo-3,4-dihydro-2H-benzo[b][1,4]oxazine (7A) was used instead of 7-bromo-1,2,3,4-tetrahydroquinoline (1E) in step 4 of example 23.

Step 2: Preparation of tert-butyl 6-(4,4,5,5-tetramethyl-1,3,2-dioxaborolan-2-yl)-2H-benzo[b][1,4]oxazine-4(3H)-carboxylate (53B).

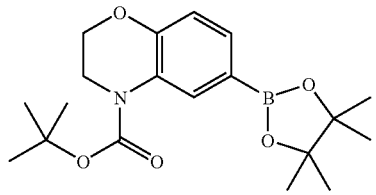
(53B)

tert-Butyl 6-(4,4,5,5-tetramethyl-1,3,2-dioxaborolan-2-yl)-2H-benzo[b][1,4]oxazine-4(3H)-carboxylate (53B) was prepared following a similar procedure as that described in example 23, except tert-butyl 6-bromo-2H-benzo[b][1,4]oxazine-4(3H)-carboxylate (53A) was used instead of tert-butyl 7-bromo-3,4-dihydroquinoline-1(2H)-carboxylate (23D) in step 5 of example 23.

Step 3: Preparation of tert-butyl 6-(6-(methoxycarbonyl)-5-(3-phenoxypropoxy)pyridin-2-yl)-2H-benzo[b][1,4]oxazine-4(3H)-carboxylate (53C)

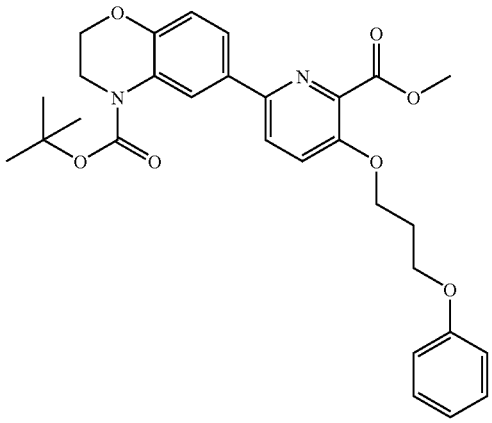
(53C)

A mixture of tert-butyl 6-(4,4,5,5-tetramethyl-1,3,2-dioxaborolan-2-yl)-2H-benzo[b][1,4]oxazine-4(3H)-carboxylate (53B) (72 mg, 0.20 mmol), methyl 6-bromo-3-(3-phenoxypropoxy)picolinate (26C) (72 mg, 0.20 mmol), $K_2CO_3$ (30 mg, 0.22 mmol in 0.5 mL of water), tetrabutyl ammonium bromide (64 mg, 0.20 mmol) and dichlorobis(triphenylphosphine)palladium (II) (10 mg, catalytic amount) in 1,4-dioxane (5 mL) was heated to 90° C. for 6 hours. The reaction mixture was cooled to rt, diluted with EtOAc, filtered through Celite, and concentrated under reduced pressure. The crude material was purified by column chromatography on silica gel eluting with 20% EtOAc in hexanes to provide the desired product tent-butyl 6-(6-(methoxycarbonyl)-5-(3-phenoxypropoxy)pyridin-2-yl)-2H-benzo[b][1,4]oxazine-4(3H)-carboxylate (53C). $^1$H NMR (300 MHz, CDCl$_3$): 8.49 (1H, s), 7.74 (1H, d), 7.60 (1H, d), 7.38 (1H, d), 7.24 (2H, m), 6.90 (4H, m), 4.31 (2H, t), 4.18 (2H, t), 4.25 (2H, t), 3.95 (3H, s), 3.85 (2H, t), 2.3 (2H, m), 1.58 (9H, s). LCMS (APCI): m/z 521.1 (M+H).

Step 4: Preparation of title compound 6-(4-(benzo[d]thiazol-2-ylcarbamoyl)-3,4-dihydro-2H-benzo[b][1,4]oxazin-6-yl)-3-(3-phenoxypropoxy)picolinic acid (53)

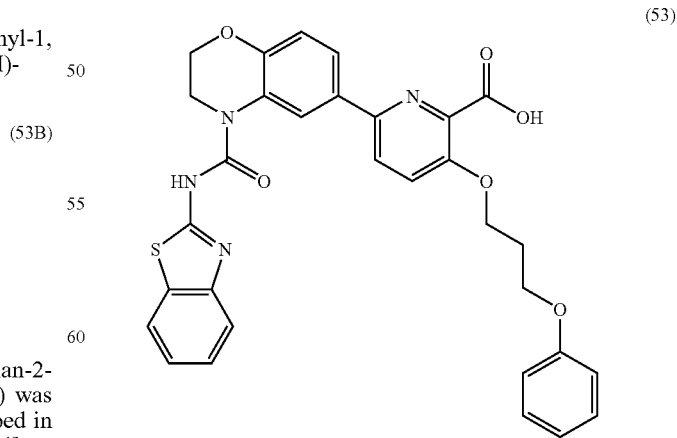
(53)

The title compound 6-(4-(benzo[d]thiazol-2-ylcarbamoyl)-3,4-dihydro-2H-benzo[b][1,4]oxazin-6-yl)-3-(3-phenoxypropoxy)picolinic acid (53) was prepared by the following procedure: 6-(4-(Benzo[d]thiazol-2-ylcarbamoyl)-3,4-dihydro-2H-benzo[b][1,4]oxazin-6-yl)-3-(3-phenoxypropoxy)picolinic acid (53) was prepared following a similar procedure as that described in example 29, except tert-butyl 6-(6-(methoxycarbonyl)-5-(3-phenoxypropoxy) pyridin-2-yl)-2H-benzo[b][1,4]oxazine-4(3H)-carboxylate (53C) was used instead of tert-butyl 7-(6-(methoxycarbonyl)-5-(trifluoromethylsulfonyloxy)pyridin-2-yl)-3,4-dihydroquinoline-1(2H)-carboxylate (29E) in step 6 of example 29. LCMS (APCI): m/z 583.1 (M+H).

Example 54

Synthesis of 6-(4-(benzo[d]thiazol-2-ylcarbamoyl)-3,4-dihydro-2H-benzo[b][1,4]oxazin-6-yl)-3-(3-(pyridin-4-yl)propoxy)picolinic acid (54)

(54)

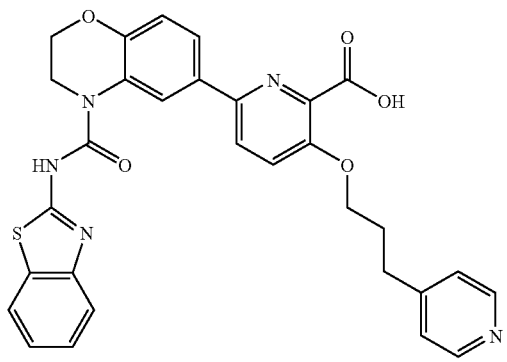

Step 1: Preparation of methyl 6-bromo-3-(3-(pyridin-4-yl)propoxy)picolinate (54A)

(54A)

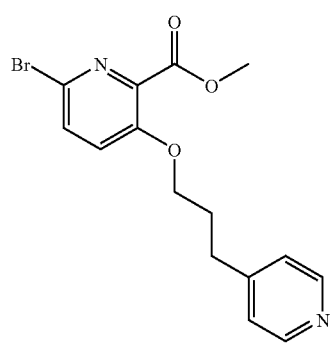

Methyl 6-bromo-3-(3-(pyridin-4-yl)propoxy)picolinate (54A) was prepared following a similar procedure as that described for example 39, except 3-(pyridin-4-yl)propan-1-ol was used instead of 2-(3-(dimethyamino)phenoxy)ethanol in step 3 of example 39.

Step 2: Preparation of title compound 6-(4-(benzo[d]thiazol-2-ylcarbamoyl)-3,4-dihydro-2H-benzo[b][1,4]oxazin-6-yl)-3-(3-(pyridin-4-yl)propoxy)picolinic acid (54)

(54)

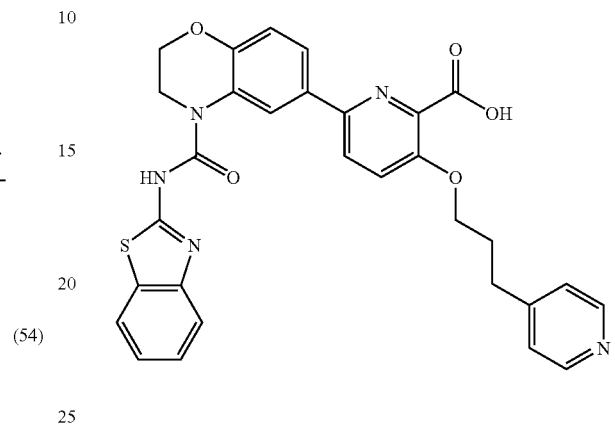

The title compound 6-(4-(benzo[d]thiazol-2-ylcarbamoyl)-3,4-dihydro-2H-benzo[b][1,4]oxazin-6-yl)-3-(3-(pyridin-4-yl)propoxy)picolinic acid (54) was prepared by the following procedure: 6-(4-(Benzo[d]thiazol-2-ylcarbamoyl)-3,4-dihydro-2H-benzo[b][1,4]oxazin-6-yl)-3-(3-(pyridin-4-yl)propoxy)picolinic acid (54) was prepared following a similar procedure as that described in example 53, except methyl 6-bromo-3-(3-(pyridin-4-yl)propoxy)picolinate (54A) was used instead of methyl 6-bromo-3-(3-phenoxypropoxy)picolinate (26C) in step 3 of example 53. $^1$H NMR (300 MHz, MeOD): 8.42 (3H, m), 7.7 (2H, m), 7.6 (1H, d)), 7.3-7.4 (5H, m), 7.2 (1H, t), 6.9 (1H, m), 4.3 (2H, t), 4.1-4.2 (4H, m), 2.9 (2H, t), 2.2 (2H, t). LCMS (APCI): m/z 568 (M+H).

Example 55

Synthesis of 6-(1-(benzo[d]thiazol-2-ylcarbamoyl)-1,2,3,4-tetrahydroquinolin-7-yl)-3-(3-morpholinopropoxy)picolinic acid (55)

(55)

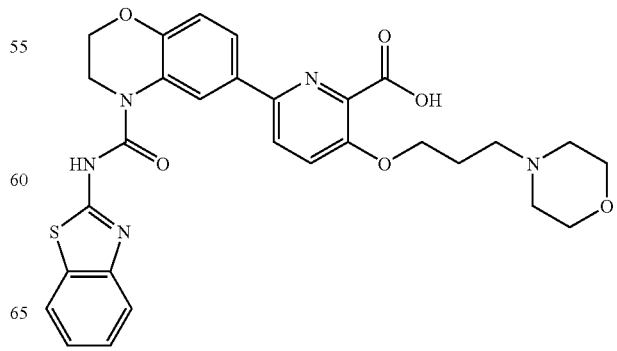

Step 1: Preparation of 6-bromo-3-hydroxypicolinic acid (55A).

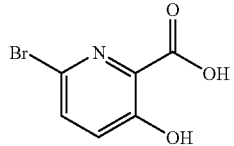
(55A)

Methyl 6-bromo-3-hydroxypicolinate (26B) (464 mg, 2 mmol) in MeOH (0.5 mL) was added to a solution of LiOH (200 mg in 2 mL water). The reaction mixture was stirred at rt for 2 h. The product precipitated out of solution and was filtered, washed with water, and dried under reduced pressure to provide the desired product 6-bromo-3-hydroxypicolinic acid (55A). $^1$H NMR (300 MHz, CDCl$_3$): 7.6 (1H, d), 7.32 (1H, d).

Step 2: Preparation of Resin 55B

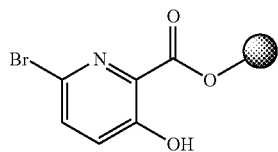
56B

Wang resin (1 g, Novabiochem, 1.1 mmol/g) was gently mixed on a shaker with a mixture of 6-bromo-3-hydroxypicolinic acid (55A) (436 mg, 2 mmol), 1,3-diisopropylcarbodiimide (252 mg, 2 mmol) and DMAP (2 mmol) in DCM/DMF (1:1, 10 mL) at 60° C. for 16 hours. The resin was carefully washed with DCM/DMF (1:1, 3×5 mL) and DCM (3×5 mL) and dried under reduced pressure for 2-3 hours to provide the resin 55B.

Step 3: Preparation of Resin 55C.

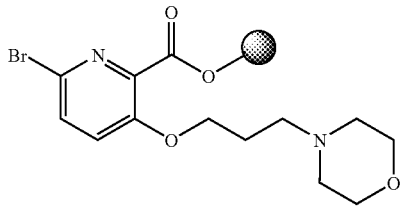
55C

Resin 55B (0.2 g, 0.22 mmol) was incubated with a mixture of 4-(3-hydroxypropyl)morpholine (145 mg, 1 mmol), diethylazodicarboxylate (174 mg, 1 mmol), and triphenylphosphine (262 mg, 1 mmol) in DCM (10 mL) at rt for 4 hours. The resulting resin was filtered and carefully washed with DMF (3×5 mL), MeOH (5 mL) and DCM (3×5 mL) and dried under reduced pressure for 30 minutes to provide the resin 55C.

Step 4: Preparation of Resin 55D

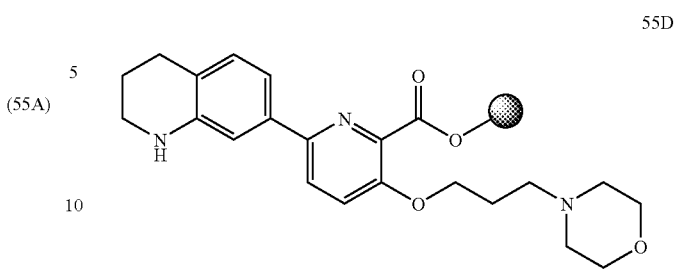
55D

Resin 55C (0.2 g, 0.11 mmol) was incubated with 7-(4,4,5,5-tetramethyl-1,3,2-dioxaborolan-2-yl)-1,2,3,4-tetrahydroquinoline (27B) (103.6 mg, 0.4 mmol), bis-(triphenylphosphine)palladium II chloride (10 mg, catalytical amount), tetrabutyl ammonium fluoride (0.5 mL of 1 M solution in THF) and K$_2$CO$_3$ (25 mg, dissolved in 3 drops of water) in 5 mL of DCM:THF (1:1) at 60° C. for 16 hours. The resulting resin was filtered and carefully washed with DMF (3×5 mL), MeOH (3×5 mL), and DCM (3×5 mL) and dried under reduced pressure for 30 minutes to provide resin 55D.

Step 5: Preparation of Resin 55E

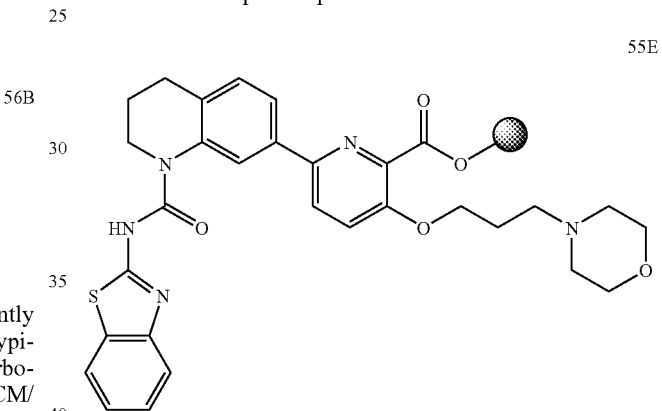
55E

Resin 55D (0.05 g, 023 mmol), was incubated with a mixture of 4-nitrophenyl benzo[d]thiazol-2-ylcarbamate (19) (1 mmol), in acetonitrile (2 mL) at 65° C. for 16 hours. The resulting resin was filtered and carefully washed with DMF (3×5 mL), MeOH (5 mL) and DCM (3×5 mL) and dried under reduced pressure for 30 minutes to provide resin 55E.

Step 6: Preparation of title compound 6-(1-(benzo[d]thiazol-2-ylcarbamoyl)-1,2,3,4-tetrahydroquinolin-7-yl)-3-(3-morpholinopropoxy)picolinic acid (55)

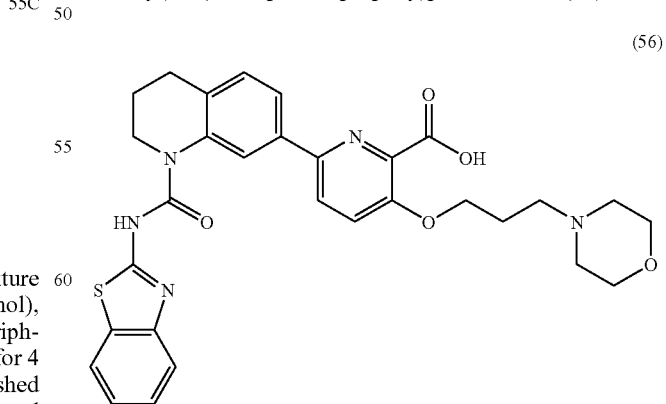
(56)

The title compound 6-(1-(benzo[d]thiazol-2-ylcarbamoyl)-1,2,3,4-tetrahydroquinolin-7-yl)-3-(3-morpholinopropoxy)picolinic acid (55) was prepared by the following procedure: Resin 55E was incubated with 20% tetrafluoroacetic acid in DCM (2 mL) for 1 hour. The resin was carefully filtered and the supernatant was dried under a stream of nitrogen. The residue was re-suspended in MeOH and purified by column chromatography on silica gel eluting with 10% EtOAc in hexanes to provide the desired product 6-(1-(benzo[d]thiazol-2-ylcarbamoyl)-1,2,3,4-tetrahydroquinolin-7-yl)-3-(3-morpholinopropoxy)picolinic acid (55): LCMS (APCI): m/z 574.0 (M+H).

Example 56

Synthesis of 6-(1-(benzo[d]thiazol-2-ylcarbamoyl)-1,2,3,4-tetrahydroquinolin-7-yl)-3-(2-(pyridin-4-yl)ethoxy)picolinic acid (56)

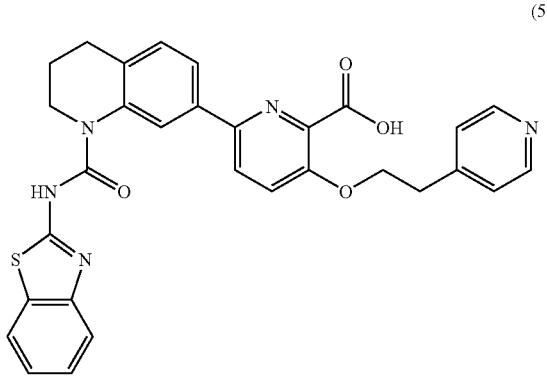

(56)

The title compound 6-(1-(benzo[d]thiazol-2-ylcarbamoyl)-1,2,3,4-tetrahydroquinolin-7-yl)-3-(2-(pyridin-4-yl)ethoxy)picolinic acid (56) was prepared by the following procedure: 6-(1-(Benzo[d]thiazol-2-ylcarbamoyl)-1,2,3,4-tetrahydroquinolin-7-yl)-3-(2-(pyridin-4-yl)ethoxy)picolinic acid (56) was prepared following a similar procedure as that described in example 56, except 4-pyridineethanol was used instead of 4-(3-hydroxypropyl)morpholine in step 3 of example 55. $^1$H NMR (300 MHz, MeOD): 8.45 (2H, d), 8.2 (1H, s), 7.7-7.6 (3H, m), 7.5-7.3 (5H, m), 7.2 (2H, d), 4.30 (2H, t), 3.95 (2H, t), 3.20 (2H, t), 2.85 (2H, t), 2.1 (2H, m). LCMS (APCI): m/z 552.0 (M+H).

Example 57

Synthesis of 6-(1-(benzo[d]thiazol-2-ylcarbamoyl)-1,2,3,4-tetrahydroquinolin-7-yl)-3-(2-(pyridin-2-yl)ethoxy)picolinic acid (57)

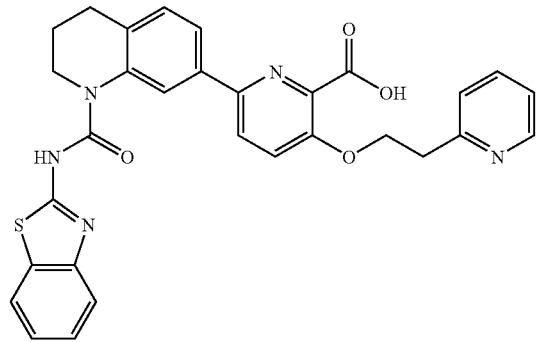

(57)

The title compound 6-(1-(benzo[d]thiazol-2-ylcarbamoyl)-1,2,3,4-tetrahydroquinolin-7-yl)-3-(2-(pyridin-2-yl)ethoxy)picolinic acid (57) was prepared by the following procedure: 6-(1-(Benzo[d]thiazol-2-ylcarbamoyl)-1,2,3,4-tetrahydroquinolin-7-yl)-3-(2-(pyridin-2-yl)ethoxy)picolinic acid (57) was prepared following a similar procedure as that described in example 56, except 2-pyridineethanol was used instead of 4-(3-hydroxypropyl)morpholine in step 3 of example 55. $^1$H NMR (300 MHz, MeOD): 8.2-8.45 (3H, m), 7.8-7.1 (10H, complex m), 4.60 (2H, t), 4.0 (2H, t), 3.1 (2H, m), 2.85 (2H, t), 2.0 (2H, m). LCMS (APCI): m/z 552.0 (M+H).

Example 58

Synthesis of 6-(1-(benzo[d]thiazol-2-ylcarbamoyl)-1,2,3,4-tetrahydroquinolin-7-yl)-3-(cyclobutylmethoxy)picolinic acid (58)

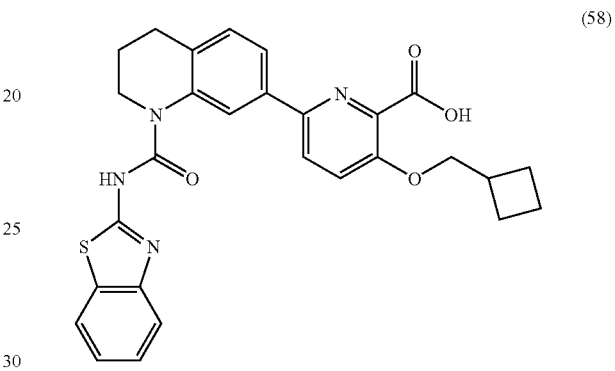

(58)

The title compound 6-(1-(benzo[d]thiazol-2-ylcarbamoyl)-1,2,3,4-tetrahydroquinolin-7-yl)-3-(cyclobutylmethoxy)picolinic acid (58) was prepared by the following procedure: 6-(1-(benzo[d]thiazol-2-ylcarbamoyl)-1,2,3,4-tetrahydroquinolin-7-yl)-3-(cyclobutylmethoxy)picolinic acid (58) was prepared following a similar procedure as that described in example 55, except cyclobutanemethanol was used instead of 4-(3-4ydroxypropyl)morpholine in step 3 of example 55. $^1$H NMR (300 MHz, MeOD): 8.15 (1H, s), 7.7-7.2 (8H, complex m), 4.10 (2H, d), 3.9 (2H, m), 2.80 (2H, t), 2.2-1.8 (9H, m). LCMS (APCI): m/z 515.1 (M+H).

Example 59

Synthesis of 6-(1-(benzo[d]thiazol-2-ylcarbamoyl)-1,2,3,4-tetrahydroquinolin-7-yl)-3-hydroxypicolinic acid (59)

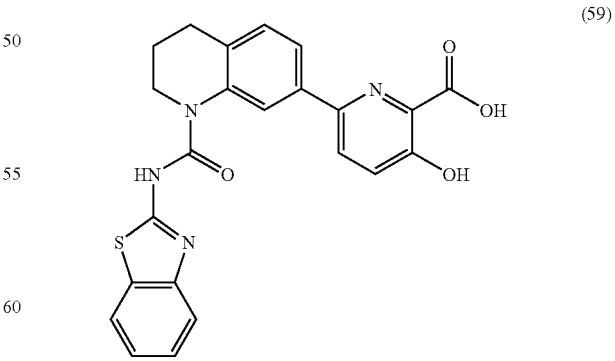

(59)

The title compound 6-(1-(benzo[d]thiazol-2-ylcarbamoyl)-1,2,3,4-tetrahydroquinolin-7-yl)-3-hydroxypicolinic acid (59) was prepared by the following procedure: 6-(1-(Benzo[d]thiazol-2-ylcarbamoyl)-1,2,3,4-tetrahydroquinolin-7-yl)-3-hydroxypicolinic acid (59) was prepared following a similar procedure as that described in example 55, except resin 55B is used instead of resin 55C step 4 of example 55. $^1$H NMR (300 MHz, MeOD): 8.2 (1H, s), 8.0 (1H, d), 7.75 (1H, d), 7.70 (1H, d), 7.5 (1H, d), 7.4-7.2 (3H, m), 6.6 (1H, d), 3.95 (2H, t), 2.85 (2H, t), 2.0 (2H, m). LCMS (APCI): m/z 447.1 (M+H).

Example 60

Synthesis of 6-(1-(benzo[d]thiazol-2-ylcarbamoyl)-1,2,3,4-tetrahydroquinolin-7-yl)-3-(4-fluorophenethoxy)picolinic acid (60)

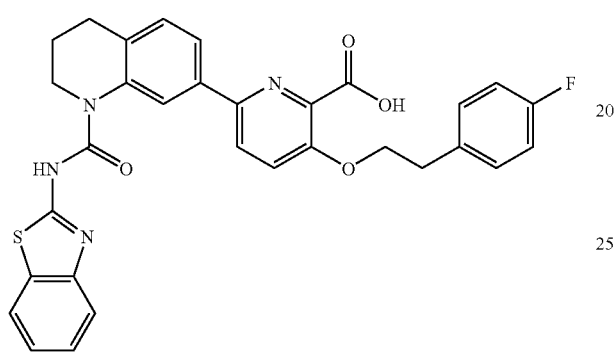

(60)

The title compound 6-(1-(benzo[d]thiazol-2-ylcarbamoyl)-1,2,3,4-tetrahydroquinolin-7-yl)-3-(4-fluorophenethoxy)picolinic acid (60) was prepared by the following procedure: 6-(1-(Benzo[d]thiazol-2-ylcarbamoyl)-1,2,3,4-tetrahydroquinolin-7-yl)-3-(4-fluorophenethoxy)picolinic acid (60) was prepared following a similar procedure as that described in example 56, except 4-fluorophenethyl alcohol was used instead of 4-(3-4ydroxypropyl)morpholine in step 3 of example 55. $^1$H NMR (300 MHz, MeOD): 8.15 (1H, s), 7.7 (2H, t), 7.60-6.90 (10H, complex m), 4.2 (2H, t), 3.9 (2H, t), 3.1 (2H, t), 2.8 (2H, t), 2.05 (2H, m). LCMS (APCI): m/z 569.2 (M+H).

Example 61

Synthesis of 6-(1-(benzo[d]thiazol-2-ylcarbamoyl)-1,2,3,4-tetrahydroquinolin-7-yl)-3-(4-(dimethylamino)phenethoxy)picolinic acid (61)

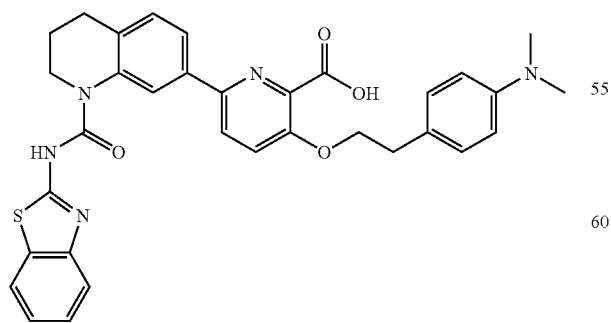

(61)

The title compound 6-(1-(benzo[d]thiazol-2-ylcarbamoyl)-1,2,3,4-tetrahydroquinolin-7-yl)-3-(4-(dimethylamino)phenethoxy)picolinic acid (61) was prepared by the following procedure: 6-(1-(Benzo[d]thiazol-2-ylcarbamoyl)-1,2,3,4-tetrahydroquinolin-7-yl)-3-(4-(dimethylamino)phenethoxy)picolinic acid (61) was prepared following a similar procedure as that described in example 55, except 4-(dimethylamino)phenethyl alcohol was used instead of 4-(3-4ydroxypropyl)morpholine in step 3 of example 55. $^1$H NMR (300 MHz, MeOD): 8.15 (1H, s), 7.7 (3H, m), 7.5 (1H, d), 7.4-7.3 (2H, m), 7.3-7.1 (4H, m), 6.75 (2H, d), 4.15 (2H, t), 3.9 (2H, t), 3.0 (2H, t), 2.85 (8H, m), 2.0 (2H, m). LCMS (APCI): m/z 594.1 (M+H).

Example 62

Synthesis of 3-amino-6-(1-(benzo[d]thiazol-2-ylcarbamoyl)-1,2,3,4-tetrahydroquinolin-7-yl)pyrazine-2-carboxylic acid (62)

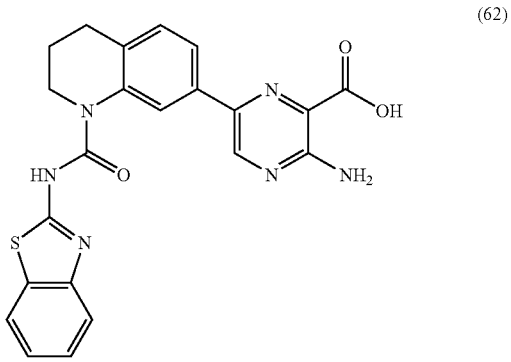

(62)

The title compound 3-amino-6-(1-(benzo[d]thiazol-2-ylcarbamoyl)-1,2,3,4-tetrahydroquinolin-7-yl)pyrazine-2-carboxylic acid (62) was prepared by the following procedure: 3-amino-6-(1-(Benzo[d]thiazol-2-ylcarbamoyl)-1,2,3,4-tetrahydroquinolin-7-yl)pyrazine-2-carboxylic acid (62) was prepared following a similar procedure as that described in for example 55. LC/MS (APCI) m/z 447 (M+H).

Example 64

The measurement of competition of compounds of the invention with F-Bak for a Bcl-2 family protein (Bcl-$x_L$) binding site using a Time Resolved Fluorescence Resonance Energy Transfer (TR-FRET) Binding Assay:

Test compounds were serially diluted in DMSO starting at 50 µM (2× starting concentration; 10% DMSO) and 10 µL transferred into a 384-well plate. Then 10 µL of a protein/probe/antibody mix is added to each well at final concentrations listed in Table 2.

TABLE 2

| Protein | Probe | Protein (nM) | Probe (nM) | Antibody | Antibody (nM) |
|---|---|---|---|---|---|
| GST-Bcl-$x_L$ | F-Bak (GQVGRQLAIIGDK(6-FAM)INR-amide) (SEQ ID NO: 1) | 1 | 100 | Tb-anti-GST | 1 |

The samples are then mixed on a shaker for 1 minute then incubated for an additional 2 hours at room temperature. For each assay plate, a probe/antibody and protein/antibody/probe mixture were included as a negative and a positive control, respectively. Fluorescence was measured on the Envision (Perkin Elmer) using a 340/35 nm excitation filter and 520/525 (F-Bak) and 495/510 nm (Tb-labeled anti-his antibody) emission filters. Dissociation constants ($K_i$) were determined using Wang's equation (see, Wang, Z. X. *An exact mathematical expression for describing competitive binding of two different ligands to a protein molecule*. FEBS Lett. 1995 360:111-114). The TR-FRET assay can be performed in the presence of varying concentrations of human serum (HS) or fetal bovine serum (FBS).

For comparison, the measurement of the competition of compounds of the invention for other Bcl-2 family protein binding sites (e.g., Bcl-2, Mcl-1) using the TR-FRET binding assay was accomplish by substituting GST-Bcl-$X_L$ in the TR-FRET assay with other GST-labeled protein, e.g., GST-Bcl-2, GST-Mcl-1 prepared in-house.

TR-FRET assay results (K, in micromolar) for compounds 1, 28, 38, 63, 68, 71, 75, 80, 81, 92, and 94 in Table 1 are 0.197, 0.0009, 0.0002, 0.012, 0.47, 0.007, 0.001, 0.0007, 0.66, 0.0005 and 0.000003, respectively.

In one embodiment, compounds of the invention selectively inhibit the Bcl-2 family protein, Bcl-$x_L$, over other Bcl-2 family proteins, such as Bcl-2 and Mcl-1. For comparison, data ($K_i$ in micromolar) from the measurement of the competition by certain compounds of the invention (i.e., compounds 1, 28, 38, 63, 71, 75, 80, 81, 92 and 94 in Table 1) with F-Bak for the Bcl-2 binding site using the TR-FRET binding assay are, 1.2, 0.15, 0.01, 0.018, 0.50, 0.272, 0.167, 0.66, 0.23 and 0.000003 respectively.

Example 65

The measurement of competition of compounds of the invention with Bim26-mer for a Bcl-2 family protein binding site using an Alpha Screen Bcl-$x_L$ Binding Assay:

The BH3 proteins ALPHASCREEN™ assay was used to identify active small molecules Bcl-2 family protein screen, e.g., Bcl-xL, hmMcl-1 screen. To determine an accurate estimation of the $IC_{50}$, the compounds were routinely tested at starting concentrations, 100 µM and/or 1 µM and serially titrated 3 fold over 11 dilutions.

The assay uses ALPHASCREEN™ technology that relies on hydrogel coated acceptor and donor beads which have functional groups for conjugation to a protein (e.g., GST-hmMcl-1, GST-Bcl-xL or GST-Biotin) and a peptide (Biotin-Bak, Biotin-Bim) respectively. The beads come in close proximity when the protein and the peptides interact. Donor beads contain a photosensitiser that converts oxygen to an excited form of $O_2$ at an excitation of 680 nm. Energy is transformed from the singlet oxygen and reacts with chemiluminescers on the acceptor bead, resulting in light emission at 520-620 nm. Compounds of the invention when added to the reaction, can reduce the intensity of the luminescence, dependent on the inhibition of proximity of the acceptor and donor beads. With this information, the $IC_{50}$ of each compound was calculated Materials GST-Bcl-xL, GST-hmMcl-1 and biotinylated GST proteins were prepared in-house and were stored as stock solutions at −80° C. The biotinylated-Bak, and biotinylated-Bim peptides were purchased from Auspep and were stored as 500 µM stock solutions in 100% DMSO at −80° C. The ALPHASCREEN™ GST (Glutathione-S-Transferase) Detection Kit was obtained from Perkin Elmer Lifesciences (Cat #6760603R). The Proxiplates, white 384 well flat-Bottom plates were purchased from Interpath Services, Melbourne (Cat #784075). The seals to cover the plates were purchased from Proscience, Melbourne (Cat#784075). DMSO was purchased from AnalaR. The 384 deep well plates and the Polypropylene 50 µL, V bottom polypropylene compound plates were purchased from Matrical.

Preparation of Compounds

Compounds of the invention were prepared as 10 mM stocks with 100% DMSO on the day prior to performing the assay. 12 µL of 100% DMSO and 6 µL of 10 mM compound (i.e. 3.333 mM, final 100 µM) was added to columns 1 and 12 in the Polypropylene 50 µL, V bottom compound plates. To achieve a final compound concentration of 1 µM, in a separate material plate, 28 µL of 100% DMSO and 2 µL of 10 mM compound was added to a well, mixed well, 2 µL of this solution was taken and added to 38 µL of 100% DMSO. 20 µL of this solution was added to the test material plate. Several control compounds were included in the test plates. For the control wells 15 µL 100% DMSO only was added to the appropriate wells of each plate. The compound plates were then serially diluted 2 fold using the MiniTrak. Once titrations were complete, the compound plate was immediately covered with a foil seal to prevent evaporation.

Buffer Preparation

The assay and bead buffers were prepared fresh. Each titrated compound plate was assayed in duplicate. The following volumes were sufficient to run 12 Proxiplates (4 assay plates run in duplicate in each of Bclxl, hmMcl and counter assays)

| Assay Buffer | | |
|---|---|---|
| [Stock] | [Final] | [Volume for 100 mL] |
| 1 M Hepes pH 7.4 | 50 mM | 5 mL |
| 1 M DTT | 10 mM | 1 mL |
| 4 M NaCl | 100 mM | 2.5 mL |
| 10% Tween-20 | 0.05% | 0.5 mL |
| 10 mg/mL Casein | 0.1 mg/mL | 1 mL |
| Milli-Q $H_2O$ | | 90 mL |

| Bead Buffer | | |
|---|---|---|
| [Stock] | [Final] | [Volume for 100 mL] |
| 1 M Tris-HCL pH 7.5 | 50 mM | 5 mL |
| 10% Tween-20 | 0.01% | 0.1 mL |
| 10 mg/mL Casein | 0.1 mg/mL | 1 mL |
| Milli-Q $H_2O$ | | 93.9 mL |

Protein and Peptide Preparation; and Assay Performance
1. The assay and bead buffers were used to prepare the acceptor and donor solutions. ALPHASCREEN™ beads are light sensitive and therefore prepared in a darkened room. 2.5 µL of beads were added per 1 mL of buffer.
2. The volume of protein or peptide to add was calculated using the following formula:

$$\frac{C1}{C2} \times V1 \times 2 = V2$$

$C_1$=Final Concentration of protein/peptide
$C_2$=Stock Concentration of protein/peptide
$V_1$=Total Volume of Acceptor/Donor Solution
$V_2$=Volume of stock protein/Peptide to add to Acceptor/Donor solution 3. The assay components were prepared as separate Acceptor and Donor Solutions. The Acceptor Solution contained Acceptor beads and target protein, while the Donor Solution contained Donor beads and biotinylated peptide.

| [Acceptor Solution] | [mL] | [Donor Solution] | [mL] |
|---|---|---|---|
| hmMcl-1 | | | |
| Assay buffer | 10 mL | Assay buffer | 10 mL |
| Bead buffer | 10 mL | Bead buffer | 10 mL |
| Acceptor Beads | 50 µL | Donor Beads | 50 µL |
| 11.1 µM hmMcl-1 | 2.9 µL | 500 µM B-Bak | 0.32 µL |
| Final Protein | [0.8 nM] | Final Peptide | [4 nM] |
| Bcl-xL | | | |
| Assay buffer | 10 mL | Assay buffer | 10 mL |
| Bead buffer | 10 mL | Bead buffer | 10 mL |
| Acceptor Beads | 50 µL | Donor Beads | 50 µL |
| 23.5 µM Bcl-XL | 1.02 µL | 500 µM B-Bim | 0.16 µL |
| Final Protein | [0.6 nM] | Final Peptide | [2 nM] |
| Counter-GST | | | |
| Assay buffer | 10 mL | Assay buffer | 8 mL |
| Bead buffer | 10 mL | Bead buffer | 8 mL |
| Acceptor Beads | 50 µL | Donor Beads | 50 µL |
| 77 µM B-GST | 1.04 µL | | |
| Final Protein | [2 nm] | | |

4. After the solutions were prepared, they were left to incubate for 30 minutes at room temperature to allow the beads to bind to the protein and the peptide.
5. 50 µL of Bcl-xL solution, 50 µL of hmMcl-1 solution and 50 µL of biotinylated-GST were added into separate deep wells on an assay plate. A control 50 µL Assay/Bead buffer was added separate well plates (no protein).
6. 50 µL of Bim solution and 50 µL of Bak solution were added into separate deep well plates.
7. Transfer 0.3 µL of sample from the compound plate into each assay plate.
8. Incubated for 30 mins at RT, then add 5 µL of the Donor solution. After addition of the Donor solution, tapped plates gently and sealed individually with adhesive film.
9. The plates were then loaded on the Envision 2103 plate reader to for analysis.

Data Analysis
The percent inhibition was calculated using the following equation:

$$\% \text{ Inhibition} = 100 * \left(1 - \left[\frac{(x - \mu^-)}{(\mu^+ - \mu^-)}\right]\right)$$

x=RFU obtained after compound treatment
$\mu^-$=RFU obtained for the negative controls (no protein controls)
$\mu^+$=RFU obtained for the positive controls (DMSO vehicle controls)

$IC_{50}$ values were obtained by non-linear least squares fitting of the above data, e.g., to XLfit3 equation 205: $y = A + ((B-A)/(1+((C/x)^{\wedge}D)))$.

The quality of the assay results were monitored by determination of the Z Prime factor for each assay plate, where Z Prime =>0.5 for the results was considered as reliable (Zhang et al, J Biomol Screening, 4:67-73, 1999).

Alphascreen results ($IC_{50}$ in micromolar) for exemplary compounds of the invention, that is compounds in Table 1, are provided below in the order as they appear in Table 1: 0.36, 0.84, 5.39, 1.44, 0.53, 0.76, 1.79, 0.36, 0.53, 0.035, 0.009, 0.005, 15.7, 0.11, 0.2, 10.09, 0.08, 0.045, 0.002, 0.53, 0.003, 100.0, 0.23, 0.095, 0.025, 0.035, 0.045, 0.007, 24.0, 0.045, 0.04, 0.01, 0.37, 0.002, 0.005, 0.007, 0.01, 0.003, 0.0009, 0.14, 0.005, 0.01, 0.008, 0.015, 0.01, 0.01, 0.69, 100, 0.295, 7.35, 12.83, 1.7, 0.66, NA, 0.01, 5.12, 0.72, 56.0, 0.40, 0.47, 0.15, 0.015, 0.05, 0.31, 0.23, 0.11, 0.20, 0.54, 0.68, 10.0, 0.04, 10.1, 0.008, 0.003, 0.007, 0.39, 0.12, 0.0006, 0.006, 0.006, 0.38, 0.0007, 0.005, 0.027, 0.0005, NA, NA, 0.065, 0.235, 0.01, 0.14, 0.002, 0.04 and 0.0005. As used herein, the abbreviation "NA" means that the data for the compound is not available.

Example 66

Cell Viability Assay

General:
The efficacy of the compounds of the present invention can also be determined in cell-based killing assays using a variety of cell lines and mouse tumor models. For example, their activity on cell viability can be assessed on a panel of cultured tumorigenic and non-tumorigenic cell lines, as well as primary mouse or human cell populations. In one exemplary set of conditions, 5,000-20,000 cells are cultured at 37° C. and 10% $CO_2$ in appropriate growth media (e.g., 100 µL Dulbecco's Modified Eagle's medium supplemented with 10% fetal calf serum, asparaginase, and 2-mercaptoethanol in the case of pre-B Eµ-Myc mouse tumors) in 96 well plates. Cell viability and total cell numbers can be monitored after several hours to several days of incubation with 1 nM-100 µM of the compounds to identify those that kill at $EC_{50}$<10 µL M. Cell viability can be determined by the ability of the cells to exclude propidium iodide (10 µg/mL by immunofluorescence analysis of emission wavelengths of 660-675 nm on a flow cytometer (BD FACScan) or by luminescent detection after incubation with CELL TITER-GLO®. Alternatively, a high throughput colorimetric assay such as the CELLTITER® 96 Aqueous Non-Radioactive Cell Proliferation Assay (Promega) may be used. Cell death by apoptosis is confirmed by pre-incubation of the cells with 50 µM of a caspase inhibitor such as zVAD-fmk.

a. Cell Viability Assay for Mcl-1$^{-/-}$ Mouse Embryonic Fibroblasts (MEF):
Neutralization of both Bcl-$x_L$ and Mcl-1 anti-apoptotic proteins in normal cells is required before a cell undergoes apoptosis via the downstream Bax/Bak pathway See, Chen, L. et al. Mol. Cell (2005) 17, 393-403; Willis, S, N. et al. Genes Dev. (2005) 19, 1294-1305. A compound that only targets Bcl-$x_L$ should not affect normal cells, but could kill certain cancer cells if they rely more on Bcl-$x_L$ and less on other anti-apoptotic proteins, e.g., Mcl-1, for survival. To mirror this, compounds of the invention were tested for its effect on survival of wild type (wt) mouse embryo fibroblasts (MEFs), Bax/Bak double knockout (BB DKO) MEFs, MEFs that expressed Noxa, and MEFs that expressed Bad. Noxa specifically neutralizes Mcl-1. Hence, MEFs that express Noxa mirror cancer cell types that are reliant on Bcl-$X_1$ for survival and should be much more sensitive to killing by a Bcl-$x_L$ targeting compound than MEFs where both Bcl-$x_L$ and Mcl-1 are protective.

In this assay, Mcl-1$^{(-/-)}$ cells were used to confirm that cell apoptosis in the presence of BH3 mimetic small molecules was due to predominantly Bcl-$x_L$ inactivation. This inactivation leaves Bax/Bak unconstrained and results in apoptosis. The CELLTITER-GLO Luminescent Cell Viability Assay is a homogeneous method of determining the number of viable cells in culture based on quantitation of the ATP present. The amount of ATP correlates with the presence of metabolically active cells such that following cell lysis the amount of ATP present is proportional to the amount of luminescence measured.

Materials

Mcl-1$^{(-/-)}$ mouse embryonic fibroblasts (MEFs) are an adherent cell line prepared in house. MEFs were grown in Iwaki 75 $cm^2$ tissue culture flasks (cat #3123-075) with FMA media which consists of:

89% DME Kelso

10% heat-inactivated foetal calf serum (FCS) (Hyclone cat #SH30396.03)

1% 10 mM asparagine (Fluka cat #11149)

275 µl of a 1:2000 dilution of 2-mercaptoethanol is added to the final 500 ml volume of FMA (Sigma cat #M7522; diluted in MT-PBS)

FMA was stored at 4° C. and used at 37° C. MEFs were cultured in FMA media and harvested in MT-PBS and trypsin. For MEF cell viability assays, cells were seeded separately in plates with 10% FCS-FMA and 1% FCS-FMA.

1% FCS-FMA consists of:

98% DME Kelso

1% heat-inactivated foetal calf serum (FCS) (Hyclone cat #SH30396.03)

1% 10 mM asparagine (Fluka cat #11149)

275 µl of a 1:2000 dilution of 2-mercaptoethanol is added to the final 500 ml volume (Sigma cat #M7522; diluted in MT-PBS)

Assays were performed using white, flat clear-bottom Greiner 384-well tissue culture grade (Interpath #781098) plates. The compounds were made up in Matrical 384-well, 25 µl V-bottomed plates (cat #MP101-2-PP), sealed with aluminium foil from Beckman Coulter (cat #538619) and stored at 12° C. overnight. Compound preparation and titrations were performed in AnalaR grade DMSO (Merck cat #1.02952.2500). The cell viability detection assay used was CELLTITRE-GLO™ which is commercially available from Promega (cat #G7572), stored at −20° C. and used at 37° C.

Automated Systems that can be used in this assay include: 1) Multidrop—The MULTIDROP 384 (ThermoLabsystems) dispenser was used to dispense cells aseptically into the assay plates; 2) MiniTrak—The MINITRAK system from Perkin Elmer was used for titration of the compound plates; 3) Zymark—The ZYMARK SCICLONE ALH3000 System with 100 nL pintool head was used for compound addition to the cells; 4) EnVision—The ENVISION plate reader was used to measure the viability via the detection of the luminescence.

Compounds of the invention were prepared as 10 mM solution in 100% DMSO and stored at −20° C. Compounds were thawed to room temperature and dispensed into a 384 well Matrical plate. Standard control compounds, e.g. 32.3 mM Etoposide, were added to the plate as controls.

The plates can be sealed with foil seals and stored at 12° C. overnight. The compound plates were left to thaw at room temperature and the compounds titrated 1:3 in 100% DMSO on the MiniTrak (see methods section below—day 3).

Method

1. Day One—Cell Splitting

The media was aspirated and the Mcl-1$^{(-/-)}$ cells washed with 10 mls of warmed MT-PBS. MT-PBS was aspirated and 1 ml of trypsin was added. The T75 flasks were incubated at 37° C. until the cells became detached. 4 ml of 10% FCS FMA media was added to the trypsinized cells and the entire volume was transferred to a 50 ml centrifuge tube and centrifuged for 3 minutes at 250 g. The supernatant was aspirated and the pellet resuspended in 10 ml of 10% FCS FMA. 3 ml of this cell suspension was added to a clean 75 $cm^2$ flask containing 17 ml of 10% FCS FMA media, thus performing a 3:10 split. The remaining cell suspension was used to perform a 1:50 split into another 75 $cm^2$ flask for further culturing.

2. Day Two—Seeding Assay Plates and Setting Up Compound Plates

Cells were harvested as per method step 1 and the pellet resuspended in 3 mls 10% FCS FMA. Cell number was determined by counting in a Neubauer haemocytometer and the dilution calculated to achieve a density of $1 \times 10^4$ cells $ml^{-1}$ (500 cells per well in 50 µl media). Separate dilutions were prepared in 50 ml 10% FCS FMA and 50 ml 1% FCS FMA solutions respectively.

Four assay plates were set up per compound plate. Two 384 well plates containing Mcl-1$^{(-/-)}$ cells in 10% FCS FMA and the other two plates containing Mcl-1$^{(-/-)}$ cells in 1% FCS FMA.

Using the Multidrop, 25 µl cells were dispensed aseptically into all 384 wells of the assay plates. Plates were left to rest in a non-stacked layer at room temperature for approximately 30 minutes (minimizes edge-effects) and then were placed as a single layer in the 37° C. incubator. The plates were left to incubate overnight.

3. Day Three—Titrating Compound Plates and Treating the Cells

The compound plates were titrated by performing a 3-fold 11-point dilution series using 100% DMSO on the MiniTrak. Following titration of the compounds, 100nl of compounds were added to the cell plates using the Zymark Sciclone Pintool. This was a 1:250 dilution of the compound so the highest final concentration of compound was 40 µM. The plates were then returned to 37° C. incubator and left to incubate overnight.

4. Day Four—Viability Analysis

The CELLTITRE-GLO™ solution was prepared according to the manufacturer's instructions by the reconstitution of CELLTITRE-GLO™Substrate with CELLTITRE-GLO™Buffer and stored after use at −80° C. Plates were removed from incubator and left to equilibrate to room temperature for 15 mins. 250 of diluted CELLTITRE-GLO™ was added to each well of the assay plates using the Multidrop. The plates were mixed on a plate shaker for 15 mins before being read on the Envision using the luminescence protocol.

Data Analysis

The percent inhibition was calculated using the following equation:

$$\% \text{ Inhibition} = 100 * \left(1 - \left[\frac{(x - \mu^-)}{(\mu^+ - \mu^-)}\right]\right)$$

x=CPS obtained after sample compound treatment
$\mu^-$=CPS obtained for the negative controls
$\mu^+$=CPS obtained for the positive controls $IC_{50}$ values were obtained by non-linear least squares fitting of the data, of the data using, e.g, the 4-parameter logistic fit (XLFit 4 eqn #205; y=A+4B−A)/(1+((C/x)^D))).

The quality of the assay results were monitored by determination of the Z' factor for each assay plate, where Z'≧0.5 for the results was considered as robust (Zhang et al, J Biomol Screening, 4:67-73, 1999).

MEF Mcl-1$^{-/-}$ KO cell viability results (i.e. EC$_{50}$ in micromolar and assay performed in the presence of 1% Fetal Bovine Serum) for certain compounds of the invention, i.e., compounds 74, 79, 90 and 92 in Table 1, are 0.06, 0.21, 0.59, 0.15, respectively.

b. Cell Viability Assay for Platelets

Platelet rich plasma (PRP) was incubated with a compound of the invention for approximately 4 hours at 37° C. After incubation, platelets were equilibrated to room temperature for 20 minutes and then and equal volume of CELLTITER-GLO™ reagent (Promega Corporation) was added. Samples were mixed for two minutes and then allowed to equilibrate for an additional 10 minutes at room temperature. The luminescence generated from the samples was quantitated using a LJL Analyst plate reader.

c. Cellular Viability of Human Tumor Cell Line NCI-H146

NCI-H146 (ATCC, Manassas, Va.) human small cell lung carcinoma cells were plated 50,000 cells per well in 96-well tissue culture plates in a total volume of 100 µL tissue culture medium supplemented with 10% human serum (Invitrogen, Carlsbad, Calif.) and treated with a 2-fold serial dilution of the compounds of interest from 10 µM to 0.020 µL. Each concentration was tested in duplicate at least 3 separate times. The number of viable cells following 48 hours of compound treatment was determined using the CELLTITER 96® Aqueous non-radioactive cell proliferation MTS assay according to manufacturer's recommendations (Promega Corp., Madison, Wis.).

or a pharmaceutically acceptable salt thereof, wherein

R$^1$ is independently a member selected from the group consisting of C$_{1-6}$ alkyl, C$_{1-6}$ heteroalkyl, C$_{2-6}$ alkenyl, C$_{2-6}$ alkynyl, C$_{1-6}$ haloalkyl and halogen;

the subscript n is an integer from 0 to 2, wherein when n is 0 then X$^1$ is —CH$_2$—, —C(H)(R$^a$)— or —C(R$^a$)$_2$;

X$^1$ is a member selected from the group consisting of —CH$_2$—, —C(H)(R$^a$)—, —C(R$^a$)$_2$, —O—, —N(H)—, —N(R$^a$)—, —N(C(O)R$^a$)—, —N(C(O) OR$^a$)—, —N(S(O)$_2$R$^a$)—, —N(S(O)R$^a$)—, —S—, —S(O)—, and —S(O)$_2$—, wherein R$^a$ is selected from the group consisting of C$_{1-6}$ alkyl, C$_{2-6}$ alkenyl, C$_{2-6}$ alkynyl, C$_{1-6}$ haloalkyl, C$_{3-6}$ cycloalkyl and halogen;

X$^{2a}$, X$^{2b}$ and X$^{2c}$ are each independently selected from the group consisting of C(H), C(R$^2$) and N, wherein at least one of X$^{2a}$ and X$^{2b}$ is C(H) or C(R$^2$); wherein R$^2$ is independently selected from the group consisting of —OR$^b$, —NR$^b$R$^c$, —SR$^b$, —C(O)OR$^c$, —C(O)NR$^b$R$^c$, —NR$^b$C(O)R$^d$, —S(O)$_2$R$^d$, —S(O)R$^d$, —S(O)$_2$NR$^b$R$^c$, —R$^d$, halogen, —CN and —NO$_2$, wherein R$^b$ and R$^c$ are each independently selected from the group consisting of hydrogen, C$_{1-4}$ alkyl, C$_{2-4}$ alkenyl, C$_{2-4}$ alkynyl, and C$_{1-4}$ haloalkyl, or optionally R$^b$ and R$^c$, together with the atom to which each is attached, are combined to form a 3- to 7-membered heterocyclic ring comprising 1 to 2 heteroatoms selected from N, O and S as ring vertices; and R$^d$ is selected from the group consisting of C$_{1-6}$ alkyl, C$_{2-6}$, alkenyl, C$_{2-6}$ alkynyl and C$_{1-6}$ haloalkyl;

---

---

We claim:

1. A compound of Formula I

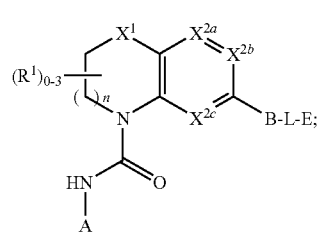

A is a member selected from the group consisting of:

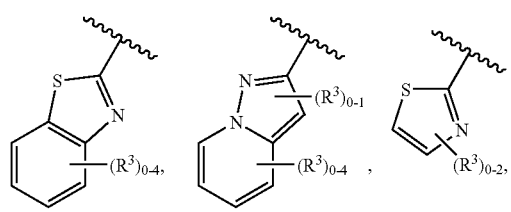

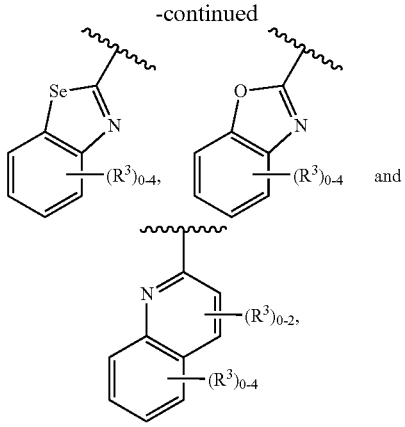

wherein $R^3$ is independently selected from the group consisting of —$NR^eR^f$, —$OR^c$, —CN, —$NO_2$, halogen, —C(O)$OR^e$, —C(O)$NR^eR^f$, —$NR^eC(O)R^f$, —$NR^eS(O)_2R^g$, —$NR^eS(O)R^g$, —S(O)$_2R^g$, S(O)$R^g$ and —$R^g$, wherein $R^e$ and $R^f$ at each occurrence are each independently selected from the group consisting of hydrogen, $C_{1-4}$ alkyl, $C_{2-4}$ alkenyl, $C_{2-4}$ alkynyl, $C_{1-4}$ haloalkyl and —$(CH_2)_{1-4}$phenyl, or $R^e$ and $R^f$, or $R^e$ and $R^g$ together with the atom to which each is attached, are optionally combined to form a 3- to 7-membered heterocyclic ring comprising 1 to 2 heteroatoms selected from N, O and S as ring vertices; and $R^g$ is selected from the group consisting of $C_{1-4}$ alkyl, $C_{2-4}$ alkenyl, $C_{2-4}$ alkynyl and $C_{1-4}$ haloalkyl;

B is a member selected from the group consisting of:

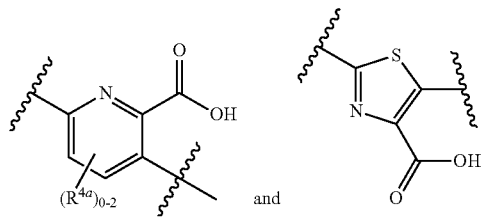

wherein $R^{4a}$, if present, is independently selected from $C_{1-4}$ alkyl, $C_{1-4}$ haloalkyl, $C_{2-4}$ alkenyl, $C_{2-4}$ alkynyl, halogen and —CN;

L is absent or is a member selected from the group consisting of $C_{6-10}$ arylene-$C_{1-6}$ heteroalkylene, $C_{5-9}$ heteroarylene-$C_{1-6}$ heteroalkylene, $C_{1-6}$ heteroalkylene, $C_{1-6}$ alkylene, $C_{1-6}$ haloalkylene, $C_{2-6}$ alkenylene, $C_{2-6}$ alkynylene, —NH—, —S— and —O—, wherein the alkylene, alkenylene, alkynylene or heteroalkylene portions of the L group are substituted with 0 to 4 $R^{5a}$ substituents selected from the group consisting of halogen, —$R^m$ and =O, and the aromatic portions of the L group are substituted with 0 to 4 $R^{5b}$ substituents selected from the group consisting of halogen, —$OR^n$, —$NR^nR^o$, —$R^n$, —$NO_2$, and CN; wherein $R^m$ is selected from the group consisting of $C_{1-6}$ alkyl, $C_{2-6}$ alkenyl, $C_{2-6}$ alkynyl, $C_{1-6}$ heteroalkyl and $C_{1-6}$ haloalkyl, and optionally any two $R^{5a}$ substituents attached to the same or different atoms of L can be combined to form a 5- to 7-membered carbocyclic ring or a 5- to 7-membered heterocyclic ring comprising 1 to 2 heteroatoms selected from N, O and S as ring vertices; and wherein $R^n$ and $R^o$, at each occurrence, are selected from the group consisting of hydrogen, $C_{1-6}$ alkyl, $C_{2-6}$ alkenyl, $C_{2-6}$ alkynyl and $C_{1-6}$ haloalkyl, and wherein optionally $R^n$ and $R^o$, together with the atoms to which each is attached, are combined to form a 3- to 7-membered heterocyclic ring comprising 1 to 2 heteroatoms selected from N, O and S as ring vertices;

E is hydrogen or halogen; or in the alternative E is selected from the group consisting of phenyl, $C_{5-6}$ heteroaryl, $C_{3-7}$ heterocycloalkyl and $C_{3-7}$ cycloalkyl, and optionally fused to E are 1 or 2 rings independently selected from the group consisting of a 3- to 7-membered carbocyclic ring, a 3- to 7-membered heterocyclic ring, a benzene ring and a 5- to 6-membered heteroaromatic ring, wherein E and each ring optionally fused to E are independently substituted with 0 to 5 $R^6$ substituents selected from the group consisting of halogen, —$NR^p R^q$, —$SR^p$, —$OR^p$, —C(O)$OR^p$, —C(O)$NR^pR^q$, —C(O)$R^p$, —$NR^pC(O)R^q$, —OC(O)$R^r$, —$NR^pC(O)NR^pR^q$, —OC(O)$NR^pR^q$, —$NR^pC(O)OR^r$, —C(=$NOR^p$)$NR^pR^q$, —$NR^pC$(=N—CN)$NR^pR^q$, —$NR^pS(O)_2NR^pR^q$, —S(O)$_2R^r$, —S(O)$_2NR^pR^q$, —$R^r$, —$R^s$, —$NO_2$, —$N_3$, =O, —CN, —$Z^1$—$NR^pR^q$, —$Z^1$—$SR^p$, —$Z^1$—$OR^p$, —$Z^1$—C(O)$OR^p$, —$Z^1$—C(O)$NR^pR^q$, —$Z^1$—C(O)$R^p$, —$Z^1$—$NR^pC(O)R^q$, —$Z^1$—OC(O)$R^r$, —$Z^1$—$NR^pC(O)NR^pR^q$, —$Z^1$—OC(O)$NR^pR^q$, —$Z^1$—$NR^pC(O)OR^r$, —$Z^1$—C(=$NOR^p$)$NR^pR^q$, —$Z^1$—$NR^pC$(=N—CN)$NR^pR^q$, —$Z^1$—$NR^pS(O)_2NR^pR^q$, —$Z^1$—S(O)$_2R^r$, —$Z^1$—S(O)$_2NR^pR^q$, —$Z^1$—$NO_2$, —$Z^1$—$N_3$, —$Z^1$—$R^s$ and —$Z^1$—CN; wherein $Z^1$ is selected from the group consisting of $C_{1-6}$ alkylene, $C_{2-6}$ alkenylene, $C_{2-6}$ alkynylene, $C_{1-6}$ heteroalkylene, $C_{3-7}$ cycloalkylene and $C_{3-7}$ heterocycloalkylene; $R^p$ and $R^q$ are each independently from hydrogen, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-phenyl; $R^r$ is selected from the group consisting of $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl, phenyl and —$(CH_2)_{1-4}$-phenyl; optionally within each $R^6$ substituent $R^p$ and $R^q$ or $R^p$ and $R^r$, together with the atom to which each is attached, are optionally combined to form a 3- to 7-membered heterocyclic ring optionally comprising 1 to 2 heteroatoms selected from N, O and S as ring vertices; $R^s$ is selected from the group consisting of phenyl, $C_{5-6}$ heteroaryl, $C_{3-7}$ heterocycloalkyl, $C_{3-7}$ cycloalkyl, and optionally fused to $R^s$ are 1 or 2 rings each independently selected from the group consisting of a 5- to 7-membered carbocyclic ring, a 5- to 7-membered heterocyclic ring, a benzene ring and a 5- to 6-membered heteroaromatic ring, and wherein $R^s$ and each ring optionally fused to $R^s$ is each independently substituted with 0 to 5 $R^7$ substituents selected from the group consisting of halogen, —$NR^tR^u$, —$SR^t$, —$OR^t$, —C(O)$OR^t$, —C(O)$NR^tR^u$, —C(O)$R^t$, —$NR^tC(O)R^v$, —OC(O)$R^v$, —$NR^tC(O)NR^tR^u$, —OC(O)$NR^tR^v$, —$NR^tC(O)OR^v$, —C(=$NOR^t$)$NR^tR^u$, —$NR^tC$(=N—CN)$NR^tR^u$, —$NR^tS(O)_2NR^tR^u$, —S(O)$_2R^v$, —S(O)$_2NR^tR^u$, —$R^v$, —$NO_2$, —$N_3$, =O, —CN, —$Z^2$—$NR^tR^u$, —$Z^2$—$SR^t$, —$Z^2$—$OR^t$, —C(O)$R^t$, —$Z^2$—C(O)$NR^tR^u$, —$Z^2$—C(O)$R^v$, —$Z^2$—$NR^tC(O)R^v$, —$Z^2$—OC(O)$R^v$, —$Z^2$—$NR^tC(O)NR^tR^u$, —$Z^2$—OC(O)$NR^tR^u$, —$Z^2$—$NR^tC(O)OR^v$, —$Z^2$—C(=$NOR^t$)$NR^tR^u$, —$Z^2$—$NR^tC$(=N—CN)$NR^tR^u$, —$Z^2$—$NR^tS(O)_2NR^tR^u$, —$Z^2$—S(O)$_2R^v$, —$Z^2$—S(O)$_2NR^tR^u$, —$Z^2$—$NO_2$, —$Z^2$—$N_3$ and —$Z^2$—CN; wherein $Z^2$ is selected from the group consisting of $C_{1-6}$ alkylene, $C_{2-6}$ alkenylene, $C_{2-6}$ alkynylene, and $C_{1-6}$ heteroalkylene; $R^t$ and $R^u$ are each independently selected from hydrogen, $C_{1-6}$ alkyl, $C_{1-6}$ haloalkyl, $C_{2-6}$ alkenyl, $C_{2-6}$ alkynyl, —$(CH_2)_{1-4}$-phenyl, $C_{3-7}$ cycloalkyl and $C_{3-7}$ heterocycloalkyl; $R^v$ is selected from $C_{1-4}$ alkyl, $C_{1-4}$ haloalkyl, $C_{2-6}$ alkenyl, $C_{3-7}$ alkynyl, $C_{3-7}$ cycloalkyl, $C_{3-7}$ heterocycloalkyl and —$(CH_2)_{1-4}$-phenyl; and within each $R^7$ substituent, $R^t$ and $R^u$ or $R^t$ and $R^v$, together with the atom to which each is attached, optionally are combined to form a 3- to 7-membered heterocyclic ring having 1 to 2 heteroatoms selected from N, O and S as ring vertices.

2. The compound of claim 1, or the pharmaceutically acceptable salt thereof, wherein the compound is of a formula selected from the group consisting of

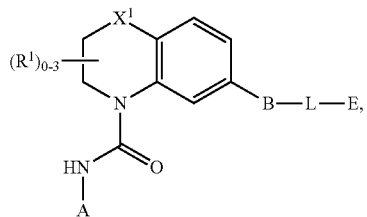
I-a

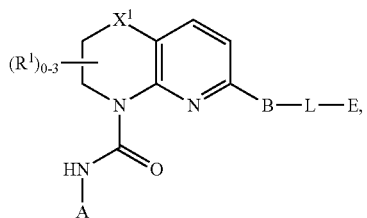
I-b

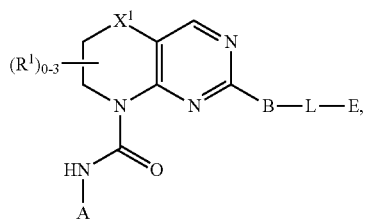
I-c

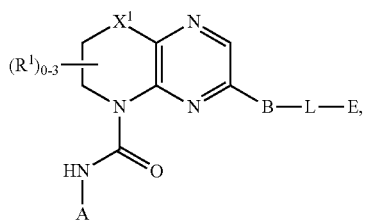
I-d

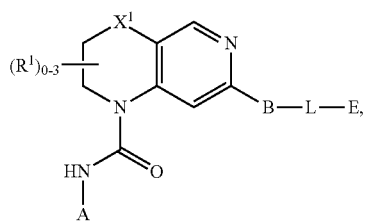
I-e

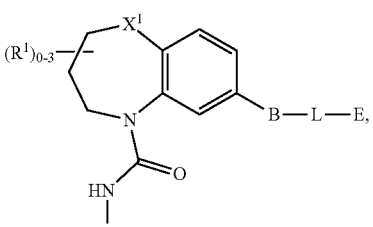
I-f

-continued

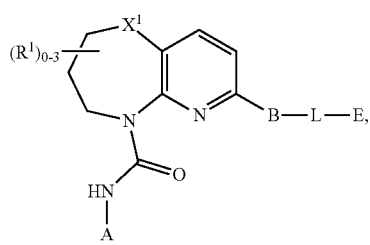
I-g

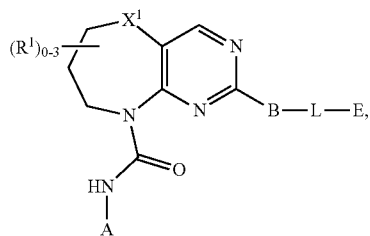
I-h

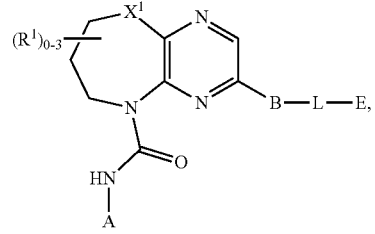
I-i

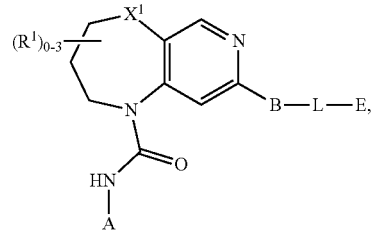
I-j

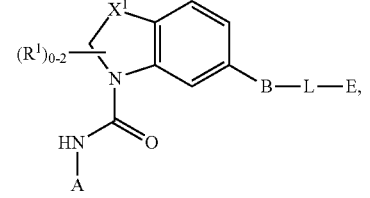
I-k

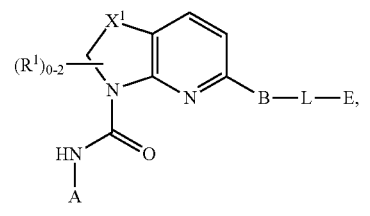
I-m

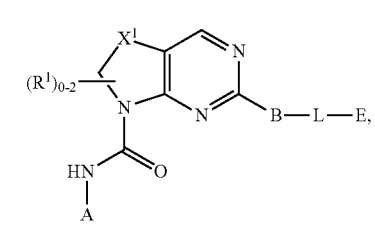
I-n

-continued

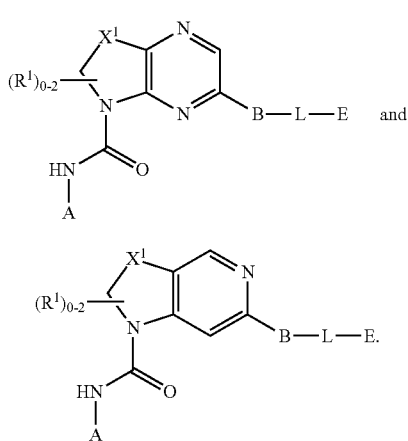
I-o

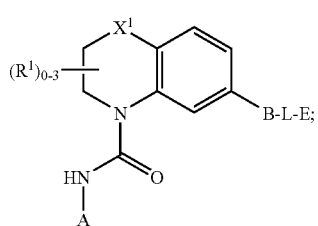
I-p

3. The compound of claim 2, or the pharmaceutically acceptable salt thereof, wherein the compound is of Formula I-a,

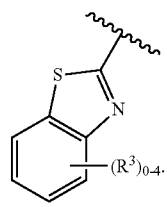
I-a wherein $R^1$ is absent;
$X^1$ is selected from the group consisting of —CH$_2$—, —C(H)(R$^a$)—, —C(R$^a$)$_2$—, —O—, —N(H)—, —N(R$^a$)—, —N(C(O)R$^a$)—, —N(C(O)OR$^a$)—, —N(S(O)$_2$R$^a$)—, —N(S(O)R$^a$)—, —S—, —S(O)—, and —S(O)$_2$—; and
A is

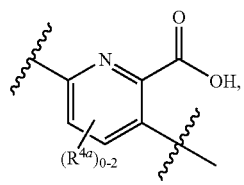

4. The compound of claim 3, or the pharmaceutically acceptable salt thereof, wherein $X^1$ is —CH$_2$— or —O—.

5. The compound of claim 1, or the pharmaceutically acceptable salt thereof, wherein in Formula I, B is

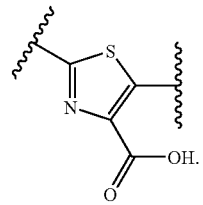

wherein $R^{4a}$, if present, is selected from the group consisting of halogen and C$_{1-4}$ alkyl.

6. The compound of claim 1, or the pharmaceutically acceptable salt thereof, wherein B is 7. The compound of claim 1, 2, 3, 5 or 6, or the pharmaceutically acceptable salt thereof, wherein L is absent or is an optionally substituted group selected from the group consisting of C$_{6-10}$ arylene-C$_{1-6}$ heteroalkylene, C$_{5-9}$ heteroarylene-C$_{1-6}$ heteroalkylene, C$_{1-6}$ heteroalkylene, C$_{2-6}$ heteroalkenylene, C$_{1-6}$ alkylene, C$_{2-6}$ alkenylene, C$_{2-6}$ alkynylene and —O—; and E is a ring selected from the group consisting of phenyl, C$_{5-6}$ heteroaryl, C$_{3-7}$ heterocycloalkyl, and C$_{3-7}$ cycloalkyl, and wherein optionally fused to E is a 5- to 7-membered heterocyclic ring, a benzene ring, or a 5- to 6-membered heteroaromatic ring, and wherein E and said ring optionally fused to E are substituted with 0 to 5 $R^6$ substituents selected from the group consisting of fluoro, chloro, bromo, —NR$^p$R$^q$, —SR$^p$, —C(O)OR$^p$, —C(O)NR$^p$R$^q$, —C(O)R$^p$, —NR$^p$C(O)R$^q$, —OC(O)R$^r$, —NR$^p$C(O)NR$^p$R$^q$, —OC(O)NR$^p$R$^q$, —NR$^p$C(O)OR$^r$, —S(O)$_2$R$^r$, —S(O)$_2$NR$^p$R$^q$, —R$^r$, —R$^s$, —NO$_2$, —N$_3$, —CN, —Z$^1$—NR$^p$R$^q$, —Z$^1$—SR$^p$, —Z$^1$—OR$^p$, —Z$^1$—OC(O)NR$^p$R$^q$, —Z$^1$—NR$^p$C(O)OR$^r$, —Z$^1$—S(O)$_2$R$^r$, —Z$^1$—R$^s$ and —Z$^1$—S(O)$_2$NR$^p$R$^q$; wherein Z$^1$ is selected from the group consisting of C$_{1-6}$ alkylene, C$_{2-6}$ alkenylene, C$_{2-6}$ alkynylene and C$_{1-6}$ heteroalkylene; R$^p$ and R$^q$ are each independently selected from hydrogen, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl, phenyl and —(CH$_2$)$_{1-4}$-phenyl; R$^r$ is selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl and —(CH$_2$)$_{1-4}$-phenyl; and optionally within each R$^6$ substituent, R$^p$ and R$^q$ or R$^p$ and R$^r$, together with the atom to which each is attached, are combined to form a 3- to 7-membered heterocyclic ring comprising 1 to 2 heteroatoms selected from N, O and S as ring vertices; —R$^s$ is phenyl, a 5- to 6-membered heteroaromatic ring or a 5- to 7 membered heterocyclic ring, wherein optionally fused to R$^5$ is a benzene ring, a 5- to 6-membered heteroaromatic ring or a 5- to 7 membered heterocyclic ring, wherein R$^s$ and said ring optionally fused to R$^s$ are substituted with 0 to 3 R$^7$ substituents selected from the group consisting of halogen, —NR$^t$R$^u$, —SR$^t$, —OR$^t$, —OC(O)NR$^t$R$^u$, —NR$^t$C(O)OR$^v$, —R$^v$, —Z$^2$—NR$^t$R$^u$, —Z$^2$—OC(O)NR$^t$R$^u$, —Z$^2$—NR$^t$C(O)OR$^v$ and —CN; wherein Z$^2$ is selected from the group consisting of C$_{1-6}$ alkylene, C$_{2-6}$ alkenylene, C$_{2-6}$ alkynylene and C$_{1-6}$ heteroalkylene, wherein R$^t$ and R$^u$ each independently selected from hydrogen, C$_{1-6}$ alkyl, C$_{1-6}$ haloalkyl, C$_{2-6}$ alkenyl, C$_{2-6}$ alkynyl, C$_{3-7}$ cycloalkyl and C$_{3-7}$ heterocycloalkyl; R$^v$ is selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ heterocycloalkyl and —(CH$_2$)$_{1-4}$-phenyl; and optionally within each R$^7$ substitutent, R$^t$ and R$^u$ or R$^t$ and R$^v$, together with the atoms to which each is attached, are combined to form a 3- to 7-membered heterocyclic ring optionally comprising 1 to 2 heteroatoms selected from N, O and S as ring vertices.

8. The compound of claim 5, or the pharmaceutically acceptable salt thereof, wherein L is absent and E is selected from the group consisting of phenyl and pyridyl, and wherein optionally fused to E is a ring selected from the group consisting of a pyrimidin-4-one ring, a pyrimidin-2-one ring, a benzene ring, a pyridine ring, a pyrrole ring, a pyrazole ring, an imidazole ring, a furan ring and a thiophene ring, wherein E and the ring optionally fused to E are each optionally independently substituted.

9. The compound of claim 1, or the pharmaceutically acceptable salt thereof, wherein L is $C_{1-4}$ alkylene or $C_{1-4}$ heteroalkylene.

10. The compound of claim 1, or the pharmaceutically acceptable salt thereof, wherein L is selected from the group consisting of:

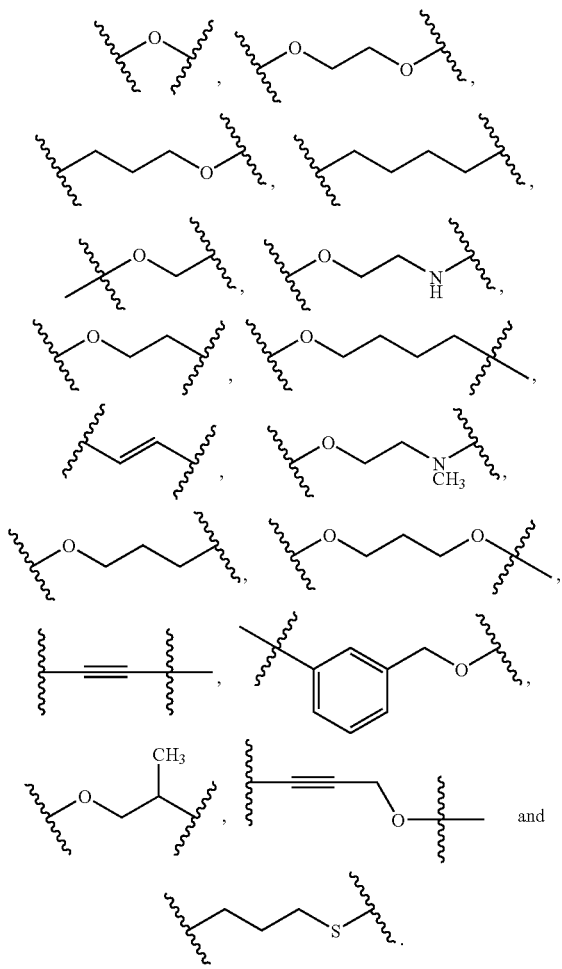

11. The compound of claim 9 or 10, or the pharmaceutically acceptable salt thereof, wherein L is present and E is selected from the group consisting of phenyl, pyridyl, pyrimidinyl, piperidinyl, piperazinyl, morpholino, pyrrolidinyl, pyrrolidonyl and cyclobutyl, and wherein optionally fused to E is a pyridine ring, a benzene ring, pyrimidin-4-one ring, a pyrimidin-2-one ring or a dioxolane ring, and wherein E and said ring optionally fused to E are substituted with 0 to 5 $R^6$ substituents selected from the group consisting of fluoro, chloro, $-NR^pR^q$, $-SR^p$, $-S(O)_2R^r$, $-OR^p$, $-NR^pC(O)OR^r$, $-R^r$, $-Z^1-NR^pR^q$, $-Z^1-NR^pC(O)OR^r$ and $-R^s$, wherein $R^p$ and $R^q$ are each independently selected from hydrogen, $C_{1-6}$ alkyl, $C_{1-6}$ haloalkyl, $C_{2-6}$ alkenylene, $C_{2-6}$ alkynylene and $C_{1-6}$ heteroalkylene; $R^r$ is selected from $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ heterocycloalkyl and $-(CH_2)_{1-4}$-phenyl; and optionally within each $R^6$ substituent $R^p$ and $R^q$ or $R^p$ and $R^r$, are combined to form a 3- to 6-membered heterocyclic ring having 1 to 2 heteroatoms selected from N, O and S as ring vertices.

12. The compound of claim 1, 3, 5 or 6, or the pharmaceutically acceptable salt thereof, wherein E is phenyl and is meta or para substituted with an optionally substituted $R^s$ group selected from the group consisting of:

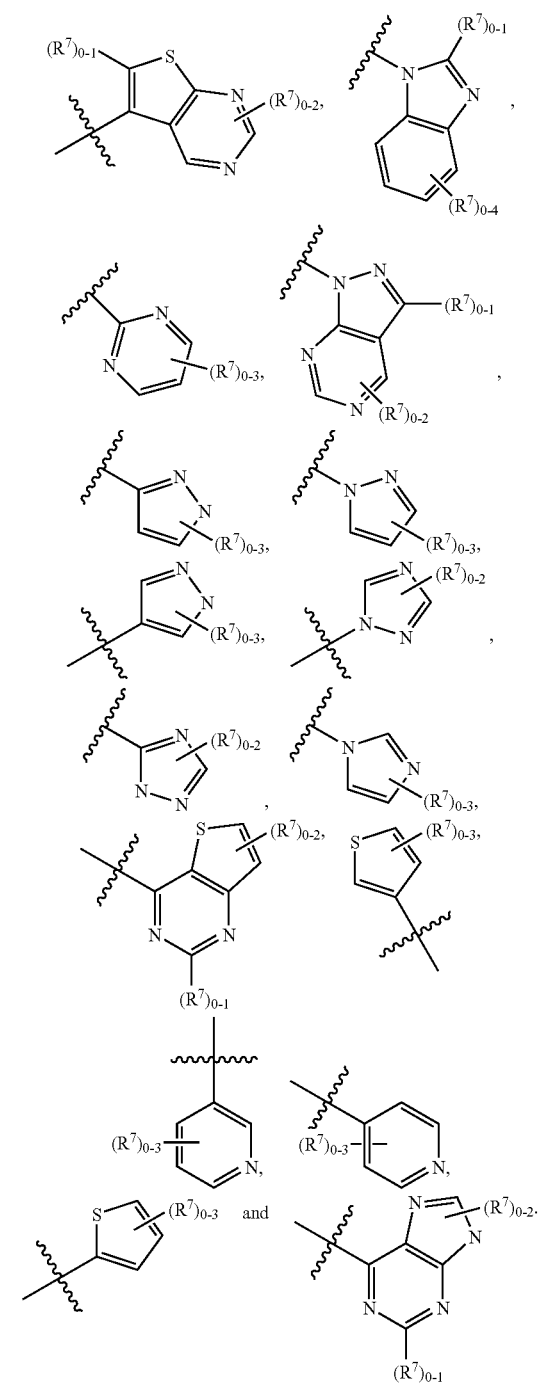

13. The compound of claim 1, 3, 5 or 6, or the pharmaceutically acceptable salt thereof, wherein E is selected from the group consisting of
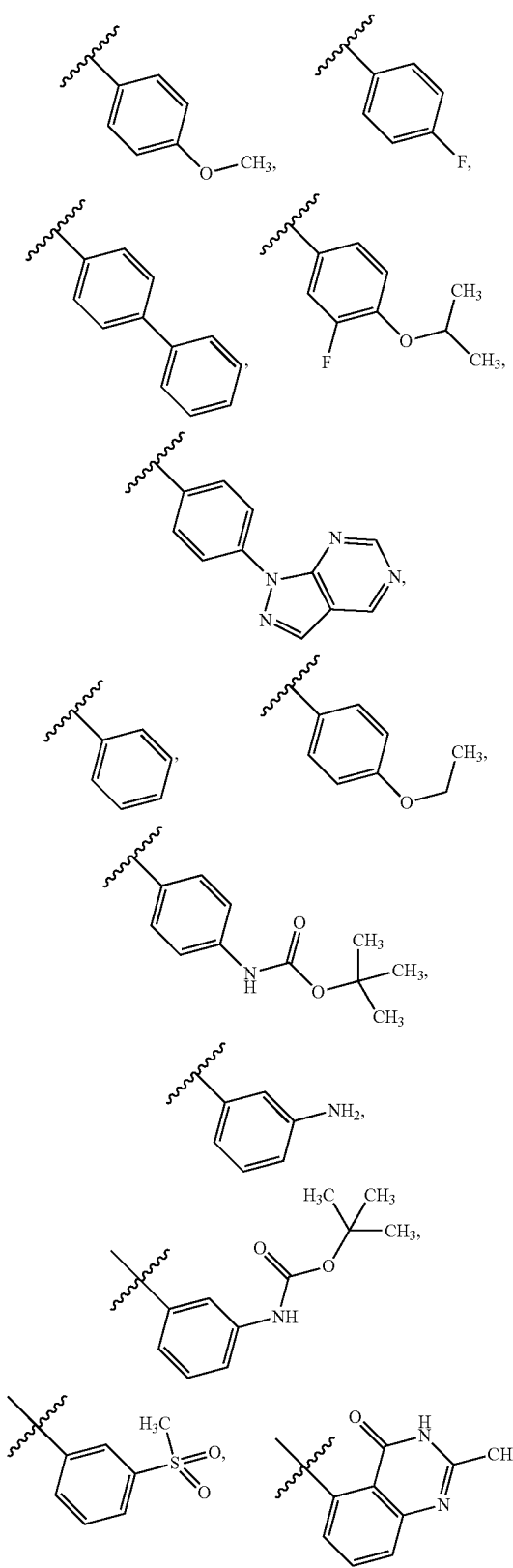
-continued
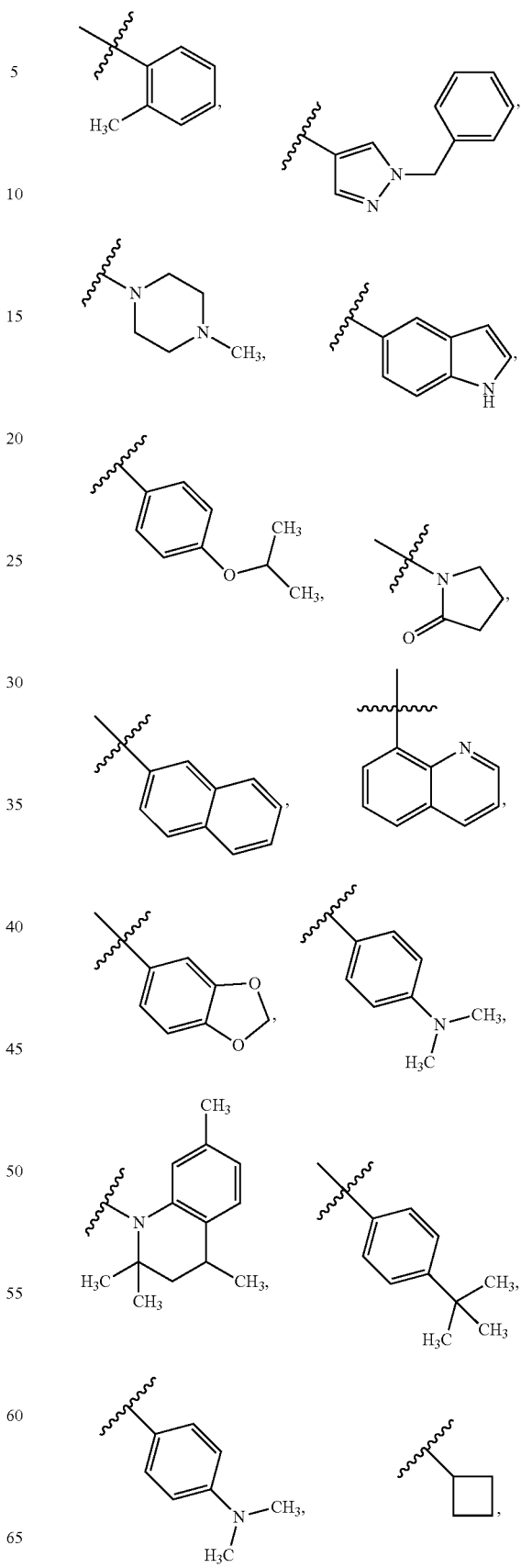

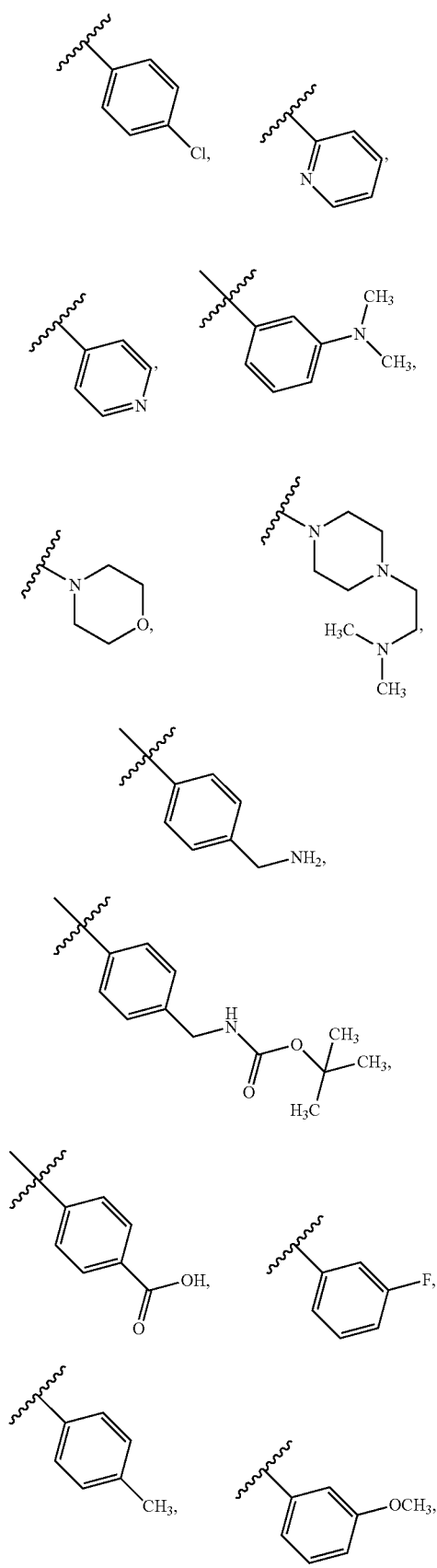
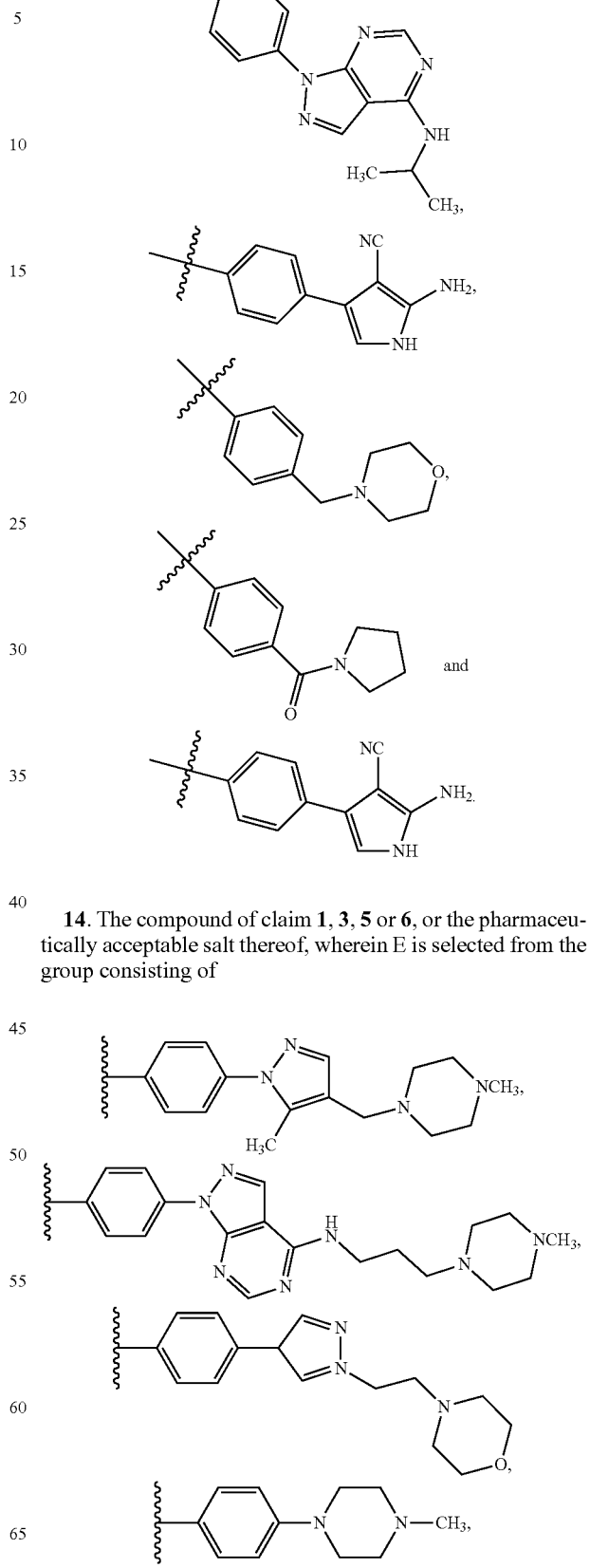
14. The compound of claim 1, 3, 5 or 6, or the pharmaceutically acceptable salt thereof, wherein E is selected from the group consisting of

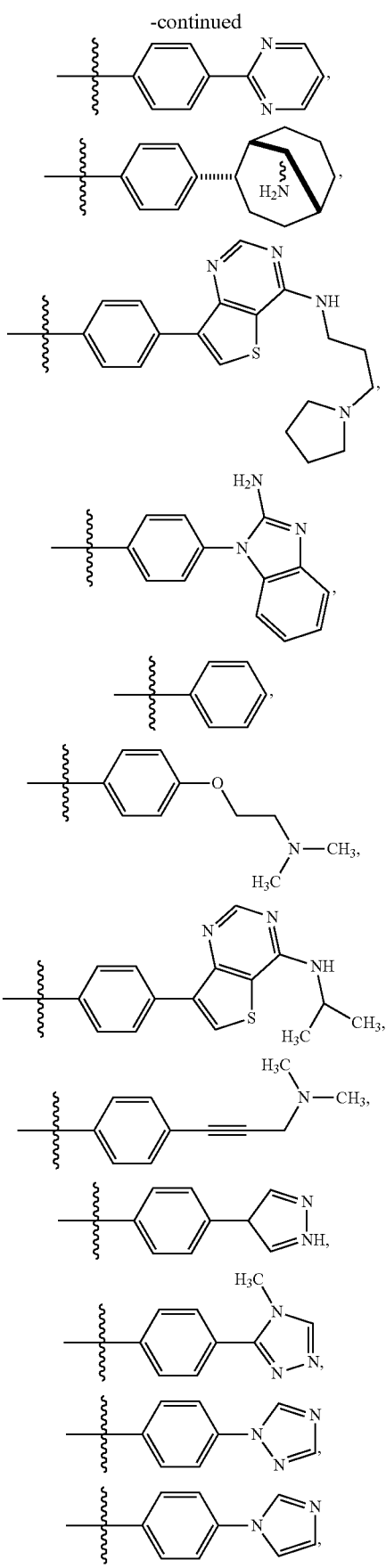
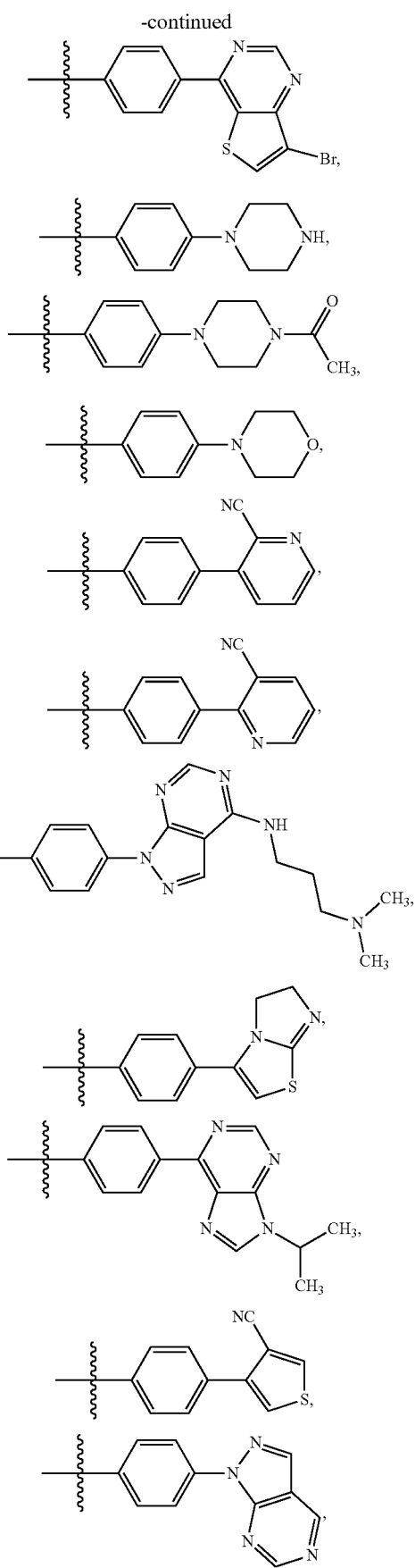

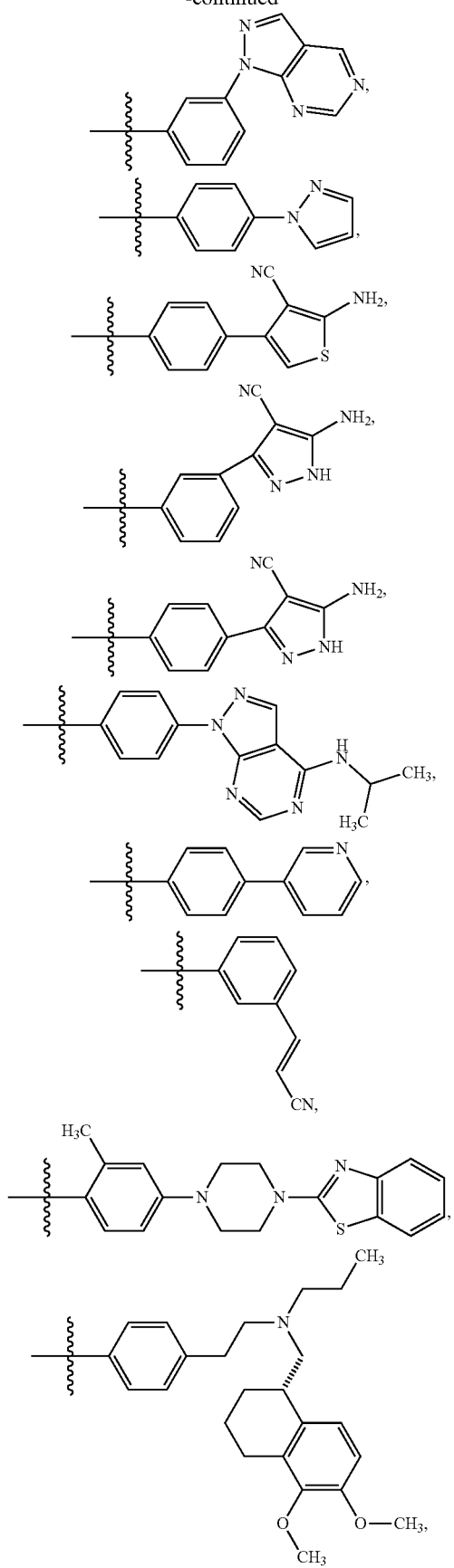
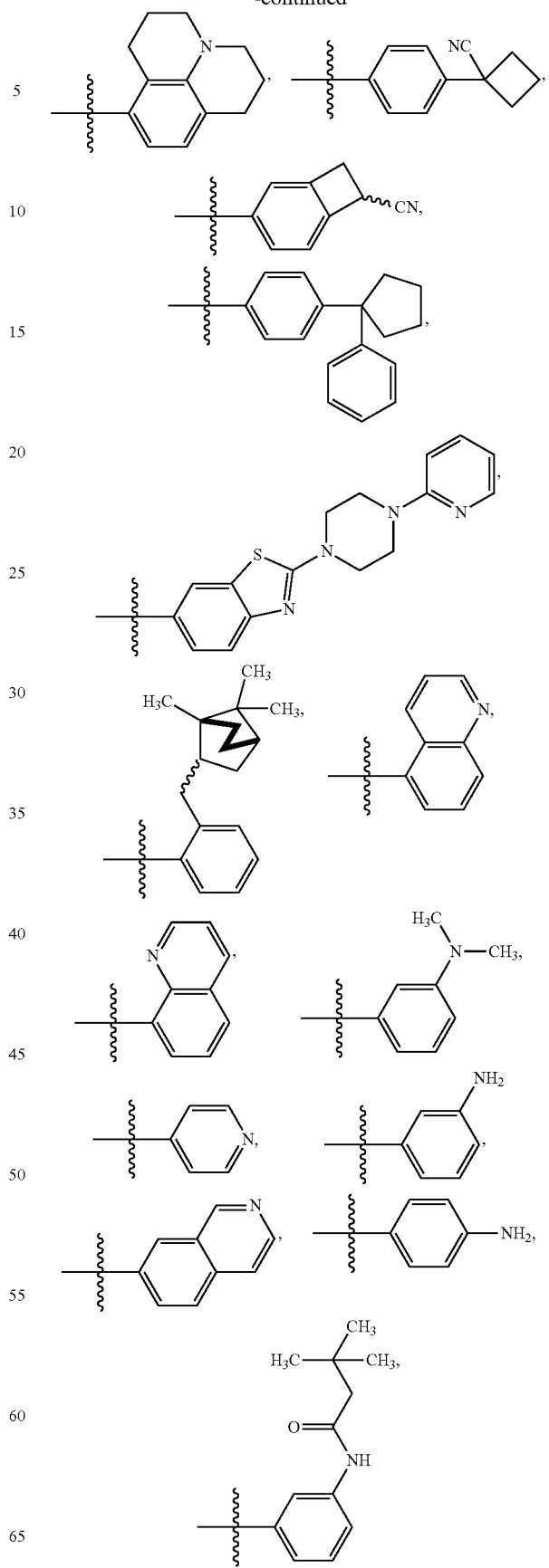

-continued

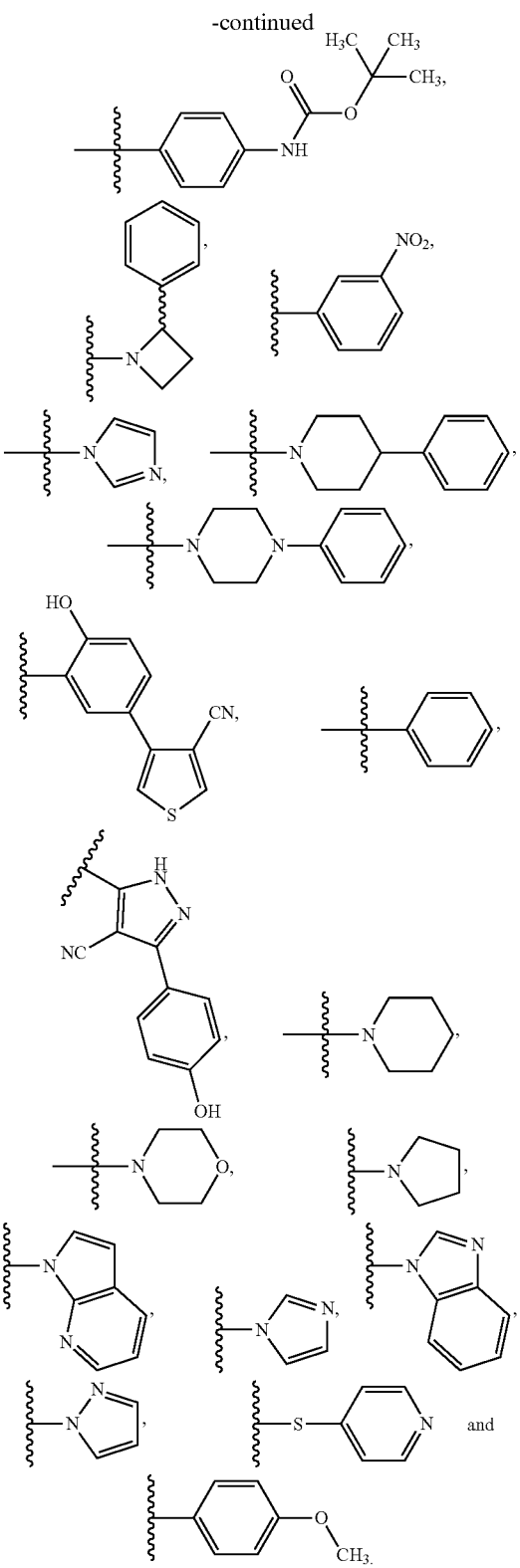

15. The compound of claim 1 or 3, or the pharmaceutically acceptable salt thereof, wherein L is absent and E is hydrogen or halogen.

16. The compound of claim 1 or 3, or the pharmaceutically acceptable salt thereof, wherein L is selected from the group consisting of $C_{1-6}$ heteroalkylene, $C_{1-6}$ alkylene, $C_{2-6}$ alkenylene and $C_{2-6}$ alkynylene, each of which is independently optionally substituted; and E is hydrogen.

17. The compound of claim 16, or the pharmaceutically acceptable salt thereof, wherein L is an optionally substituted $C_{1-4}$ heteroalkylene.

18. A compound, or a pharmaceutically acceptable salt thereof, wherein said compound is selected from the group consisting of 2-(1-(benzo[d]thiazol-2-ylcarbamoyl)-1,2,3,4-tetrahydroquinolin-7-yl)thiazole-4-carboxylic acid;

6-(1-(benzo[d]thiazol-2-ylcarbamoyl)-1,2,3,4-tetrahydroquinolin-7-yl)-3-hydroxypicolinic acid;

6-(4-(benzo[d]thiazol-2-ylcarbamoyl)-1-methyl-1,2,3,4-tetrahydroquinoxalin-6-yl)picolinic acid;

6-(1-(benzo[d]thiazol-2-ylcarbamoyl)-1,2,3,4-tetrahydroquinolin-7-yl)-3-isobutoxypicolinic acid;

6-(1-(benzo[d]thiazol-2-ylcarbamoyl)-1,2,3,4-tetrahydroquinolin-7-yl)-3-butoxypicolinic acid;

6-(1-(benzo[d]thiazol-2-ylcarbamoyl)-1,2,3,4-tetrahydroquinolin-7-yl)-3-(cyclobutylmethoxy)picolinic acid;

6-(1-(benzo[d]thiazol-2-ylcarbamoyl)-1,2,3,4-tetrahydroquinolin-7-yl)-3-(2-(2-oxopyrrolidin-1-yl)ethoxy)picolinic acid;

6-(1-(benzo[d]thiazol-2-ylcarbamoyl)-1,2,3,4-tetrahydroquinolin-7-yl)-3-(3-morpholinopropoxy)picolinic acid;

6-(1-(benzo[d]thiazol-2-ylcarbamoyl)-1,2,3,4-tetrahydroquinolin-7-yl)-3-(2-(4-(2-(dimethylamino)ethyl)piperazin-1-yl)ethoxy)picolinic acid;

6-(1-(benzo[d]thiazol-2-ylcarbamoyl)-1,2,3,4-tetrahydroquinolin-7-yl)-3-phenylpicolinic acid;

6-(1-(benzo[d]thiazol-2-ylcarbamoyl)-1,2,3,4-tetrahydroquinolin-7-yl)-3-o-tolylpicolinic acid;

6-(1-(benzo[d]thiazol-2-ylcarbamoyl)-1,2,3,4-tetrahydroquinolin-7-yl)-3-(3-(methylsulfonyl)phenyl)picolinic acid;

6-(1-(benzo[d]thiazol-2-ylcarbamoyl)-1,2,3,4-tetrahydroquinolin-7-yl)-3-(2-(pyridin-2-yl)ethoxy)picolinic acid;

6-(1-(benzo[d]thiazol-2-ylcarbamoyl)-1,2,3,4-tetrahydroquinolin-7-yl)-3-(2-(pyridin-4-yl)ethoxy)picolinic acid:

6-(4-(benzo[d]thiazol-2-ylcarbamoyl)-3,4-dihydro-2H-benzo[b][1,4]oxazin-6-yl)-3-(3-(pyridin-4-yl)propoxy)picolinic acid;

6-(1-(benzo[d]thiazol-2-ylcarbamoyl)-1,2,3,4-tetrahydroquinolin-7-yl)-3-(phenylethynyl)picolinic acid;

(E)-6-(1-(benzo[d]thiazol-2-ylcarbamoyl)-1,2,3,4-tetrahydroquinolin-7-yl)-3-(4-fluorophenethoxy)picolinic acid;

6-(1-(benzo[d]thiazol-2-ylcarbamoyl)-1,2,3,4-tetrahydroquinolin-7-yl)-3-(4-fluorophenethoxy)picolinic acid;

6-(1-(benzo[d]thiazol-2-ylcarbamoyl)-1,2,3,4-tetrahydroquinolin-7-yl)-3-(2-phenoxyethoxy)picolinic acid;

6-(4-(benzo[d]thiazol-2-ylcarbamoyl)-3,4-dihydro-2H-benzo[b][1,4]oxazin-6-yl)-3-(3-phenoxypropoxy)picolinic acid;

3-(2-(3-aminophenoxy)ethoxy)-6-(1-(benzo[d]thiazol-2-ylcarbamoyl)-1,2,3,4-tetrahydroquinolin-7-yl)picolinic acid;

6-(1-(benzo[d]thiazol-2-ylcarbamoyl)-1,2,3,4-tetrahydroquinolin-7-yl)-3-(3-(4-chlorophenyl)propoxy)picolinic acid;

6-(1-(benzo[d]thiazol-2-ylcarbamoyl)-1,2,3,4-tetrahydroquinolin-7-yl)-3-(4-methoxyphenethoxy)picolinic acid;

6-(4-(benzo[d]thiazol-2-ylcarbamoyl)-1-methyl-1,2,3,4-tetrahydroquinoxalin-6-yl)-3-(3-phenoxypropoxy)picolinic acid;

3-(2-(4-(aminomethyl)phenoxy)ethoxy)-6-(1-(benzo[d]thiazol-2-ylcarbamoyl)-1,2,3,4-tetrahydroquinolin-7-yl)picolinic acid;

6-(1-(benzo[d]thiazol-2-ylcarbamoyl)-1,2,3,4-tetrahydroquinolin-7-yl)-3-(4-tert-butylphenyl)picolinic acid;

6-(1-(benzo[d]thiazol-2-ylcarbamoyl)-1,2,3,4-tetrahydroquinolin-7-yl)-3-(4-(dimethylamino)phenethoxy)picolinic acid;

6-(1-(benzo[d]thiazol-2-ylcarbamoyl)-1,2,3,4-tetrahydroquinolin-7-yl)-3-(2-(3-(dimethylamino)phenoxy)ethoxy)picolinic acid;

6-(1-(benzo[d]thiazol-2-ylcarbamoyl)-1,2,3,4-tetrahydroquinolin-7-yl)-3-(4-(4-methoxyphenyl)butoxy)picolinic acid;

6-(1-(benzo[d]thiazol-2-ylcarbamoyl)-1,2,3,4-tetrahydroquinolin-7-yl)-3-(3-(4-(dimethylamino)phenyl)propoxy)picolinic acid;

6-(1-(benzo[d]thiazol-2-ylcarbamoyl)-1,2,3,4-tetrahydroquinolin-7-yl)-3-(3-(4-(dimethylamino)phenoxy)propoxy)picolinic acid;

6-(1-(benzo[d]thiazol-2-ylcarbamoyl)-1,2,3,4-tetrahydroquinolin-7-yl)-3-(3-(3-(dimethylamino)phenoxy)propoxy)picolinic acid;

6-(1-(benzo[d]thiazol-2-ylcarbamoyl)-1,2,3,4-tetrahydroquinolin-7-yl)-3-(2-(4-(dimethylamino)benzylamino)ethoxy)picolinic acid;

6-(1-(benzo[d]thiazol-2-ylcarbamoyl)-1,2,3,4-tetrahydroquinolin-7-yl)-3-(2-(4-(tert-butoxycarbonylamino)phenoxy)ethoxy)picolinic acid;

6-(1-(benzo[d]thiazol-2-ylcarbamoyl)-1,2,3,4-tetrahydroquinolin-7-yl)-3-(2-(3-(tert-butoxycarbonylamino)phenoxy)ethoxy)picolinic acid;

6-(1-(benzo[d]thiazol-2-ylcarbamoyl)-1,2,3,4-tetrahydroquinolin-7-yl)-6'-(4-methylpiperazin-1-yl)-3,3'-bipyridine-2-carboxylic acid;

3-(3-(benzo[d][1,3]dioxol-5-yloxy)propoxy)-6-(1-(benzo[d]thiazol-2-ylcarbamoyl)-1,2,3,4-tetrahydroquinolin-7-yl)picolinic acid;

6-(1-(benzo[d]thiazol-2-ylcarbamoyl)-1,2,3,4-tetrahydroquinolin-7-yl)-3-(2-(2,2,4,7-tetramethyl-3,4-dihydroquinolin-1(2H)-yl)ethoxy)picolinic acid;

6-(1-(benzo[d]thiazol-2-ylcarbamoyl)-1,2,3,4-tetrahydroquinolin-7-yl)-3-(1-benzyl-1H-pyrazol-4-yl)picolinic acid;

6-(1-(benzo[d]thiazol-2-ylcarbamoyl)-1,2,3,4-tetrahydroquinolin-7-yl)-3-(biphenyl-4-ylmethoxy)picolinic acid;

3-(3-((3-aminophenoxy)methyl)phenyl)-6-(1-(benzo[d]thiazol-2-ylcarbamoyl)-1,2,3,4-tetrahydroquinolin-7-yl)picolinic acid;

6-(1-(benzo[d]thiazol-2-ylcarbamoyl)-1,2,3,4-tetrahydroquinolin-7-yl)-3-(3-((3-(tert-butoxycarbonylamino)phenoxy)methyl)phenyl)picolinic acid;

6-(1-(benzo[d]thiazol-2-ylcarbamoyl)-1,2,3,4-tetrahydroquinolin-7-yl)-3-(1-indol-5-yl)picolinic acid;

6-(1-(benzo[d]thiazol-2-ylcarbamoyl)-1,2,3,4-tetrahydroquinolin-7-yl)-3-(2-methyl-4-oxo-3,4-dihydroquinazolin-6-yl)picolinic acid;

6-1-(benzo[d]thiazol-2-ylcarbamoyl)-1,2,3,4-tetrahydroquinolin-7-yl)-3-(naphthalen-2-yl)picolinic acid;

6-(1-(benzo[d]thiazol-2-ylcarbamoyl)-1,2,3,4-tetrahydroquinolin-7-yl)-3-(3-(quinolin-8-yloxy)propoxy)picolinic acid;

2-(1-(benzo[d]thiazol-2-ylcarbamoyl)indolin-6-yl)thiazole-4-carboxylic acid;

6-(1-(benzo[d]thiazol-2-ylcarbamoyl)-2,3,4,5-tetrahydro-1H-benzo[b]azepin-8-yl)-3-(3-phenylpropoxy)picolinic acid;

5-(4-methoxyphenyl)-2-(1-(thiazol-2-ylcarbamoyl)-1,2,3,4-tetrahydroquinolin-7-yl)thiazole-4-carboxylic acid;

5-(4-methoxyphenyl)-2-(1-(4-methylthiazol-2-ylcarbamoyl)-1,2,3,4-tetrahydroquinolin-7-yl)thiazole-4-carboxylic acid;

5-(4-methoxyphenyl)-2-(1-(5-methylthiazol-2-ylcarbamoyl)-1,2,3,4-tetrahydroquinolin-7-yl)thiazole-4-carboxylic acid;

2-(4-(benzo[d]thiazol-2-ylcarbamoyl)-3,4-dihydro-2H-benzo[b][1,4]oxazin-6-yl)thiazole-4-carboxylic acid;

2-(4-(benzo[d]thiazol-2-ylcarbamoyl)-3,4-dihydro-2H-benzo[h][1,4]oxazin-6-yl)-5-chlorothiazole-4-carboxylic acid;

2-(4-(benzo[d]oxazol-2-ylcarbamoyl)-3,4-dihydro-2H-benzo[b][1,4]oxazin-6-yl)thiazole-4-carboxylic acid;

(E)-2-(1-(benzo[d]thiazol-2-ylcarbamoyl)-1,2,3,4-tetrahydroquinolin-7-yl)-5-(prop-1-enyl)thiazole-4-carboxylic acid;

6-(4-(benzo[d]thiazol-2-ylcarbamoyl)-3,4-dihydro-2H-benzo[b][1,4]oxazin-6-yl)picolinic acid;

6-(1-(benzo[d]thiazol-2-ylcarbamoyl)-1,2,3,4-tetrahydroquinolin-7-yl)picolinic acid;

2-(4-(quinolin-2-ylcarbamoyl)-3,4-dihydro-2H-benzo[b][1,4]oxazin-6-yl)thiazole-4-carboxylic acid;

2-(4-(benzo[d]thiazol-2-ylcarbamoyl)-3,4-dihydro-2H-benzo[b][1,4]oxazin-6-yl)-5-phenylthiazole-4-carboxylic acid;

2-(4-(benzo[d]thiazol-2-ylcarbamoyl)-3,4-dihydro-2H-benzo[b][1,4]oxazin-6-yl)-5-(4-fluorophenyl)thiazole-4-carboxylic acid;

2-(4-(benzo[d]thiazol-2-ylcarbamoyl)-3,4-dihydro-2H-benzo[b][1,4]oxazin-6-yl)-5-(3-fluorophenyl)thiazole-4-carboxylic acid;

2-(1-(benzo[d]thiazol-2-ylcarbamoyl)-1,2,3,4-tetrahydroquinolin-7-yl)-5-phenylthiazole-4-carboxylic acid;

2-(1-(benzo[d]thiazol-2-ylcarbamoyl)-1,2,3,4-tetrahydroquinolin-7-yl)-5-phenoxythiazole-4-carboxylic acid;

2-(4-(benzo[d]thiazol-2-ylcarbamoyl)-3,4-dihydro-2H-benzo[b][1,4]oxazin-6-yl)-5-p-tolylthiazole-4-carboxylic acid;

2-(1-(benzo[d]thiazol-2-ylcarbamoyl)-1,2,3,4-tetrahydroquinolin-7-yl)-5-(4-fluorophenoxy)thiazole-4-carboxylic acid;

2-(4-(benzol dithiazol-2-ylcarbamoyl)-3,4-dihydro-2H-benzo[b][1,4]oxazin-6-yl)-5-(4-methoxyphenyl)thiazole-4-carboxylic acid;

2-(4-(benzo[d]thiazol-2-ylcarbamoyl)-3,4-dihydro-2H-benzo[b][1,4]oxazin-6-yl)-5-(3-methoxyphenyl)thiazole-4-carboxylic acid;

2-(4-(benzo[d]thiazol-2-ylcarbamoyl)-3,4-dihydro-2H-benzo[b][1,4]oxazin-6-yl)-5-(4-carboxyphenyl)thiazole-4-carboxylic acid;

2-(4-(benzo[d]thiazol-2-ylcarbamoyl)-3,4-dihydro-2H-benzo[b][1,4]oxazin-6-yl)-5-(4-methoxyphenoxy)thiazole-4-carboxylic acid;

2-(4-(benzo[d]thiazol-2-ylcarbamoyl)-3,4-dihydro-2H-benzo[b][1,4]oxazin-6-yl)-5-(4-methoxyphenoxy)thiazole-4-carboxylic acid;

2-(1-(benzo[d]thiazol-2-ylcarbamoyl)-1,2,3,4-tetrahydroquinolin-7-yl)-5-(4-fluorophenoxy)thiazole-4-carboxamide;

2-(1-(benzo[d]thiazol-2-ylcarbamoyl)-1,2,3,4-tetrahydroquinolin-7-yl)-5-(4-methoxyphenyl)thiazole-4-carboxylic acid;

2-(1-(6-fluorobenzo[d]thiazol-2-ylcarbamoyl)-1,2,3,4-tetrahydroquinolin-7-yl)-5-(4-methoxyphenyl)thiazole-4-carboxylic acid;

2-(4-(benzo[d]thiazol-2-ylcarbamoyl)-3,4-dihydro-2H-benzo[b][4]oxazin-6-yl)-5-(3-(pyridin-4-ylthio)propyl)thiazole-4-carboxylic acid;

(E)-2-(1-(benzo[d]thiazol-2-ylcarbamoyl)-1,2,3,4-tetrahydroquinolin-7-yl)-5-styrylthiazole-4-carboxylic acid;

2-(1-(benzo[d]thiazol-2-ylcarbamoyl)-1,2,3,4-tetrahydroquinolin-7-yl)-5-(4-ethoxyphenyl)thiazole-4-carboxylic acid;

2-(4-(benzo[d]thiazol-2-ylcarbamoyl)-3,4-dihydro-2H-benzo[b][1,4]oxazin-6-yl)-5-(methyl(2-phenoxyethyl)amino)thiazole-4-carboxylic acid;

2-(4-(benzo[d]thiazol-2-ylcarbamoyl)-3,4-dihydro-2H-benzo[b][1,4]oxazin-6-yl)-5-(4-phenylbutyl)thiazole-4-carboxylic acid;

2-(1-(benzo[d]thiazol-2-ylcarbamoyl)-1,2,3,4-tetrahydroquinolin-7-yl)-5-(3-phenoxypropyl)thiazole-4-carboxylic acid;

2-1-(benzo[d]thiazol-2-ylcarbamoyl)-1,2,3,4-tetrahydroquinolin-7-yl)-5-(4-isopropoxyphenyl)thiazole-4-carboxylic acid;

2-(1-(benzo[d]thiazol-2-yl carbamoyl)-1,2,3,4-tetrahydroquinolin-7-yl)-5-(3-fluoro-4-isopropoxyphenyl)thiazole-4-carboxylic acid;

2-(1-(benzo[d]thiazol-2-ylcarbamoyl)-1,2,3,4-tetrahydroquinolin-7-yl)-5-(4-methoxyphenyl)-N,N-dimethylthiazole-4-carboxamide;

5-(3-(3-aminophenoxy)propyl)-2-(1-(benzo[d]thiazol-2-ylcarbamoyl)-1,2,3,4-tetrahydroquinolin-7-yl)thiazole-4-carboxylic acid;

5-(3-(4-(aminomethyl)phenoxy)propyl)-2-(4-(benzo[d]thiazol-2-ylcarbamoyl)-3,4-dihydro-2H-benzo[b][1,4]oxazin-6-yl)thiazole-4-carboxylic acid;

2-(1-(benzo[d]thiazol-2-ylcarbamoyl)-1,2,3,4-tetrahydroquinolin-7-yl)-5-(3-(4-tert-butylphenoxy)propyl)thiazole-4-carboxylic acid;

2-(1-(benzo[d]thiazol-2-ylcarbamoyl)-1,2,3,4-tetrahydroquinolin-7-yl)-5-(3-(4-(tert-butoxycarbonylamino)phenoxy)propyl)thiazole-4-carboxylic acid;

2-(1-(benzo[d]thiazol-2-ylcarbamoyl)-1,4-tetrahydroquinolin-7-yl)-5-(3-(3-(tert-butoxycarbonylamino)phenoxy)propyl)thiazole-4-carboxylic acid;

2-(4-(benzo[d]thiazol-2-ylcarbamoyl)-3,4-dihydro-2H-benzo[b][1,4]oxazin-6-yl)-5-(3-(4-((tert-butoxycarbonylamino)methyl)phenoxy)propyl)thiazole-4-carboxylic acid;

6-(4-(benzo[d]thiazol-2-ylcarbamoyl)-3,4-dihydro-2H-benzo[b][1,4]oxazin-6-yl)-3-(3-phenylpropoxy)picolinic acid;

3-(3-phenylpropoxy)-6-(4-(pyrazolo[1,5-a]pyridin-2-ylcarbamoyl)-3,4-dihydro-2H-benzo[b][1,4]oxazin-6-yl)picolinic acid;

6-(1-(benzo[d]thiazol-2-ylcarbamoyl)-1,2,3,4-tetrahydroquinolin-7-yl)-3-(3-phenylpropoxy)picolinic acid;

N-(benzo[d]thiazol-2-yl)-6-(6-(methylsulfonylcarbamoyl)-5-(3-phenylpropoxy)pyridin-2-yl)-2H-benzo[b][1,4]oxazine-4(3H)-carboxamide;

2-(1-(benzo[d]thiazol-2-ylcarbamoyl)-1,2,3,4-tetrahydroquinolin-7-yl)-5-(biphenyl-4-yl)thiazole-4-carboxylic acid;

5-(4-(1H-pyrazolo[3,4-d]pyrimidin-1-yl)phenoxy)-2-(1-(benzo[d]thiazol-2-ylcarbamoyl)-1,2,3,4-tetrahydroquinolin-7-yl)thiazole-4-carboxylic acid; and 5-(3-(4-(1H-pyrazolo[3,4-d]pyrimidin-1-yl)phenoxy)propyl)-2-(1-(benzo[d]thiazol-2-ylcarbamoyl)-1,2,3,4-tetrahydroquinolin-7-yl)thiazole-4-carboxylic acid.

19. A pharmaceutical composition comprising the compound of claim 1 or the pharmaceutically acceptable salt thereof, and at least one pharmaceutically acceptable diluent, carrier or excipient.

20. 6-(1-(benzo[d]thiazol-2-ylcarbamoyl)-1,2,3,4-tetrahydroquinolin-7-yl)-3-(3-(4-(dimethylamino)phenoxy)propoxy)picolinic acid, or a pharmaceutically acceptable salt thereof.

* * * * *

UNITED STATES PATENT AND TRADEMARK OFFICE
CERTIFICATE OF CORRECTION

PATENT NO. : 8,114,893 B2
APPLICATION NO. : 12/641063
DATED : February 14, 2012
INVENTOR(S) : Baell et al.

It is certified that error appears in the above-identified patent and that said Letters Patent is hereby corrected as shown below:

In the Specification

In column 198, line 30, replace " $C_{2-6}$, alkenyl " with -- $C_{2-6}$ alkenyl --.

In column 199, line 20, replace " $-OR^c$ " with -- $-OR^e$ --.

In column 200, line 57, replace " $-C(O)OR^t$ " with -- $-Z^2-C(O)OR^t$ --.

In the Claims

Claim 1
In column 201, line 2, replace " $C_{3-7}$ alkynyl " with -- $C_{2-6}$ alkynyl --.

Claim 7
In column 204, line 28, add -- $-OR^p$ -- after " $-SR^p$ ".

Claim 18
In column 216, lines 47–49, replace "(E)-6-(1-(benzo[d]thiazol-2-ylcarbamoyl)-1,2,3,4-tetrahydroquinolin-7-yl)-3-(4-fluorophenethoxy)picolinic acid" with -- (E)-6-(1-(benzo[d]thiazol-2-ylcarbamoyl)-1,2,3,4-tetrahydroquinolin-7-yl)-3-(4-fluorostyryl)picolinic acid --.

Claim 18
In column 217, lines 52–53, replace "6-(1-(benzo[d]thiazol-2-ylcarbamoyl)-1,2,3,4-tetrahydroquinolin-7-yl)-3-(1-indol-5-yl)picolinic acid" with -- 6-(1-(benzo[d]thiazol-2-ylcarbamoyl)-1,2,3,4-tetrahydroquinolin-7-yl)-3-(1H-indol-5-yl)picolinic acid --.

Claim 18
In column 217, lines 57–58, replace "6-1-(benzo[d]thiazol-2-ylcarbamoyl)-1,2,3,4-tetrahydroquinolin-7-yl)-3-(naphthalen-2-yl)picolinic acid" with -- 6-(1-(benzo[d]thiazol-2-ylcarbamoyl)-1,2,3,4-tetrahydroquinolin-7-yl)-3-(naphthalen-2-yl)picolinic acid --.

Signed and Sealed this
Twenty-seventh Day of August, 2013

Teresa Stanek Rea
*Acting Director of the United States Patent and Trademark Office*

CERTIFICATE OF CORRECTION (continued)
U.S. Pat. No. 8,114,893 B2

Claim 18

In column 218, lines 9–11, replace "2-(4-(benzo[d]thiazol-2-ylcarbamoyl)-3,4-dihydro-2H-benzo[h][1,4]oxazin-6-yl)-5-chlorothiazole-4-carboxylic acid" with -- 2-(4-(benzo[d]thiazol-2-ylcarbamoyl)-3,4-dihydro-2H-benzo[b][1,4]oxazin-6-yl)-5-chlorothiazole-4-carboxylic acid --.

Claim 18

In column 218, lines 42–44, replace "2-(4-(benzol dithiazol-2-ylcarbamoyl)-3,4-dihydro-2H-benzo[b][1,4]oxazin-6-yl)-5-(4-methoxyphenyl)thiazole-4-carboxylic acid" with -- 2-(4-(benzo[d]thiazol-2-ylcarbamoyl)-3,4-dihydro-2H-benzo[b][1,4]oxazin-6-yl)-5-(4-methoxyphenyl)thiazole-4-carboxylic acid --.

Claim 18

In column 218, lines 65–67, replace "2-(4-(benzo[d]thiazol-2-ylcarbamoyl)-3,4-dihydro-2H-benzo[b][4]oxazin-6-yl)-5-(3-(pyridin-4-ylthio)propyl)thiazole-4-carboxylic acid" with -- 2-(4-(benzo[d]thiazol-2-ylcarbamoyl)-3,4-dihydro-2H-benzo[b][1,4]oxazin-6-yl)-5-(3-(pyridin-4-ylthio)propyl)thiazole-4-carboxylic acid --.

Claim 18

In column 219, lines 16–18, replace "2-1-(benzo[d]thiazol-2-ylcarbamoyl)-1,2,3,4-tetrahydroquinolin-7-yl)-5-(4-isopropoxyphenyl)thiazole-4-carboxylic acid" with -- 2-(1-(benzo[d]thiazol-2-ylcarbamoyl)-1,2,3,4-tetrahydroquinolin-7-yl)-5-(4-isopropoxyphenyl)thiazole-4-carboxylic acid --.

Claim 18

In column 219, lines 19–21, replace "2-(1-(benzo[d]thiazol-2-yl carbamoyl)-1,2,3,4-tetrahydroquinolin-7-yl)-5-(3-fluoro-4-isopropoxyphenyl)thiazole-4-carboxylic acid" with -- 2-(1-(benzo[d]thiazol-2-ylcarbamoyl)-1,2,3,4-tetrahydroquinolin-7-yl)-5-(3-fluoro-4-isopropoxyphenyl)thiazole-4-carboxylic acid --.

Claim 18

In column 220, lines 1–3, replace "2-(1-(benzo[d]thiazol-2-ylcarbamoyl)-1,4-tetrahydroquinolin-7-yl)-5-(3-(3-(tert-butoxycarbonylamino)phenoxy)propyl)thiazole-4-carboxylic acid" with -- 2-(1-(benzo[d]thiazol-2-ylcarbamoyl)-1,2,3,4-tetrahydroquinolin-7-yl)-5-(3-(3-(tert-butoxycarbonylamino)phenoxy)propyl)thiazole-4-carboxylic acid --.

SEQUENCE LISTING

```
<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Probe Peptide
<220> FEATURE:
<221> NAME/KEY: MOD_RES
<222> LOCATION: 13
<223> OTHER INFORMATION: Lys is modified with 6-FAM
<220> FEATURE:
<221> NAME/KEY: MOD_RES
<222> LOCATION: 16
<223> OTHER INFORMATION: Arg is modified with amide

<400> SEQUENCE: 1

Gly Gln Val Gly Arg Gln Leu Ala Ile Ile Gly Asp Lys Ile Asn Arg
 1               5                   10                  15
```